United States Patent
Lin et al.

(10) Patent No.: US 11,845,799 B2
(45) Date of Patent: Dec. 19, 2023

(54) ANTI-LY6G6D ANTIBODIES AND METHODS OF USE

(71) Applicant: Genentech, Inc., South San Francisco, CA (US)

(72) Inventors: WeiYu Lin, Millbrae, CA (US); Christoph Spiess, Mountain View, CA (US); Liping Sun, San Ramon, CA (US); Yan Wu, Foster City, CA (US); Cecilia P. C. Chiu, Redwood City, CA (US); Walter Christian Darbonne, Burlingame, CA (US); Michael Andrew Dillon, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 262 days.

(21) Appl. No.: 17/119,753

(22) Filed: Dec. 11, 2020

(65) Prior Publication Data
US 2021/0179715 A1    Jun. 17, 2021

Related U.S. Application Data

(60) Provisional application No. 62/948,097, filed on Dec. 13, 2019.

(51) Int. Cl.
*C07K 16/28*    (2006.01)
*A61K 39/00*    (2006.01)

(52) U.S. Cl.
CPC ...... *C07K 16/2824* (2013.01); *C07K 16/2809* (2013.01); *A61K 2039/507* (2013.01); *C07K 2317/565* (2013.01); *C07K 2317/567* (2013.01); *C07K 2317/92* (2013.01)

(58) Field of Classification Search
CPC ............ C07K 16/2824; C07K 16/2809; C07K 2317/565; C07K 2317/567; C07K 2317/92; C07K 14/70539; C07K 16/468; C07K 2317/41; C07K 2317/71; C07K 2317/72; C07K 2317/90; C07K 2317/73; A61K 2039/507; A61P 35/00
See application file for complete search history.

(56) References Cited

U.S. PATENT DOCUMENTS

| | | | |
|---|---|---|---|
| 5,821,337 A | 10/1998 | Carter et al. | |
| 6,194,551 B1 | 2/2001 | Idusogie et al. | |
| 6,248,516 B1 | 6/2001 | Winter et al. | |
| 6,455,043 B1 | 9/2002 | Grillo-Lopez | |
| 6,602,684 B1 | 8/2003 | Umana et al. | |
| 6,737,056 B1 | 5/2004 | Presta | |
| 7,332,581 B2 | 2/2008 | Presta | |
| 7,371,826 B2 | 5/2008 | Presta | |
| 7,612,181 B2 | 11/2009 | Wu et al. | |
| 7,695,936 B2 | 4/2010 | Carter et al. | |
| 7,951,546 B2 | 5/2011 | Frantz et al. | |
| 8,258,268 B2 | 9/2012 | Wu et al. | |
| 8,722,859 B2 | 5/2014 | Miller et al. | |
| 9,011,864 B2 | 4/2015 | Schulz et al. | |
| 9,017,676 B2 | 4/2015 | Lindhofer | |
| 9,308,257 B2 | 4/2016 | Sharma, Sr. et al. | |
| 9,315,567 B2 | 4/2016 | Chang et al. | |
| 9,587,021 B2 | 3/2017 | Huang et al. | |
| 9,657,102 B2 | 5/2017 | Smith et al. | |
| 10,174,124 B2 | 1/2019 | Chen et al. | |
| 10,501,545 B2 | 12/2019 | Kelley et al. | |
| 10,640,572 B2 | 5/2020 | Chen et al. | |
| 11,007,267 B2 | 5/2021 | Lee et al. | |
| 11,116,840 B2 | 9/2021 | Carter et al. | |
| 2012/0244577 A1 | 9/2012 | Dixit et al. | |
| 2013/0129723 A1 | 5/2013 | Blankenship et al. | |
| 2013/0150558 A1 | 6/2013 | Williams et al. | |
| 2013/0287774 A1 | 10/2013 | Zugmaier et al. | |
| 2014/0088295 A1 | 3/2014 | Smith et al. | |
| 2014/0112914 A1 | 4/2014 | Nezu et al. | |
| 2014/0170149 A1 | 6/2014 | Neijssen et al. | |
| 2014/0187753 A1 | 7/2014 | Blein et al. | |
| 2014/0221244 A1 | 8/2014 | Chapman et al. | |
| 2014/0302064 A1 | 10/2014 | Moore | |
| 2014/0377270 A1 | 12/2014 | Moore et al. | |
| 2015/0166661 A1* | 6/2015 | Chen ..................... A61P 17/06 435/254.2 |
| 2015/0266966 A1 | 9/2015 | Smith et al. | |
| 2015/0284475 A1 | 10/2015 | Zhou et al. | |
| 2016/0000916 A1 | 1/2016 | Crotts et al. | |
| 2016/0017058 A1 | 1/2016 | Kim et al. | |
| 2016/0075785 A1 | 3/2016 | Ast et al. | |

(Continued)

FOREIGN PATENT DOCUMENTS

| CN | 101675077 B | 3/2010 |
|---|---|---|
| EP | 1923072 A1 | 5/2008 |

(Continued)

OTHER PUBLICATIONS

Atwell et al., "Stable Heterodimers from Remodeling the Domain Interface of a Homodimer using a Phage Display Library," J Mol Biol. 270(1):26-35 (1997).
Baeuerle et al., "Bispecific T-cell engaging antibodies for cancer therapy," Cancer Res. 69(12):4941-4. (2009) doi: 10.1158/0008-5472.CAN-09-0547.
Bortoletto et al., "Optimizing anti-CD3 affinity for effective T cell targeting against tumor cells," Eur J Immunol. 32(11):3102-7 (2002).
Brack et al., "A Bispecific HER2-Targeting FynomAb with Superior Antitumor Activity and Novel Mode of Action," Mol Cancer Ther. 13(8):2030-39 (2014) (11 pages).
Brinkmann et al., "The making of bispecific antibodies," mAbs. 9(2):182-212 (2017).

(Continued)

*Primary Examiner* — Nelson B Moseley, II
(74) *Attorney, Agent, or Firm* — Clark & Elbing LLP; Karen L. Elbing

(57) ABSTRACT

Provided herein are anti-Ly6G6D (lymphocyte antigen 6 complex, locus G61) antibodies and methods of using the same.

44 Claims, 107 Drawing Sheets
(97 of 107 Drawing Sheet(s) Filed in Color)
Specification includes a Sequence Listing.

(56) References Cited

U.S. PATENT DOCUMENTS

| | | |
|---|---|---|
| 2016/0090416 A1 | 3/2016 | Gunde et al. |
| 2016/0145339 A1 | 5/2016 | Zhou et al. |
| 2017/0022274 A1 | 1/2017 | Chang et al. |
| 2017/0204194 A1 | 7/2017 | Chen et al. |
| 2017/0224818 A1 | 8/2017 | Lindhofer et al. |
| 2018/0057593 A1 | 3/2018 | Dennis |
| 2018/0117152 A1 | 5/2018 | Lee et al. |
| 2018/0177873 A1 | 6/2018 | Carter et al. |
| 2021/0244815 A1 | 8/2021 | Lee et al. |

FOREIGN PATENT DOCUMENTS

| | | | |
|---|---|---|---|
| EP | 2482212 A1 | 8/2012 | |
| EP | 2769989 A1 | 8/2014 | |
| EP | 2789630 A1 | 10/2014 | |
| EP | 2840091 A1 | 2/2015 | |
| JP | 2009-539413 A | 11/2009 | |
| JP | 2010-524435 A | 7/2010 | |
| JP | 2013-515509 A | 5/2013 | |
| JP | 2013-528569 A | 7/2013 | |
| JP | 2015-509952 A | 4/2015 | |
| WO | WO-94/04679 A1 | 3/1994 | |
| WO | WO-94/29351 A2 | 12/1994 | |
| WO | WO-96/01126 A1 | 1/1996 | |
| WO | WO-96/27011 A1 | 9/1996 | |
| WO | WO-97/30087 A1 | 8/1997 | |
| WO | WO-98/50431 A2 | 11/1998 | |
| WO | WO-98/58964 A1 | 12/1998 | |
| WO | WO-98/50431 A3 | 1/1999 | |
| WO | WO-99/22764 A1 | 5/1999 | |
| WO | WO-99/51642 A1 | 10/1999 | |
| WO | WO-00/61739 A1 | 10/2000 | |
| WO | WO-01/29246 A1 | 4/2001 | |
| WO | WO-02/31140 A1 | 4/2002 | |
| WO | WO-03/011878 A2 | 2/2003 | |
| WO | WO-03/084570 A1 | 10/2003 | |
| WO | WO-03/085107 A1 | 10/2003 | |
| WO | WO-03/085119 A1 | 10/2003 | |
| WO | WO-03/087131 A2 | 10/2003 | |
| WO | WO-2004/056312 A2 | 7/2004 | |
| WO | WO-2004/106380 A2 | 12/2004 | |
| WO | WO-2005/035586 A1 | 4/2005 | |
| WO | WO-2005/035778 A1 | 4/2005 | |
| WO | WO-2005/053742 A1 | 6/2005 | |
| WO | WO-2005/100402 A1 | 10/2005 | |
| WO | WO-2006/029879 A2 | 3/2006 | |
| WO | WO-2007/018316 A1 | 2/2007 | |
| WO | WO-2007/042261 A2 | 4/2007 | |
| WO | WO-2007/110205 A2 | 10/2007 | |
| WO | WO-2007/146968 A2 | 12/2007 | |
| WO | WO-2008/077546 A1 | 7/2008 | |
| WO | WO-2008/119566 A2 | 10/2008 | |
| WO | WO-2008/119567 A2 | 10/2008 | |
| WO | WO-2009/070642 A1 | 6/2009 | |
| WO | WO-2010/081173 A2 | 7/2010 | |
| WO | WO-2010/114940 A1 | 10/2010 | |
| WO | WO-2011/028952 A1 | 3/2011 | |
| WO | WO-2011/090754 A1 | 7/2011 | |
| WO | WO-2011/090762 A1 | 7/2011 | |
| WO | WO-2011/121110 A1 | 10/2011 | |
| WO | WO-2011/131746 A2 | 10/2011 | |
| WO | WO-2011/143545 A1 | 11/2011 | |
| WO | WO-2012/058768 A1 | 5/2012 | |
| WO | WO-2012/058768 A8 | 6/2012 | |
| WO | WO-2012/073985 A1 | 6/2012 | |
| WO | WO-2012/075581 A1 | 6/2012 | |
| WO | WO-2012/123949 A1 | 9/2012 | |
| WO | WO-2012/143524 A2 | 10/2012 | |
| WO | WO-2012/158818 A2 | 11/2012 | |
| WO | WO-2012/162067 A2 | 11/2012 | |
| WO | WO-2013/128194 A1 | 9/2013 | |
| WO | WO-2013/163631 A2 | 10/2013 | |
| WO | WO-2013/192546 A1 | 12/2013 | |
| WO | WO-2013/192550 A2 | 12/2013 | |
| WO | WO-2014/012085 A2 | 1/2014 | |
| WO | WO-2014/022540 A1 | 2/2014 | |
| WO | WO-2014/028560 A2 | 2/2014 | |
| WO | WO-2014/047231 A1 | 3/2014 | |
| WO | WO-2014/028560 A3 | 5/2014 | |
| WO | WO-2014/083178 A1 | 6/2014 | |
| WO | WO-2014/107599 A2 | 7/2014 | |
| WO | WO-2014/108483 A1 | 7/2014 | |
| WO | WO-2014/122251 A2 | 8/2014 | |
| WO | WO-2014/141152 A2 | 9/2014 | |
| WO | WO-2014/144722 A2 | 9/2014 | |
| WO | WO-2014/153002 A1 | 9/2014 | |
| WO | WO-2014/122251 A3 | 10/2014 | |
| WO | WO-2014/170063 A1 | 10/2014 | |
| WO | WO-2014/141152 A3 | 12/2014 | |
| WO | WO-2014/191113 A1 | 12/2014 | |
| WO | WO-2015/006749 A2 | 1/2015 | |
| WO | WO-2015/013671 A1 | 1/2015 | |
| WO | WO-2014/191113 A8 | 2/2015 | |
| WO | WO-2015/018527 A1 | 2/2015 | |
| WO | WO-2015/095392 A1 | 6/2015 | |
| WO | WO-2015/143079 A1 | 9/2015 | |
| WO | WO-2015/184203 A1 | 12/2015 | |
| WO | WO-2015/184207 A1 | 12/2015 | |
| WO | WO-2016/014942 A1 | 1/2016 | |
| WO | WO-2016/019969 A1 | 2/2016 | |
| WO | WO-2016/020065 A1 | 2/2016 | |
| WO | WO-2016/036678 A1 | 3/2016 | |
| WO | WO-2016/081490 A1 | 5/2016 | |
| WO | WO-2016/110576 A1 | 7/2016 | |
| WO | WO-2016/179003 A1 | 11/2016 | |
| WO | WO-2016/191750 A1 | 12/2016 | |
| WO | WO-2016/201300 A1 | 12/2016 | |
| WO | WO 2016/204966 | * 12/2016 | ............ C07K 16/28 |
| WO | WO-2016/204966 A1 | 12/2016 | |
| WO | WO-2016/205531 A2 | 12/2016 | |
| WO | WO-2017/132279 A1 | 8/2017 | |

OTHER PUBLICATIONS

Brüggemann et al., "Comparison of the Effector Functions of Human Immunoglobulins Using a Matched set of Chimeric Antibodies," J Exp Med. 166(5):1351-61 (1987).

Buhmann et al., "Immunotherapy of recurrent B-cell malignancies after allo-SCT with Bi20 (FBTA05), a trifunctional anti-CD3 x anti-CD20 antibody and donor lymphocyte infusion," Bone Marrow Transplant. 43(5):383-97 (2009).

Carter, "Bispecific human IgG by design," J Immunol Methods. 248(1-2):7-15 (2001).

Chatenoud et al., "CD3-specific antibodies: a portal to the treatment of autoimmunity," Nat Rev Immunol. 7(8):622-32 (2007).

Che-Leung Law et al., "Expression and characterization of recombinant soluble human CD3 molecules: presentation of antigenic epitopes defined on the native TCR-CD3 complex," Int Immunol. 14(4):389-400 (2002).

Choi et al., "Bispecific antibodies engage T cells for antitumor immunotherapy," Expert Opin Biol Ther. 11(7):843-53 (2011).

Clynes et al., "Fc receptors are required in passive and active immunity to melanoma," Proc Natl Acad Sci U S A. 95(2):652-6 (1998).

Cragg et al., "Antibody specificity controls in vivo effector mechanisms of anti-CD20 reagents," Blood. 103(7):2738-43 (2004).

Desnoyers et al., "Tumor-Specific Activation of an EGFR-Targeting Probody Enhances Therapeutic Index," Sci Transl Med. 5(207):207ra144 (2013) (10 pages).

Drent et al., "A Rational Strategy for Reducing On-Target Off-Tumor Effects of CD38-Chimeric Antigen Receptors by Affinity Optimization," Mol Ther. 25(8):1946-58 (2017).

Duncan et al., "The binding site for C1q on IgG," Nature. 332(6166):738-40 (1988).

Durben et al., "Characterization of a Bispecific FLT3 X CD3 Antibody in an Improved, Recombinant Format for the Treatment of Leukemia," Mol Ther. 23(4):648-55 (2015).

Edelman et al., "The covalent structure of an entire gammaG immunoglobulin molecule," Proc Natl Acad Sci U S A. 63(1):78-85 (1969).

(56) References Cited

OTHER PUBLICATIONS

Guyer et al., "Immunoglobulin binding by mouse intestinal epithelial cell receptors," J Immunol. 117(2):587-93 (1976).
Haile et al., "Soluble CD80 Restores T Cell Activation and Overcomes Tumor Cell Programmed Death Ligand 1-Mediated Immune Suppression," J Immunol. 191(5):2829-36 (2013) (9 pages).
Hellström et al., "Antitumor effects of L6, an IgG2a antibody that reacts with most human carcinomas," Proc Natl Acad Sci U S A. 83(18):7059-63 (1986).
Hellström et al., "Strong antitumor activities of IgG3 antibodies to a human melanoma-associated ganglioside," Proc Natl Acad Sci U S A. 82(5):1499-502 (1985).
Holliger et al., "'Diabodies': small bivalent and bispecific antibody fragments," Proc Natl Acad Sci U S A. 90(14):6444-8 (1993).
Holliger et al., "Specific killing of lymphoma cells by cytotoxic T-cells mediated by a bispecific diabody," Protein Eng. 9(3):299-305 (1996).
Honeychurch et al., "Bispecific Ab therapy of B-cell lymphoma: target cell specificity of antibody derivatives appears critical in determining therapeutic outcome," Cancer Immunol Immunother. 45(3-4):171-3 (1997).
Hosseini et al., "Abstract B043: Systems pharmacology modeling of anti-CD20/CD3 T-cell dependent bispecific antibody and its application to clinical trial design," Proceedings of the Second CRI-CIMT-EATI-AACR International Cancer Immunotherapy Conference: Translating Science into Survival; Sep. 25-28; New York, NY. Cancer Immunol Res. 4(11 Suppl):Abstract nr B043 (2016) (4 pages).
Huang et al., "In Vivo Deamidation Characterization of Monoclonal Antibody by LC/MS/MS," Anal Chem. 77(5):1432-9 (2005).
Huang, "Structural chemistry and therapeutic intervention of protein-protein interactions in immune response, human immunodeficiency virus entry, and apoptosis," Pharmacol Ther. 86(3):201-215 (2000).
Hudson et al., "Engineered antibodies," Nat Med. 9(1):129-34 (2003).
Huehls et al., "Bispecific T-cell engagers for cancer immunotherapy," Immunol Cell Biol. 93(3):290-6 (2015).
Idusogie et al., "Mapping of the C1q Binding Site on Rituxan, A Chimeric Antibody with a Human IgG1 Fc," J Immunol. 164(8):4178-84 (2000).
Igawa et al., "VH/VL interface engineering to promote selective expression and inhibit conformational isomerization of thrombopoietin receptor agonist single-chain diabody," Protein Eng Des Sei. 23(8):667-77 (2010) (11 pages).
Jager et al., "The trifunctional antibody ertumaxomab destroys tumor cells that express low levels of human epidermal growth factor receptor 2," Cancer Res. 69(10):4270-6 (2009).
Kanda et al., "Comparison of cell lines for stable production of fucose-negative antibodies with enhanced ADCC," Biotechnol Bioeng. 94(4):680-8 (2006).
Kelley et al.,"Thermodynamic Analysis of an Antibody Functional Epitope," Biochemistry. 32(27):6828-35(1993).
Kim et al., "Localization of the site of the murine IgG1 molecule that is involved in binding to the murine intestinal Fc receptor," Eur J Immunol. 24(10):2429-34 (1994).
Kipriyanov et al., "Bispecific Tandem Diabody for Tumor Therapy with Improved Antigen Binding and Pharmacokinetics," J Mol Biol. 293(1):41-56 (1999).
Klein et al., "Progress in overcoming the chain association issue in bispecific heterodimeric IgG antibodies," MAbs. 4(6):653-63 (2012).
Kontermann, "Dual targeting strategies with bispecific antibodies," MAbs. 4(2):182-97 (2012).
Kortt et al., "Dimeric and trimeric antibodies: high avidity scFvs for cancer targeting," Biomol Eng. 18(3):95-108 (2001) (15 pages).
Leabman et al., "Effects of altered FcgammaR binding on antibody pharmacokinetics in cynomolgus monkeys," MAbs. 5(6):896-903 (2013).
Lee et al., "Current concepts in the diagnosis and management of cytokine release syndrome," retrieved from <www.ncbi.nlm.nih.gov/pmc/articles/PMC4093690/?report=printable> on Feb. 19, 2020, Blood 124(2):188-95 (2014) (18 pages).
Lippow et al., "Computational design of antibody affinity improvement beyond in vivo maturation," available in PMC Jan. 7, 2010, published in final edited form as: Nat Biotechnol. 25(10):1171-6 (2007) (14 pages).
Liu et al., "Affinity-Tuned ErbB2 or EGFR Chimeric Antigen Receptor T Cells Exhibit an Increased Therapeutic Index against Tumors in Mice," Cancer Res. 75(17):3596-607 (2015) (13 pages).
Liu et al., "Heteroantibody duplexes target cells for lysis by cytotoxic T lymphocytes," Proc Natl Acad Sci U S A. 82(24):8648-52 (1985).
Lum et al., "Targeting T cells with bispecific antibodies for cancer therapy," available in PMC Oct. 8, 2013, published in final edited form as: BioDrugs. 25(6):365-79 (2011) (24 pages).
Mallya et al., "Characterization of the five novel Ly-6 superfamily members encoded in the MHC, and detection of cells expressing their potential ligands," Protein Sci. 15(10):2244-56 (2006).
Merchant et al., "An efficient route to human bispecific IgG," Nat Biotechnol. 16(7):677-81 (1998).
Metz et al., "Bispecific antibody derivatives with restricted binding functionalities that are activated by proteolytic processing," Protein Eng Des Sel. 25(10):571-80 (2012).
Milne et al., "Systematic Analysis of Immune Infiltrates in High-Grade Serous Ovarian Cancer Reveals CD20, FoxP3 and TIA-1 as Positive Prognostic Factors," PLoS One. 4(7):e6412 (2009) (14 pages).
Milner et al. "Differential responses of invariant V alpha 24J alpha Q T cells and MHC class II-restricted CD4+ T cells to dexamethasone," J Immunol. 163(5):2522-9 (1999).
Moore et al., "Application of dual affinity retargeting molecules to achieve optimal redirected T-cell killing of B-cell lymphoma," Blood. 117(17):4542-51 (2011) (11 pages).
Nagorsen et al., "Immunomodulatory therapy of cancer with T cell-engaging BiTE antibody blinatumomab," Exp Cell Res. 317(9):1255-60 (2011).
Nishimoto et al., "Toxicity, pharmacokinetics, and dose-finding study of repetitive treatment with the humanized anti-interleukin 6 receptor antibody MRA in rheumatoid arthritis. Phase I/II clinical study," J Rheumatol. 30(7):1426-35 (2003).
Okazaki et al., "Fucose depletion from human IgG1 oligosaccharide enhances binding enthalpy and association rate between IgG1 and FcgammaRllla," J Mol Biol. 336(5):1239-49 (2004).
Paino et al., "Reply to 'Response to "CD20 Positive Cells Are Undetectable in the Majority of Multiple Myeloma Cell Lines and Are Not Associated With a Cancer Stem Cell Phenotype,"'" Haematologica. 97(7):1110-1114 (2012) (1 page).
Pessano et al., "The T3/T cell receptor complex: antigenic distinction between the two 20-kd T3 (T3-delta and T3-epsilon) subunits," EMBO J. 4(2):337-44 (1985).
Petkova et al., "Enhanced half-life of genetically engineered human IgG1 antibodies in a humanized FcRn mouse model: potential application in humorally mediated autoimmune disease," Int Immunol. 18(12):1759-69 (2006).
Ravetch et al., "Fc receptors," Annu Rev Immunol. 9:457-92 (1991).
Reusch et al., "A tetravalent bispecific TandAb (CD19/CD3), AFM11, efficiently recruits T cells for the potent lysis of CD19(+) tumor cells," MAbs. 7(3):584-604 (2015) (22 pages).
Ridgway et al., "'Knobs-into-holes' engineering of antibody CH3 domains for heavy chain heterodimerization," Protein Eng. 9(7):617-21 (1996).
Riedle et al., "In vivo activation and expansion of T cells by a bi-specific antibody abolishes metastasis formation of human melanoma cells in SCID mice," Int J Cancer. 75(6):908-18 (1998).
Ripka et al., "Two Chinese hamster ovary glycosylation mutants affected in the conversion of GDP-mannose to GDP-fucose," Arch Biochem Biophys. 249(2):533-45 (1986).
Roosnek et al., "Triggering T Cells by Otherwise Inert Hybrid Anti-CD3/Antitumor Antibodies Requires Encounter with the Specific Target Cell," J Exp Med. 170(1):297-302 (1989) (6 pages).
Seung et al., "Immunotherapy with long-lived anti-CD20 x anti-CD3 bispecific antibodies stimulates potent t cell-mediated killing

(56) References Cited

OTHER PUBLICATIONS of human b cell lines and of circulating and lymphoid b cells in monkeys: a potential therapy for b cell lymphomas and leukemias," 56th ASH Annual Meeting and Exposition, Dec. 6-9, San Francisco, CA. 124(21):3111 (2014) (1 page).
Shi et al., "Margin-Infiltrating CD20+ B Cells Display an Atypical Memory Phenotype and Correlate with Favorable Prognosis in Hepatocellular Carcinoma," Clin Cancer Res. 19(21):5994-6005 (2013) (13 pages).
Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem. 276(9):6591-604 (2001).
Somasundaram et al., "Will Engineered T Cells Expressing CD20 scFv Eradicate Melanoma?" Mol Ther. 19(4):638-40 (2011).
Sondermann et al., "The 3.2-A crystal structure of the human IgG1 Fc fragment-Fc gammaRIII complex," Nature. 406(6793):267-73 (2000).
Spiess et al., "Alternative molecular formats and therapeutic applications for bispecific antibodies," Mol Immunol. 67(2 Pt A):95-106 (2015).
Spiess et al., "Bispecific antibodies with natural architecture produced by co-culture of bacteria expressing two distinct half-antibodies," Nat Biotechnol. 31(8):753-8 (2013) (7 pages).
Stein et al., "Novel and Emerging Drugs for Acute Myeloid Leukemia," available in PMC May 22, 2014, published in final edited form as: Curr Cancer Drug Targets. 12(5):522-530 (2012) (19 pages).
Stieglmaier et al., "Utilizing the BiTE (bispecific T-cell engager) platform for immunotherapy of cancer," Expert Opin Biol Ther. 15(8):1093-1099 (2015) (8 pages).
Stubenrauch et al., "Impact of molecular processing in the hinge region of therapeutic IgG4 antibodies on disposition profiles in cynomolgus monkeys," Drug Metab Dispos. 38(1):84-91 (2010).
Sun et al., "Anti-CD20/CD3 T cell-dependent bispecific antibody for the treatment of B cell malignancies," Sci Transl Med. 7(287):287ra70 (2015) (11 pages).
Wark et al., "Latest technologies for the enhancement of antibody affinity," Adv Drug Deliv Rev. 58(5-6):657-70 (2006).
Weidle et al., "The Intriguing Options of Multispecific Antibody Formats for Treatment of Cancer," Cancer Genomics Proteomics. 10(1):1-18 (2013) (18 pages).
Wells et al., "Reaching for high-hanging fruit in drug discovery at protein-protein interfaces," Nature. 450(7172):1001-9 (2007).
Wright et al., "Effect of glycosylation on antibody function: implications for genetic engineering," Trends Biotechnol. 15(1):26-32 (1997).
Wu et al., "Humanization of a murine monoclonal antibody by simultaneous optimization of framework and CDR residues," J Mol Biol. 294(1):151-62 (1999).
Wuellner et al., "Bispecific CD3/HER2 Targeting FynomAb Induces Redirected T Cell-Mediated Cytolysis with High Potency and Enhanced Tumor Selectivity," Antibodies. 4(4):426-440 (2015) (15 pages).
Yamane-Ohnuki et al., "Establishment of FUT8 knockout Chinese hamster ovary cells: an ideal host cell line for producing completely defucosylated antibodies with enhanced antibody-dependent cellular cytotoxicity," Biotechnol Bioeng. 87(5):614-22 (2004).
Yan et al., "Succinimide Formation at Asn 55 in the Complementarity Determining Region of a Recombinant Monoclonal Antibody IgG1 Heavy Chain," J Pharm Sci. 98(10):3509-21 (2009).
Zhu et al., "Identification of heavy chain residues in a humanized anti-CD3 antibody important for efficient antigen binding and T cell activation," J Immunol. 155(4):1903-10 (1995).
International Preliminary Report on Patentability for International Patent Application No. PCT/US2020/064635, dated Jun. 23, 2022 (7 pages).
Search Report dated Aug. 8, 2017, for Chen et al., "ANTI-CD3 Antibodies and Methods of Use," Singaporean Patent Application No. 11201604990P, filed Dec. 17, 2014 (6 pages).
Giordano et al., "JAK/Stat5-mediated subtype-specific lymphocyte antigen 6 complex, locus G6D (LY6G6D) expression drives mismatch repair proficient colorectal cancer," J Exp Clin Cancer Res. 38(1):28 (2019) (11 pages).
First Examination Report for Gulf Cooperation Council Patent Application No. 2020-41120, dated Oct. 11, 2021 (4 pages).
Search Report and Written Opinion for International Patent Application No. PCT/US2020/064635, dated Mar. 18, 2021 (9 pages).
Calvanese et al., "Regulation of expression of two LY-6 family genes by intron retension and transcription and transcription induced chimerism," BMC Mol Biol. 9:81 (2008).
Sewda et al., "Cell-surface markers for colon adenoma and adenocarcinoma," Oncotarget. 7(14):17773-17789 (2016).
Beliakov et al, "Exon-intron structure of the LY6G6D gene," Molecular Biology. 43(4):543-551 (2009) (20 pages).
Wang et al., "Novel Anti-LY6G6D/CD3 T-Cell-Dependent Bispecific Antibody for the Treatment of Colorectal Cancer," Mol Cancer Ther. 21(6):974-85 (Jun. 2022).
Office Action and English Translation for Russian Patent Application No. 2022118470 dated Jan. 24, 2023. (14 pages).
Rejection Notice for Iranian Patent Application No. 140150140003002065, dated Mar. 12, 2023 (14 pages).

* cited by examiner

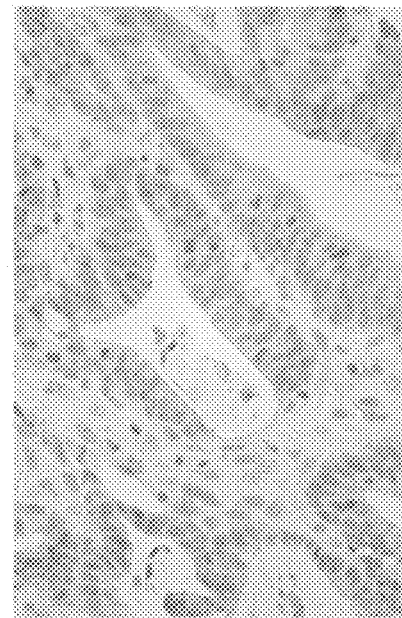
FIG. 2A
Normal colon
FIG. 2C 2+
FIG. 2B 1+
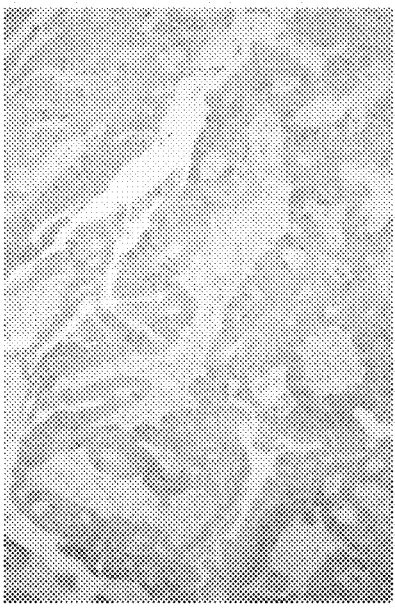
FIG. 2D 3+

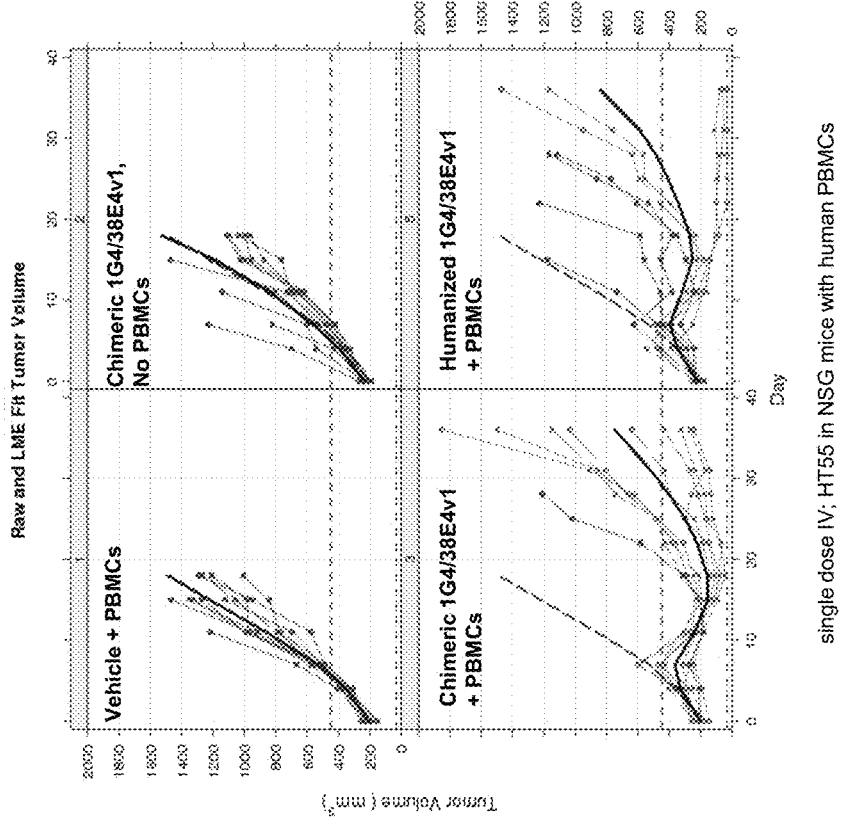
FIG. 3D
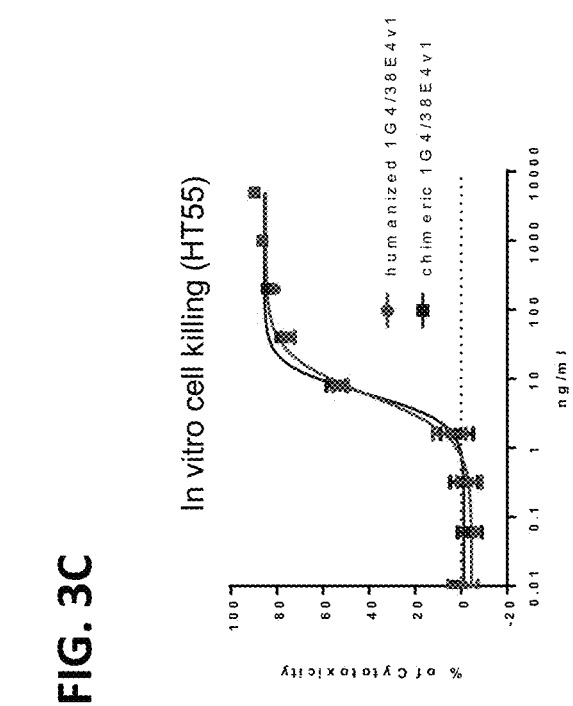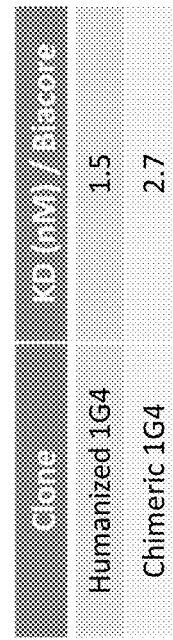
FIG. 3C

FIG. 5A

Heavy chain variable region

| Kabat number | 1 2 3 4 5 6 7 8 9 10 11 12 13 14 15 16 17 18 19 20 21 22 23 24 25 26 27 28 29 30 31 32 33 34 35 36 37 38 39 40 41 42 |
|---|---|
| 20A12.QNTv12 | E V Q L L E S G G G L V Q P G G S L R L S C A A S G F D F Y N N A M I W V R Q A P G |

CDR H1 - Contact: positions 27-32
CDR H1 - Kabat: positions 31-35

| Kabat number | 43 44 45 46 47 48 49 50 51 52 52A 53 54 55 56 57 58 59 60 61 62 63 64 65 66 67 68 69 70 71 72 73 74 75 76 77 78 79 80 81 82 82A |
|---|---|
| 20A12.QNTv12 | K G L E W V S A L S F A D N T A Y Y A T W A S G R F T I S R D S S K T T V Y L Q M N |

CDR H2 - Contact: positions 52-56
CDR H2 - Kabat: positions 50-65

| Kabat number | 82B 82C 83 84 85 86 87 88 89 90 91 92 93 94 95 96 97 98 99 100 101 102 103 104 105 106 107 108 109 110 111 112 113 |
|---|---|
| 20A12.QNTv12 | S L R A E D T A V Y Y C M R G D L W G P G T L V T V S S |

CDR H3: positions 95-102

SEQ ID NO: 22

FIG. 5B

Light chain variable region

```
Kabat number      1  2  3  4  5  6  7  8  9  10 11 12 13 14 15 16 17 18 19 20 21 22 23 24 25 26 27 28 29 30 31 32 33 34 35 36 37 38 39 40 41 42
20A12.QNTv12      D  I  Q  M  T  Q  S  P  S  T  L  S  A  S  V  G  D  R  V  T  I  T  C  Q  A  S  E  S  I  T  R  Y  L  N  W  Y  Q  Q  K  P  G  K
                                                                                 |_____CDR L1 - Kabat_____|
                                                                              |_____CDR L1 - Contact_____|

Kabat number      43 44 45 46 47 48 49 50 51 52 53 54 55 56 57 58 59 60 61 62 63 64 65 66 67 68 69 70 71 72 73 74 75 76 77 78 79 80 81 82 83 84
20A12.QNTv12      A  P  K  L  L  I  Y  D  A  S  K  L  P  S  G  V  P  S  R  F  S  G  S  G  S  G  T  E  F  T  L  T  I  S  S  L  Q  P  D  D  F  A
                           |___CDR L2 - Contact___|
                                 |___CDR L2 - Kabat___|

Kabat number      85 86 87 88 89 90 91 92 93 94 95 96 96b 96c 96d 97 98 99 100 101 102 103 104 105 106 107
20A12.QNTv12      T  Y  Y  C  Q  S  T  S  F  R  G  R  S   Y   Q   N  T  F  G   G   G   T   K   V   E   I   K
                           |_____CDR L3 - Contact_____|
                                 |_____CDR L3 - Kabat_____|
```

SEQ ID NO: 23

FIG. 5D

Light chain variable region

```
Kabat number    1  2  3  4  5  6  7  8  9  10 11 12 13 14 15 16 17 18 19 20 21 22 23 24 25 26 27 28 29 30 31 32 33 34 35 36 37 38 39 40 41 42
20A12.QNT.v12   D  I  Q  M  T  Q  S  P  S  T  L  S  A  S  V  G  D  R  V  T  I  T  C  Q  A  S  E  S  I  T  R  Y  L  N  W  Y  Q  Q  K  P  G  K
                                                                                         |————————CDR L1 - Kabat————————|
                                                                                                           |———CDR L1 - Contact———|

Kabat number    43 44 45 46 47 48 49 50 51 52 53 54 55 56 57 58 59 60 61 62 63 64 65 66 67 68 69 70 71 72 73 74 75 76 77 78 79 80 81 82 83 84
20A12.QNT.v12   A  P  K  L  L  I  Y  D  A  S  K  L  P  S  G  V  P  S  R  F  S  G  S  G  S  G  T  E  F  T  L  T  I  S  S  L  Q  P  D  D  F  A
                      |——CDR L2 - Contact——|
                                  |—CDR L2 - Kabat—|

Kabat number    85 86 87 88 89 90 91 92 93 94 95 95a 95b 95c 95d 96 97 98 99 100 101 102 103 104 105 106 107
20A12.QNT.v12   T  Y  Y  C  Q  Q  S  T  S  F  R  G   R   S   Y   Q  N  T  F  G   G   G   T   K   V   E   I  K
                         |——————CDR L3 - Contact——————|
                            |————————CDR L3 - Kabat————————|
```

SEQ ID NO: 11

10 complexes overlaid epitope: HRDCYLGDLCNS (SEQ ID NO: 87)

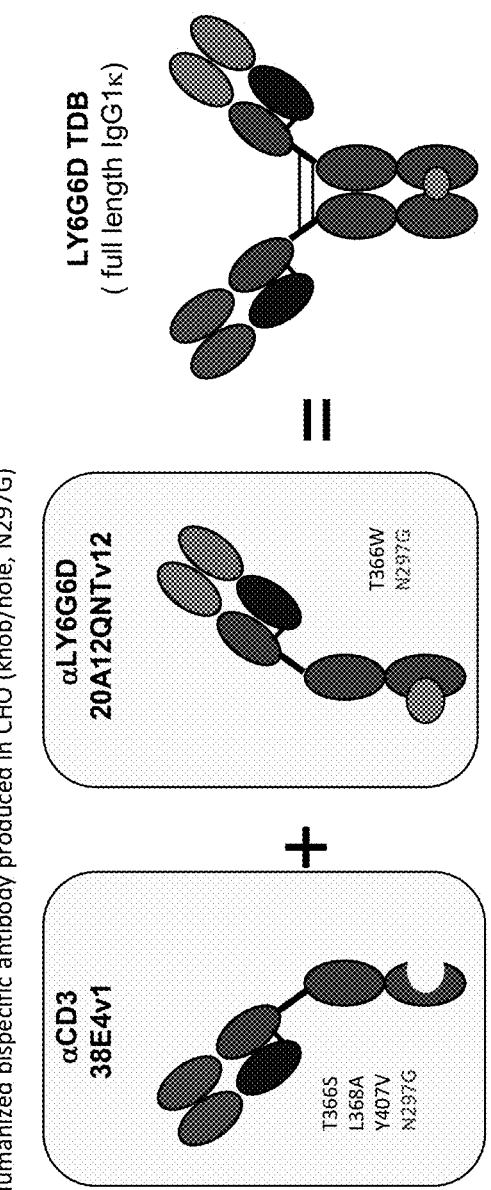
FIG. 8A Humanized bispecific antibody produced in CHO (knob/hole, N297G)

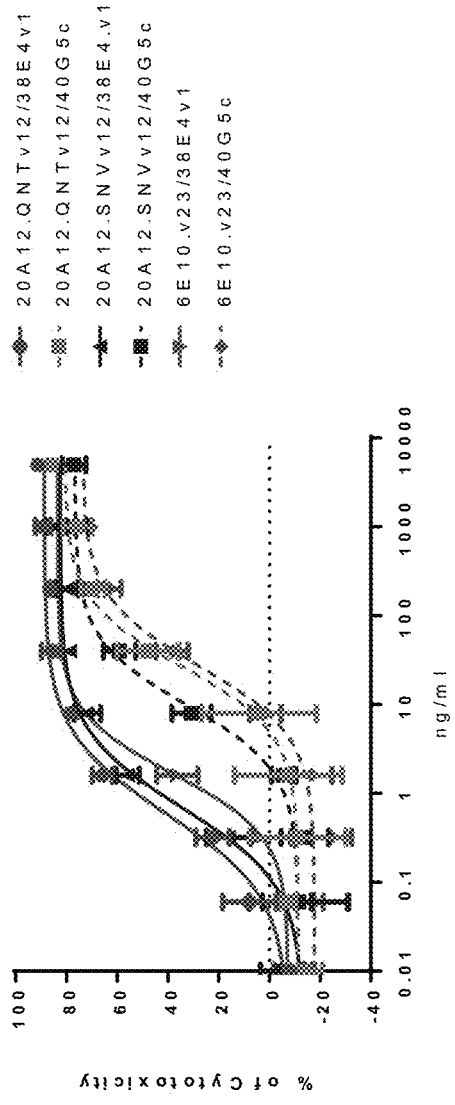

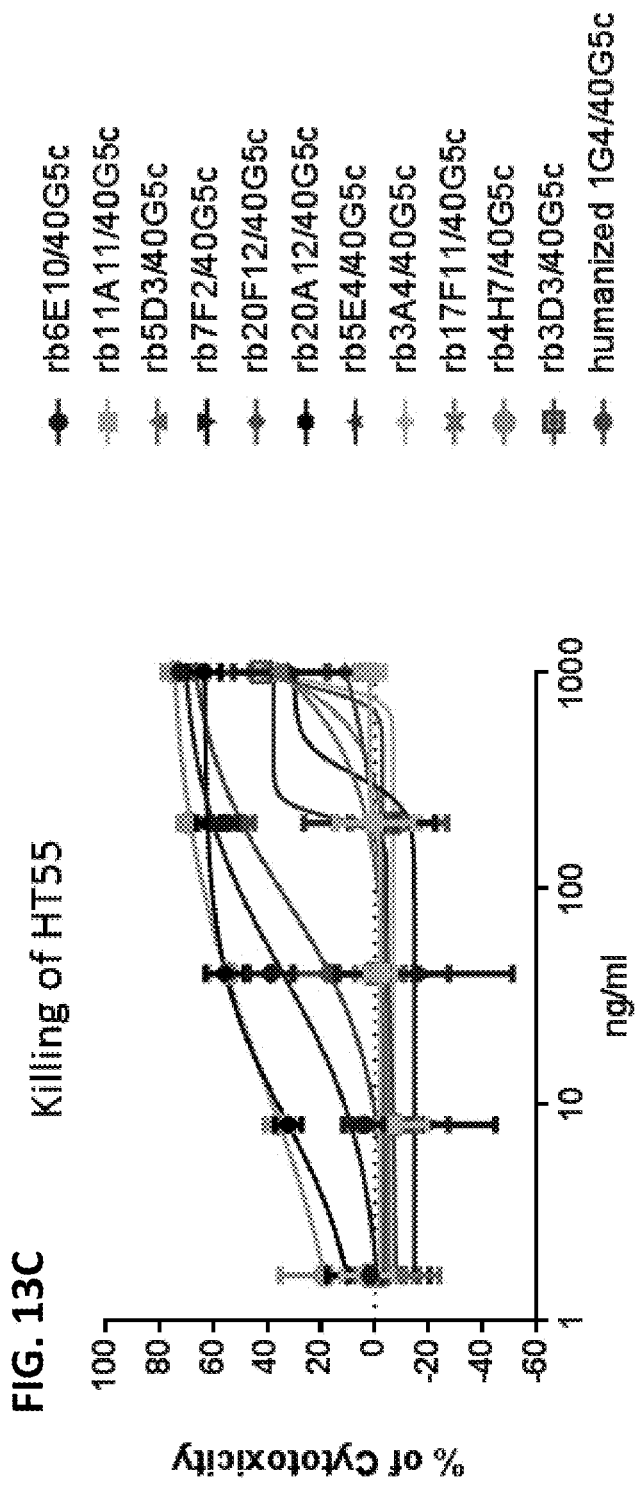

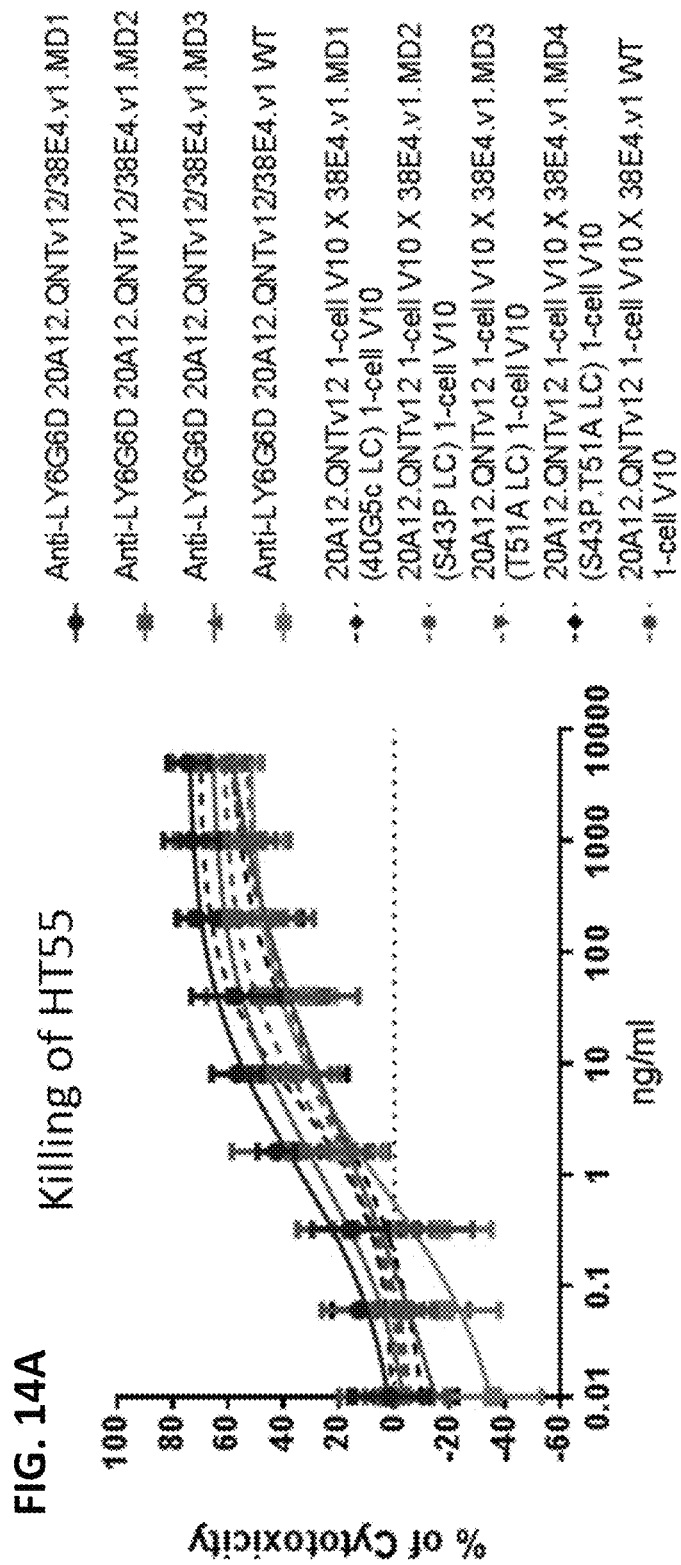

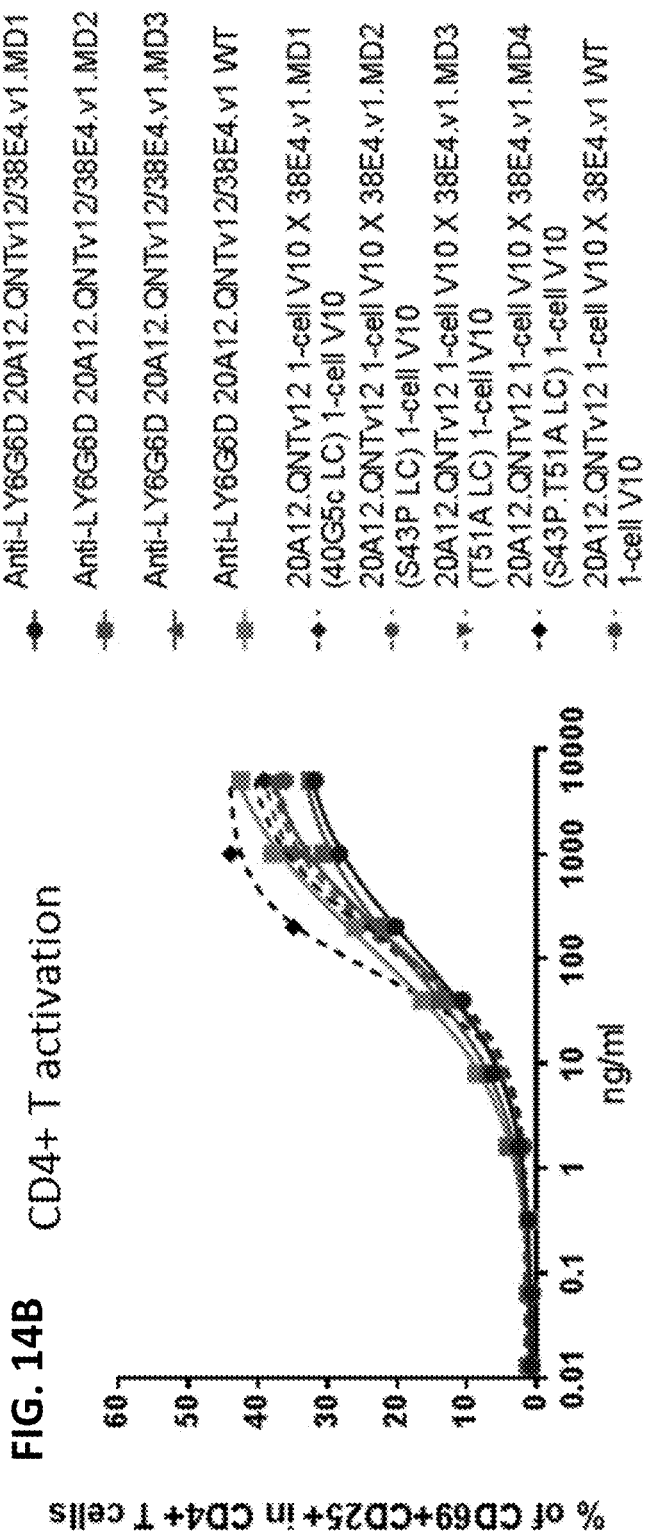
FIG. 14B CD4+ T activation

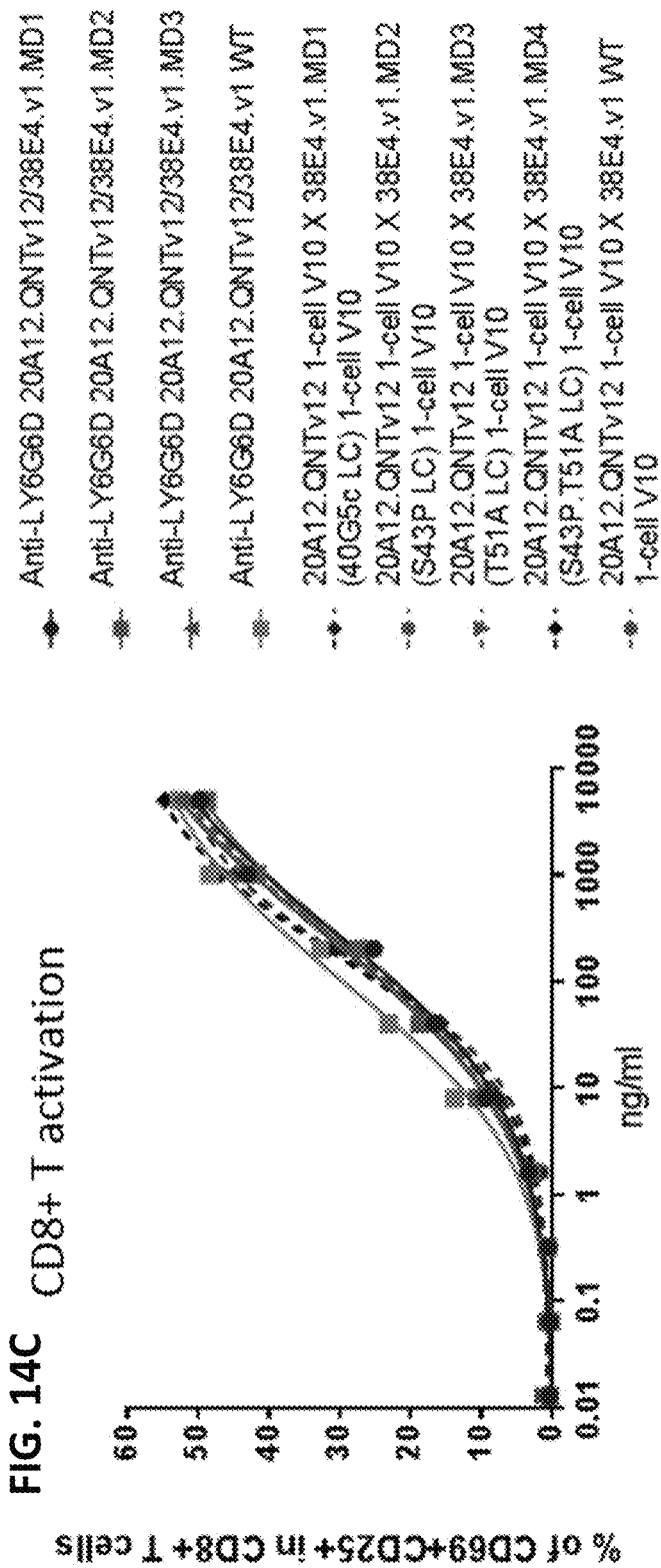
FIG. 14C CD8+ T activation

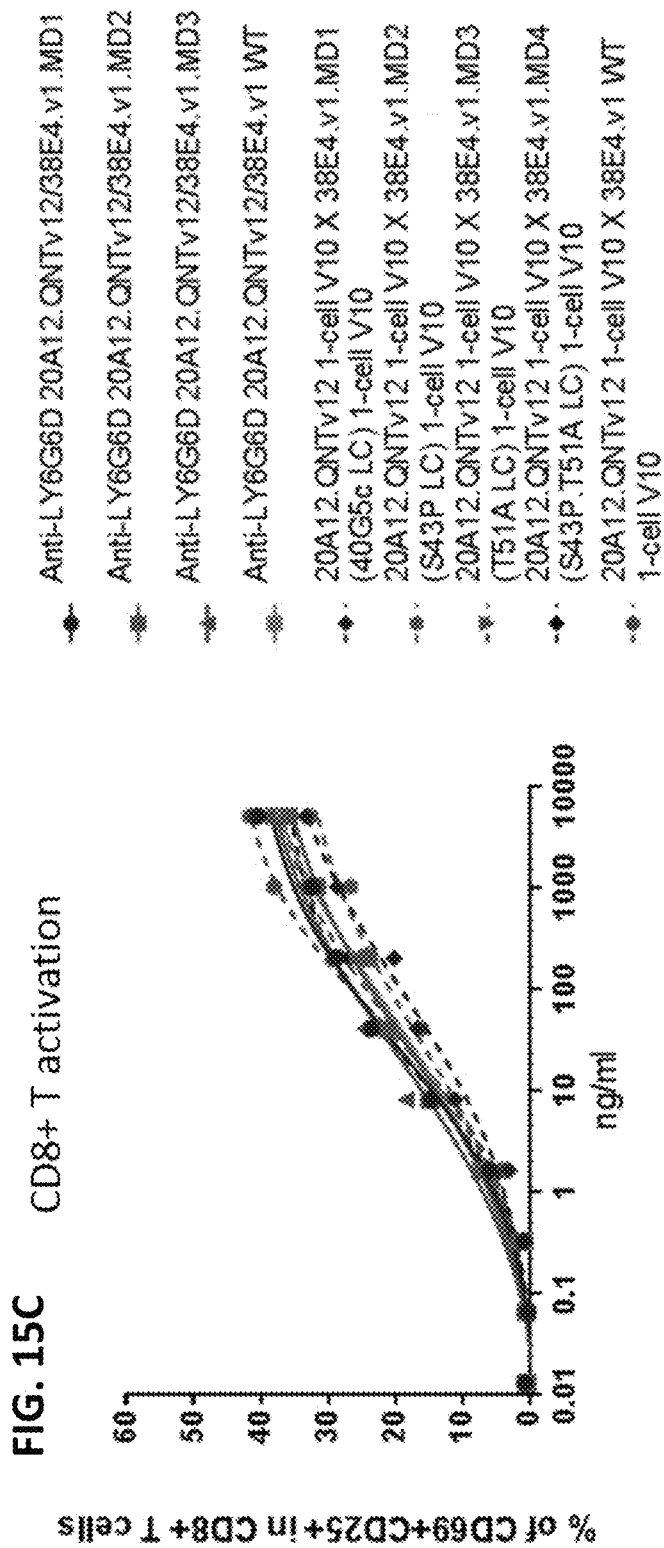

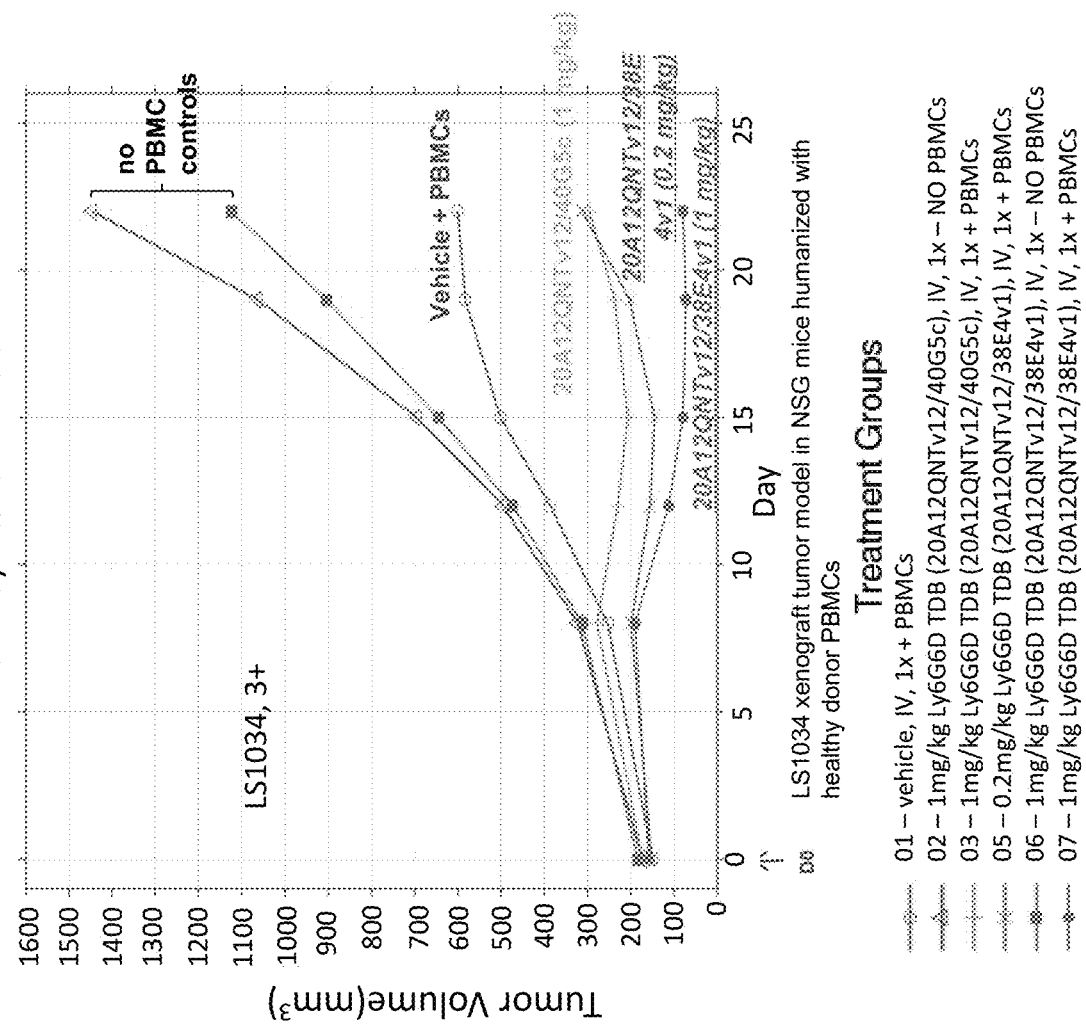

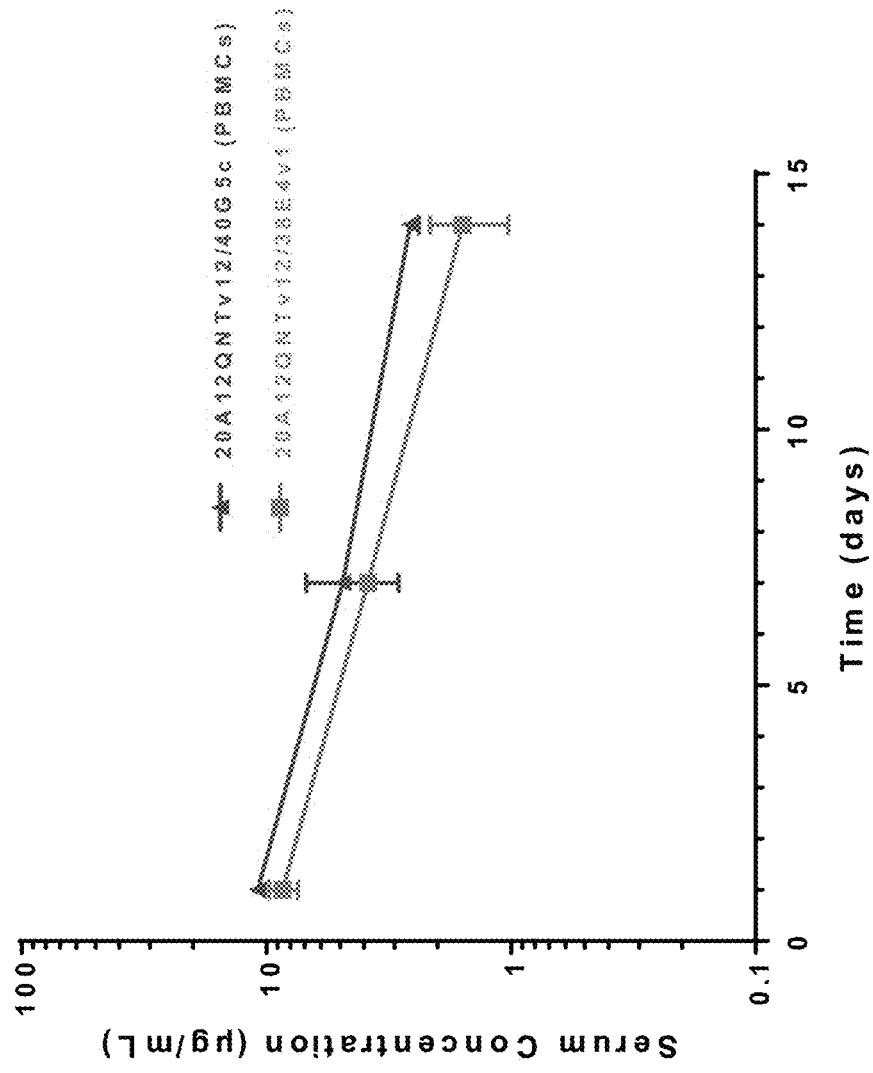
FIG. 17C  PK of LY6G6D TDBs in HT55 mouse model

FIG. 24B
human
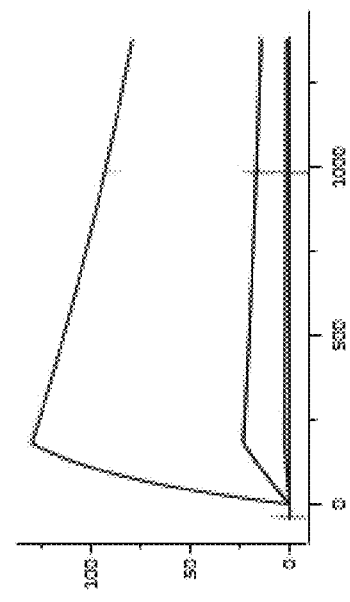
cyno
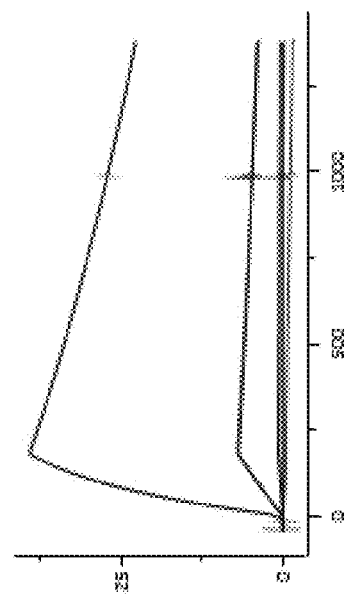

FIG. 29B

Heavy chain variable region

| Kabat number | 1 2 3 4 5 6 7 8 9 10 11 12 13 14 15 16 17 18 19 20 21 22 23 24 25 26 27 28 29 30 31 32 33 34 35 36 37 38 39 40 41 42 |
|---|---|
| 38E4v1 | E V Q L V Q S G A E V K K P G A S V K V S C K A S G F T F T S Y Y I H W V R Q A P G |
| 38E4v1MD1 | E V Q L V Q S G A E V K K P G A S V K V S C K A S G F T F T S Y Y I H W V R Q A P G |
| 38E4v1MD4 | E V Q L V Q S G A E V K K P G A S V K V S C K A S G F T F T S Y Y I H W V R Q A P G |
| 40G5c | E V Q L V Q S G A E V K K P G A S V K V S C K A S G Y T F T N Y Y I H W V R Q A P G |

CDR H1 - Contact: 27-33
CDR H1 - Kabat: 31-35

| Kabat number | 43 44 45 46 47 48 49 50 51 52 53 54 55 56 57 58 59 60 61 62 63 64 65 66 67 68 69 70 71 72 73 74 75 76 77 78 79 80 81 82 83 |
|---|---|
| 38E4v1 | Q G L E W I G W I Y P E N D N T K Y N E K F K D R V T I T A D T S T S T A Y L E L S |
| 38E4v1MD1 | Q G L E W I G W I Y P E N D N T K Y N E K F K D R V T I T A D T S T S T A Y L E L S |
| 38E4v1MD4 | Q G L E W I G W I Y P E N D N T K Y N E K F K D R V T I T A D T S T S T A Y L E L S |
| 40G5c | Q G L E W I G W I Y P G D G N T K Y N E K F K G R A T L T A D T S T S T A Y L E L S |

CDR H2 - Contact
CDR H2 - Kabat

| Kabat number | 82a 82b 82c 83 84 85 86 87 88 89 90 91 92 93 94 95 96 97 98 99 100 100a 100b 100c 101 102 103 104 105 106 107 108 109 110 111 112 113 |
|---|---|
| 38E4v1 | S L R S E D T A V Y Y C A R D G V S R Y Y F D Y W G Q G T L V T V S S | SEQ ID NO: 52 |
| 38E4v1MD1 | S L R S E D T A V Y Y C A R D G V S R Y Y F D Y W G Q G T L V T V S S | SEQ ID NO: 52 |
| 38E4v1MD4 | S L R S E D T A V Y Y C A R D G V S R Y Y F D Y W G Q G T L V T V S S | SEQ ID NO: 52 |
| 40G5c | S L R S E D T A V Y Y C A R D S Y S N Y Y F D Y W G Q G T L V T V S S | SEQ ID NO: 98 |

CDR H3 - Contact
CDR H3 - Kabat

FIG. 29F

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 27a | 27b | 27c | 27d | 27e | 28 | 29 | 30 | 31 | 32 | 33 | 34 | 35 | 36 |
|---|---|---|---|---|---|---|---|---|---|---|---|---|---|---|---|---|---|---|---|---|---|---|---|---|---|---|---|---|---|---|---|---|---|---|---|---|---|---|---|---|---|
| 38E4v1     | D | I | V | M | T | Q | S | P | D | S | L | A | V | S | L | G | E | R | A | T | I | N | C | K | S | S | Q | S | L | L | N | S | R | T | R | K | N | Y | L | A | W | Y |
| 38E4v1MD1  | D | I | V | M | T | Q | S | P | D | S | L | A | V | S | L | G | E | R | A | T | I | N | C | K | S | S | Q | S | L | L | N | S | R | T | R | K | N | Y | L | A | W | Y |
| 38E4v1MD4  | D | I | V | M | T | Q | S | P | D | S | L | A | V | S | L | G | E | R | A | T | I | N | C | K | S | S | Q | S | L | L | N | S | R | T | R | K | N | Y | L | A | W | Y |
| 40G5c      | D | I | V | M | T | Q | S | P | D | S | L | A | V | S | L | G | E | R | A | T | I | N | C | K | S | S | Q | S | L | L | N | S | R | T | R | K | N | Y | L | A | W | Y |

| Kabat number | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 38E4v1     | Q | E | K | P | G | Q | S | P | K | L | L | I | Y | W | T | S | T | R | K | S | G | V | P | D | R | F | S | G | S | G | S | G | T | D | F | T | L | T | I | S | S | L |
| 38E4v1MD1  | Q | E | K | P | G | Q | P | P | K | L | L | I | Y | W | T | S | T | R | K | S | G | V | P | D | R | F | S | G | S | G | S | G | T | D | F | T | L | T | I | S | S | L |
| 38E4v1MD4  | Q | E | K | P | G | Q | P | P | K | L | L | I | Y | W | A | S | T | R | K | S | G | V | P | D | R | F | S | G | S | G | S | G | T | D | F | T | L | T | I | S | S | L |
| 40G5c      | Q | E | K | P | G | Q | P | P | K | L | L | I | Y | W | A | S | T | R | E | S | G | V | P | D | R | F | S | G | S | G | S | G | T | D | F | T | L | T | I | S | S | L |

| Kabat number | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | |
|---|---|---|---|---|---|---|---|---|---|---|---|---|---|---|---|---|---|---|---|---|---|---|---|---|---|---|---|---|---|---|
| 38E4v1     | Q | A | E | D | V | A | V | Y | Y | C | K | Q | S | F | I | L | - | R | T | F | G | Q | G | T | K | V | E | I | K | SEQ ID NO: 108 |
| 38E4v1MD1  | Q | A | E | D | V | A | V | Y | Y | C | K | Q | S | F | I | L | - | R | T | F | G | Q | G | T | K | V | E | I | K | SEQ ID NO: 21 |
| 38E4v1MD4  | Q | A | E | D | V | A | V | Y | Y | C | T | Q | S | F | I | L | - | R | T | F | G | Q | G | T | K | V | E | I | K | SEQ ID NO: 55 |
| 40G5c      | Q | A | E | D | V | A | V | Y | Y | C | T | Q | S | F | I | L | - | R | T | F | G | Q | G | T | K | V | E | I | K | SEQ ID NO: 21 |

FIG. 29G

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 38E4v1 | E | V | Q | L | V | Q | S | G | A | E | V | K | K | P | G | A | S | V | K | V | S | C | K | A | S | G | F | T | F | T | S | Y | Y | I | H | W | V | R | K | A | P | G |
| 38E4v1MD1 | E | V | Q | L | V | Q | S | G | A | E | V | K | K | P | G | A | S | V | K | V | S | C | K | A | S | G | F | T | F | T | S | Y | Y | I | H | W | V | R | K | A | P | G |
| 38E4v1MD4 | E | V | Q | L | V | Q | S | G | A | E | V | K | K | P | G | A | S | V | K | V | S | C | K | A | S | G | F | T | F | T | S | Y | Y | I | H | W | V | R | K | A | P | G |
| 40G5c | E | V | Q | L | V | Q | S | G | A | E | V | K | K | P | G | A | S | V | K | V | S | C | K | A | S | G | Y | T | F | T | N | Y | Y | I | H | W | V | R | K | A | P | G |

CDR H1 - Contact: positions 27-32
CDR H1 - Kabat: positions 31-35

| Kabat number | 43 | 44 | 45 | 46 | 47 | 48 | 49 | 50 | 51 | 52 | 52a | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 |
|---|---|---|---|---|---|---|---|---|---|---|---|---|---|---|---|---|---|---|---|---|---|---|---|---|---|---|---|---|---|---|---|---|---|---|---|---|---|---|---|---|---|
| 38E4v1 | Q | G | L | E | W | I | G | W | I | Y | P | E | N | D | N | T | K | Y | N | E | K | F | K | D | R | V | T | I | T | A | D | T | S | T | S | T | A | Y | L | E | L | S |
| 38E4v1MD1 | Q | G | L | E | W | I | G | W | I | Y | P | E | N | D | N | T | K | Y | N | E | K | F | K | D | R | V | T | I | T | A | D | T | S | T | S | T | A | Y | L | E | L | S |
| 38E4v1MD4 | Q | G | L | E | W | I | G | W | I | Y | P | E | N | D | N | T | K | Y | N | E | K | F | K | D | R | V | T | I | T | A | D | T | S | T | S | T | A | Y | L | E | L | S |
| 40G5c | Q | G | L | E | W | I | G | W | I | Y | P | G | D | G | N | T | K | Y | N | E | K | F | K | G | R | A | T | L | T | A | D | T | S | T | S | T | A | Y | L | E | L | S |

CDR H2 - Contact: positions 47-52
CDR H2 - Kabat: positions 50-65

| Kabat number | 82a | 82b | 82c | 83 | 84 | 85 | 86 | 87 | 88 | 89 | 90 | 91 | 92 | 93 | 94 | 95 | 96 | 97 | 98 | 99 | 100 | 100a | 101 | 102 | 103 | 104 | 105 | 106 | 107 | 108 | 109 | 110 | 111 | 112 | 113 | |
|---|---|---|---|---|---|---|---|---|---|---|---|---|---|---|---|---|---|---|---|---|---|---|---|---|---|---|---|---|---|---|---|---|---|---|---|---|
| 38E4v1 | S | L | R | S | E | D | T | A | V | Y | Y | C | A | R | D | G | Y | S | R | Y | Y | F | D | Y | W | G | Q | G | T | L | V | T | V | S | S | SEQ ID NO: 20 |
| 38E4v1MD1 | S | L | R | S | E | D | T | A | V | Y | Y | C | A | R | D | G | Y | S | R | Y | Y | F | D | Y | W | G | Q | G | T | L | V | T | V | S | S | SEQ ID NO: 20 |
| 38E4v1MD4 | S | L | R | S | E | D | T | A | V | Y | Y | C | A | R | D | G | Y | S | R | Y | Y | F | D | Y | W | G | Q | G | T | L | V | T | V | S | S | SEQ ID NO: 20 |
| 40G5c | S | L | R | S | E | D | T | A | V | Y | Y | C | A | R | D | S | Y | S | N | Y | Y | F | D | Y | W | G | Q | G | T | L | V | T | V | S | S | SEQ ID NO: 109 |

CDR H3 - Contact: positions 93-100a
CDR H3 - Kabat: positions 95-102

FIG. 31C

| ID | Human VL germline | Vernier positions | Partial charge: Non-human Vernier | Human identity: Low | Partial charge: All human Vernier | Human identity: High | Prevalence in repertoire |
|---|---|---|---|---|---|---|---|
| 1 | hIGKV1D-39*01 | 1 | 3.8 | 85.3% | 3.8 | 85.3% | 13.3% |
| 2 | **hIGKV1-39*01 | 1 | 3.8 | 85.3% | 3.8 | 86.3% | 12.7%** |
| 3 | **hIGKV1-5*01 | 1 | 3.8 | 85.3% | 3.8 | 86.3% | 4.7%** |
| 4 | hIGKV1-5*02 | 1 | 3.8 | 85.3% | 3.8 | 86.3% | 4.7% |
| 5 | hIGKV1D-33*01 | 1 | 3.8 | 85.3% | 3.8 | 86.3% | 3.1% |
| 6 | hIGKV1-33*01 | 1 | 3.8 | 85.3% | 3.8 | 86.3% | 1.6% |
| 7 | hIGKV1-5*03 | 1 | 3.8 | 84.2% | 3.8 | 85.3% | 4.7% |
| 8 | hIGKV1-9*01 | 2 | 3.8 | 83.2% | 3.8 | 85.3% | 2.2% |
| 9 | hIGKV1-27*01 | 1 | 3.8 | 83.2% | 3.8 | 84.2% | 1.8% |
| 10 | hIGKV1-8*01 | 1 | 5.8 | 83.2% | 5.8 | 84.2% | 0.7% |
| 11 | hIGKV1-12*01 | 1 | 3.8 | 82.1% | 3.8 | 83.2% | 1.7% |
| 12 | hIGKV1-12*02 | 1 | 3.8 | 82.1% | 3.8 | 83.2% | 1.7% |
| 13 | hIGKV1D-12*01 | 1 | 3.8 | 82.1% | 3.8 | 83.2% | 1.6% |
| 14 | hIGKV1D-12*02 | 1 | 3.8 | 82.1% | 3.8 | 83.2% | 1.6% |
| 15 | hIGKV1-16*01 | 3 | 3.8 | 82.1% | 3.8 | 85.3% | 1.3% |
| 16 | hIGKV1-16*02 | 3 | 3.8 | 82.1% | 3.8 | 85.3% | 1.3% |
| 17 | hIGKV1-6*01 | 1 | 4.8 | 82.1% | 4.8 | 83.2% | 0.9% |
| 18 | hIGKV1-6*02 | 3 | 4.8 | 81.1% | 4.8 | 83.2% | 0.9% |
| 19 | hIGKV3-11*01 | 1 | 2.0 | 81.1% | 2.0 | 84.2% | 8.0% |
| 20 | hIGKV1-17*01 | 3 | 3.8 | 81.1% | 4.8 | 83.2% | 1.1% |
| 21 | hIGKV1-17*02 | 2 | 3.8 | 81.1% | 4.8 | 84.2% | 1.1% |
| 22 | hIGKV3-11*02 | 3 | 3.8 | 81.1% | 4.8 | 84.2% | 1.1% |
| 23 | hIGKV3-11*02 | 2 | 2.0 | 80.0% | 3.0 | 84.2% | 8.0% |
| 24 | hIGKV3-15*01 | 3 | 2.9 | 78.9% | 2.9 | 81.1% | 6.3% |
| 25 | hIGKV3-20*01 | 2 | 2.0 | 78.1% | 2.0 | 81.3% | 21.8% |
| 26 | **hIGKV4-1*01 | 0 | 0.8 | 77.2% | 0.8 | 77.2% | 4.9%** |
| 27 | hIGKV2D-29*01 | 0 | 1.8 | 76.0% | 1.8 | 76.0% | 2.0% |
| 28 | hIGKV2D-28*01 | 1 | 0.9 | 75.0% | 0.9 | 76.0% | 2.5% |
| 29 | hIGKV2-28*01 | 1 | 0.9 | 75.0% | 0.9 | 76.0% | 2.0% |
| 30 | hIGKV2D-29*02 | 1 | 1.8 | 75.0% | 1.8 | 76.0% | 2.0% |
| 31 | hIGKV2-24*01 | 1 | 2.8 | 73.0% | 2.8 | 76.0% | 0.9% |
| 32 | hIGKV2-30*01 | 4 | 2.8 | 73.0% | 3.8 | 77.0% | 2.0% |
| 33 | hIGKV2-30*02 | 4 | 2.8 | 73.0% | 3.8 | 77.0% | 2.0% |

FIG. 31D

| ID | Human VH germline | Vernier positions | Partial charge: Non-human Vernier | Human identity: Low | Partial charge: All human Vernier | Human identity: High | Prevalence in repertoire |
|---|---|---|---|---|---|---|---|
| 1 | hIGHV3-23*01 | 9 | -0.2 | 75.5% | 0.8 | 82.7% | 7.6% |
| 2 | hIGHV3-23*04 | 9 | -0.2 | 75.5% | 0.8 | 82.7% | 7.6% |
| 3 | hIGHV3-23*02 | 9 | -0.2 | 74.5% | 0.8 | 81.6% | 7.6% |
| 4 | hIGHV3-30*01 | 8 | 0.8 | 74.5% | 1.8 | 80.6% | 6.6% |
| 5 | hIGHV3-30*04 | 8 | 0.8 | 74.5% | 1.8 | 80.6% | 6.6% |
| 6 | hIGHV3-30*07 | 8 | 0.8 | 74.5% | 1.8 | 80.6% | 6.6% |
| 7 | hIGHV3-30*09 | 8 | 0.8 | 74.5% | 1.8 | 80.6% | 6.6% |
| 8 | hIGHV3-30*11 | 8 | 0.8 | 74.5% | 1.8 | 80.6% | 6.6% |
| 9 | hIGHV3-30*14 | 8 | 0.8 | 74.5% | 1.8 | 80.6% | 6.6% |
| 10 | hIGHV3-30*15 | 8 | 0.8 | 74.5% | 1.8 | 80.6% | 6.6% |
| 11 | hIGHV3-30*16 | 8 | 0.8 | 74.5% | 1.8 | 80.5% | 6.6% |
| 12 | hIGHV3-30*17 | 8 | 0.8 | 74.5% | 1.8 | 80.5% | 6.6% |
| 13 | hIGHV3-48*01 | 9 | -0.2 | 74.5% | 0.8 | 81.6% | 2.4% |
| 14 | hIGHV3-48*02 | 9 | -1.2 | 74.5% | -0.2 | 81.6% | 2.4% |
| 15 | hIGHV3-48*03 | 8 | -0.2 | 74.5% | 0.8 | 81.6% | 2.4% |
| 16 | hIGHV3-30-3*01 | 8 | 0.8 | 74.5% | 1.8 | 80.6% | 2.1% |
| 17 | hIGHV3-64*01 | 10 | -0.2 | 74.5% | 0.8 | 82.7% | 0.7% |
| 18 | hIGHV3-64*02 | 10 | -1.1 | 74.5% | -0.1 | 82.7% | 0.7% |
| 19 | hIGHV3-23*03 | 9 | -0.2 | 73.5% | 0.8 | 80.6% | 7.6% |
| 20 | hIGHV3-30*03 | 8 | 1.8 | 73.5% | 2.8 | 79.6% | 6.6% |
| 21 | hIGHV3-30*05 | 8 | 0.8 | 73.5% | 1.8 | 79.6% | 6.6% |
| 22 | hIGHV3-30*06 | 8 | 0.8 | 73.5% | 1.8 | 79.6% | 6.6% |
| 23 | hIGHV3-30*08 | 8 | 0.8 | 73.5% | 1.8 | 79.6% | 6.6% |
| 24 | hIGHV3-30*10 | 8 | 0.8 | 73.5% | 1.8 | 79.6% | 6.6% |
| 25 | hIGHV3-30*12 | 8 | 1.8 | 73.5% | 2.8 | 79.6% | 6.6% |
| 26 | hIGHV3-30*13 | 8 | 0.8 | 73.5% | 1.8 | 79.6% | 6.6% |
| 27 | hIGHV3-30*19 | 8 | 0.8 | 73.5% | 1.8 | 79.6% | 6.6% |
| 28 | hIGHV3-7*01 | 8 | -0.2 | 73.5% | 0.8 | 79.6% | 3.5% |
| 29 | hIGHV3-3*02 | 8 | -0.2 | 73.5% | 0.8 | 79.6% | 2.8% |
| 30 | hIGHV3-33*05 | 8 | 0.8 | 73.5% | 1.8 | 79.6% | 2.8% |
| 31 | hIGHV3-21*01 | 9 | 0.8 | 73.5% | 1.8 | 80.6% | 2.4% |
| 32 | hIGHV3-21*02 | 9 | 0.8 | 73.5% | 1.8 | 80.6% | 2.4% |
| 33 | hIGHV3-11*01 | 10 | 0.8 | 73.5% | 1.8 | 81.6% | 2.1% |

| Rab/humanized Variant | | KD (nM) |
|---|---|---|
| rb20A32 | | 0.122 |
| rb20A12.5A | | 0.705 |
| L1H1 | All rabbit Vernier | 2.447 |
| L1H2 | H: Q2V | 1.585 |
| L1H3 | H: I48V | 0.963 |
| L1H4 | H: A49S | 1.377 |
| L1H5 | H: K71R | 1.824 |
| L1H6 | H: S73N | 2.241 |
| L1H7 | H: V78L | 3.262 |
| L1H8 | H: F91Y | 1.749 |
| L1H9 | H: P105R | 2.014 |
| L1H10 | H: all human Vernier | 2.792 |
| L2H1 | L: P43A | 2.456 |
| L2H10 | All human Vernier | 2.450 |

| ID | Human VL germline | Vernier positions | Partial charge: Non-human vernier | Human identity: Low | Partial charge: All human vernier | Human identity: High | Prevalence in repertoire |
|---|---|---|---|---|---|---|---|
| 1 | hIGKV3-20*01 | 4 | 0.5 | 78.4% | -0.5 | 82.5% | 21.8% |
| 2 | hIGKV1-5*01 | 4 | 2.3 | 78.4% | 1.3 | 82.5% | 4.7% |
| 3 | hIGKV1-5*02 | 4 | 2.3 | 78.4% | 1.3 | 82.5% | 4.7% |
| 4 | hIGKV1-5*03 | 4 | 2.3 | 78.4% | 1.3 | 82.5% | 4.7% |
| 5 | hIGKV1-9*01 | 3 | 2.4 | 78.4% | 1.4 | 81.4% | 2.2% |
| 6 | hIGKV1-27*01 | 4 | 2.3 | 78.4% | 1.3 | 82.5% | 1.8% |
| 7 | hIGKV4-1*01 | 4 | -0.6 | 78.2% | -1.6 | 82.2% | 4.9% |
| 8 | hIGKV1D-39*01 | 4 | 2.3 | 77.3% | 1.3 | 81.4% | 13.3% |
| 9 | hIGKV1-39*01 | 4 | 2.3 | 77.3% | 1.3 | 81.4% | 12.7% |
| 10 | hIGKV3-15*01 | 5 | 1.4 | 77.3% | 0.4 | 82.5% | 6.3% |
| 11 | hIGKV1-12*01 | 4 | 2.3 | 77.3% | 1.3 | 81.4% | 1.7% |
| 12 | hIGKV1-12*02 | 4 | 2.3 | 77.3% | 1.3 | 81.4% | 1.7% |
| 13 | hIGKV1D-12*01 | 4 | 2.3 | 77.3% | 1.3 | 81.4% | 1.6% |
| 14 | hIGKV1D-12*02 | 4 | 2.3 | 77.3% | 1.3 | 81.4% | 1.6% |
| 15 | hIGKV1-16*01 | 4 | 2.3 | 77.3% | 1.3 | 81.4% | 1.3% |
| 16 | hIGKV1-16*02 | 4 | 2.3 | 77.3% | 1.3 | 81.4% | 1.3% |
| 17 | hIGKV1-17*03 | 4 | 2.4 | 77.3% | 2.4 | 81.4% | 1.1% |
| 18 | hIGKV1-8*01 | 5 | 4.3 | 76.3% | 3.3 | 81.4% | 0.7% |
| 19 | hIGKV3-11*01 | 4 | 0.4 | 76.3% | -0.6 | 80.4% | 8.0% |
| 20 | hIGKV1-6*01 | 4 | 3.3 | 76.3% | 2.3 | 80.4% | 0.9% |
| 21 | hIGKV1-6*02 | 4 | 0.4 | 75.3% | 0.4 | 80.4% | 8.0% |
| 22 | hIGKV3-11*02 | 5 | 2.3 | 75.3% | 1.3 | 79.4% | 3.1% |
| 23 | hIGKV1D-33*01 | 4 | 2.3 | 75.3% | 2.4 | 79.4% | 1.6% |
| 24 | hIGKV1-33*01 | 4 | 2.4 | 75.3% | 2.4 | 80.4% | 1.1% |
| 25 | hIGKV1-17*01 | 4 | 2.4 | 74.0% | 2.4 | 80.4% | 1.1% |
| 26 | hIGKV1-17*02 | 5 | -0.6 | 74.0% | -1.6 | 78.0% | 2.5% |
| 27 | hIGKV2D-28*01 | 5 | -0.6 | 74.0% | -1.6 | 78.0% | 2.0% |
| 28 | hIGKV2-28*01 | 5 | 1.4 | 74.0% | 1.4 | 78.0% | 2.0% |
| 29 | hIGKV2-30*01 | 4 | 1.4 | 74.0% | 1.4 | 78.0% | 2.0% |
| 30 | hIGKV2-30*02 | 4 | 1.4 | 74.0% | 1.4 | 78.0% | 2.0% |

FIG. 33B

| ID | Human VH germline | Vernier positions | Partial charge: Non-human Vernier | Human identity: Low | Partial charge: All human Vernier | Human identity: High | Prevalence in repertoire |
|---|---|---|---|---|---|---|---|
| 1 | hIGHV3-53*01 | | 1.6 | 74.5% | 2.6 | 82.7% | 1.1% |
| 2 | hIGHV3-53*02 | | 1.6 | 74.5% | 2.6 | 82.7% | 1.1% |
| 3 | hIGHV3-53*03 | | 1.6 | 74.5% | 2.6 | 82.7% | 1.1% |
| 4 | hIGHV3-53*04 | | 3.3 | 74.5% | 4.3 | 82.7% | 1.1% |
| 5 | hIGHV3-66*01 | | 1.6 | 74.5% | 2.6 | 82.7% | 0.8% |
| 6 | hIGHV3-66*02 | | 1.6 | 74.5% | 2.6 | 82.7% | 0.8% |
| 7 | hIGHV3-66*04 | | 1.6 | 74.5% | 2.6 | 82.7% | 0.8% |
| 8 | hIGHV4-4*01 | 8 | 2.5 | 73.7% | 3.5 | 79.8% | 1.7% |
| 9 | hIGHV4-4*02 | 0 | 2.5 | 73.7% | 3.5 | 79.8% | 1.7% |
| 10 | hIGHV4-48*03 | | 1.6 | 73.5% | 2.6 | 81.6% | 2.4% |
| 11 | hIGHV4-48*02 | | 0.6 | 73.5% | 1.6 | 81.6% | 0.8% |
| 12 | hIGHV3-66*03 | | 1.6 | 73.2% | 2.6 | 80.4% | 3.3% |
| 13 | hIGHV4-59*03 | | 1.6 | 73.2% | 1.6 | 80.4% | 3.3% |
| 14 | hIGHV4-59*08 | | 1.7 | 72.4% | 2.7 | 80.6% | 7.7% |
| 15 | hIGHV1-69*02 | | 1.7 | 72.4% | 2.7 | 80.6% | 7.7% |
| 16 | hIGHV1-69*04 | | 1.7 | 72.4% | 2.7 | 80.6% | 7.7% |
| 17 | hIGHV1-69*09 | | 1.7 | 72.4% | 2.7 | 80.6% | 7.7% |
| 18 | hIGHV1-69*10 | | 1.6 | 72.4% | 2.6 | 80.6% | 7.6% |
| 19 | hIGHV3-23*03 | | 2.6 | 72.4% | 3.6 | 80.6% | 6.0% |
| 20 | hIGHV5-51*01 | | 2.6 | 72.4% | 3.6 | 80.6% | 6.0% |
| 21 | hIGHV5-51*03 | | 2.6 | 72.4% | 3.6 | 80.6% | 6.0% |
| 22 | hIGHV5-51*04 | | 2.6 | 72.4% | 3.6 | 80.6% | 6.0% |
| 23 | hIGHV4-59*01 | | 1.6 | 72.4% | 1.6 | 79.6% | 3.3% |
| 24 | hIGHV4-59*02 | | 1.6 | 72.4% | 1.6 | 79.6% | 3.3% |
| 25 | hIGHV4-59*07 | | 1.6 | 72.4% | 1.6 | 79.6% | 3.3% |
| 26 | hIGHV3-21*01 | | 2.6 | 72.4% | 3.6 | 80.6% | 2.4% |
| 27 | hIGHV3-21*02 | | 2.6 | 72.4% | 3.6 | 80.6% | 2.4% |
| 28 | hIGHV3-48*03 | | 1.6 | 72.4% | 2.6 | 80.6% | 2.4% |
| 29 | hIGHV4-4*08 | | 1.6 | 72.4% | 1.6 | 79.6% | 1.7% |
| 30 | hIGHV4-59*04 | | 1.6 | 72.3% | 1.6 | 80.4% | 3.3% |

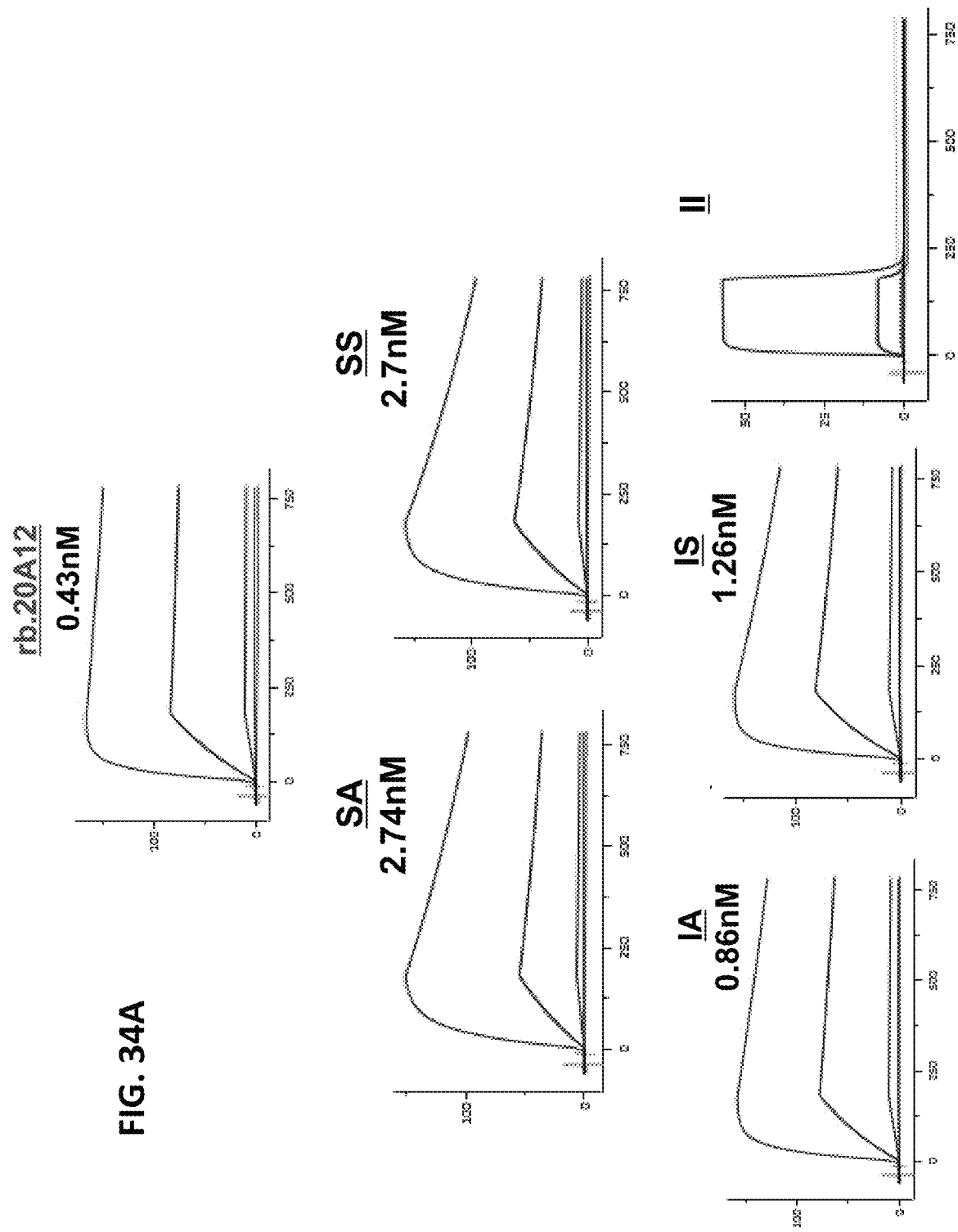

| Mutation | KD (nM) |
|---|---|
| Parental NNT | 0.43 |
| QNT | 0.28 |
| QNV | 0.22 |
| SNT | 0.25 |
| SNA | 0.27 |
| ANT | 0.26 |
| NNA | 0.26 |
| NNV | 0.22 |
| GNT | 0.34 |
| SNV | 0.23 |

-GRSYNNT-
(SEQ ID NO: 116)

FIG. 34C
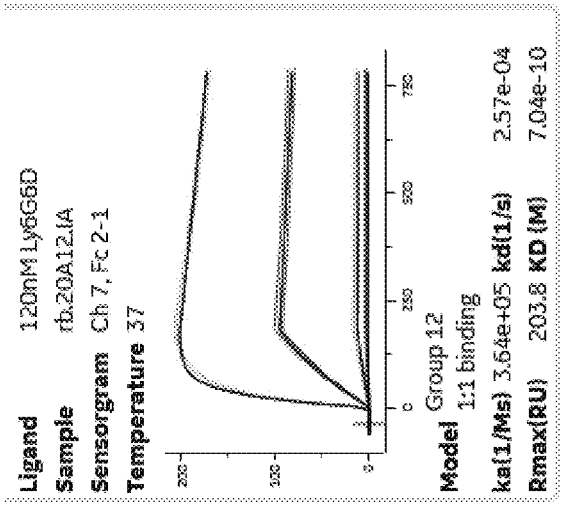
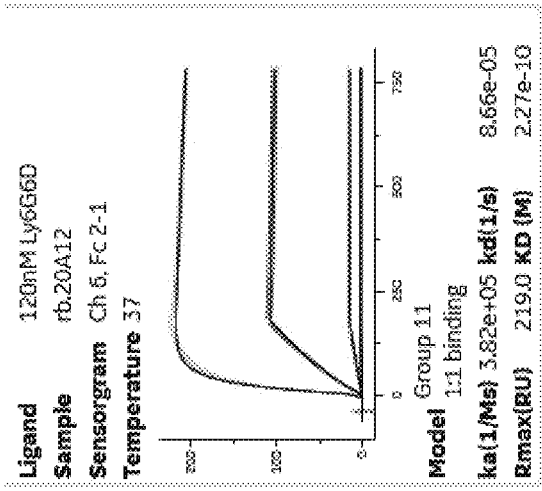
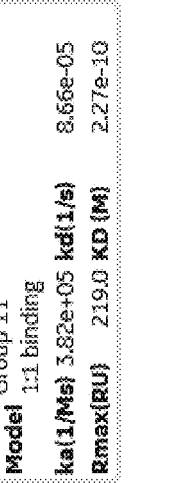

FIG. 35A Rabbit 20A12
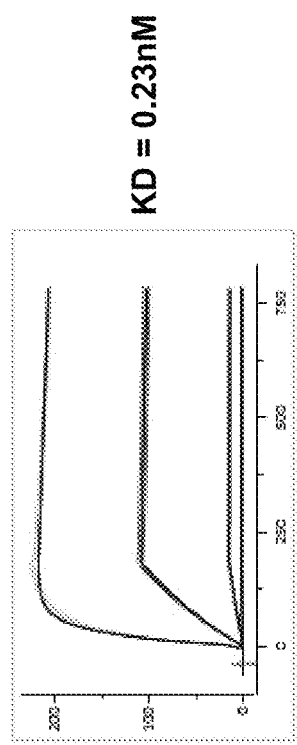
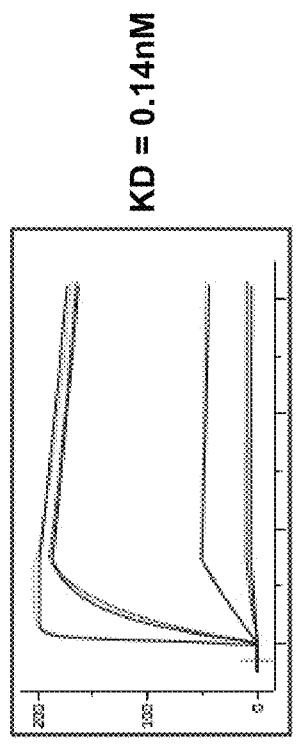 KD = 0.23nM
FIG. 35B Humanized 20A12 polished (20A12.QNTv12)
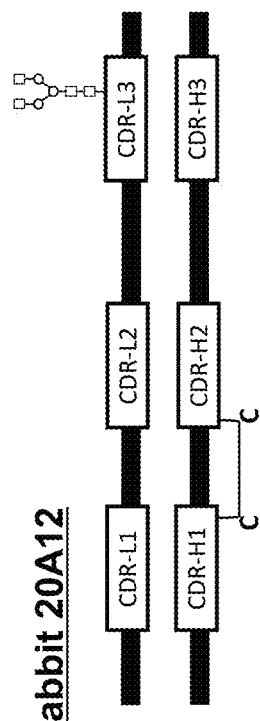
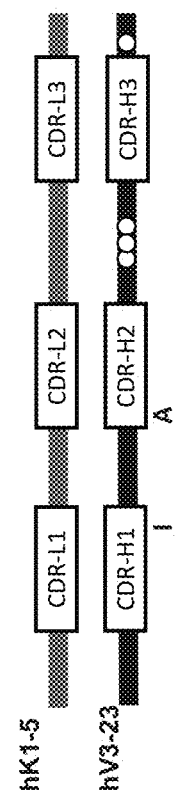 KD = 0.14nM

| | |
|---|---|
| SEC | Low Con His-Acetate, pH 5.5: Monomer loss (<0.1%) is acceptable at t=2-wk |
| Reduced mass | Masses are as expected with no change upon stress |
| Peptide mapping | Thermal Stress Platform Test Data (Low Con His-Acetate, pH 5.5)<br>- N(30)N<br>- D(95a)A<br>- N(32)S<br>- D(54)G and D(58)Y in CDR-H2 is unstable.<br>30.2% increase in isomerization (17.0% in t=0 and 47.2% in t=2-wk)<br>*unable to determine site of isomerization<br><br>Thermal Stress PBS Test Data (PBS, pH 7.4)<br>- 0.3% increase in N(30)N deamidation (2.9% in t=0 and 3.2% in t=2-wk)<br>- 0.5% increase in D(95a)A isomerization (1.5% in t=0 and 2.0% in t=2-wk)<br>- -0.4% decrease in N(32)S deamidation (3.3% in t=0 and 2.9% in t=2-wk)<br>- 18.0% increase in D(54)G and D(58)Y isomerization (16.9% in t=0 and 34.9% in t=2-wk)<br>*unable to determine site of isomerization |

ANTI-LY6G6D ANTIBODIES AND METHODS OF USE

SEQUENCE LISTING

The instant application contains a Sequence Listing which has been submitted electronically in ASCII format and is hereby incorporated by reference in its entirety. Said ASCII copy, created on Dec. 10, 2020, is named 50474-184003_Sequence_Listing_12.10.20_ST25 and is 146,127 bytes in size.

FIELD OF THE INVENTION

Provided herein are anti-Ly6G6D (lymphocyte antigen 6 complex, locus G61) antibodies and methods of using the same.

BACKGROUND

Cancer remains one of the most deadly threats to human health. In the U.S., cancer affects more than 1.7 million new patients each year and is the second leading cause of death after heart disease, accounting for approximately one in four deaths. Colorectal cancer (CRC), in particular, is the third leading cause of cancer death in the U.S., and five-year survival rates are low for advanced CRC patients. Cancers, such as CRC, represent a significant and ever-increasing societal threat and burden.

Longstanding approaches to cancer treatment include chemotherapy, radiation therapy, and surgery to remove solid tumors. Recently, bispecific antibody-based immunotherapies have been developed. Such bispecific antibodies are capable of simultaneously binding cell surface antigens on cytotoxic cells and tumor cells, with the intent that the bound cytotoxic cell will destroy the bound tumor cell.

There is an unmet need in the field for the development of effective bispecific antibody-based immunotherapies (e.g., bispecific anti-LY6G6D antibody-based immunotherapies) for use in cancer (e.g., CRC) treatment.

SUMMARY OF THE INVENTION

The present invention provides compositions for the treatment of cancer. Also provided are formulations and methods of use.

In a first aspect, the invention features an isolated antibody that binds to anti-lymphocyte antigen 6 family member G6D (LY6G6D), wherein the antibody comprises a LY6G6D binding domain comprising a heavy chain polypeptide (H1) and a light chain polypeptide (L1), wherein the H1 comprises a heavy chain variable (VH) domain (VH1) comprising the following complementarity determining regions (CDRs): (a) a CDR-H1 comprising the amino acid sequence of SEQ ID NO: 4 or SEQ ID NO: 111; (b) a CDR-H2 comprising the amino acid sequence of SEQ ID NO: 5, SEQ ID NO: 112, or SEQ ID NO: 113; and (c) a CDR-H3 comprising the amino acid sequence of SEQ ID NO: 6; and the L1 comprises a light chain variable (VL) domain (VL1) comprising the following CDRs: (d) a CDR-L1 comprising the amino acid sequence of SEQ ID NO: 1; (e) a CDR-L2 comprising the amino acid sequence of SEQ ID NO: 2; and (f) a CDR-L3 comprising the amino acid sequence of SEQ ID NO: 3 or any of SEQ ID NOs: 99-107. In some aspects, the antibody comprises a LY6G6D binding domain comprising a heavy chain polypeptide (H1) and a light chain polypeptide (L1), wherein the H1 comprises a heavy chain variable (VH) domain (VH1) comprising the following complementarity determining regions (CDRs): (a) a CDR-H1 comprising the amino acid sequence of SEQ ID NO: 4; (b) a CDR-H2 comprising the amino acid sequence of SEQ ID NO: 5; and (c) a CDR-H3 comprising the amino acid sequence of SEQ ID NO: 6; and the L1 comprises a light chain variable (VL) domain (VL1) comprising the following CDRs: (d) a CDR-L1 comprising the amino acid sequence of SEQ ID NO: 1; (e) a CDR-L2 comprising the amino acid sequence of SEQ ID NO: 2; and (f) a CDR-L3 comprising the amino acid sequence of SEQ ID NO: 3. In some aspects, the antibody comprises a LY6G6D binding domain comprising a heavy chain polypeptide (H1) and a light chain polypeptide (L1), wherein the H1 comprises a heavy chain variable (VH) domain (VH1) comprising the following complementarity determining regions (CDRs): (a) a CDR-H1 comprising the amino acid sequence of SEQ ID NO: 4; (b) a CDR-H2 comprising the amino acid sequence of SEQ ID NO: 5; and (c) a CDR-H3 comprising the amino acid sequence of SEQ ID NO: 6; and the L1 comprises a light chain variable (VL) domain (VL1) comprising the following CDRs: (d) a CDR-L1 comprising the amino acid sequence of SEQ ID NO: 1; (e) a CDR-L2 comprising the amino acid sequence of SEQ ID NO: 2; and (f) a CDR-L3 comprising the amino acid sequence of any one of SEQ ID NOs: 99-107. In some aspects, the antibody comprises a LY6G6D binding domain comprising a heavy chain polypeptide (H1) and a light chain polypeptide (L1), wherein the H1 comprises a heavy chain variable (VH) domain (VH1) comprising the following complementarity determining regions (CDRs): (a) a CDR-H1 comprising the amino acid sequence of SEQ ID NO: 111; (b) a CDR-H2 comprising the amino acid sequence of SEQ ID NO: 5; and (c) a CDR-H3 comprising the amino acid sequence of SEQ ID NO: 6; and the L1 comprises a light chain variable (VL) domain (VL1) comprising the following CDRs: (d) a CDR-L1 comprising the amino acid sequence of SEQ ID NO: 1; (e) a CDR-L2 comprising the amino acid sequence of SEQ ID NO: 2; and (f) a CDR-L3 comprising the amino acid sequence of SEQ ID NO: 3. In some aspects, the antibody comprises a LY6G6D binding domain comprising a heavy chain polypeptide (H1) and a light chain polypeptide (L1), wherein the H1 comprises a heavy chain variable (VH) domain (VH1) comprising the following complementarity determining regions (CDRs): (a) a CDR-H1 comprising the amino acid sequence of SEQ ID NO: 4; (b) a CDR-H2 comprising the amino acid sequence of SEQ ID NO: 112 or SEQ ID NO: 113; and (c) a CDR-H3 comprising the amino acid sequence of SEQ ID NO: 6; and the L1 comprises a light chain variable (VL) domain (VL1) comprising the following CDRs: (d) a CDR-L1 comprising the amino acid sequence of SEQ ID NO: 1; (e) a CDR-L2 comprising the amino acid sequence of SEQ ID NO: 2; and (f) a CDR-L3 comprising the amino acid sequence of SEQ ID NO: 3.

In some aspects, (a) the VH1 comprises an amino sequence having at least 95% sequence identity to the amino acid sequence of SEQ ID NO: 10; (b) the VL1 comprises an amino acid sequence having at least 95% identity to the amino acid sequence of SEQ ID NO: 11; or (c) the antibody comprises a VH1 as in (a) and a VL1 as in (b).

In some aspects, the VH1 comprises the following framework regions (FRs): (a) an FR-H1 comprising the amino acid sequence of SEQ ID NO: 34; (b) an FR-H2 comprising the amino acid sequence of SEQ ID NO: 35; (c) an FR-H3 comprising the amino acid sequence of SEQ ID NO: 36; and (d) an FR-H4 comprising the amino acid sequence of SEQ ID NO: 37. In some aspects, the VH1 comprises the amino acid sequence of SEQ ID NO: 10.

In some aspects, the VH1 comprises the following FRs: (a) an FR-H1 comprising the amino acid sequence of SEQ ID NO: 34; (b) an FR-H2 comprising the amino acid sequence of SEQ ID NO: 58; (c) an FR-H3 comprising the amino acid sequence of SEQ ID NO: 36; and (d) an FR-H4 comprising the amino acid sequence of SEQ ID NO: 37. In some aspects, the VH1 comprises the amino acid sequence of SEQ ID NO: 59.

In some aspects, the VL1 comprises the following FRs: (a) an FR-L1 comprising the amino acid sequence of SEQ ID NO: 38; (b) an FR-L2 comprising the amino acid sequence of SEQ ID NO: 39; (c) an FR-L3 comprising the amino acid sequence of SEQ ID NO: 40; and (d) an FR-L4 comprising the amino acid sequence of SEQ ID NO: 41. In some aspects, the VL1 comprises the amino acid sequence of SEQ ID NO: 11.

In some aspects, the VL1 comprises the following FRs: (a) an FR-L1 comprising the amino acid sequence of SEQ ID NO: 38; (b) an FR-L2 comprising the amino acid sequence of SEQ ID NO: 61; (c) an FR-L3 comprising the amino acid sequence of SEQ ID NO: 40; and (d) an FR-L4 comprising the amino acid sequence of SEQ ID NO: 41. In some aspects, the VL1 comprises the amino acid sequence of SEQ ID NO: 60.

In another aspect, the disclosure features an isolated antibody that binds to LY6G6D, wherein the antibody comprises a LY6G6D binding domain comprising a heavy chain polypeptide (H1) and a light chain polypeptide (L1), wherein the H1 comprises a VH domain (VH1) comprising the amino acid sequence of SEQ ID NO: 10 and the L1 comprises a VL domain (VL1) comprising the amino acid sequence of SEQ ID NO: 11.

In another aspect, the disclosure features an isolated antibody that binds to LY6G6D, wherein the antibody comprises a LY6G6D binding domain comprising a heavy chain polypeptide (H1) and a light chain polypeptide (L1), wherein the H1 comprises a VH domain (VH1) comprising the amino acid sequence of SEQ ID NO: 59 and the L1 comprises a VL domain (VL1) comprising the amino acid sequence of SEQ ID NO: 60.

In some aspects, the antibody binds a human LY6G6D polypeptide with a $K_D$ of between about 100 pM and 10 nM at 37° C. as measured using a BIAcore assay. In some aspects, the antibody binds the human LY6G6D polypeptide with a $K_D$ of 6.0 nM or lower; 4 nM or lower; or 2 nM or lower.

In some aspects, the antibody is monoclonal, human, humanized, or chimeric.

In some aspects, the antibody is an antibody fragment that binds LY6G6D. In some aspects, the antibody fragment is selected from the group consisting of Fab, Fab'-SH, Fv, scFv, and (Fab')$_2$ fragments.

In some aspects, the antibody is a full-length antibody or an IgG antibody.

In some aspects, the antibody is a monospecific antibody, a multispecific antibody, or a bispecific antibody.

In some aspects, the bispecific antibody binds to cluster of differentiation 3 (CD3) and comprises a CD3 binding domain comprising a heavy chain polypeptide (H2) and a light chain polypeptide (L2), wherein the H2 comprises a VH domain (VH2) and the L2 comprises VL domain (VL2).

In some aspects, the CD3 binding domain is capable of binding to a human CD3 polypeptide or a cyno CD3 polypeptide. In some aspects, the human CD3 polypeptide or the cyno CD3 polypeptide is a human CD3ε polypeptide or a cyno CD3ε polypeptide, respectively. In some aspects, the human CD3 polypeptide or the cyno CD3 polypeptide is a human CD3γ polypeptide or a cyno CD3γ polypeptide, respectively.

In some aspects, the antibody binds a human CD3ε polypeptide with a $K_D$ of between about 1 nM and 500 nM at 37° C. as measured using a BIAcore assay. In some aspects, the CD3 binding domain binds the human CD3ε polypeptide with a $K_D$ of 250 nM or lower. In some aspects, the CD3 binding domain binds the human CD3ε polypeptide with a $K_D$ of 100 nM or lower. In some aspects, the CD3 binding domain binds the human CD3ε polypeptide with a $K_D$ of 15 nM or lower. In some aspects, the CD3 binding domain binds the human CD3ε polypeptide with a $K_D$ of 10 nM or lower. In some aspects, the CD3 binding domain binds the human CD3ε polypeptide with a $K_D$ of 5 nM or lower.

In some aspects, the VH2 comprises the following CDRs: (a) a CDR-H1 comprising the amino acid sequence of SEQ ID NO: 15; (b) a CDR-H2 comprising the amino acid sequence of SEQ ID NO: 16; and (c) a CDR-H3 comprising the amino acid sequence of SEQ ID NO: 17; and the VL2 comprises the following CDRs: (d) a CDR-L1 comprising the amino acid sequence of SEQ ID NO: 12; (e) a CDR-L2 comprising the amino acid sequence of SEQ ID NO: 13; and (f) a CDR-L3 comprising the amino acid sequence of SEQ ID NO: 14.

In some aspects, the VH2 comprises an amino sequence having at least 95% sequence identity to the amino acid sequence of SEQ ID NO: 20; (b) the VL2 comprises an amino acid sequence having at least 95% identity to the amino acid sequence of SEQ ID NO: 21; or (c) the antibody comprises a VH2 as in (a) and a VL2 as in (b). In some aspects, the VH2 comprises the amino acid sequence of SEQ ID NO: 20. In some aspects, the VL2 comprises the amino acid sequence of SEQ ID NO: 21.

In some aspects, the VH2 comprises the following CDRs: (a) a CDR-H1 comprising the amino acid sequence of SEQ ID NO: 15; (b) a CDR-H2 comprising the amino acid sequence of SEQ ID NO: 16; and (c) a CDR-H3 comprising the amino acid sequence of SEQ ID NO: 17; and the VL2 comprises the following CDRs: (d) a CDR-L1 comprising the amino acid sequence of SEQ ID NO: 12; (e) a CDR-L2 comprising the amino acid sequence of SEQ ID NO: 50; and (f) a CDR-L3 comprising the amino acid sequence of SEQ ID NO: 51;

In some aspects, (a) the VH2 comprises an amino sequence having at least 95% sequence identity to the amino acid sequence of SEQ ID NO: 20; (b) the VL2 comprises an amino acid sequence having at least 95% identity to the amino acid sequence of SEQ ID NO: 55; or (c) the antibody comprises a VH2 as in (a) and a VL2 as in (b). In some aspects, the VH2 comprises the amino acid sequence of SEQ ID NO: 20. In some aspects, the VL2 comprises the amino acid sequence of SEQ ID NO: 55.

In some aspects, the VH2 comprises the following FRs: (a) an FR-H1 comprising the amino acid sequence of SEQ ID NO: 42; (b) an FR-H2 comprising the amino acid sequence of SEQ ID NO: 43; (c) an FR-H3 comprising the amino acid sequence of SEQ ID NO: 44; and (d) an FR-H4 comprising the amino acid sequence of SEQ ID NO: 45.

In some aspects, the VH2 comprises the following FRs: (a) an FR-H1 comprising the amino acid sequence of SEQ ID NO: 42; (b) an FR-H2 comprising the amino acid sequence of SEQ ID NO: 62; (c) an FR-H3 comprising the amino acid sequence of SEQ ID NO: 44; and (d) an FR-H4 comprising the amino acid sequence of SEQ ID NO: 45.

In some aspects, the VL2 comprises the following FRs: (a) an FR-L1 comprising the amino acid sequence of SEQ ID NO: 46; (b) an FR-L2 comprising the amino acid sequence of SEQ ID NO: 47; (c) an FR-L3 comprising the amino acid sequence of SEQ ID NO: 48; and (d) an FR-L4 comprising the amino acid sequence of SEQ ID NO: 49.

In some aspects, the VL2 comprises the following FRs: (a) an FR-L1 comprising the amino acid sequence of SEQ ID NO: 46; (b) an FR-L2 comprising the amino acid sequence of SEQ ID NO: 63; (c) an FR-L3 comprising the amino acid sequence of SEQ ID NO: 48; and (d) an FR-L4 comprising the amino acid sequence of SEQ ID NO: 49.

In some aspects, the H1 and H2 each further comprise a heavy chain constant domain (CH1) and the L1 and L2 each further comprise a light chain constant domain (CL). In some aspects, the CH1 of H1 comprises an amino acid substitution at S183 (EU numbering) and the CL of L1 comprises an amino acid substitution at V133 (EU numbering). In some aspects, the CH1 of H1 comprises a S183K mutation and the CL of L1 comprises a V133E mutation. In some aspects, the CH1 of H2 comprises a S183E mutation and the CL of L2 comprises a V133K mutation. In some aspects, the CH1 of H1 comprises a S183E mutation and the CL of L1 comprises a V133K mutation. In some aspects, the CH1 of H2 comprises a S183K mutation and the CL of L2 comprises a V133E mutation.

In another aspect, the disclosure features a bispecific antibody that binds to LY6G6D and CD3, wherein the bispecific antibody comprises: a LY6G6D binding domain comprising a heavy chain polypeptide (H1) and a light chain polypeptide (L1) and a CD3 binding domain comprising a heavy chain polypeptide (H2) and a light chain polypeptide (L2), wherein each H1 and H2 comprises a heavy chain variable domain (VH) and a heavy chain constant domain (CH1) and each L1 and L2 comprises a light chain variable domain (VL) and a light chain constant domain (CL), wherein: (a) the LY6G6D binding domain comprises the following six CDRs: (i) a CDR-H1 comprising the amino acid sequence of SEQ ID NO: 4 or SEQ ID NO: 111; (ii) a CDR-H2 comprising the amino acid sequence of SEQ ID NO: 5, SEQ ID NO: 112, or SEQ ID NO: 113; (iii) a CDR-H3 comprising the amino acid sequence of SEQ ID NO: 6; (iv) a CDR-L1 comprising the amino acid sequence of SEQ ID NO: 1; (v) a CDR-L2 comprising the amino acid sequence of SEQ ID NO: 2; and (vi) a CDR-L3 comprising the amino acid sequence of SEQ ID NO: 3 or any of SEQ ID NOs: 99-107; (b) the CD3 binding domain comprises the following six CDRs: (i) a CDR-H1 comprising the amino acid sequence of SEQ ID NO: 15; (ii) a CDR-H2 comprising the amino acid sequence of SEQ ID NO: 16; (iii) a CDR-H3 comprising the amino acid sequence of SEQ ID NO: 17; (iv) a CDR-L1 comprising the amino acid sequence of SEQ ID NO: 12; (v) a CDR-L2 comprising the amino acid sequence of SEQ ID NO: 13; and (vi) a CDR-L3 comprising the amino acid sequence of SEQ ID NO: 14; (c) the CH1 of H1 comprises an amino acid substitution at S183 (EU numbering) and the CL of L1 comprises an amino acid substitution at V133 (EU numbering) and/or the CH1 of H2 comprises an amino acid substitution at S183 (EU numbering) and the CL of L2 comprises an amino acid substitution at V133 (EU numbering); and (d) the VH of H1 comprises an amino acid substitution at position Q39 and the VL of L1 comprises an amino acid substitutions at position Q38 and/or the VH of H2 comprises an amino acid substitution at position Q39 and the VL of L2 comprises an amino acid substitution at position Q38 (all Kabat numbering). In some aspects, (a) the LY6G6D binding domain comprises the following six CDRs: (i) a CDR-H1 comprising the amino acid sequence of SEQ ID NO: 4; (ii) a CDR-H2 comprising the amino acid sequence of SEQ ID NO: 5; (iii) a CDR-H3 comprising the amino acid sequence of SEQ ID NO: 6; (iv) a CDR-L1 comprising the amino acid sequence of SEQ ID NO: 1; (v) a CDR-L2 comprising the amino acid sequence of SEQ ID NO: 2; and (vi) a CDR-L3 comprising the amino acid sequence of SEQ ID NO: 3; (b) the CD3 binding domain comprises the following six CDRs: (i) a CDR-H1 comprising the amino acid sequence of SEQ ID NO: 15; (ii) a CDR-H2 comprising the amino acid sequence of SEQ ID NO: 16; (iii) a CDR-H3 comprising the amino acid sequence of SEQ ID NO: 17; (iv) a CDR-L1 comprising the amino acid sequence of SEQ ID NO: 12; (v) a CDR-L2 comprising the amino acid sequence of SEQ ID NO: 13; and (vi) a CDR-L3 comprising the amino acid sequence of SEQ ID NO: 14; (c) the CH1 of H1 comprises an amino acid substitution at S183 (EU numbering) and the CL of L1 comprises an amino acid substitution at V133 (EU numbering) and/or the CH1 of H2 comprises an amino acid substitution at S183 (EU numbering) and the CL of L2 comprises an amino acid substitution at V133 (EU numbering); and (d) the VH of H1 comprises an amino acid substitution at position Q39 and the VL of L1 comprises an amino acid substitutions at position Q38 and/or the VH of H2 comprises an amino acid substitution at position Q39 and the VL of L2 comprises an amino acid substitution at position Q38 (all Kabat numbering).

In some aspects, (a) the LY6G6D binding domain comprises the following six CDRs: (i) a CDR-H1 comprising the amino acid sequence of SEQ ID NO: 4; (ii) a CDR-H2 comprising the amino acid sequence of SEQ ID NO: 5; (iii) a CDR-H3 comprising the amino acid sequence of SEQ ID NO: 6; (iv) a CDR-L1 comprising the amino acid sequence of SEQ ID NO: 1; (v) a CDR-L2 comprising the amino acid sequence of SEQ ID NO: 2; and (vi) a CDR-L3 comprising the amino acid sequence of any one of SEQ ID NOs: 99-107; (b) the CD3 binding domain comprises the following six CDRs: (i) a CDR-H1 comprising the amino acid sequence of SEQ ID NO: 15; (ii) a CDR-H2 comprising the amino acid sequence of SEQ ID NO: 16; (iii) a CDR-H3 comprising the amino acid sequence of SEQ ID NO: 17; (iv) a CDR-L1 comprising the amino acid sequence of SEQ ID NO: 12; (v) a CDR-L2 comprising the amino acid sequence of SEQ ID NO: 13; and (vi) a CDR-L3 comprising the amino acid sequence of SEQ ID NO: 14; (c) the CH1 of H1 comprises an amino acid substitution at S183 (EU numbering) and the CL of L1 comprises an amino acid substitution at V133 (EU numbering) and/or the CH1 of H2 comprises an amino acid substitution at S183 (EU numbering) and the CL of L2 comprises an amino acid substitution at V133 (EU numbering); and (d) the VH of H1 comprises an amino acid substitution at position Q39 and the VL of L1 comprises an amino acid substitutions at position Q38 and/or the VH of H2 comprises an amino acid substitution at position Q39 and the VL of L2 comprises an amino acid substitution at position Q38 (all Kabat numbering).

In some aspects, (a) the LY6G6D binding domain comprises the following six CDRs: (i) a CDR-H1 comprising the amino acid sequence of SEQ ID NO: 111; (ii) a CDR-H2 comprising the amino acid sequence of SEQ ID NO: 5; (iii) a CDR-H3 comprising the amino acid sequence of SEQ ID NO: 6; (iv) a CDR-L1 comprising the amino acid sequence of SEQ ID NO: 1; (v) a CDR-L2 comprising the amino acid sequence of SEQ ID NO: 2; and (vi) a CDR-L3 comprising the amino acid sequence of SEQ ID NO: 3; (b) the CD3 binding domain comprises the following six CDRs: (i) a CDR-H1 comprising the amino acid sequence of SEQ ID NO: 15; (ii) a CDR-H2 comprising the amino acid sequence of SEQ ID NO: 16; (iii) a CDR-H3 comprising the amino acid sequence of SEQ ID NO: 17; (iv) a CDR-L1 comprising the amino acid sequence of SEQ ID NO: 12; (v) a CDR-L2 comprising the amino acid sequence of SEQ ID NO: 13; and (vi) a CDR-L3 comprising the amino acid sequence of SEQ ID NO: 14; (c) the CH1 of H1 comprises an amino acid substitution at S183 (EU numbering) and the CL of L1 comprises an amino acid substitution at V133 (EU numbering) and/or the CH1 of H2 comprises an amino acid substitution at S183 (EU numbering) and the CL of L2 comprises an amino acid substitution at V133 (EU numbering); and (d) the VH of H1 comprises an amino acid substitution at position Q39 and the VL of L1 comprises an amino acid substitutions at position Q38 and/or the VH of H2 comprises an amino acid substitution at position Q39 and the VL of L2 comprises an amino acid substitution at position Q38 (all Kabat numbering). In some aspects, (a) the LY6G6D binding domain comprises the following six CDRs: (i) a CDR-H1 comprising the amino acid sequence of SEQ ID NO: 4; (ii) a CDR-H2 comprising the amino acid sequence of SEQ ID NO: 112 or SEQ ID NO: 113; (iii) a CDR-H3 comprising the amino acid sequence of SEQ ID NO: 6; (iv) a CDR-L1 comprising the amino acid sequence of SEQ ID NO: 1; (v) a CDR-L2 comprising the amino acid sequence of SEQ ID NO: 2; and (vi) a CDR-L3 comprising the amino acid sequence of SEQ ID NO: 3; (b) the CD3 binding domain comprises the following six CDRs: (i) a CDR-H1 comprising the amino acid sequence of SEQ ID NO: 15; (ii) a CDR-H2 comprising the amino acid sequence of SEQ ID NO: 16; (iii) a CDR-H3 comprising the amino acid sequence of SEQ ID NO: 17; (iv) a CDR-L1 comprising the amino acid sequence of SEQ ID NO: 12; (v) a CDR-L2 comprising the amino acid sequence of SEQ ID NO: 13; and (vi) a CDR-L3 comprising the amino acid sequence of SEQ ID NO: 14; (c) the CH1 of H1 comprises an amino acid substitution at S183 (EU numbering) and the CL of L1 comprises an amino acid substitution at V133 (EU numbering) and/or the CH1 of H2 comprises an amino acid substitution at S183 (EU numbering) and the CL of L2 comprises an amino acid substitution at V133 (EU numbering); and (d) the VH of H1 comprises an amino acid substitution at position Q39 and the VL of L1 comprises an amino acid substitutions at position Q38 and/or the VH of H2 comprises an amino acid substitution at position Q39 and the VL of L2 comprises an amino acid substitution at position Q38 (all Kabat numbering).

In another aspect, the invention features a bispecific antibody that binds to LY6G6D and CD3, wherein the bispecific antibody comprises: a LY6G6D binding domain comprising a heavy chain polypeptide (H1) and a light chain polypeptide (L) and a CD3 binding domain comprising a heavy chain polypeptide (H2) and a light chain polypeptide (L2), wherein each H1 and H2 comprises a heavy chain variable domain (VH) and a heavy chain constant domain (CH1) and each L1 and L2 comprises a light chain variable domain (VL) and a light chain constant domain (CL), wherein: (a) the LY6G6D binding domain comprises the following six CDRs: (i) a CDR-H1 comprising the amino acid sequence of SEQ ID NO: 4 or SEQ ID NO: 111; (ii) a CDR-H2 comprising the amino acid sequence of SEQ ID NO: 5, SEQ ID NO: 112, or SEQ ID NO: 113; (iii) a CDR-H3 comprising the amino acid sequence of SEQ ID NO: 6; (iv) a CDR-H1 comprising the amino acid sequence of SEQ ID NO: 1; (v) a CDR-L2 comprising the amino acid sequence of SEQ ID NO: 2; and (vi) a CDR-L3 comprising the amino acid sequence of SEQ ID NO: 3 or any of SEQ ID NOs: 99-107; (b) the CD3 binding domain comprises the following six CDRs: (i) a CDR-H1 comprising the amino acid sequence of SEQ ID NO: 15; (ii) a CDR-H2 comprising the amino acid sequence of SEQ ID NO: 16; (iii) a CDR-H3 comprising the amino acid sequence of SEQ ID NO: 17; (iv) a CDR-L1 comprising the amino acid sequence of SEQ ID NO: 12; (v) a CDR-L2 comprising the amino acid sequence of SEQ ID NO: 50; and (vi) a CDR-L3 comprising the amino acid sequence of SEQ ID NO: 51; (c) the CH1 of H1 comprises an amino acid substitution at S183 (EU numbering) and the CL of L1 comprises an amino acid substitution at V133 (EU numbering) and/or the CH1 of H2 comprises an amino acid substitution at S183 (EU numbering) and the CL of L2 comprises an amino acid substitution at V133 (EU numbering); and (d) the VH of H1 comprises an amino acid substitution at position Q39 and the VL of L1 comprises an amino acid substitutions at position Q38 and/or the VH of H2 comprises an amino acid substitution at position Q39 and the VL of L2 comprises an amino acid substitution at position Q38 (all Kabat numbering). In some aspects, (a) the LY6G6D binding domain comprises the following six CDRs: (i) a CDR-H1 comprising the amino acid sequence of SEQ ID NO: 4; (ii) a CDR-H2 comprising the amino acid sequence of SEQ ID NO: 5; (iii) a CDR-H3 comprising the amino acid sequence of SEQ ID NO: 6; (iv) a CDR-H1 comprising the amino acid sequence of SEQ ID NO: 1; (v) a CDR-L2 comprising the amino acid sequence of SEQ ID NO: 2; and (vi) a CDR-L3 comprising the amino acid sequence of any one of SEQ ID NOs: 99-107; (b) the CD3 binding domain comprises the following six CDRs: (i) a CDR-H1 comprising the amino acid sequence of SEQ ID NO: 15; (ii) a CDR-H2 comprising the amino acid sequence of SEQ ID NO: 16; (iii) a CDR-H3 comprising the amino acid sequence of SEQ ID NO: 17; (iv) a CDR-L1 comprising the amino acid sequence of SEQ ID NO: 12; (v) a CDR-L2 comprising the amino acid sequence of SEQ ID NO: 50; and (vi) a CDR-L3 comprising the amino acid sequence of SEQ ID NO: 51; (c) the CH1 of H1 comprises an amino acid substitution at S183 (EU numbering) and the CL of L1 comprises an amino acid substitution at V133 (EU numbering) and/or the CH1 of H2 comprises an amino acid substitution at S183 (EU numbering) and the CL of L2 comprises an amino acid substitution at V133 (EU numbering); and (d) the VH of H1 comprises an amino acid substitution at position Q39 and the VL of L1 comprises an amino acid substitutions at position Q38 and/or the VH of H2 comprises an amino acid substitution at position Q39 and the VL of L2 comprises an amino acid substitution at position Q38 (all Kabat numbering).

In some aspects, (a) the LY6G6D binding domain comprises the following six CDRs: (i) a CDR-H1 comprising the amino acid sequence of SEQ ID NO: 111; (ii) a CDR-H2 comprising the amino acid sequence of SEQ ID NO: 5; (iii) a CDR-H3 comprising the amino acid sequence of SEQ ID NO: 6; (iv) a CDR-H1 comprising the amino acid sequence of SEQ ID NO: 1; (v) a CDR-L2 comprising the amino acid sequence of SEQ ID NO: 2; and (vi) a CDR-L3 comprising the amino acid sequence of SEQ ID NO: 3; (b) the CD3 binding domain comprises the following six CDRs: (i) a CDR-H1 comprising the amino acid sequence of SEQ ID NO: 15; (ii) a CDR-H2 comprising the amino acid sequence of SEQ ID NO: 16; (iii) a CDR-H3 comprising the amino acid sequence of SEQ ID NO: 17; (iv) a CDR-L1 comprising the amino acid sequence of SEQ ID NO: 12; (v) a CDR-L2 comprising the amino acid sequence of SEQ ID NO: 50; and (vi) a CDR-L3 comprising the amino acid sequence of SEQ ID NO: 51; (c) the CH1 of H1 comprises an amino acid substitution at S183 (EU numbering) and the CL of L1 comprises an amino acid substitution at V133 (EU numbering) and/or the CH1 of H2 comprises an amino acid substitution at S183 (EU numbering) and the CL of L2 comprises an amino acid substitution at V133 (EU numbering); and (d) the VH of H1 comprises an amino acid substitution at position Q39 and the VL of L1 comprises an amino acid substitutions at position Q38 and/or the VH of H2 comprises an amino acid substitution at position Q39 and the VL of L2 comprises an amino acid substitution at position Q38 (all Kabat numbering). In some aspects, (a) the LY6G6D binding domain comprises the following six CDRs: (i) a CDR-H1 comprising the amino acid sequence of SEQ ID NO: 111; (ii) a CDR-H2 comprising the amino acid sequence of SEQ ID NO: 112 or SEQ ID NO: 113; (iii) a CDR-H3 comprising the amino acid sequence of SEQ ID NO: 6; (iv) a CDR-H1 comprising the amino acid sequence of SEQ ID NO: 1; (v) a CDR-L2 comprising the amino acid sequence of SEQ ID NO: 2; and (vi) a CDR-L3 comprising the amino acid sequence of SEQ ID NO: 3; (b) the CD3 binding domain comprises the following six CDRs: (i) a CDR-H1 comprising the amino acid sequence of SEQ ID NO: 15; (ii) a CDR-H2 comprising the amino acid sequence of SEQ ID NO: 16; (iii) a CDR-H3 comprising the amino acid sequence of SEQ ID NO: 17; (iv) a CDR-L1 comprising the amino acid sequence of SEQ ID NO: 12; (v) a CDR-L2 comprising the amino acid sequence of SEQ ID NO: 50; and (vi) a CDR-L3 comprising the amino acid sequence of SEQ ID NO: 51; (c) the CH1 of H1 comprises an amino acid substitution at S183 (EU numbering) and the CL of L1 comprises an amino acid substitution at V133 (EU numbering) and/or the CH1 of H2 comprises an amino acid substitution at S183 (EU numbering) and the CL of L2 comprises an amino acid substitution at V133 (EU numbering); and (d) the VH of H1 comprises an amino acid substitution at position Q39 and the VL of L1 comprises an amino acid substitutions at position Q38 and/or the VH of H2 comprises an amino acid substitution at position Q39 and the VL of L2 comprises an amino acid substitution at position Q38 (all Kabat numbering).

In some aspects, the VH of H1 comprises an amino acid substitution at Q39 (Kabat numbering) and the VL of L1 comprises an amino acid substitution at Q38 (Kabat numbering). In some aspects, the CH1 of H2 comprises an amino acid substitution at S183 (EU numbering) and the CL of L2 comprises an amino acid substitution at V133 (EU numbering). In some aspects, the VH of H2 further comprises an amino acid substitution at position Q39 (Kabat numbering) and the VL of L2 further comprises an amino acid substitution at position Q38 (Kabat numbering). In some aspects, the CH1 of H1 comprises a S183K mutation (EU numbering) and CL of L1 comprises a V133E mutation (EU numbering), and CH1 of H2 comprises a S183E mutation (EU numbering) and the CL of L2 comprises a V133K mutation (EU numbering). In some aspects, the VH of H1 comprises a Q39E (Kabat numbering) mutation, the VL of L1 comprises a Q38K mutation, the VH of H2 comprises a Q39K mutation, and the VL of L2 comprises a Q38E mutation (Kabat numbering). In some aspects, the CH1 of H1 comprises a S183E mutation (EU numbering) and the CL of L1 comprises a V133K mutation (EU numbering), and the CH1 of H2 comprises a S183K mutation (EU numbering) and the CL of L2 comprises a V133E mutation (EU numbering). In some aspects, the VH of H1 comprises a Q39K mutation (Kabat numbering), the VL of L1 comprises a Q38E mutation (Kabat numbering), the VH of H2 comprises a Q39E mutation (Kabat numbering), and the VL of L2 comprises a Q38K mutation (Kabat numbering).

In some aspects, the VH of H2 comprises the amino acid sequence of SEQ ID NO: 20 and/or the VL of L2 comprises the amino acid sequence of SEQ ID NO: 21. In some aspects, the VH of H1 comprises the amino acid sequence of SEQ ID NO: 10 and the VL of L1 comprises the amino acid sequence of SEQ ID NO: 11.

In some aspects, the VH of H2 comprises the amino acid sequence of SEQ ID NO: 20 and/or the VL of L2 comprises the amino acid sequence of SEQ ID NO: 55. In some aspects, the VH of H1 comprises the amino acid sequence of SEQ ID NO: 10 and the VL of L1 comprises the amino acid sequence of SEQ ID NO: 11.

In some aspects, a first CH3 domain ($CH3_1$) of an Fc region of the H1 and a second CH3 domain ($CH3_2$) of an Fc region of the H2 each comprise a protuberance or a cavity, and wherein the protuberance or cavity in the $CH3_1$ is positionable in the cavity or protuberance, respectively, in the $CH3_2$. In some aspects, the $CH3_1$ and the $CH3_2$ meet at an interface between the protuberance and cavity.

In some aspects, the $CH3_1$ of the Fc region of the H1 comprises a protuberance and the $CH3_2$ of the Fc region of the H2 comprises a cavity. In some aspects, (a) the $CH3_1$ of the Fc region of the H1 comprises a protuberance comprising a T366W amino acid substitution mutation (EU numbering); (b) the $CH3_2$ of the Fc region of the H2 comprises a cavity comprising a T366S, L368A, or Y407V amino acid substitution mutation (EU numbering), or a combination thereof; or (c) both (a) and (b).

In some aspects, (a) the $CH3_1$ of the Fc region of the H1 comprises a protuberance comprising a T366W amino acid substitution mutation (EU numbering); (b) the $CH3_2$ of the Fc region of the H2 comprises a cavity comprising T366S, L368A, and Y407V amino acid substitution mutations (EU numbering); or (c) both (a) and (b). In some aspects, (a) the $CH3_1$ of the Fc region of the H1 comprises a protuberance comprising a T366W amino acid substitution mutation (EU numbering) and (b) the CH3$_2$ of the Fc region of the H2 comprises a cavity comprising T366S, L368A, and Y407V amino acid substitution mutations (EU numbering).

In some aspects, the CH3$_1$ of the Fc region of the H1 comprises a cavity and the CH3$_2$ of the Fc region of the H2 comprises a protuberance. In some aspects, (a) the CH3$_1$ of the Fc region of the H1 comprises a cavity comprising a T366S, L368A, or Y407V amino acid substitution mutation (EU numbering), or a combination thereof; (b) the CH3$_2$ of the Fc region of the H2 comprises a protuberance comprising a T366W amino acid substitution mutation (EU numbering); or (c) both (a) and (b). In some aspects, (a) the CH3$_1$ of the Fc region of the H1 comprises a cavity comprising T366S, L368A, and Y407V amino acid substitution mutations (EU numbering); (b) the CH3$_2$ of the Fc region of the H2 comprises a protuberance comprising a T366W amino acid substitution mutation (EU numbering); or (c) both (a) and (b). In some aspects, (a) the CH3$_1$ of the Fc region of the H1 comprises a cavity comprising T366S, L368A, and Y407V amino acid substitution mutations (EU numbering) and (b) the CH3$_2$ of the Fc region of the second heavy chain polypeptide comprises a protuberance comprising a T366W amino acid substitution mutation (EU numbering).

In some aspects, the Fc regions are human IgG isotype Fc regions, or Fc region variants thereof. In some aspects, the Fc regions are human IgG isotype Fc region variants. In some aspects, the human IgG isotype Fc region variants each comprise a mutation at amino acid residue N297 (EU numbering) that results in the absence of glycosylation. In some aspects, the mutation at amino acid residue N297 is a substitution mutation. In some aspects, the mutation at amino acid residue N297 reduces effector function of the Fc region.

In some aspects, the substitution mutation is an N297G or N297A mutation. In some aspects, the human IgG isotype Fc region variants each comprise the N297G mutation. In some aspects, the human IgG isotype Fc region variants each comprise a mutation that reduces effector function of the Fc region.

In some aspects, the mutation that reduces effector function of the Fc region is a substitution mutation. In some aspects, the substitution mutation is at amino acid residue E233, L234, L235, D265, and/or P329 (EU numbering). In some aspects, the substitution mutation is a E233P, L234A, L234V, L235A, D265A, or P329G mutation. In some aspects, the human IgG isotype Fc region variants each comprise the P329G mutation. In some aspects, the human IgG isotype Fc region variants each comprise the N297G and P329G mutations.

In some aspects, the human IgG isotype Fc region variants are human IgG1 or IgG3 isotype Fc region variants, each further comprising the L234A or L235A mutation. In some aspects, the human IgG isotype Fc region variants are human IgG1 or IgG3 isotype Fc region variants, each further comprising the L234A and L235A mutations.

In some aspects, the human IgG isotype Fc region variants are human IgG1 or IgG3 isotype Fc region variants, each further comprising the following substitution mutations E233P, L234V, and L235A (EU numbering) and a deletion of residue G236 (EU numbering). In some aspects, the human IgG isotype Fc region variants are human IgG1 isotype Fc region variants.

In some aspects, the human IgG isotype Fc region variants are human IgG4 isotype Fc region variants, each further comprising the following substitution mutations E233P, F234V, and L235A (EU numbering) and a deletion of residue G236 (EU numbering).

In some aspects, the Fc regions of the Fc complex are effectorless Fc regions.

In some aspects, the H1 comprises the amino acid sequence of SEQ ID NO: 7 and the L2 comprises the amino acid sequence of SEQ ID NO: 9. In some aspects, the H2 comprises the amino acid sequence of SEQ ID NO: 18 and the L2 comprises the amino acid sequence of SEQ ID NO: 19. In some aspects, the H2 comprises the amino acid sequence of SEQ ID NO: 18 and the L2 comprises the amino acid sequence of SEQ ID NO: 57.

In another aspect, the disclosure features a bispecific antibody that binds to LY6G6D and CD3, wherein the bispecific antibody comprises a LY6G6D binding domain comprising a heavy chain polypeptide (H1) and a light chain polypeptide (L1) and a CD3 binding domain comprising a heavy chain polypeptide (H2) and a light chain polypeptide (L2), and wherein: (a) H1 comprises the amino acid sequence of SEQ ID NO: 7; (b) L1 comprises the amino acid sequence of SEQ ID NO: 9; (c) H2 comprises the amino acid sequence of SEQ ID NO: 18; and (d) L2 comprises the amino acid sequence of SEQ ID NO: 19.

In another aspect, the disclosure features a bispecific antibody that binds to LY6G6D and CD3, wherein the bispecific antibody comprises a LY6G6D binding domain comprising a heavy chain polypeptide (H1) and a light chain polypeptide (L1) and a CD3 binding domain comprising a heavy chain polypeptide (H2) and a light chain polypeptide (L2), and wherein: (a) H1 comprises the amino acid sequence of SEQ ID NO: 64; (b) L1 comprises the amino acid sequence of SEQ ID NO: 65; (c) H2 comprises the amino acid sequence of SEQ ID NO: 69; and (d) L2 comprises the amino acid sequence of SEQ ID NO: 70.

In another aspect, the disclosure features a bispecific antibody that binds to LY6G6D and CD3, wherein the bispecific antibody comprises a LY6G6D binding domain comprising a heavy chain polypeptide (H1) and a light chain polypeptide (L1) and a CD3 binding domain comprising a heavy chain polypeptide (H2) and a light chain polypeptide (L2), and wherein: (a) H1 comprises the amino acid sequence of SEQ ID NO: 8; (b) L1 comprises the amino acid sequence of SEQ ID NO: 9; (c) H2 comprises the amino acid sequence of SEQ ID NO: 67; and (d) L2 comprises the amino acid sequence of SEQ ID NO: 19.

In another aspect, the disclosure features a bispecific antibody that binds to LY6G6D and CD3, wherein the bispecific antibody comprises a LY6G6D binding domain comprising a heavy chain polypeptide (H1) and a light chain polypeptide (L1) and a CD3 binding domain comprising a heavy chain polypeptide (H2) and a light chain polypeptide (L2), and wherein: (a) H1 comprises the amino acid sequence of SEQ ID NO: 66; (b) L1 comprises the amino acid sequence of SEQ ID NO: 65; (c) H2 comprises the amino acid sequence of SEQ ID NO: 68; and (d) L2 comprises the amino acid sequence of SEQ ID NO: 70.

In another aspect, the disclosure features a bispecific antibody that binds to LY6G6D and CD3, wherein the bispecific antibody comprises a LY6G6D binding domain comprising a heavy chain polypeptide (H1) and a light chain polypeptide (L1) and a CD3 binding domain comprising a heavy chain polypeptide (H2) and a light chain polypeptide (L2), and wherein: (a) H1 comprises the amino acid sequence of SEQ ID NO: 7; (b) L1 comprises the amino acid sequence of SEQ ID NO: 9; (c) H2 comprises the amino acid sequence of SEQ ID NO: 18; and (d) L2 comprises the amino acid sequence of SEQ ID NO: 57.

In another aspect, the disclosure features a bispecific antibody that binds to LY6G6D and CD3, wherein the bispecific antibody comprises a LY6G6D binding domain comprising a heavy chain polypeptide (H1) and a light chain polypeptide (L1) and a CD3 binding domain comprising a heavy chain polypeptide (H2) and a light chain polypeptide (L2), and wherein: (a) H1 comprises the amino acid sequence of SEQ ID NO: 64; (b) L1 comprises the amino acid sequence of SEQ ID NO: 65; (c) H2 comprises the amino acid sequence of SEQ ID NO: 69; and (d) L2 comprises the amino acid sequence of SEQ ID NO: 73.

In another aspect, the disclosure features a bispecific antibody that binds to LY6G6D and CD3, wherein the bispecific antibody comprises a LY6G6D binding domain comprising a heavy chain polypeptide (H1) and a light chain polypeptide (L1) and a CD3 binding domain comprising a heavy chain polypeptide (H2) and a light chain polypeptide (L2), and wherein: (a) H1 comprises the amino acid sequence of SEQ ID NO: 8; (b) L1 comprises the amino acid sequence of SEQ ID NO: 9; (c) H2 comprises the amino acid sequence of SEQ ID NO: 67; and (d) L2 comprises the amino acid sequence of SEQ ID NO: 57.

In another aspect, the disclosure features a bispecific antibody that binds to LY6G6D and CD3, wherein the bispecific antibody comprises a LY6G6D binding domain comprising a heavy chain polypeptide (H1) and a light chain polypeptide (L1) and a CD3 binding domain comprising a heavy chain polypeptide (H2) and a light chain polypeptide (L2), and wherein: (a) H1 comprises the amino acid sequence of SEQ ID NO: 66; (b) L1 comprises the amino acid sequence of SEQ ID NO: 65; (c) H2 comprises the amino acid sequence of SEQ ID NO: 68; and (d) L2 comprises the amino acid sequence of SEQ ID NO: 73.

In some aspects, the antibody has a clearance following intravenous injection of between about 10 ml/kg/day to about 35 ml/kg/day.

In another aspect, the disclosure features one or more isolated nucleic acids encoding the antibody of any one of the above aspects, or a portion thereof comprising a binding domain that binds to LY6G6D.

In another aspect, the disclosure features one or more vectors comprising the one or more isolated nucleic acids of the above aspect.

In another aspect, the disclosure features one or more host cells comprising the one or more vectors of the above aspect.

In some aspects, the one or more host cells are one or more mammalian host cells. In some aspects, the one or more mammalian host cells are one or more Chinese hamster ovary (CHO) host cells.

In some aspects, the one or more host cells are one or more prokaryotic host cells. In some aspects, the one or more prokaryotic host cells are one or more *E. coli* host cells.

In another aspect, the disclosure features a method of producing the antibody of any one of the above aspects, the method comprising culturing the one or more host cells of the above aspect in a culture medium. In some aspects, the method further comprises recovering the anti-LY6G6D antibody from the one or more host cells or the culture medium.

In another aspect, the disclosure features a composition comprising the antibody of any one of the above aspects. In some aspects, the composition further comprises a pharmaceutically acceptable excipient or diluent. In some aspects, the pharmaceutically acceptable excipient is a buffer, carrier, stabilizer, or preservative. In some aspects, the composition is a pharmaceutical composition.

In another aspect, the disclosure features the antibody of any one of the above aspects for use as a medicament.

In another aspect, the disclosure features the antibody of any one of the above aspects or the composition of any one of the above aspects for use in treating or delaying progression of a LY6G6D-positive cancer in a subject in need thereof. In some aspects, the LY6G6D-positive cancer is a colorectal cancer. In some aspects, the LY6G6D-positive cancer has a microsatellite instability (MSI) status of microsatellite stable (MSS) or microsatellite instability low (MSI-L).

In another aspect, the disclosure features use of the antibody of any one of the above aspects or the composition of any one of the above aspects in the manufacture of a medicament for treating or delaying progression of an LY6G6D-positive cancer in a subject. In some aspects, the LY6G6D-positive cancer is a colorectal cancer. In some aspects, the LY6G6D-positive cancer has a MSI status of MSS or MSI-L.

In another aspect, the disclosure features a method of treating or delaying the progression of an LY6G6D-positive cancer in a subject in need thereof, the method comprising administering to the subject the antibody of any one of the above aspects or the composition of any one of the above aspects. In some aspects, the LY6G6D-positive cancer is a colorectal cancer. In some aspects, the LY6G6D-positive cancer has a MSI status of MSS or MSI-L.

In another aspect, the disclosure features a kit comprising the antibody of any of the above aspects and a package insert comprising instructions for using the antibody for treating or delaying progression of a LY6G6D-positive cancer in a subject. In some aspects, the LY6G6D-positive cancer is a colorectal cancer. In some aspects, the LY6G6D-positive cancer has a MSI status of MSS or MSI-L. In some aspects, the subject is a human.

In another aspect, the disclosure features an isolated antibody that binds to CD3, wherein the antibody comprises a binding domain comprising the following CDRs: (a) a CDR-H1 comprising the amino acid sequence of SEQ ID NO: 15; (b) a CDR-H2 comprising the amino acid sequence of SEQ ID NO: 16; (c) a CDR-H3 comprising the amino acid sequence of SEQ ID NO: 17; (d) a CDR-L1 comprising the amino acid sequence of SEQ ID NO: 12; (e) a CDR-L2 comprising the amino acid sequence of SEQ ID NO: 13; and (f) a CDR-L3 comprising the amino acid sequence of SEQ ID NO: 14. In some aspects, the antibody comprises (a) a VH comprising an amino acid sequence having at least 95% sequence identity to the amino acid sequence of SEQ ID NO: 20; (b) a VL comprising an amino acid sequence having at least 95% identity to the amino acid sequence of SEQ ID NO: 21; or (c) a VH as in (a) and a VL as in (b). In some aspects, the VH comprises the amino acid sequence of SEQ ID NO: 20. In some aspects, the VL comprises the amino acid sequence of SEQ ID NO: 21.

In another aspect, the disclosure features an isolated antibody that binds to CD3, wherein the antibody comprises a binding domain comprising the following CDRs: (a) a CDR-H1 comprising the amino acid sequence of SEQ ID NO: 15; (b) a CDR-H2 comprising the amino acid sequence of SEQ ID NO: 16; (c) a CDR-H3 comprising the amino acid sequence of SEQ ID NO: 17; (d) a CDR-L1 comprising the amino acid sequence of SEQ ID NO: 12; (e) a CDR-L2 comprising the amino acid sequence of SEQ ID NO: 50; and (f) a CDR-L3 comprising the amino acid sequence of SEQ ID NO: 51. In some aspects, the antibody comprises (a) a VH comprising an amino sequence having at least 95% sequence identity to the amino acid sequence of SEQ ID NO: 20; (b) a VL comprising an amino acid sequence having at least 95% identity to the amino acid sequence of SEQ ID NO: 55; or (c) a VH as in (a) and a VL as in (b). In some aspects, the VH comprises the amino acid sequence of SEQ ID NO: 20. In some aspects, the VL comprises the amino acid sequence of SEQ ID NO: 55.

In some aspects, the VH comprises the following FRs: (a) an FR-H1 comprising the amino acid sequence of SEQ ID NO: 42; (b) an FR-H2 comprising the amino acid sequence of SEQ ID NO: 43; (c) an FR-H3 comprising the amino acid sequence of SEQ ID NO: 44; and (d) an FR-H4 comprising the amino acid sequence of SEQ ID NO: 45.

In some aspects, the VH comprises the following FRs: (a) an FR-H1 comprising the amino acid sequence of SEQ ID NO: 42; (b) an FR-H2 comprising the amino acid sequence of SEQ ID NO: 62; (c) an FR-H3 comprising the amino acid sequence of SEQ ID NO: 44; and (d) an FR-H4 comprising the amino acid sequence of SEQ ID NO: 45.

In some aspects, the VL comprises the following FRs: (a) an FR-L1 comprising the amino acid sequence of SEQ ID NO: 46; (b) an FR-L2 comprising the amino acid sequence of SEQ ID NO: 47; (c) an FR-L3 comprising the amino acid sequence of SEQ ID NO: 48; and (d) an FR-L4 comprising the amino acid sequence of SEQ ID NO: 49.

In some aspects, the VL comprises the following FRs: (a) an FR-L1 comprising the amino acid sequence of SEQ ID NO: 46; (b) an FR-L2 comprising the amino acid sequence of SEQ ID NO: 63; (c) an FR-L3 comprising the amino acid sequence of SEQ ID NO: 48; and (d) an FR-L4 comprising the amino acid sequence of SEQ ID NO: 49.

In some aspects, the antibody binds a human CD3ε polypeptide with a $K_D$ of between about 1 nM and 500 nM at 37° C. as measured using a BIAcore assay. In some aspects, the antibody binds the human CD3ε polypeptide with a $K_D$ of 250 nM or lower; 100 nM or lower; 15 nM or lower; 10 nM or lower; or 5 nM or lower.

In some aspects, the antibody is monoclonal, human, humanized, or chimeric.

In some aspects, the antibody is an antibody fragment that binds CD3. In some aspects, the antibody fragment is selected from the group consisting of Fab, Fab'-SH, Fv, scFv, and (Fab')$_2$ fragments.

In some aspects, the antibody is a full-length antibody.

In some aspects, the antibody is an IgG antibody.

In some aspects, the anti-CD3 antibody is a monospecific antibody.

In another aspect, the disclosure features an isolated antibody that binds to LY6G6D, wherein the antibody comprises a binding domain comprising the following complementarity determining regions (CDRs): (a) a CDR-H1 comprising the amino acid sequence of SEQ ID NO: 27; (b) a CDR-H2 comprising the amino acid sequence of SEQ ID NO: 28; (c) a CDR-H3 comprising the amino acid sequence of SEQ ID NO: 29; (d) a CDR-L1 comprising the amino acid sequence of SEQ ID NO: 24; (e) a CDR-L2 comprising the amino acid sequence of SEQ ID NO: 25; and (f) a CDR-L3 comprising the amino acid sequence of SEQ ID NO: 26.

In some aspects, the antibody comprises (a) a VH comprising an amino sequence having at least 95% sequence identity to the amino acid sequence of SEQ ID NO: 32; (b) a VL comprising an amino acid sequence having at least 95% identity to the amino acid sequence of SEQ ID NO: 33; or (c) a VH as in (a) and a VL as in (b). In some aspects, the VH comprises the amino acid sequence of SEQ ID NO: 32. In some aspects, the VL comprises the amino acid sequence of SEQ ID NO: 33.

In another aspect, the disclosure features an isolated antibody that binds to LY6G6D, wherein the antibody comprises a heavy chain comprising the amino acid sequence of SEQ ID NO: 30 and a light chain comprising the amino acid sequence of SEQ ID NO: 31.

BRIEF DESCRIPTION OF THE DRAWINGS

The application file contains at least one drawing executed in color. Copies of this patent or patent application with color drawings will be provided by the Office upon request and payment of the necessary fee.

FIG. 2A is a photomicrograph of normal colon tissue showing immunohistochemistry (IHC) staining for LY6G6D.

FIG. 2B is a photomicrograph of a primary colon tumor showing weak (1+) IHC staining for LY6G6D.

FIG. 2C is a photomicrograph of a primary colon tumor showing moderate (2+) IHC staining for LY6G6D.

FIG. 2D is a photomicrograph of a primary colon tumor showing strong (3+) IHC staining for LY6G6D.

FIG. 3C is a graph showing in vitro killing of HT55 cells supplemented with human PBMCs by a LY6G6D TDB comprising a chimeric or humanized anti-LY6G6D 1G4 arm and an anti-CD3 38E4v1 arm and accompanying table showing affinity of the chimeric or humanized 1G4 arm in a BIAcore assay.

FIG. 3D is a set of graphs showing tumor volume (mm$^2$) of xenograft HT55 tumors in NSG™ mice following treatment with a LY6G6D TDB comprising a chimeric or humanized anti-LY6G6D 1G4 arm and an anti-CD3 38E4v1arm. Mice were humanized with healthy donor PBMCs. Treatments comprising the delivery vehicle and PMBCs or comprising the LY6G6D TDB and not comprising PMBCs are provided as controls.

Glycosylation at the site marked by the pink circle disrupted the binding of 16D7. Glycosylation at the sites marked by blue circles did not disrupt the binding of 1G4 or 16D7. The green circle marks an engineered glycosylation site in the linker to the Fc.

FIG. 4B is a chart showing binding of candidate anti-LY6G6D antibodies to LY6G6D polypeptides comprising engineered glycosylation sites at the indicated residues. Cells marked with an X indicate that no binding was detected. Cells marked with a W indicate that binding was significantly reduced.

FIG. 4C is a pair of diagrams showing the location of engineered glycosylation sites in a structural homology model of the LY6G6D polypeptide at a first orientation and a second orientation that has been rotated 180°. Glycosylation sites that disrupted binding of the antibodies of Bins 1, 2, 3, and 4 of FIG. 4A are indicated by green, purple, blue, and orange circles, respectively.

FIG. 4D is an annotated LY6G6D polypeptide sequence in which the amino acid residues affected by glycosylation mutations are color-coded as in FIG. 4C and the Bins 1, 2, 3, and 4 of FIG. 4A are indicated by underlining.

FIG. 4E is a diagram showing rabbit anti-LY6G6D antibody clones placed into four distinct epitope bins. Bin 1 includes three groups of sequences and includes 20A12, rf.1G4, 6E10, and 4H7. Bin 2 includes six groups of sequences and includes f.16D7. Bins 3 and 4 each include three groups of sequences.

FIG. 4F is a graph showing binding of rabbit anti-human LY6G6D TDBs comprising the indicated anti-LY6G6D arm from Bin 1, 2, 3, or 4 of FIG. 4E and the anti-CD3 40G5c arm to HT55 cells (human colon carcinoma cell line). Binding is measured as mean fluorescence intensity (MFI).

FIG. 4G is a graph showing in vitro killing of HT55 cells supplemented with human PBMCs by a LY6G6D TDB comprising an anti-LY6G6D arm from Bin 1, 2, 3, or 4 of FIG. 4E and the anti-CD3 40G5c arm.

FIG. 4H is a set of graphs showing binding of 1G4 and the rabbit anti-LY6G6D antibodies 6E10, 20A12, and 4H7 to a Ly6G6D polypeptide as measured using a BIAcore assay. Rabbit antibodies were expressed as chimeric antigen-binding fragments (Fabs) with rabbit variable domains and human constant domains. Ly6G6D-Fc was directly immobilized on the chip, and the Fab was flowed through at 37° C. KD is indicated below each graph.

FIG. 5A is a diagram showing the amino acid sequence of the heavy chain variable region of 20A12.QNTv12 (two-cell) (SEQ ID NO: 22) according to the Kabat numbering system. The complementarity-determining regions (CDRs) CDR H1, CDR H2, and CDR H3 are indicated. CDR sequences according to the Kabat numbering system are underlined.

FIG. 5B is a diagram showing the amino acid sequence of the light chain variable region of 20A12.QNTv12 (two-cell) (SEQ ID NO: 23) according to the Kabat numbering system. The CDRs CDR H1, CDR H2, and CDR H3 are indicated. CDR sequences according to the Kabat definition are underlined.

FIG. 5C is a diagram showing the amino acid sequence of the heavy chain variable region of 20A12.QNTv12 (one-cell) comprising a Q39E amino acid substitution mutation (boxed) in framework region (FR) 2 (SEQ ID NO: 10). This heavy chain variable region sequence is particularly useful for single-cell manufacturing of TDBs. The complementarity-determining regions (CDRs) CDR H1, CDR H2, and CDR H3 are indicated according to the contact, Chothia, and Kabat definitions. CDR sequences according to the Kabat definition are underlined.

FIG. 5D is a diagram showing the amino acid sequence of the light chain variable region of 20A12.QNTv12 (one-cell) comprising a Q38K mutation (boxed) in FR2 (SEQ ID NO: 11). This light chain variable region sequence is particularly useful for single-cell manufacturing of TDBs. The complementarity-determining regions (CDRs) CDR H1, CDR H2, and CDR H3 are indicated according to the contact, Chothia, and Kabat definitions. CDR sequences according to the Kabat definition are underlined.

FIG. 6A is a protein structure model showing the fragment antigen-binding region (Fab) of the 20A12.QNTv12 antibody bound to a polypeptide comprising amino acid residues 94-103 of LY6G6D (RDCYLGDLCN; SEQ ID NO: 78).

FIG. 6B is a region of a protein structure model showing ten overlaid complexes comprising the Fab of the 20A12.QNTv12 antibody bound to amino acid residues 94-103 of LY6G6D. 20A12.QNTv12 is shown as a ribbon diagram. The polypeptide comprising LY6G6D residues 94-103 is shown as a stick diagram, and amino acid residues are labeled.

FIG. 6C is a region of a protein structure model showing the heavy chain (HC; pink) and light chain (LC; green) of the 20A12.QNTv12 antibody bound to amino acid residues 94-103 of LY6G6D. The polypeptide comprising LY6G6D residues 94-103 is shown as a stick diagram, and amino acid residues are labeled.

FIG. 6D is a region of a protein structure model showing the HC (pink) and LC (green) of the 20A12.QNTv12 antibody bound to amino acid residues 94-103 of LY6G6D. The polypeptide comprising LY6G6D residues 94-103 is shown as a stick diagram with an 2Fo-Fc electron density map contoured at 1.0σ (blue).

FIG. 6E is a region of a protein structure model showing the 20A12.QNTv12 antibody bound to amino acid residues 94-103 of LY6G6D. CDR H1, CDR H2, and CDR H3 (H1, H2, and H3, respectively) of the heavy chain variable region of 20A12.QNTv12 and CDR L1, CDR L2, and CDR L3 (L1, L2, and L3, respectively) of the light chain variable region of 20A12.QNTv12 are labeled and indicated by color in a ribbon model. The polypeptide comprising LY6G6D residues 94-103 is shown as a stick diagram.

FIG. 6F is a region of a protein structure model showing the 20A12.QNTv12 antibody bound to amino acid residues 94-103 of LY6G6D. 20A12.QNTv12 is shown as a space-filling model. CDR H1, CDR H2, and CDR H3 (H1, H2, and H3, respectively) of the heavy chain variable region of 20A12.QNTv12 and CDR L1, CDR L2, and CDR L3 (L1, L2, and L3, respectively) of the light chain variable region of 20A12.QNTv12 are labeled. Selected residues of 20A12.QNTv12 are labeled, and interactions between 20A12.QNTv12 and the LY6G6D polypeptide are indicated by red dashed lines. The polypeptide comprising LY6G6D residues 94-103 is shown as a stick diagram.

FIG. 7A is a region of a protein structure model showing the 1G4 antibody bound to amino acid residues 94-103 of LY6G6D. CDR H1, CDR H2, and CDR H3 of the heavy chain variable region of 1G4 and CDR L1, CDR L2, and CDR L3 of the light chain variable region of 1G4 are labeled and indicated by color in a ribbon model. The polypeptide comprising LY6G6D residues 94-103 is shown as a stick diagram.

FIG. 7B is a region of a protein structure model showing the 20A12.QNTv12 antibody bound to amino acid residues 94-103 of LY6G6D. CDR H1, CDR H2, and CDR H3 of the heavy chain variable region of 20A12.QNTv12 and CDR L1, CDR L2, and CDR L3 of the light chain variable region of 20A12.QNTv12 are labeled and indicated by color in a ribbon model. The polypeptide comprising LY6G6D residues 94-103 is shown as a stick diagram.

Figure 7A:
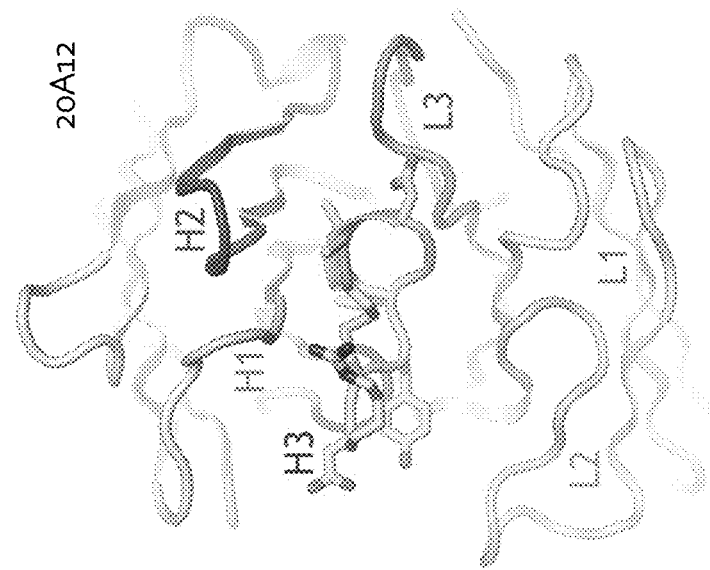
Figure 7B:
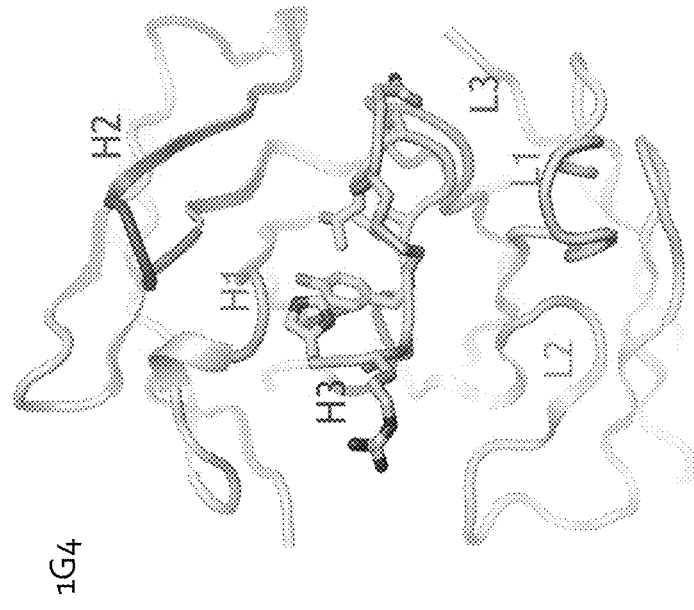
Figure 7D:
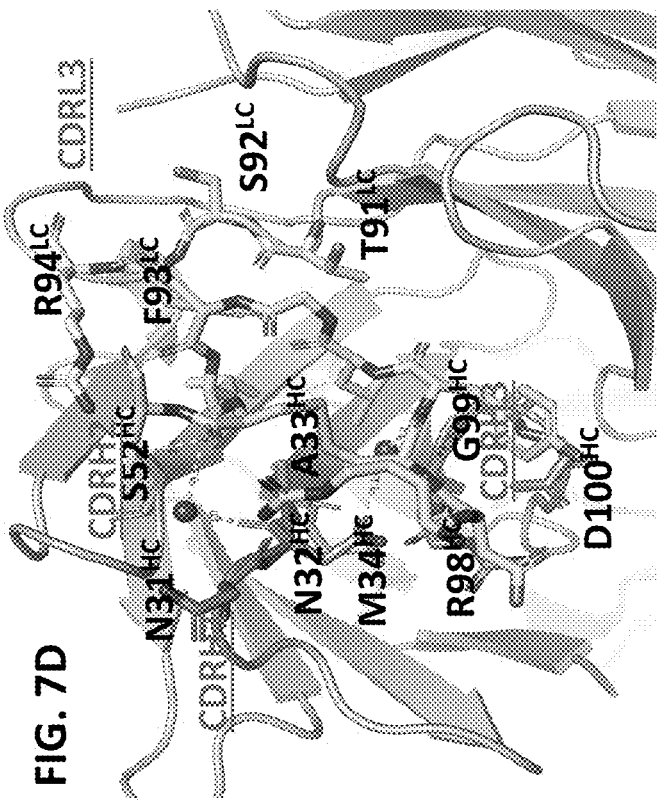
Figure 7C:
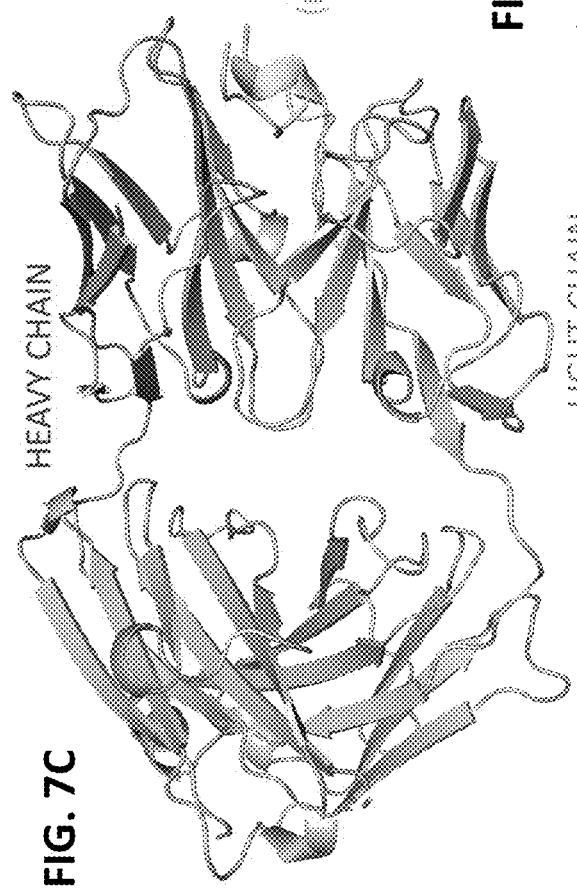

FIG. 7C is a protein structure model showing the heavy chain (SEQ ID NO: 96) and light chain (SEQ ID NO: 97) of the fragment antigen-binding region (Fab) of the 20A12.QNTv12 antibody bound to a polypeptide comprising amino acid residues 93-104 of LY6G6D (HRDCYLGDLCNS; SEQ ID NO: 87) and a sequence diagram of LY6G6D residues 93-104 showing the specific residues with which 20A12.QNTv12 interacts (orange and underlined). Each of these residues is positioned within 5 Å of the Fab.

FIG. 7D is a region of a protein structure model showing the heavy chain (SEQ ID NO: 96) and light chain (SEQ ID NO: 97) of the fragment antigen-binding region (Fab) of the 20A12.QNTv12 antibody bound to a polypeptide comprising amino acid residues 93-104 of LY6G6D (HRDCYLGDLCNS; SEQ ID NO: 87). Residues in 20A12.QNTv12 that interact with the LY6G6D polypeptide are labeled. $^{HC}$ indicates that the residue is in the 20A12.QNTv12 heavy chain; $^{LC}$ indicates that the residue is in the 20A12.QNTv12 light chain.

Figure 7E:
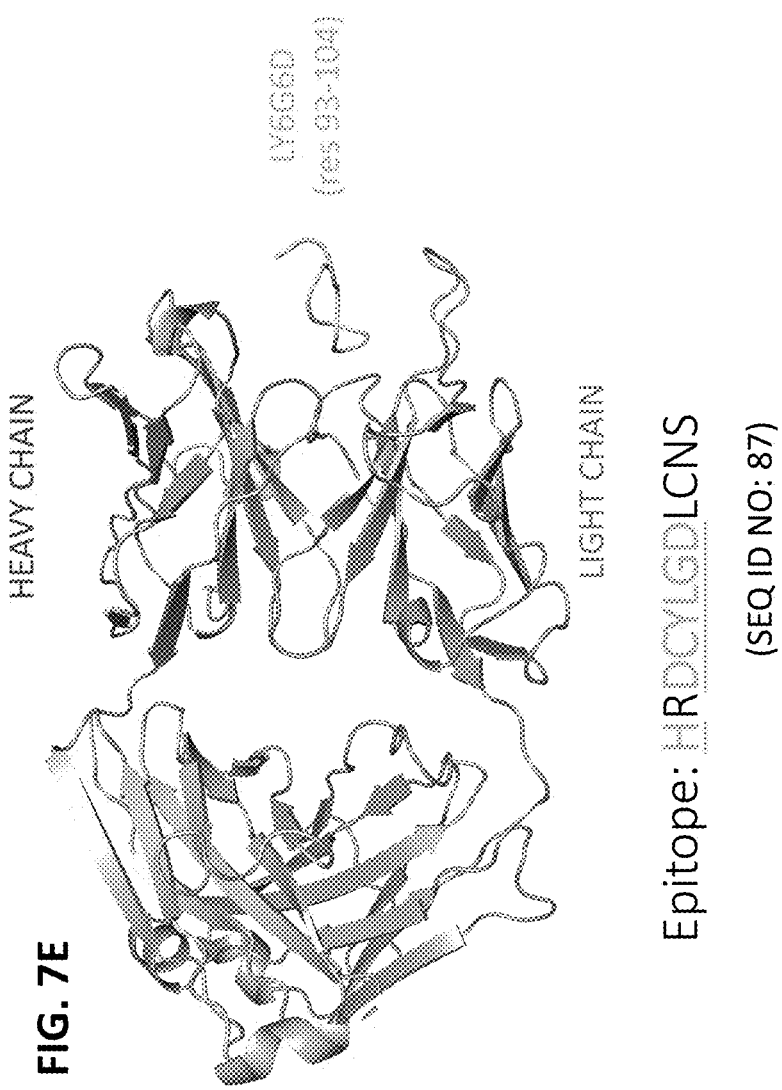

FIG. 7E is a protein structure model showing the heavy chain (SEQ ID NO: 94) and light chain (SEQ ID NO: 95) of the fragment antigen-binding region (Fab) of the 1G4 antibody bound to a polypeptide comprising amino acid residues 93-104 of LY6G6D (HRDCYLGDLCNS; SEQ ID NO: 87) and a sequence diagram of LY6G6D residues 93-104 showing the specific residues with which 1G4 interacts (orange and underlined). Each of these residues is positioned within 5 Å of the Fab.

Figure 7F:
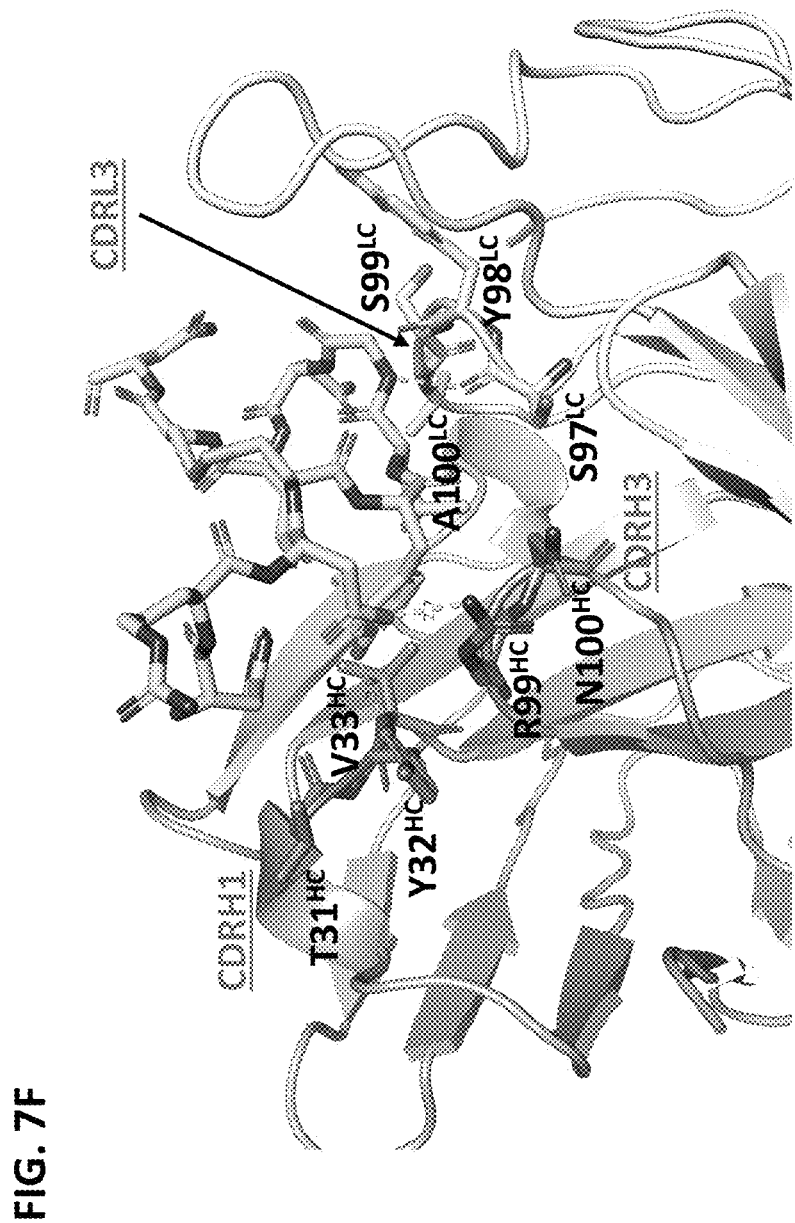

FIG. 7F is a region of a protein structure model showing the heavy chain (SEQ ID NO: 94) and light chain (SEQ ID NO: 95) of the fragment antigen-binding region (Fab) of the 1G4 antibody bound to a polypeptide comprising amino acid residues 93-104 of LY6G6D (HRDCYLGDLCNS; SEQ ID NO: 87). Residues in 1G4 that interact with the LY6G6D polypeptide are labeled. $^{HC}$ indicates that the residue is in the 1G4 heavy chain; $^{LC}$ indicates that the residue is in the 1G4 light chain.

FIG. 8A is a schematic diagram showing manufacturing of a LY6G6D TDB having an anti-CD3 38E4v1 arm comprising an Fc region having T366S, L368A, and Y407V amino acid substitution mutations forming a "hole" region and an N297G mutation, paired with an anti-LY6G6D 20A12.QNTv12 arm (two-cell) comprising an Fc region having a T366W amino acid substitution mutation that forms a "knob" region and an N297G mutation, wherein the anti-CD3 arm and the anti-LY6G6D arm form a full-length IgG1K TDB.

Figure 8B:
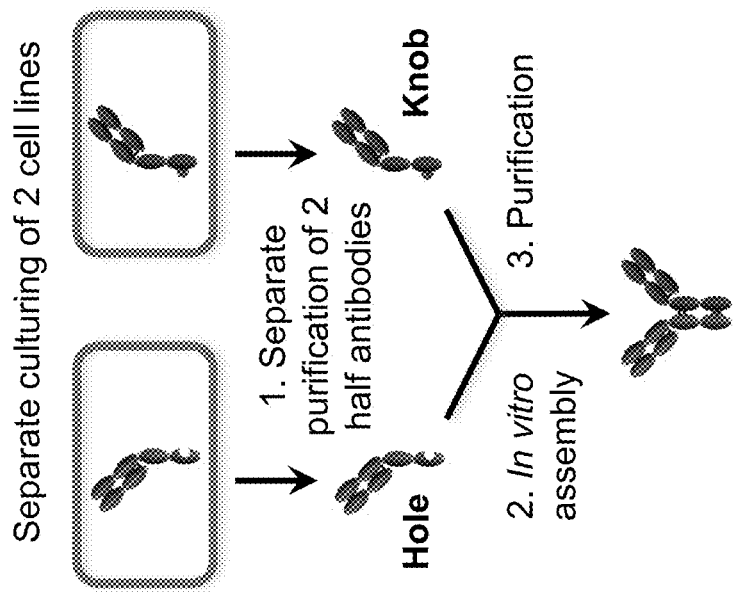

FIG. 8B is a schematic diagram showing a workflow for manufacturing a bispecific antibody using two host cell lines (two-cell technology). A first arm of the antibody comprising a hole region is produced in a first host cell line, and a second arm of the antibody comprising a knob region is produced in a second host cell line. The arms of the antibody are purified from the host cell lines and are assembled in vitro.

Figure 8D:
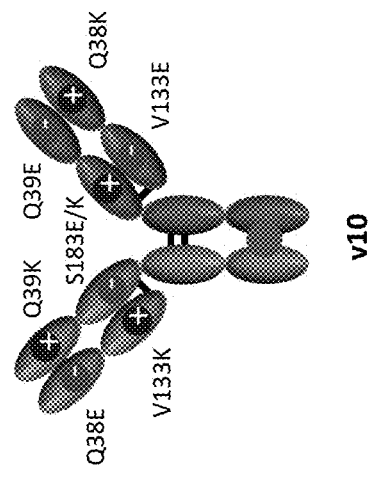
Figure 8C:
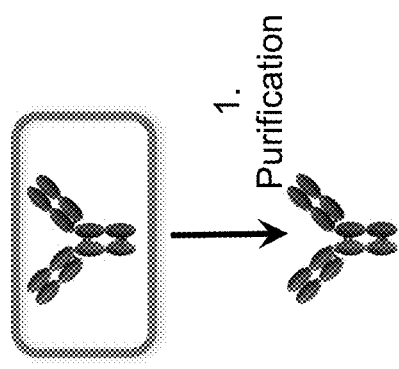

FIG. 8C is a schematic diagram showing a workflow for manufacturing a bispecific antibody using a single host cell line (one-cell technology). A first arm of the antibody comprising a hole region and a second arm of the antibody comprising a knob region are produced in and purified from a single host cell line. The first arm and second arm of the antibody comprise amino acid substitution mutations as shown in FIG. 8D or FIG. 8E.

FIG. 8D is a diagram showing a bispecific antibody produced using a single cell line. Amino acid substitution mutations introducing charge pairs are indicated. The charge pairs comprise a Q39K substitution mutation in the VH of the first arm and a Q38E substitution mutation in the VL of the first arm; a S183E substitution mutation in the CH1 of the first arm and a V133K substitution mutation in the CL of the first arm; a Q39E substitution mutation in the VH of the second arm and a Q38K substitution mutation in the VL of the second arm; and a S183K substitution mutation in the CH1 of the second arm and a V133E substitution mutation in the CL of the second arm.

Figure 8E:
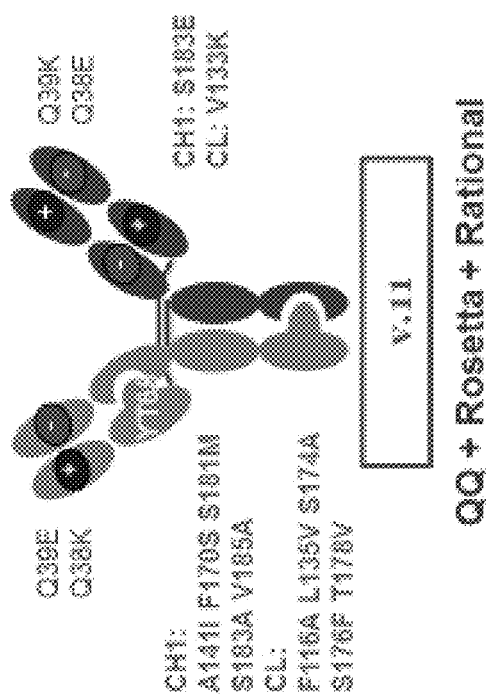

FIG. 8E is a diagram showing a bispecific antibody produced using a single cell line. Amino acid substitution mutations are indicated. Amino acid substitution mutations introducing charge pairs are indicated. The charge pairs comprise a Q39E substitution mutation in the VH of the first arm and a Q38E substitution mutation in the VL of the first arm; a Q39K substitution mutation in the VH of the second arm and a Q38E substitution mutation in the VL of the second arm; and a S183E substitution mutation in the CH1 of the second arm and a V133K substitution mutation in the CL of the second arm. The antibody also comprises the Rosetta YT65 mutations A141I, F170S, S181M, S183A, and V185A mutations in the CH1 of the first arm and F116A, L135V, S174A, S176F, and T178V mutations in the CL of the first arm.

Figure 9B:
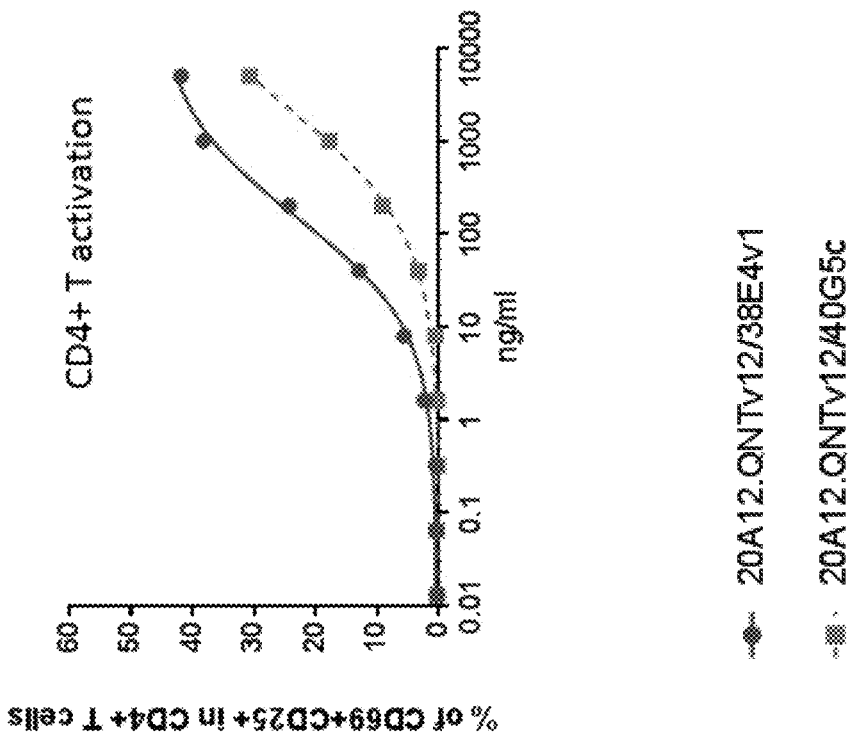
Figure 9A:
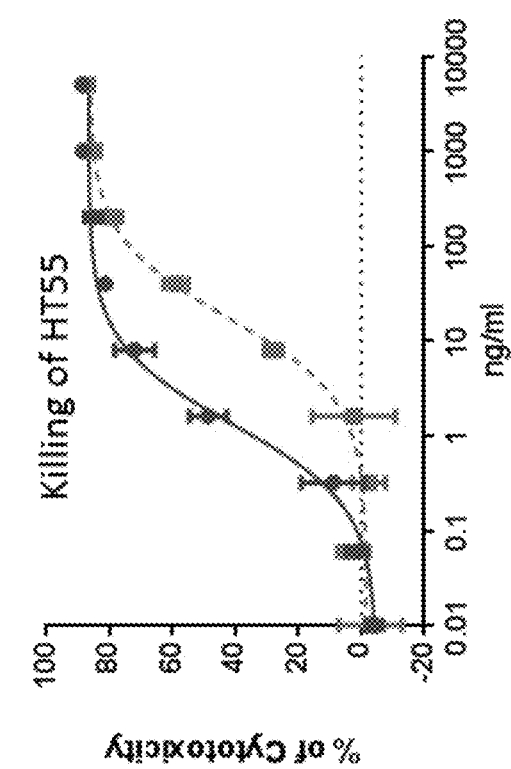

FIG. 9A is a graph showing in vitro killing of HT55 cells by a LY6G6D TDB comprising an anti-LY6G6D 20A12.QNTv12 arm (two-cell) and an anti-CD3 38E4v1 or 40G5c arm. Killing is quantified as % of cytotoxicity in a CELLTITER-GLO® assay. The TDB was provided at concentrations of between 0.01 and 10,000 ng/mL.

FIG. 9B is a graph showing in vitro activation of CD4+ T cells by a LY6G6D TDB comprising an anti-LY6G6D 20A12.QNTv12 arm (two-cell) and an anti-CD3 38E4v1 or 40G5c arm. CD4+ T cell activation was measured using fluorescence activated cell sorting (FACS).

Figure 9C:
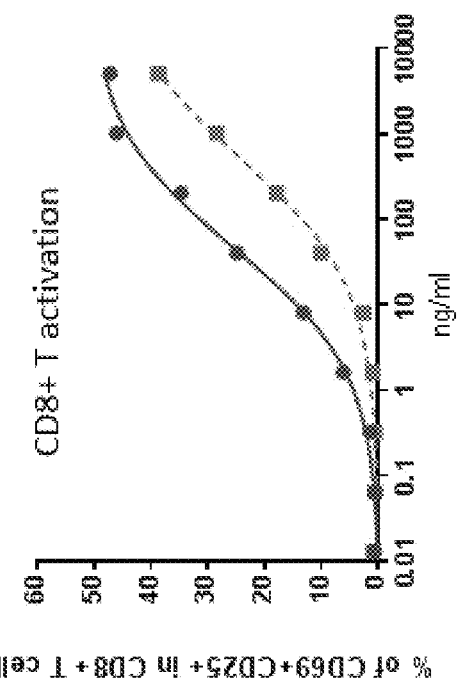

FIG. 9C is a graph showing in vitro activation of CD8+ T cells by a LY6G6D TDB comprising an anti-LY6G6D arm 20A12.QNTv12 (two-cell) and an anti-CD3 arm 38E4v1 or 40G5c. CD8+ T cell activation was measured using FACS.

Figure 10B:
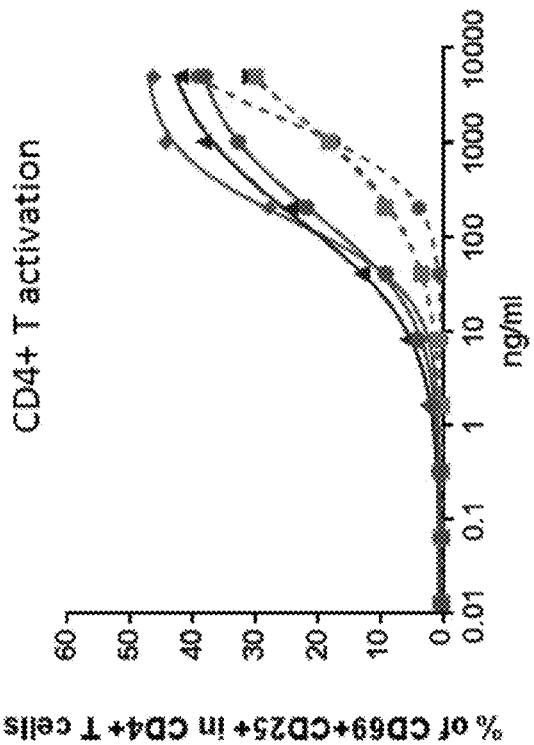
Figure 10A:
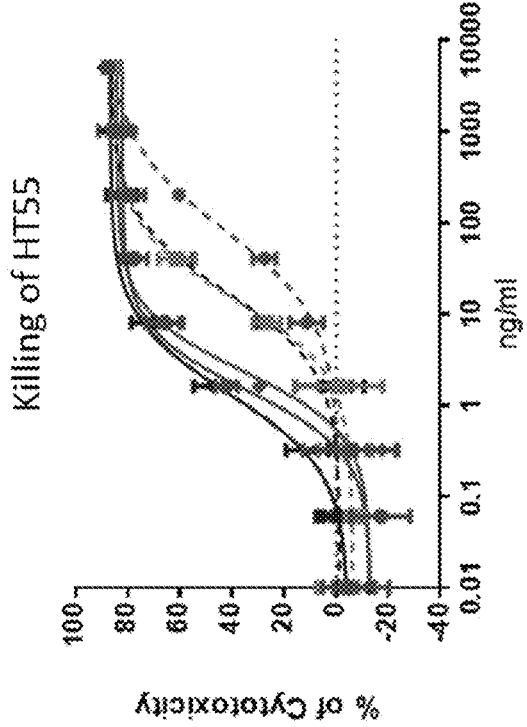

FIG. 10A is a graph showing in vitro killing of HT55 cells by a LY6G6D TDB comprising the anti-LY6G6D 20A12.v1 arm and an anti-CD3 38E4v1 or 40G5c arm, the anti-LY6G6D 20A12.QNTv12 arm (two-cell) and an anti-CD3 38E4v1 or 40G5c arm, or the anti-LY6G6D 1G4 arm and an anti-CD3 38E4v1 or 40G5c arm. Killing is quantified as % of cytotoxicity in a CELLTITER-GLO® assay. The TDB was provided at concentrations of between 0.01 and 10,000 ng/mL.

FIG. 10B is a graph showing in vitro activation of CD4+ T cells by a LY6G6D TDB comprising the anti-LY6G6D 20A12.v1 arm and an anti-CD3 38E4v1 or 40G5c arm, the anti-LY6G6D 20A12.QNTv12 arm (two-cell) and an anti-CD3 38E4v1 or 40G5c arm, or the anti-LY6G6D 1G4 arm and an anti-CD3 38E4v1 or 40G5c arm. CD4+ T cell activation was measured using FACS.

Figure 10C:
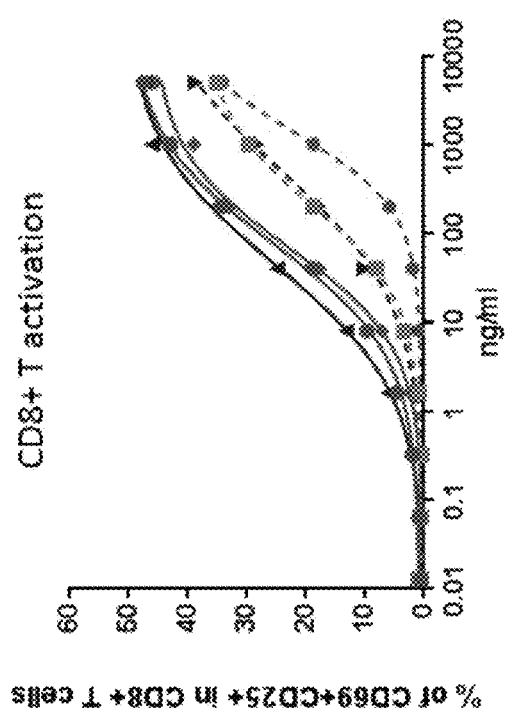

FIG. 10C is a graph showing in vitro activation of CD8+ T cells by a LY6G6D TDB comprising the anti-LY6G6D 20A12.v1 arm and an anti-CD3 38E4v1 or 40G5c arm, the anti-LY6G6D 20A12.QNTv12 arm (two-cell) and an anti-CD3 38E4v1 or 40G5c arm, or the anti-LY6G6D 1G4 arm and an anti-CD3 38E4v1 or 40G5c arm. CD8+ T cell activation was measured using FACS.

FIG. 10D is a graph showing in vitro killing of HT55 cells by a LY6G6D TDB comprising the anti-LY6G6D 20A12.QNTv12 arm (two-cell) and an anti-CD3 38E4v1 or 40G5c arm, the anti-LY6G6D 20A12.SNVv12 arm and an anti-CD3 38E4v1 or 40G5c arm, or the anti-LY6G6D 6E10.v23 arm and an anti-CD3 38E4v1 or 40G5c arm. Killing is quantified as % of cytotoxicity in a CELLTITER-GLO® assay.

Figure 11A:
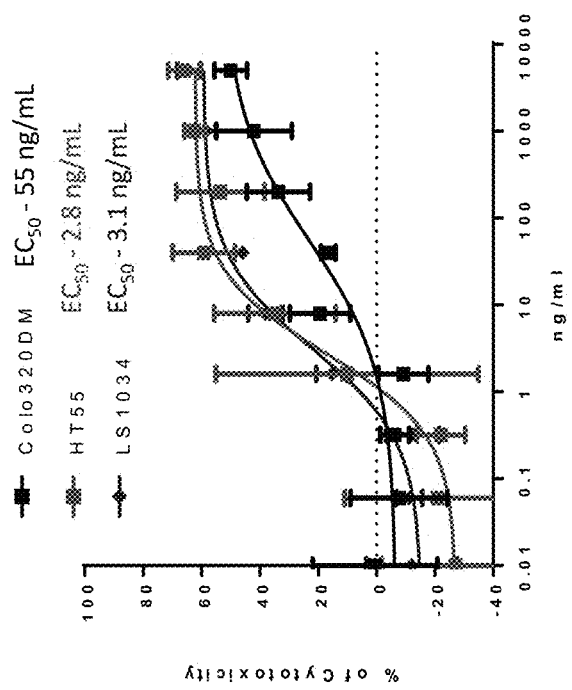

FIG. 11A is a graph showing in vitro killing of Colo320DM, HT55, and LS1034 cells by a LY6G6D TDB comprising an anti-LY6G6D 20A12.QNTv12 arm (two-cell) and an anti-CD3 38E4v1 arm. Killing is quantified as % of cytotoxicity in a CELLTITER-GLO® assay.

Figure 11B:
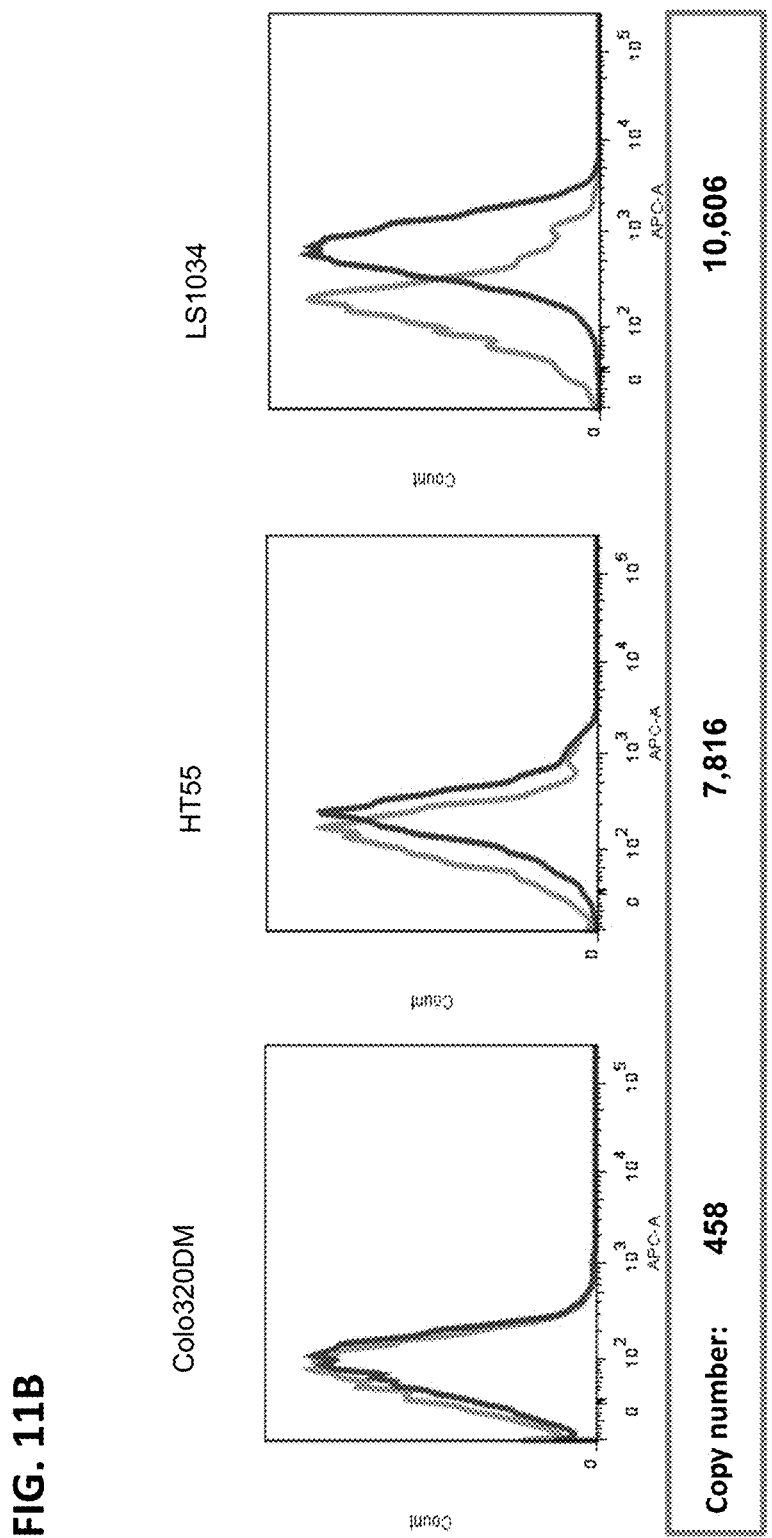

FIG. 11B is a set of graphs showing antigen binding capacity of a LY6G6D TDB comprising an anti-LY6G6D 20A12.QNTv12 arm (two-cell) and an anti-CD3 38E4v1 arm to Colo320DM, HT55, and LS1034 cells as measured by FACS.

Figure 11C:
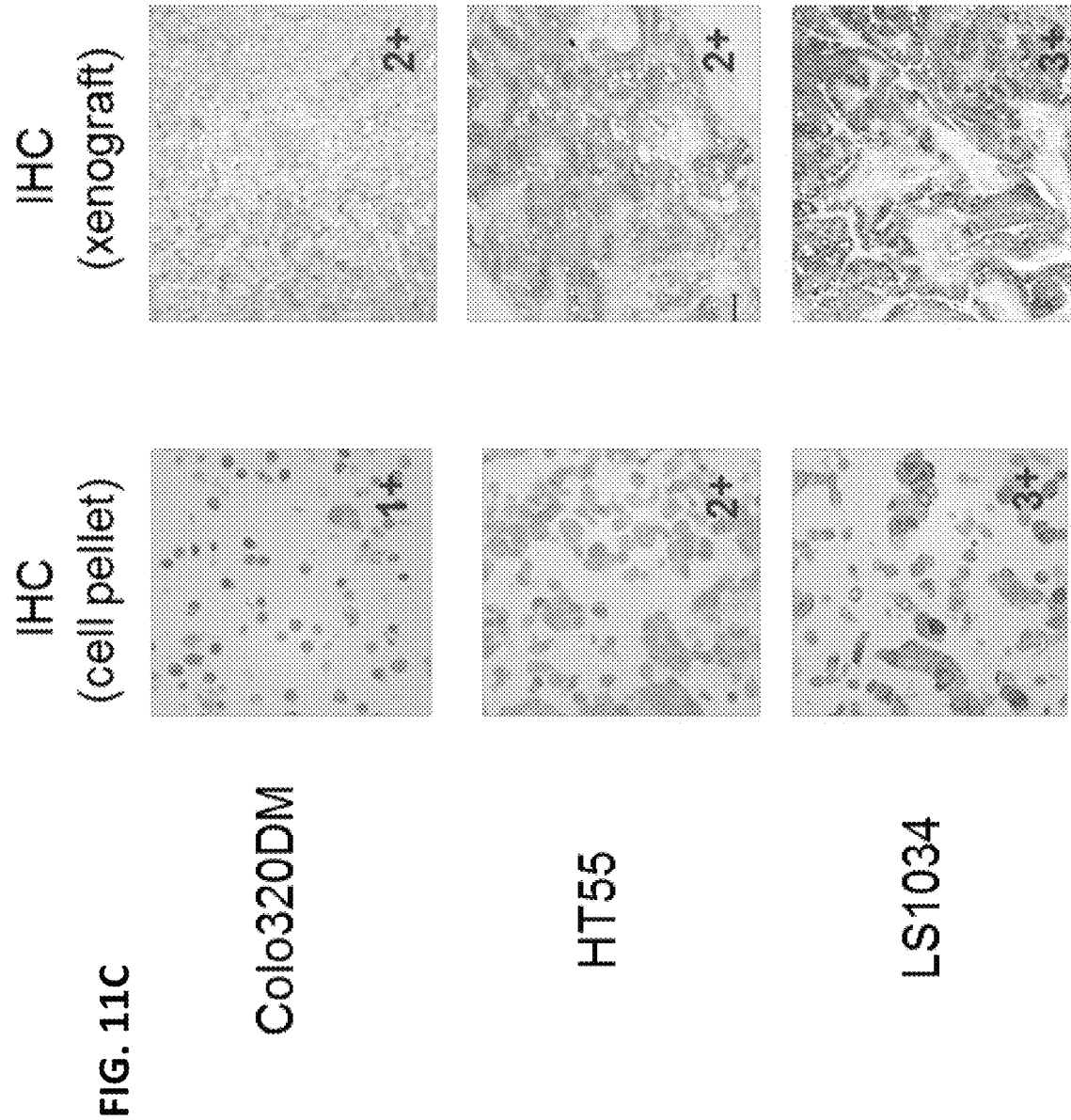

FIG. 11C is a set of photomicrographs showing IHC staining in cell pellets and in xenograft tumor samples.

Figure 11D:
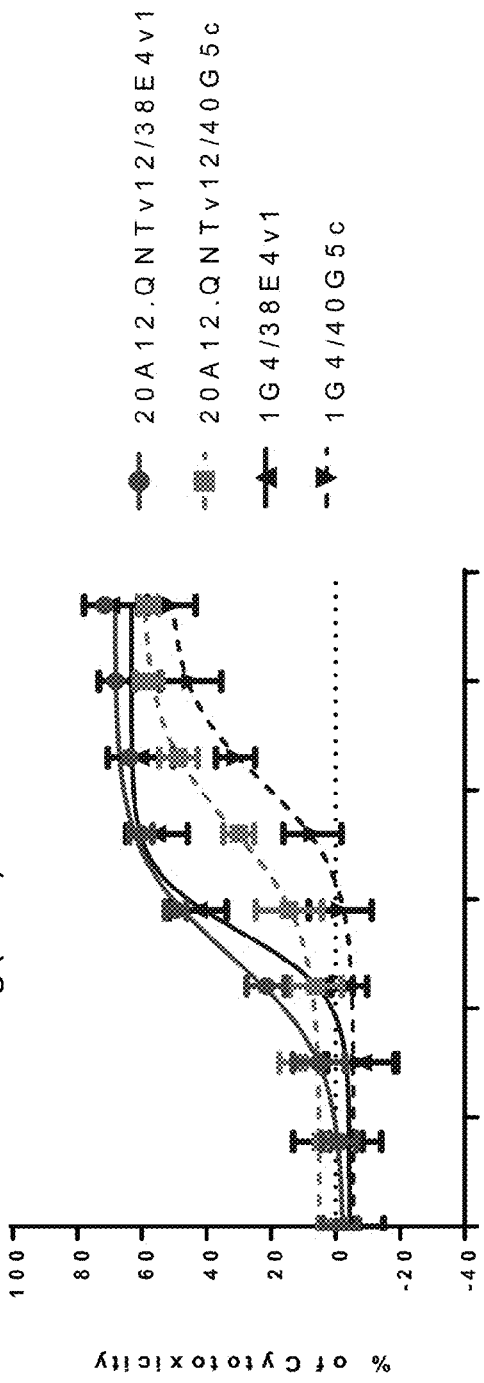

FIG. 11D is a graph showing in vitro killing of HT55 cells supplemented with human PBMCs from a healthy donor by a LY6G6D TDB comprising the anti-LY6G6D 20A12.QNTv12 arm (two-cell) and an anti-CD3 38E4v1 or 40G5c arm or the anti-LY6G6D 1G4 arm and an anti-CD3 38E4v1 or 40G5c arm after 24 hours.

Figure 11E:
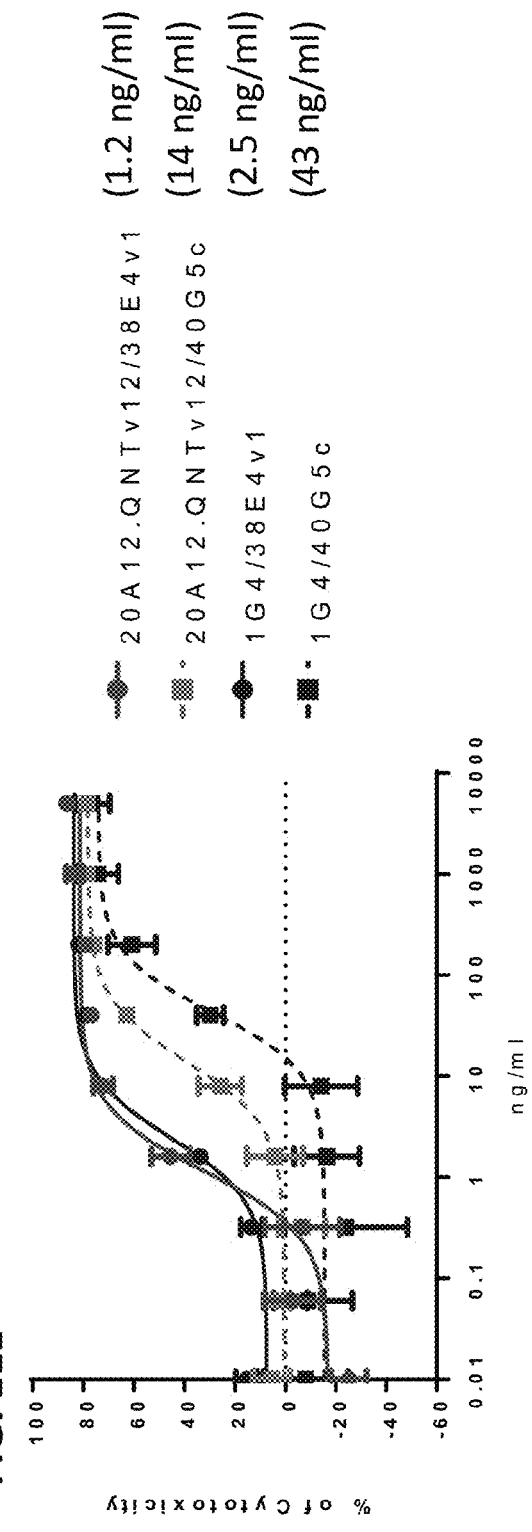

FIG. 11E is a graph showing in vitro killing of HT55 cells supplemented with human PBMCs from a healthy donor by a LY6G6D TDB comprising the anti-LY6G6D 20A12.QNTv12 arm (two-cell) and an anti-CD3 38E4v1 or 40G5c arm or the anti-LY6G6D 1G4 arm and an anti-CD3 38E4v1 or 40G5c arm after 48 hours. $K_D$ for each TDB is indicated in parentheses.

Figures 11F, 11G, 11H:
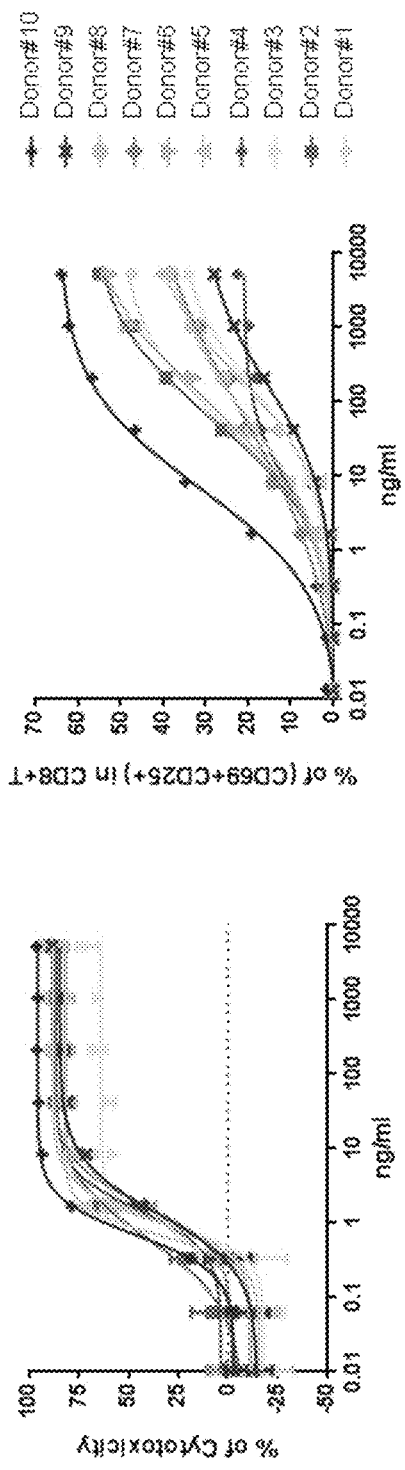

FIG. 11F is a graph showing in vitro killing of HT55 cells supplemented with human PBMCs from ten donors by a LY6G6D TDB comprising the anti-LY6G6D 20A12.QNTv12 arm (two-cell) and the anti-CD3 38E4v1 arm.

FIG. 11G is a graph showing is a graph showing in vitro activation of CD8+ T cells by a LY6G6D TDB comprising the anti-LY6G6D 20A12.QNTv12 arm (two-cell) and the anti-CD3 38E4v1 arm. CD8+ T cell activation was measured using FACS.

FIG. 11H is a table showing EC50 values for cell killing and CD8+ T cell activation for ten PBMC donors.

Figure 11I:
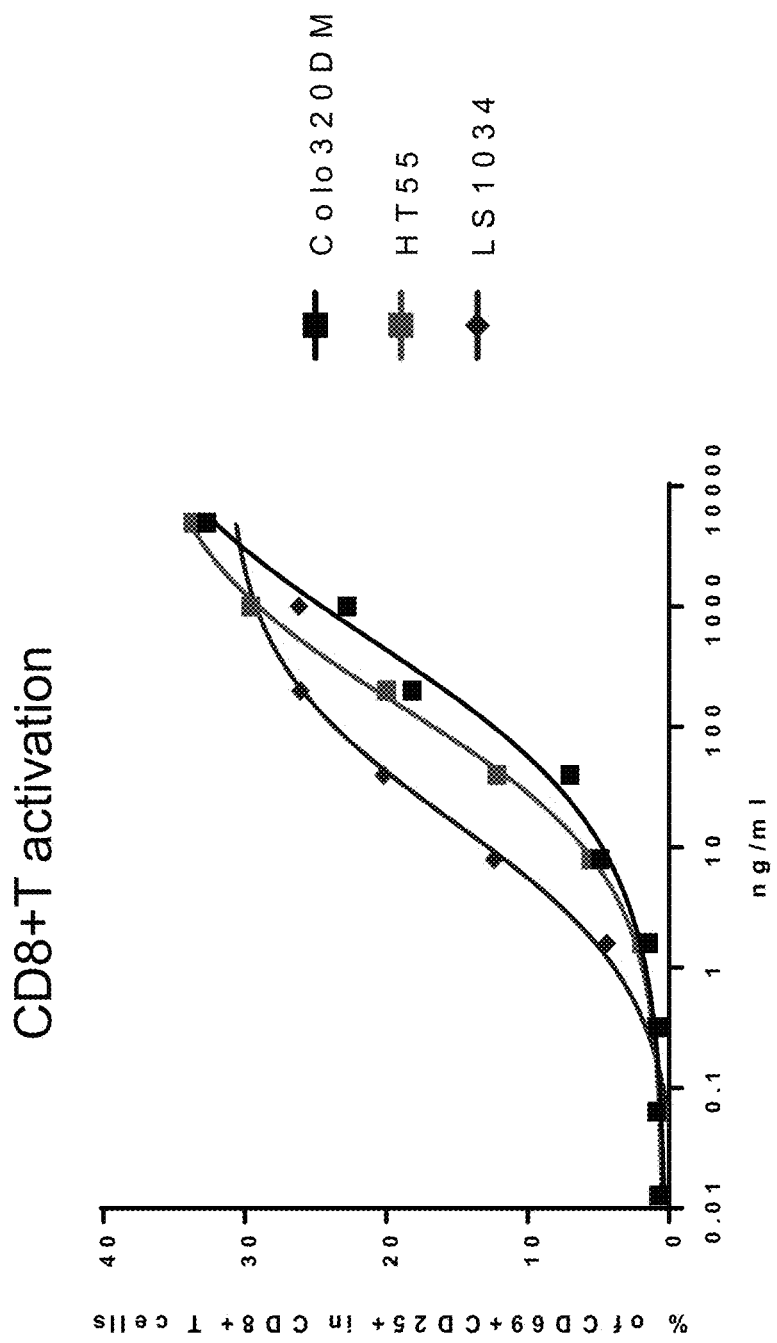

FIG. 11I is a graph showing is a graph showing in vitro activation of CD8+ T cells by a LY6G6D TDB comprising the anti-LY6G6D 20A12.QNTv12 arm (two-cell) and the anti-CD3 38E4v1 arm in Colo320DM, HT55, and LS1034 cells. CD8+ T cell activation was measured using FACS.

Figure 12:
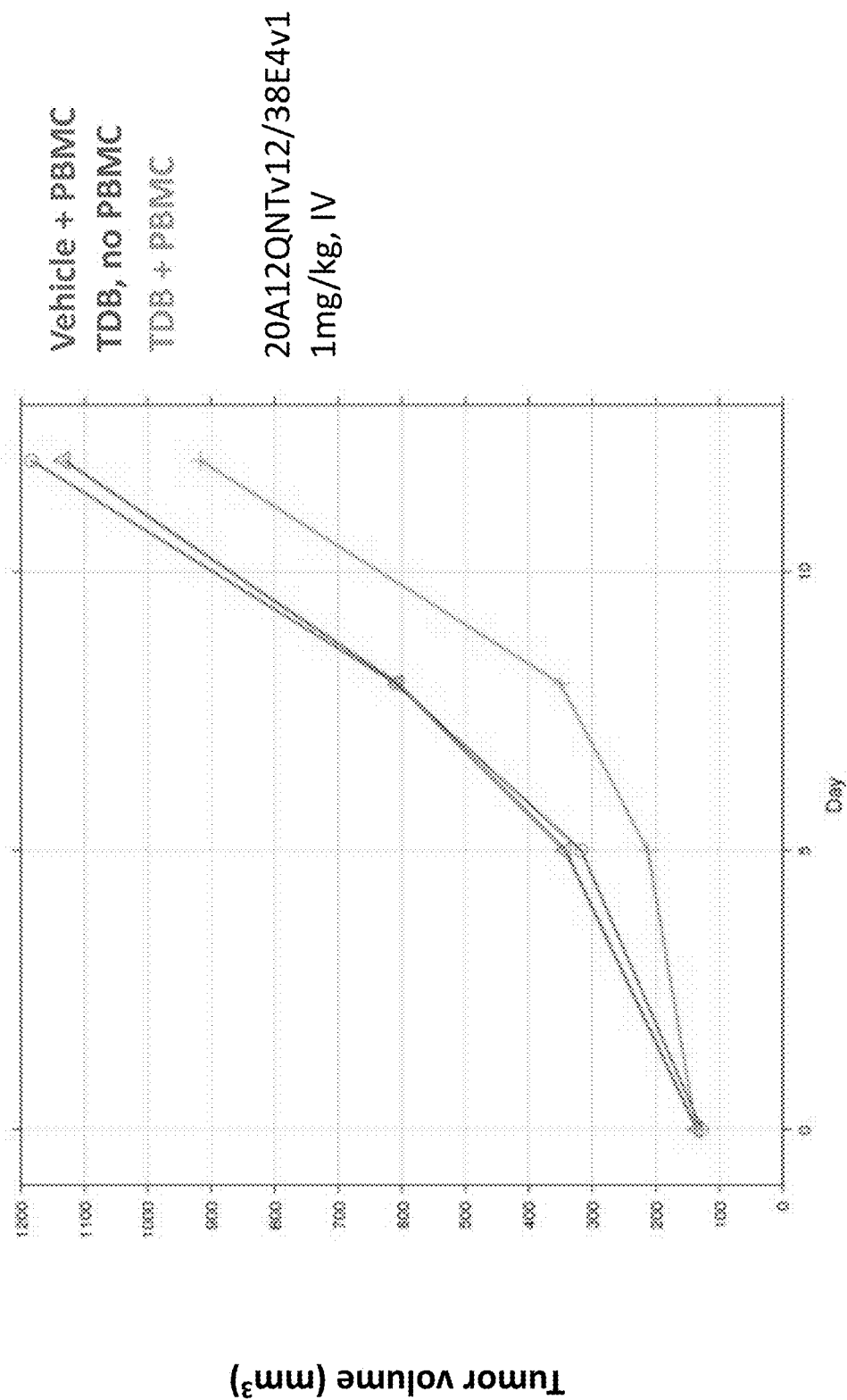

FIG. 12 is a graph showing tumor volume (mm$^2$) of xenograft COLO320DM tumors in mice following treatment with a LY6G6D TDB comprising the anti-LY6G6D 20A12.QNTv12 arm (two-cell) and an anti-CD3 38E4.v1 arm. Mice were humanized with healthy donor peripheral blood mononuclear cells (PBMCs). Treatments comprising the delivery vehicle and PMBCs or comprising the TDB and not comprising PMBCs are provided as controls.

Figure 13A:
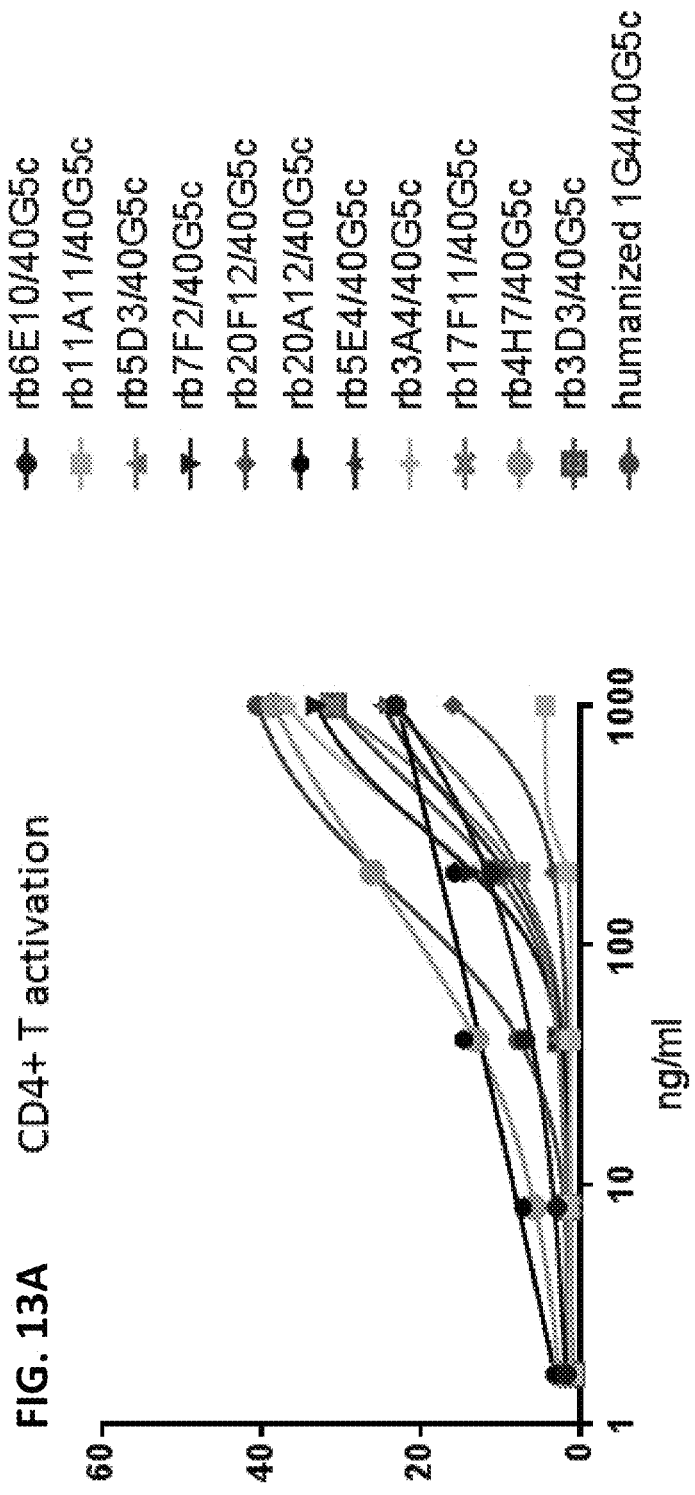

FIG. 13A is a graph showing in vitro activation of CD4+ T cells by a LY6G6D TDB comprising an anti-LY6G6D arm rb6E, rb11A11, rb5D3, rb7F2, rb20F12, rb20A12, rb5E4, rb3A4, rb17F11, rb4H7, rb3D3, or humanized 1G4 and the anti-CD3 40G5c arm. CD4+ T cell activation was measured using FACS.

Figure 13B:
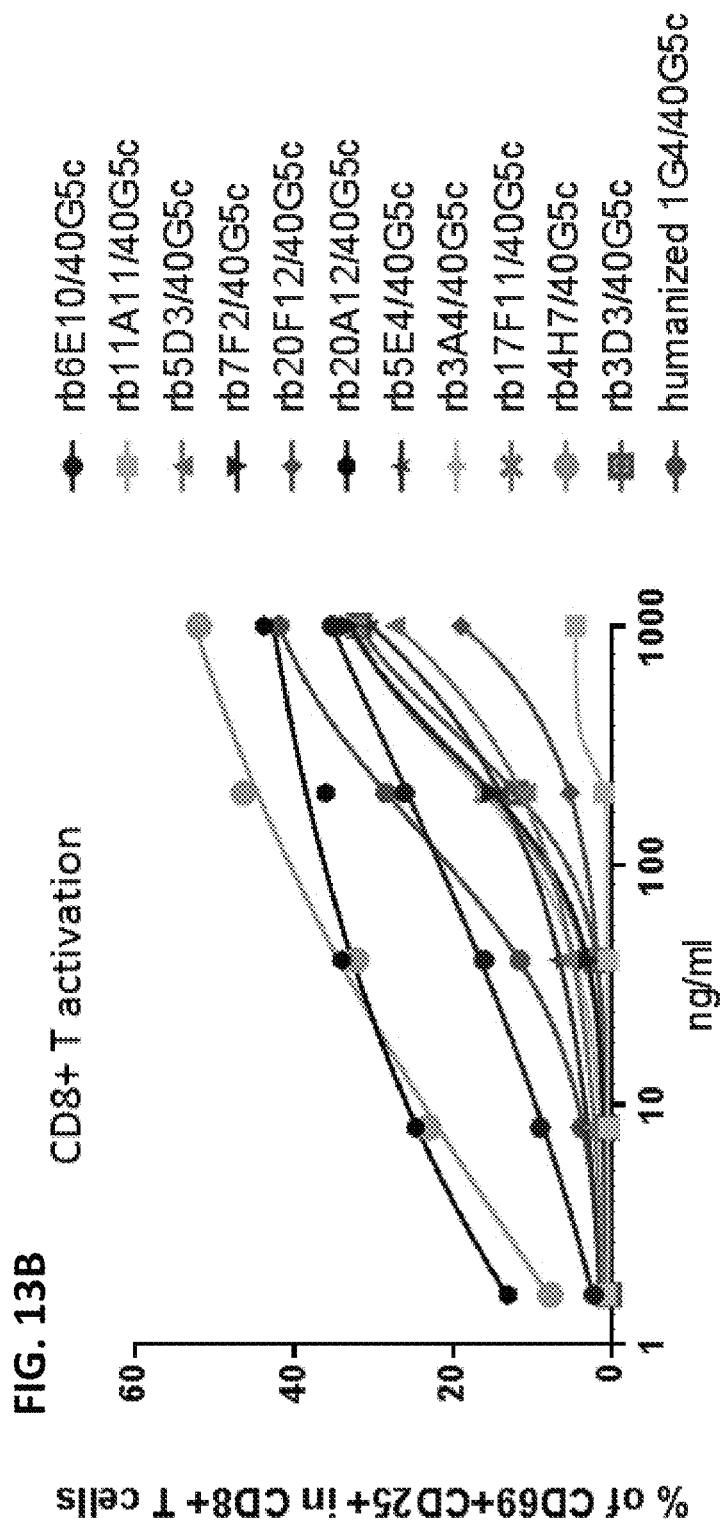

FIG. 13B is a graph showing in vitro activation of CD8+ T cells by a LY6G6D TDB comprising an anti-LY6G6D arm rb6E, rb11A11, rb5D3, rb7F2, rb20F12, rb20A12, rb5E4, rb3A4, rb17F11, rb4H7, rb3D3, or humanized 1G4 and the anti-CD3 40G5c arm. CD8+ T cell activation was measured using FACS.

FIG. 13C is a graph showing in vitro killing of HT55 cells supplemented with PMBCs from Donor #2 by a LY6G6D TDB comprising an anti-LY6G6D arm rb6E, rb11A11, rb5D3, rb7F2, rb20F12, rb20A12, rb5E4, rb3A4, rb17F11, rb4H7, rb3D3, or humanized 1G4 and the anti-CD3 40G5c arm. Killing is quantified as % of cytotoxicity in a CELL-TITER-GLO® assay.

Figure 13D:
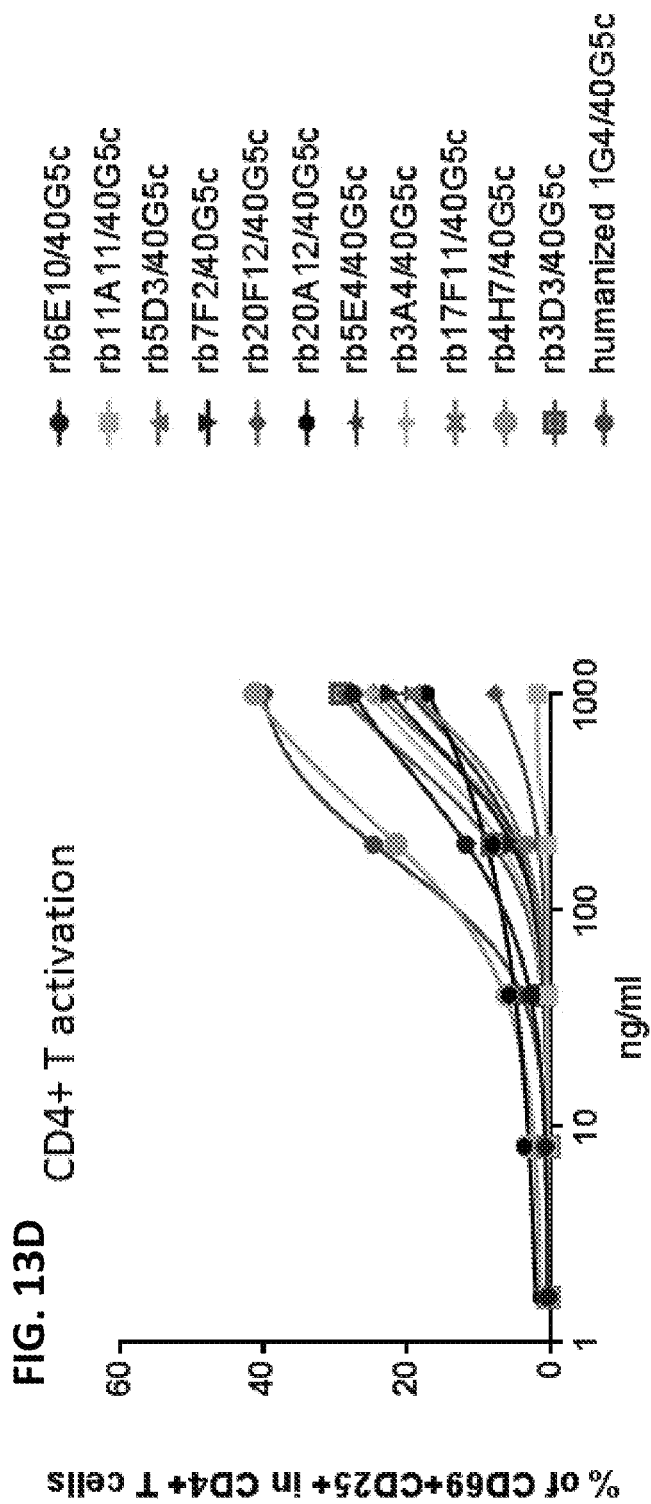

FIG. 13D is a graph showing in vitro activation of CD4+ T cells by a LY6G6D TDB comprising an anti-LY6G6D arm rb6E, rb11A11, rb5D3, rb7F2, rb20F12, rb20A12, rb5E4, rb3A4, rb17F11, rb4H7, rb3D3, or humanized 1G4 and the anti-CD3 40G5c arm. CD4+ T cell activation was measured using FACS.

Figure 13E:
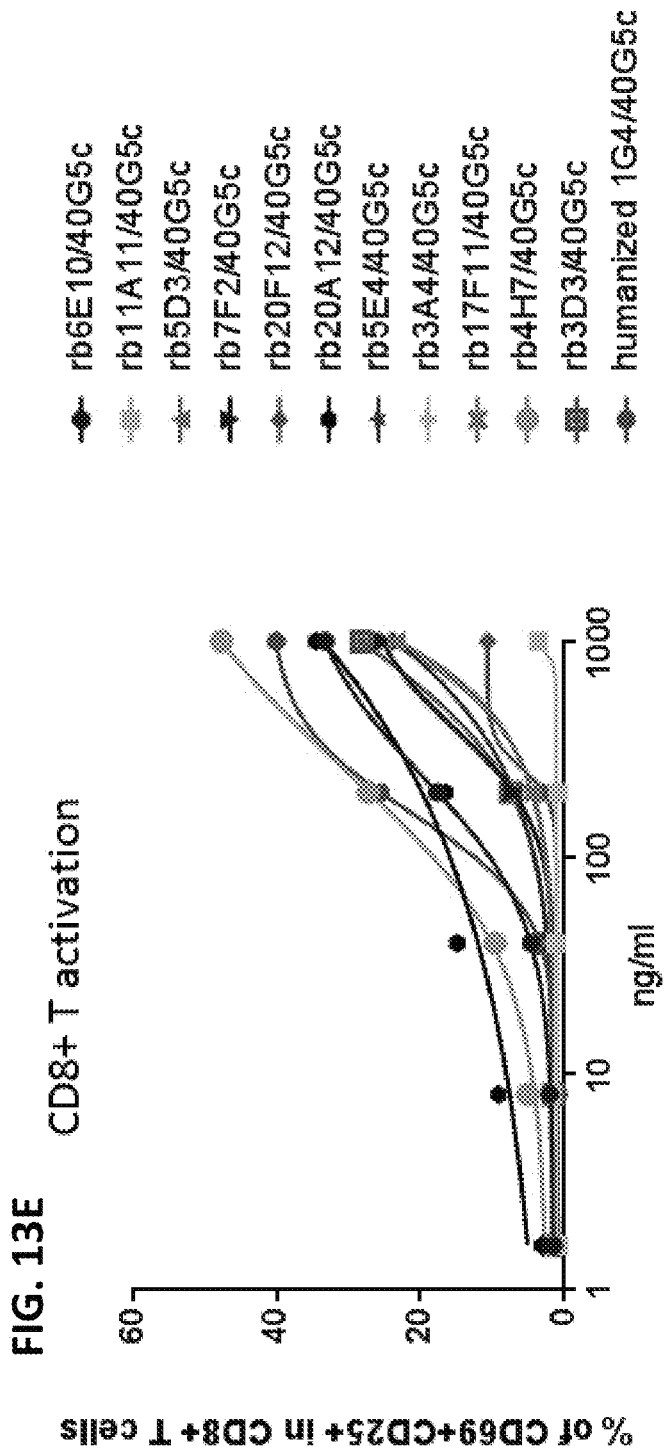

FIG. 13E is a graph showing in vitro activation of CD8+ T cells by a LY6G6D TDB comprising an anti-LY6G6D arm rb6E, rb11A11, rb5D3, rb7F2, rb20F12, rb20A12, rb5E4, rb3A4, rb17F11, rb4H7, rb3D3, or humanized 1G4 and the anti-CD3 arm 40G5c. CD8+ T cell activation was measured using FACS.

FIG. 14A is a graph showing in vitro killing of HT55 cells supplemented with PMBCs from Donor #1 by LY6G6D TDBs assembled using a two-cell system and comprising the anti-LY6G6D 20A12.QNTv12 arm (two-cell) and an anti-CD3 arm 38E4.v1 MD1, 38E4.v1 MD2, 38E4.v1 MD3, or 38E4.v1 (WT) and by TDBs assembled using a one-cell system and comprising the anti-LY6G6D 20A12.QNTv12 arm (one-cell) and an anti-CD3 arm 38E4.v1 MD1, 38E4.v1 MD2, 38E4.v1 MD3, 38E4.v1 MD4, or 38E4.v1 (WT). Specific residues in MD2, MD3, and MD4 that have been mutated relative to the WT 38E4.v1 sequence are indicated in parentheses. Killing is quantified as % of cytotoxicity in a CELLTITER-GLO® assay.

FIG. 14B is a graph showing in vitro activation of CD4+ T cells by LY6G6D TDBs assembled using a two-cell system and comprising the anti-LY6G6D 20A12.QNTv12 arm (two-cell) and an anti-CD3 arm 38E4.v1 MD1, 38E4.v1 MD2, 38E4.v1 MD3, or 38E4.v1 (WT) and by TDBs assembled using a one-cell system and comprising the anti-LY6G6D 20A12.QNTv12 arm (one-cell) and an anti-CD3 arm 38E4.v1 MD1, 38E4.v1 MD2, 38E4.v1 MD3, 38E4.v1 MD4, or 38E4.v1 (WT). CD4+ T cell activation was measured using FACS.

FIG. 14C is a graph showing in vitro activation of CD8+ T cells by LY6G6D TDBs assembled using a two-cell system and comprising the anti-LY6G6D 20A12.QNTv12 arm (two-cell) and an anti-CD3 arm 38E4.v1 MD1, 38E4.v1 MD2, 38E4.v1 MD3, or 38E4.v1 (WT) and by LY6G6D TDBs assembled using a one-cell system and comprising the anti-LY6G6D 20A12.QNTv12 arm (one-cell) and an anti-CD3 arm 38E4.v1 MD1, 38E4.v1 MD2, 38E4.v1 MD3, 38E4.v1 MD4, or 38E4.v1 (WT). CD8+ T cell activation was measured using FACS.

Figure 15A:
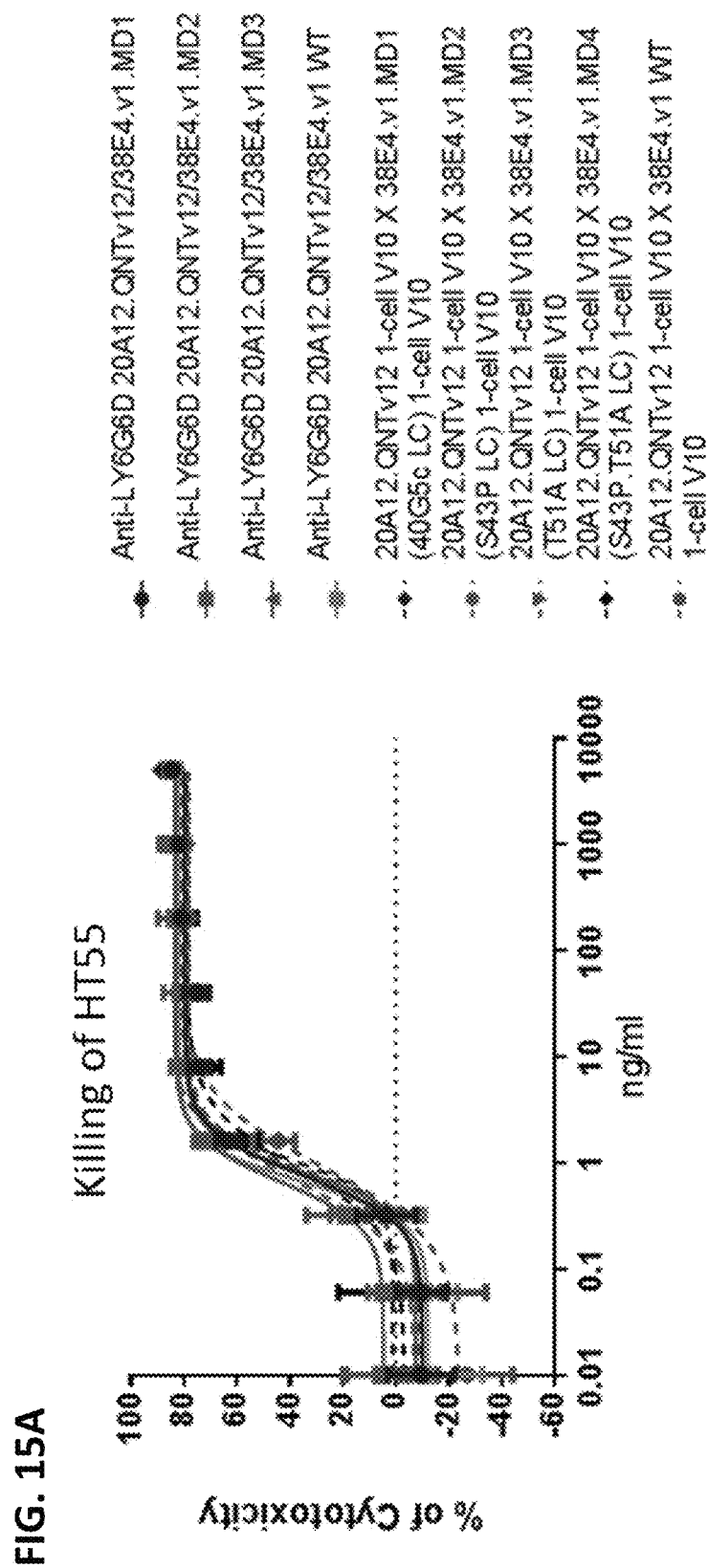

FIG. 15A is a graph showing in vitro killing of HT55 cells supplemented with PMBCs from Donor #2 by LY6G6D TDBs assembled using a two-cell system and comprising the anti-LY6G6D 20A12.QNTv12 arm (two-cell) and an anti-CD3 arm 38E4.v1 MD1, 38E4.v1 MD2, 38E4.v1 MD3, or 38E4.v1 (WT) and by TDBs assembled using a one-cell system and comprising the anti-LY6G6D 20A12.QNTv12 arm (one-cell) and an anti-CD3 arm 38E4.v1 MD1, 38E4.v1 MD2, 38E4.v1 MD3, 38E4.v1 MD4, or 38E4.v1 (WT). Killing is quantified as % of cytotoxicity in a CELLTITER-GLO® assay.

Figure 15B:
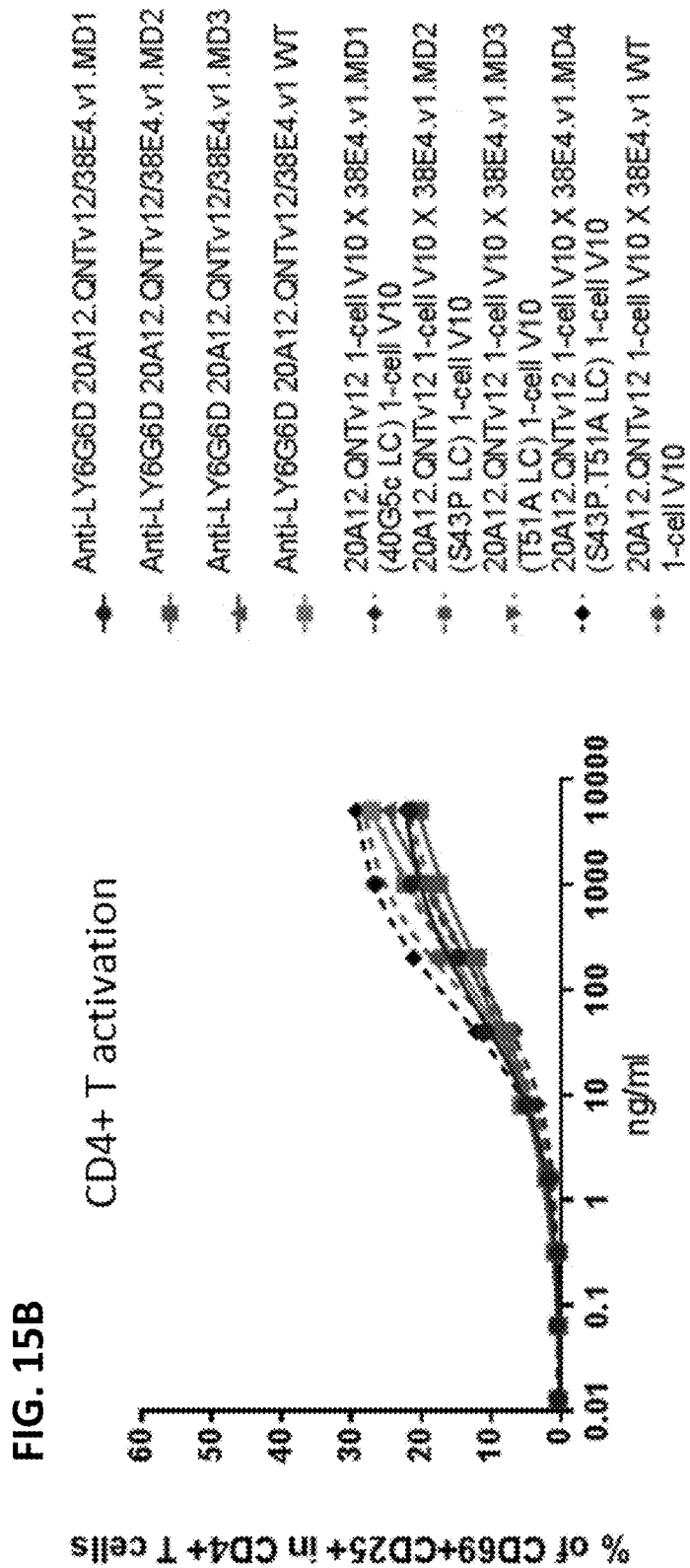

FIG. 15B is a graph showing in vitro activation of CD4+ T cells by LY6G6D TDBs assembled using a two-cell system and comprising the anti-LY6G6D 20A12.QNTv12 arm (two-cell) and an anti-CD3 arm 38E4.v1 MD1, 38E4.v1 MD2, 38E4.v1 MD3, or 38E4.v1 (WT) and by LY6G6D TDBs assembled using a one-cell system and comprising the anti-LY6G6D 20A12.QNTv12 arm (one-cell) and an anti-CD3 arm 38E4.v1 MD1, 38E4.v1 MD2, 38E4.v1 MD3, 38E4.v1 MD4, or 38E4.v1 (WT). CD4+ T cell activation was measured using FACS.

FIG. 15C is a graph showing in vitro activation of CD8+ T cells by LY6G6D TDBs assembled using a two-cell system and comprising the anti-LY6G6D 20A12.QNTv12 arm (two-cell) and an anti-CD3 arm 38E4.v1 MD1, 38E4.v1 MD2, 38E4.v1 MD3, or 38E4.v1 (WT) and by LY6G6D TDBs assembled using a one-cell system and comprising the anti-LY6G6D 20A12.QNTv12 arm (one-cell) and an anti-CD3 arm 38E4.v1 MD1, 38E4.v1 MD2, 38E4.v1 MD3, 38E4.v1 MD4, or 38E4.v1 (WT). CD8+ T cell activation was measured using FACS.

FIG. 16A is a graph showing tumor volume (mm$^2$) of xenograft LS1034 tumors in NSG™ mice following treatment with a LY6G6D TDB comprising the anti-LY6G6D 20A12.QNTv12 arm (two-cell) and an anti-CD3 40G5c or 38E4.v1 arm. Mice were humanized with healthy donor peripheral blood mononuclear cells (PBMCs). Treatments comprising the delivery vehicle and PMBCs or comprising the LY6G6D TDB and not comprising PMBCs are provided as controls. "3+" indicates the LY6G6D IHC score of the cell line.

Figure 16B:
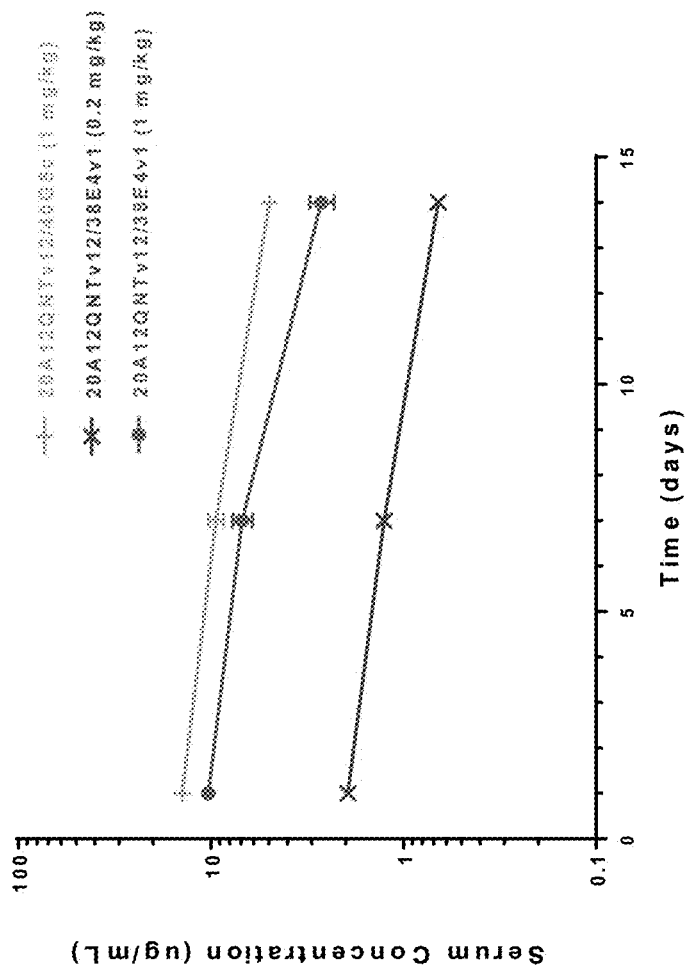

FIG. 16B is a graph showing serum concentration (in μg/mL) of LY6G6D TDBs comprising the anti-LY6G6D 20A12.QNTv12 arm (two-cell) and an anti-CD3 40G5c or 38E4.v1 arm in LS1034 NSG™ mice following administration of a single dose of the TDB.

Figure 16C:
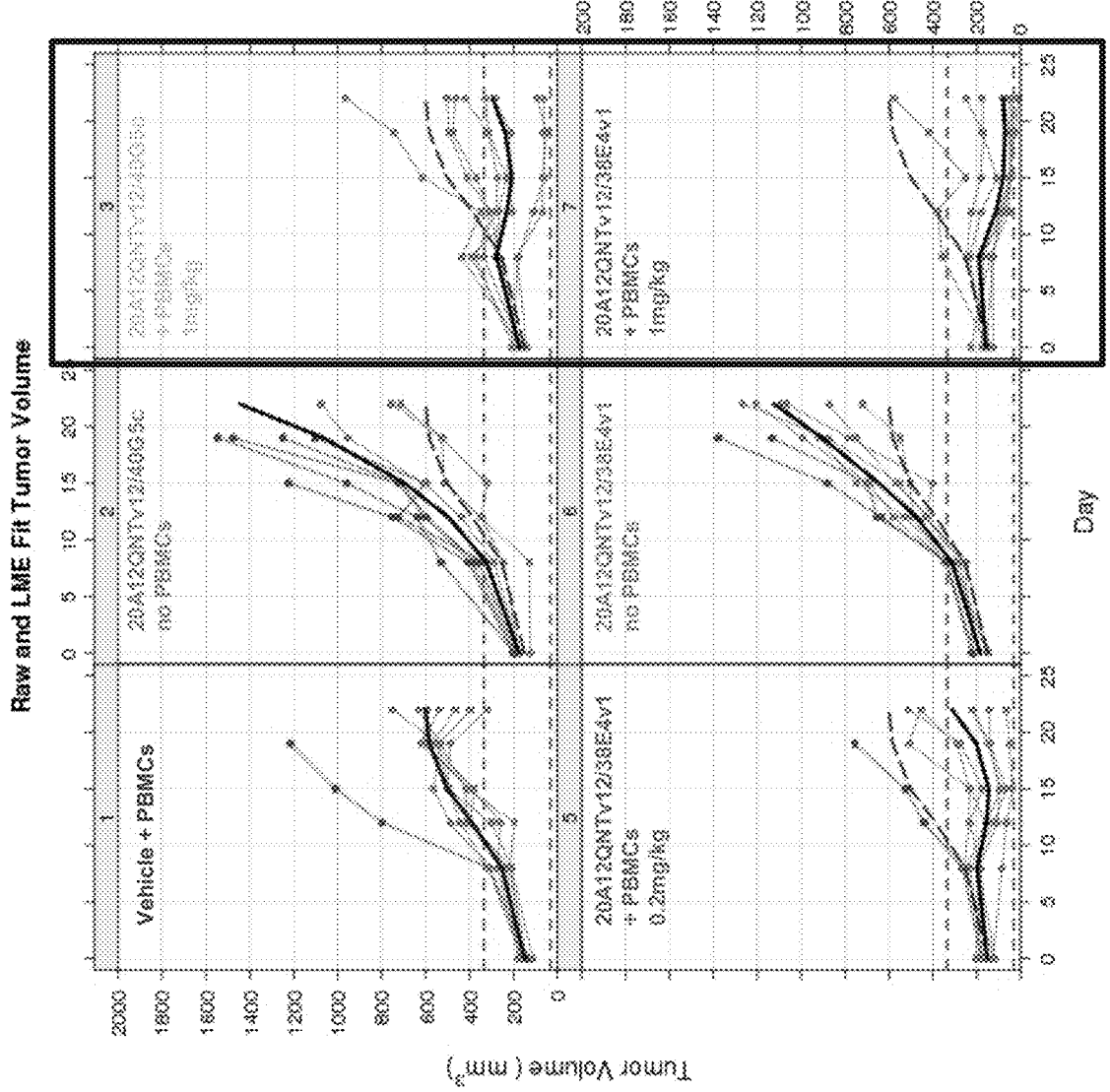

FIG. 16C is a set of graphs showing raw data for the tumor volume assay shown in FIG. 16A.

Figure 17A:
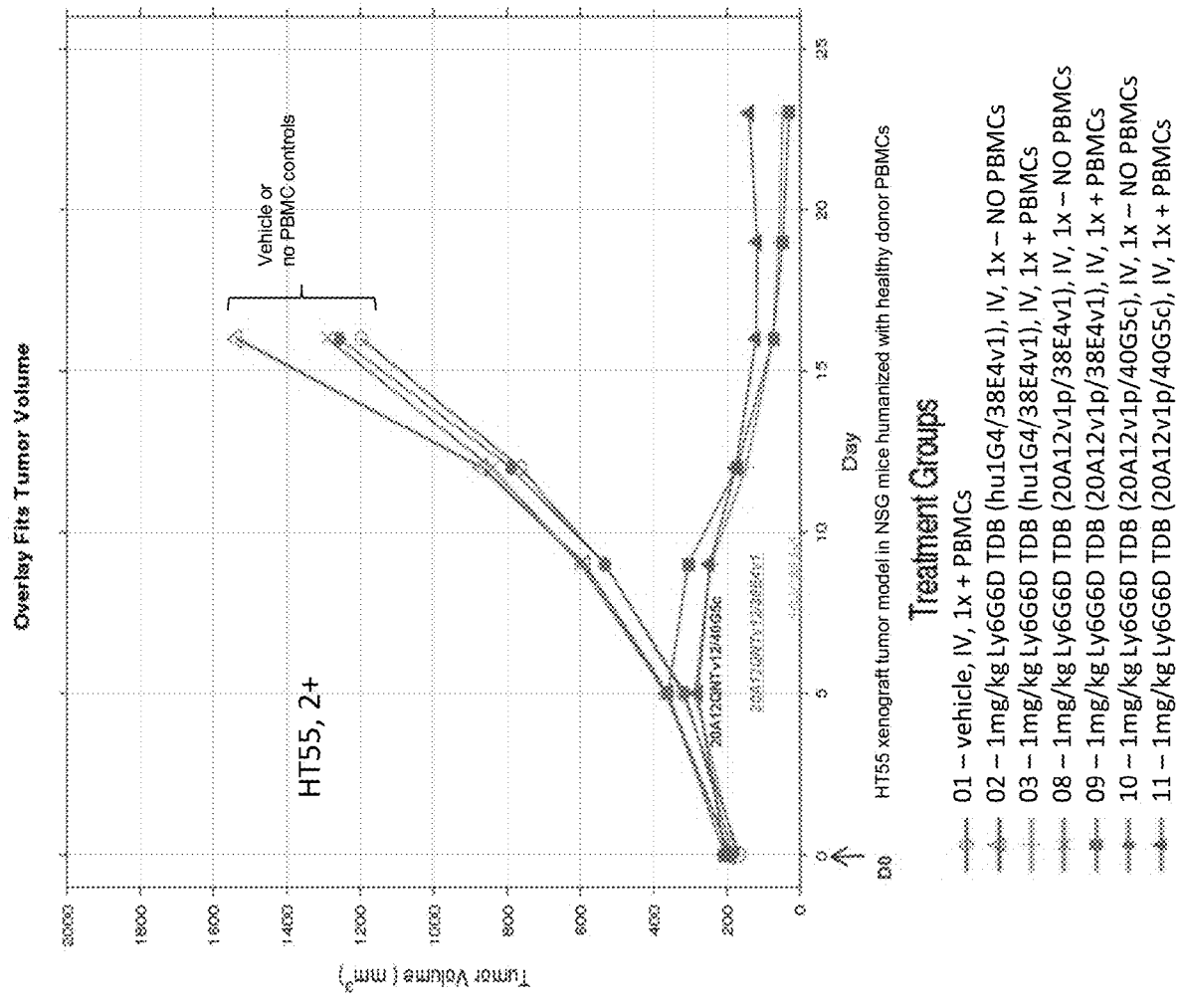

FIG. 17A is a graph showing tumor volume (mm$^2$) of xenograft HT55 tumors in NSG™ mice following treatment with a LY6G6D TDB comprising the anti-LY6G6D 20A12.QNTv12 arm (two-cell) and an anti-CD3 40G5c or 38E4.v1arm. Mice were humanized with healthy donor PBMCs. Treatments comprising the delivery vehicle and PMBCs or comprising the TDB and not comprising PMBCs are provided as controls. "2+" indicates the LY6G6D IHC score of the cell line.

Figure 17B:
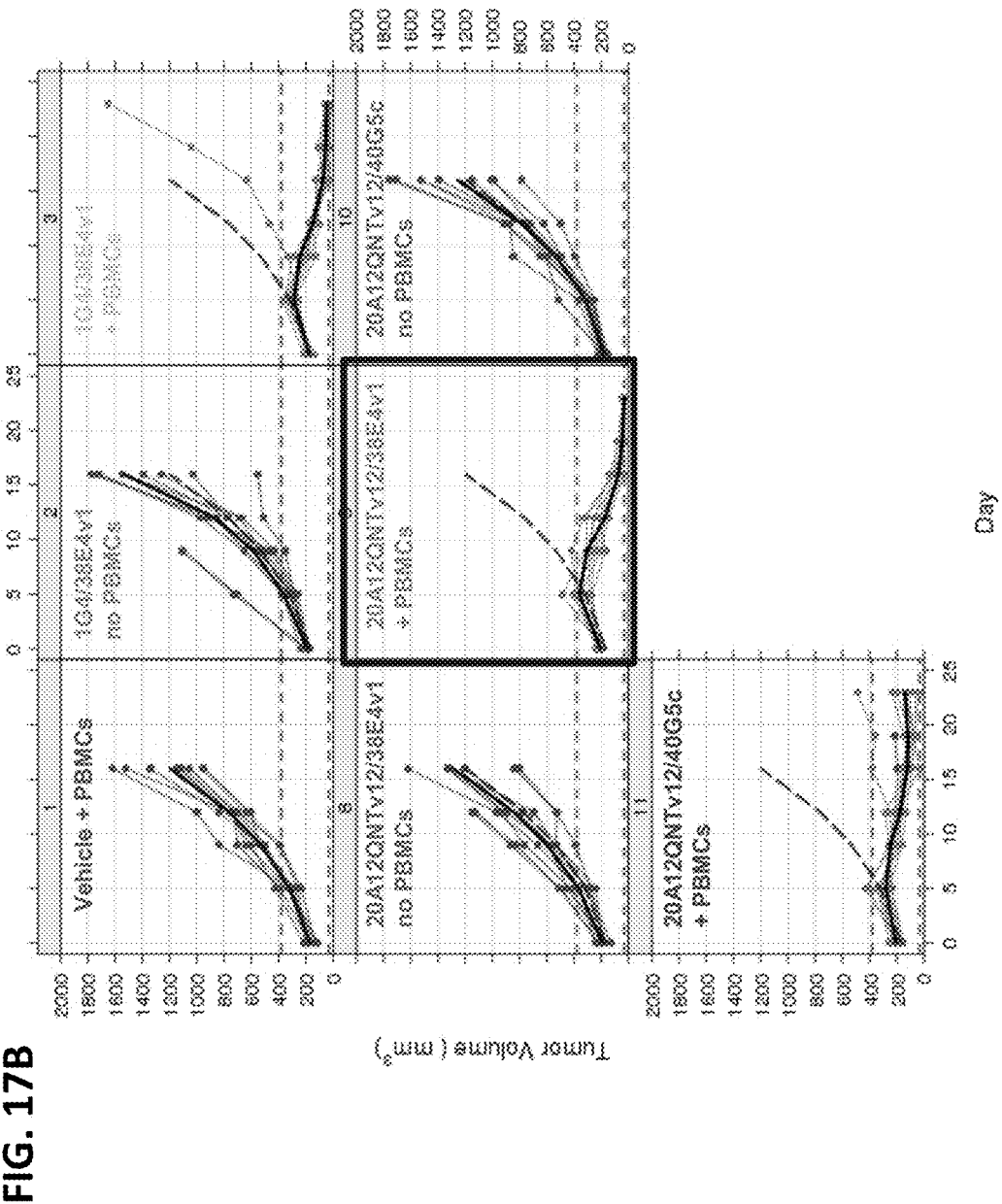

FIG. 17B is a set of graphs showing raw data for the tumor volume assay shown in FIG. 17A.

FIG. 17C is a graph showing serum concentration (in μg/mL) of LY6G6D TDBs comprising the anti-LY6G6D 20A12.QNTv12 arm (two-cell) and an anti-CD3 40G5c or 38E4.v1 arm in HTT55 NSG™ mice following administration of a single dose of the TDB, as measured using a Generic Immunoglobulin Pharmacokinetic (GRIP) ELISA.

Figure 18:
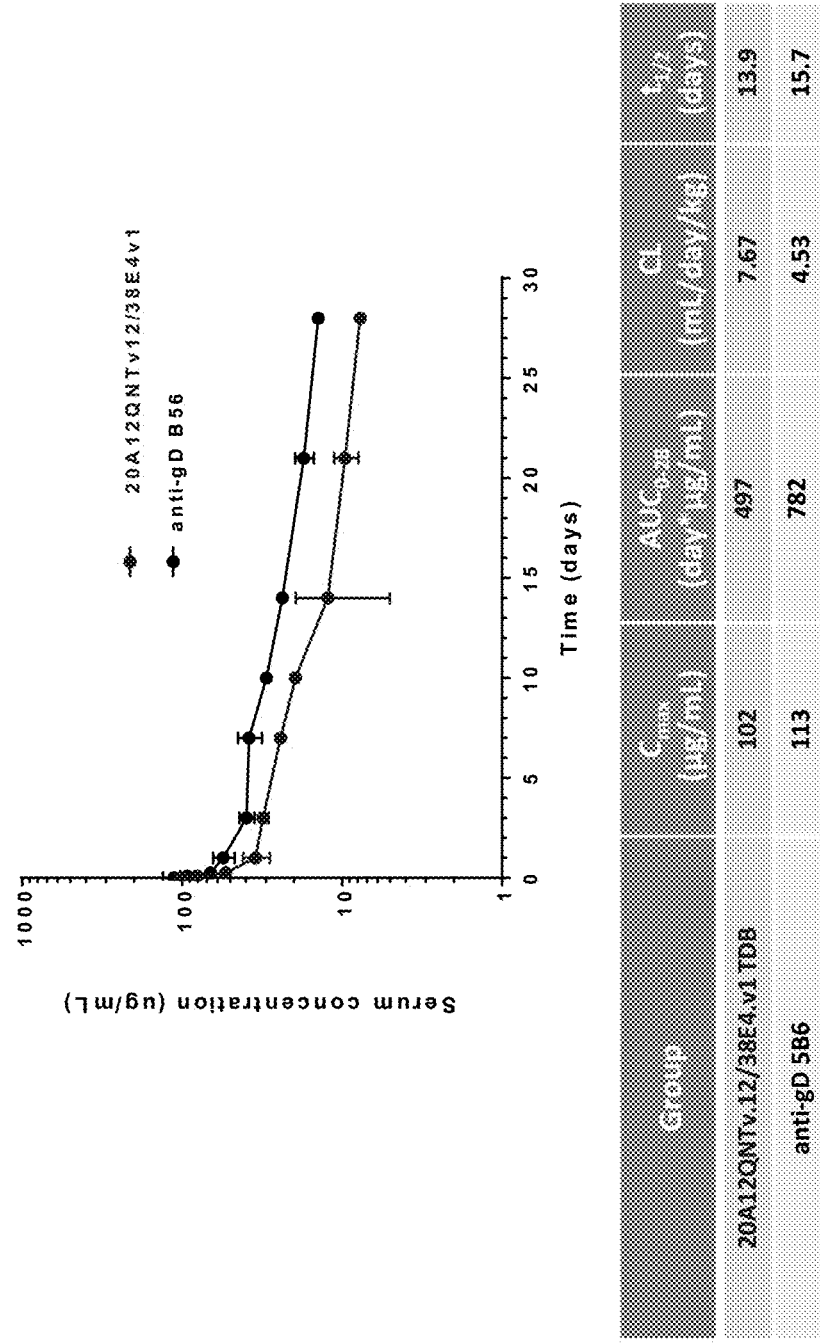

FIG. 18 is a graph and a table showing serum concentration (in μg/mL) of a LY6G6D TDB comprising the anti-LY6G6D arm 20A12.QNTv12 (two-cell) and an anti-CD3 arm 40G5c or 38E4.v1 and an anti-gD B56 antibody in severe combined immunodeficient (SCID) mice following intravenous administration of a single 5 mg/kg dose of the antibody. $C_{max}$: maximum serum concentration; $AUC_{0-28}$: area under curve; CL: clearance rate; $t_{1/2}$: half-life.

Figure 19:
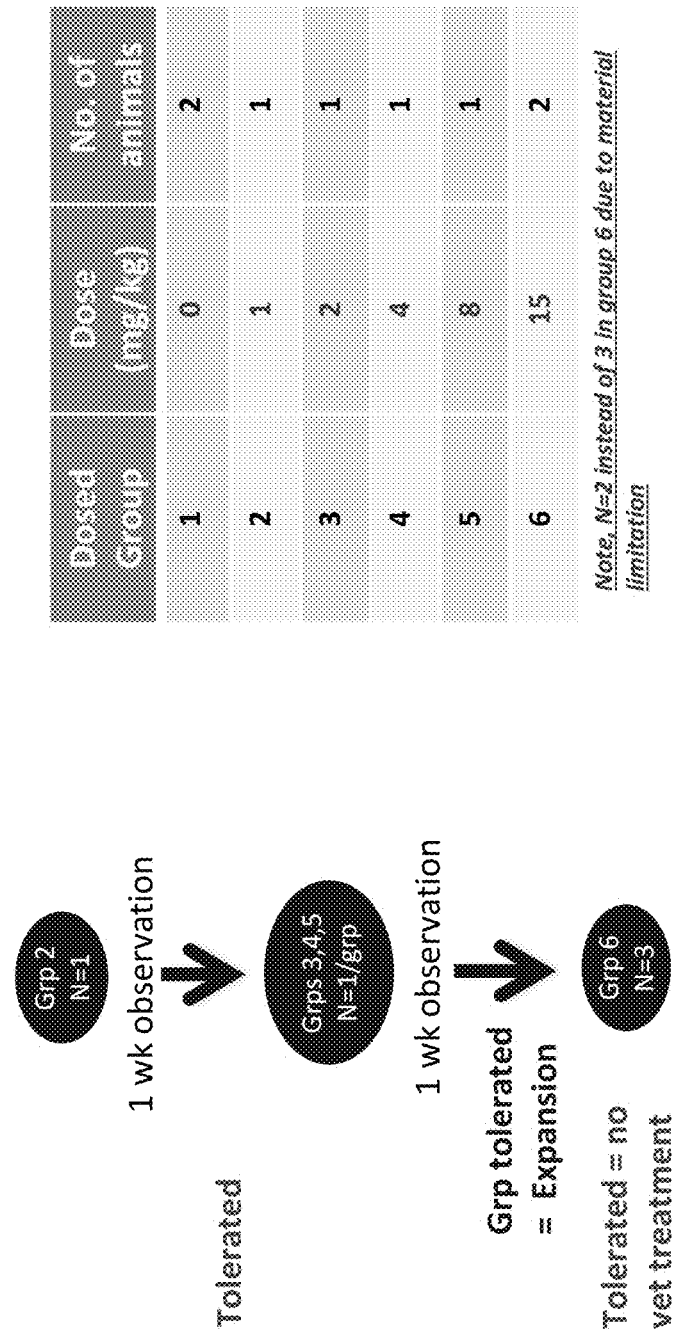

FIG. 19 is a schematic diagram and a table showing a toxicity study for a LY6G6D TDB comprising the anti-LY6G6D 20A12.QNTv12 arm (two-cell) and the anti-CD3 38E4.v1 arm in cynomolgus monkeys (cyno).

Figure 20A:
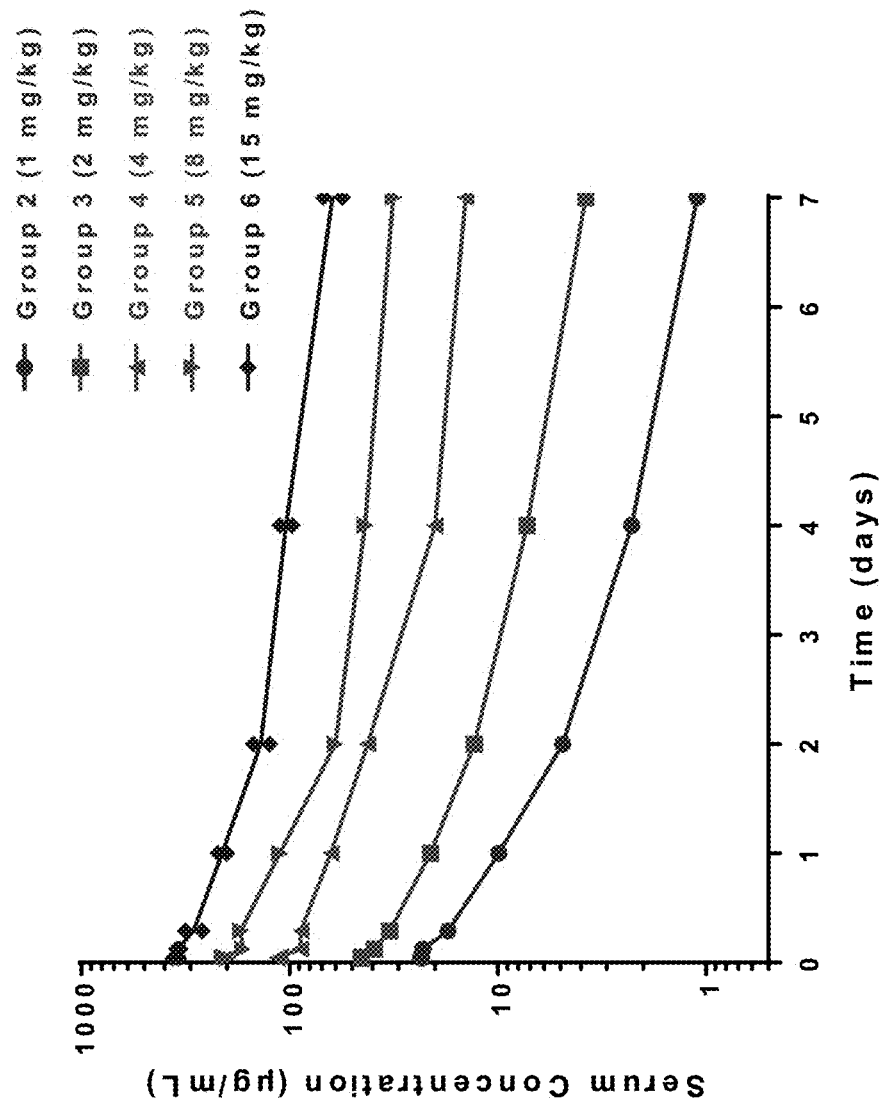

FIG. 20A is a graph showing serum concentration (in μg/mL) of a LY6G6D TDB comprising the anti-LY6G6D 20A12.QNTv12 arm (two-cell) and the anti-CD3 38E4.v1 arm in cynomolgus monkeys following intravenous administration of a single dose of the TDB at the indicated dosages.

Figure 20B:
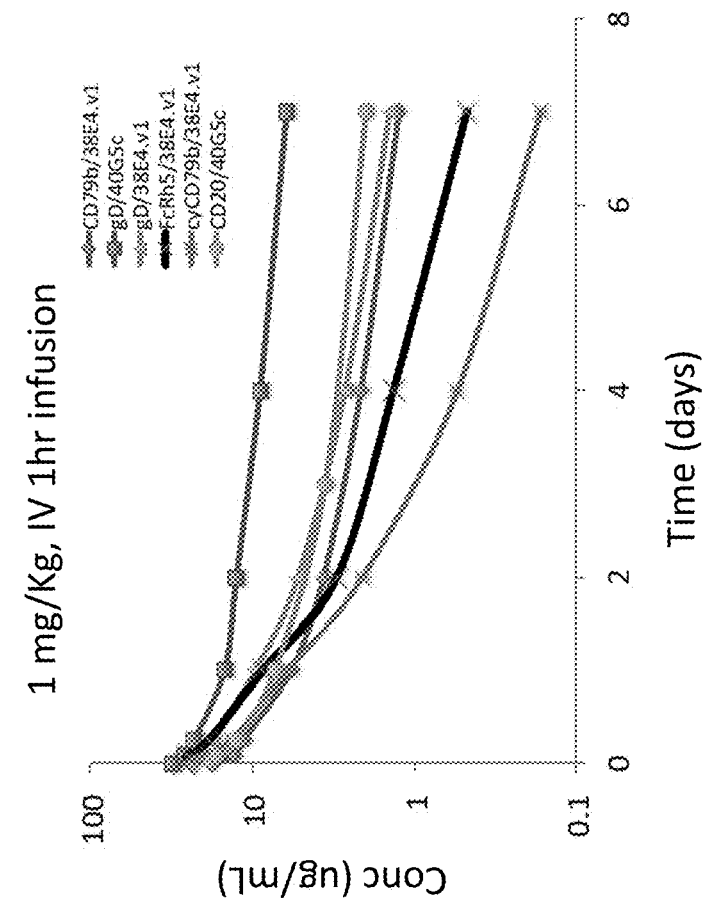

FIG. 20B is a graph and a table showing serum concentration (in μg/mL) and clearance (CL) of TDBs comprising various tumor-targeting arms paired with the anti-CD3 38E4v1 or 405Gc arm in cynomolgus monkeys following intravenous administration of a single 1 mg/kg dose of the TDB.

Figure 21:
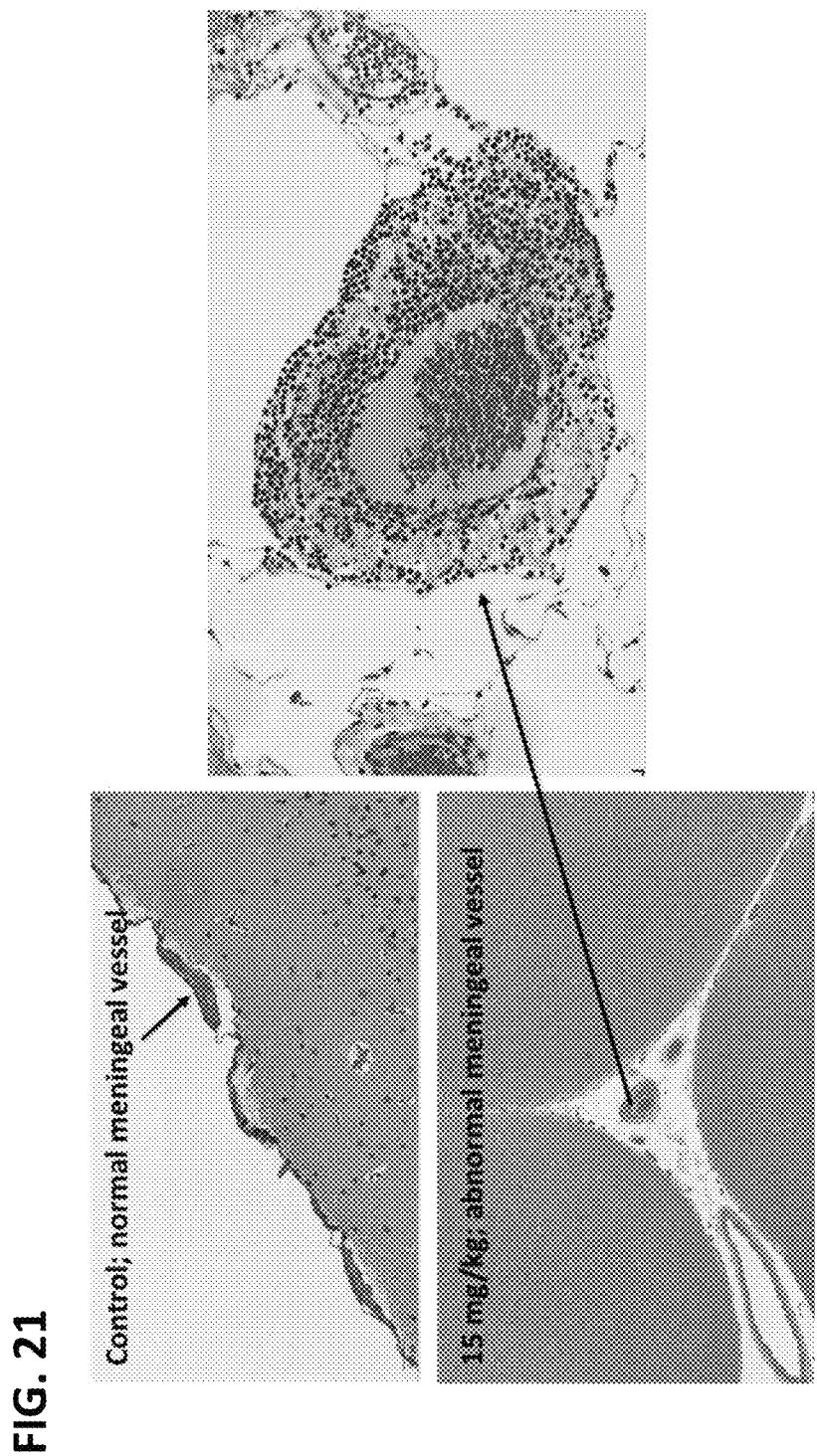

FIG. 21 is a set of photomicrographs showing perivascular/vascular mononuclear infiltrates in the brain of Animal No. 6003, which was dosed with a LY6G6D TDB comprising the anti-LY6G6D 20A12.QNTv12 arm (two-cell) and the anti-CD3 38E4.v1 arm at 15 mg/kg. The upper left panel shows a control (normal) meningeal vessel. The lower left panel shows an abnormal meningeal vessel of Animal No. 6003. The right panel shows a magnified view of the abnormal meningeal vessel.

Figure 22A:
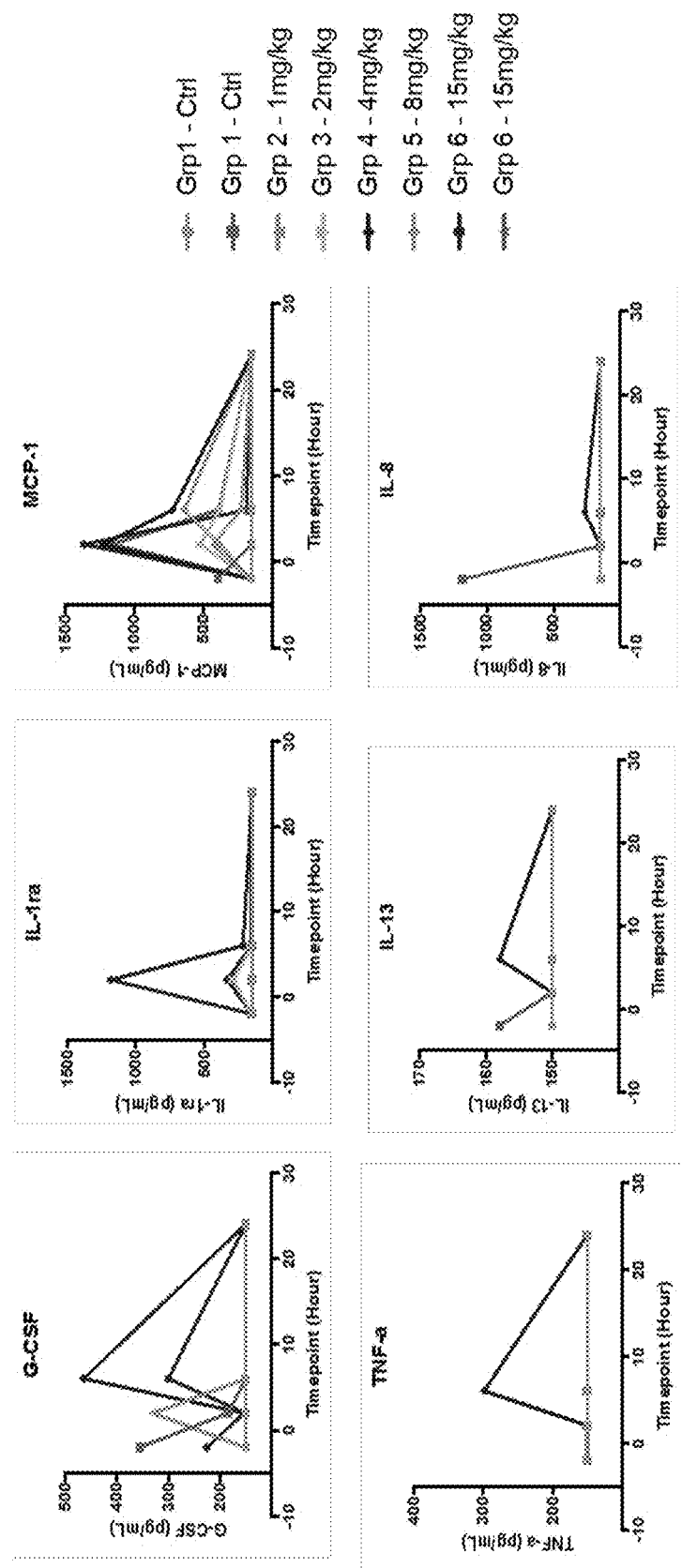

FIG. 22A is a set of graphs showing concentration of the cytokines G-CSF, IL-1Ra, MCP-1, TNF-a, IL-13, and IL-8 (in μg/mL) following treatment of cynomolgus monkeys with a single dose of a LY6G6D TDB comprising the anti-LY6G6D 20A12.QNTv12 arm (two-cell) and the anti-CD3 38E4.v1 arm at the indicated dosages and in control (untreated) cynomolgus monkeys.

Figure 22B:
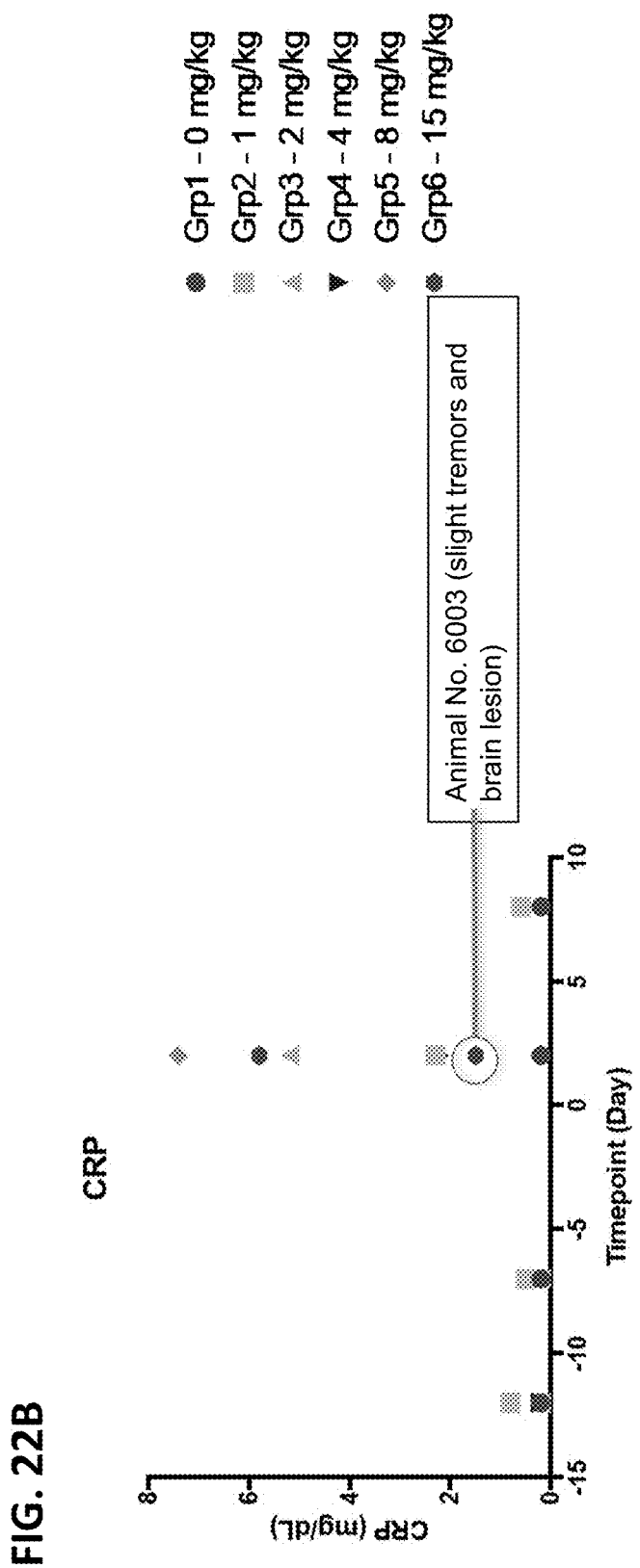

FIG. 22B is a scatter plot showing concentration of C-reactive protein (CRP; in μg/mL) following treatment of cynomolgus monkeys with a single dose of a LY6G6D TDB comprising the anti-LY6G6D 20A12.QNTv12 arm (two-cell) and the anti-CD3 38E4.v1 arm at the indicated dosages and in control (untreated) cynomolgus monkeys.

Figure 23A:
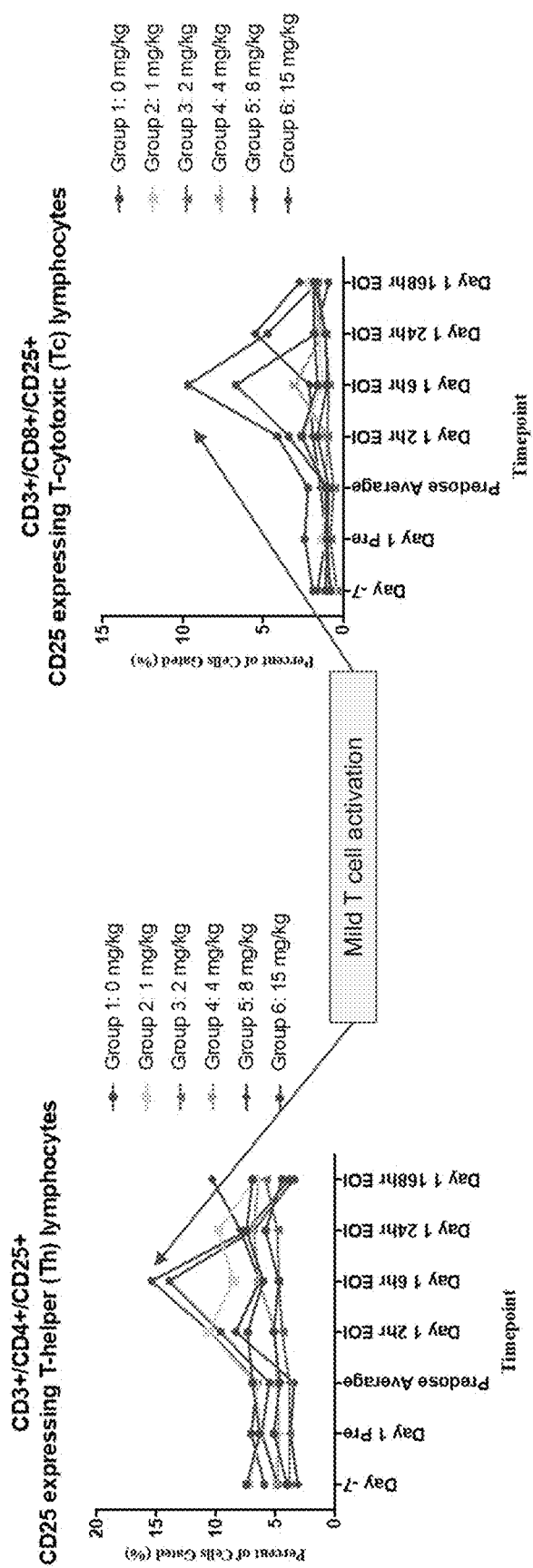

FIG. 23A is a pair of graphs showing the percent of cells that were gated as CD3+/CD4+/CD5+CD25 expressing T-helper (Th) lymphocytes (left panel) and CD3+/CD8+/CD5+CD25 expressing T-cytotoxic (Tc) lymphocytes (right panel) in a flow cytometry assay in cynomolgus monkeys treated with a single dose of a LY6G6D TDB comprising the anti-LY6G6D 20A12.QNTv12 arm (two-cell) and the anti-CD3 38E4.v1 arm at the indicated dosages and in control (untreated) cynomolgus monkeys. Measurements were taken at 7 days before treatment (Day −7) and on the day of treatment (Day 1 Pre) and were averaged (Predose average). After the end of infusion (EOI), measurements were taken at 2 hours, 6 hours, 24 hours, and 168 hours. A peak showing mild T cell activation is labeled by an arrow.

Figure 23B:
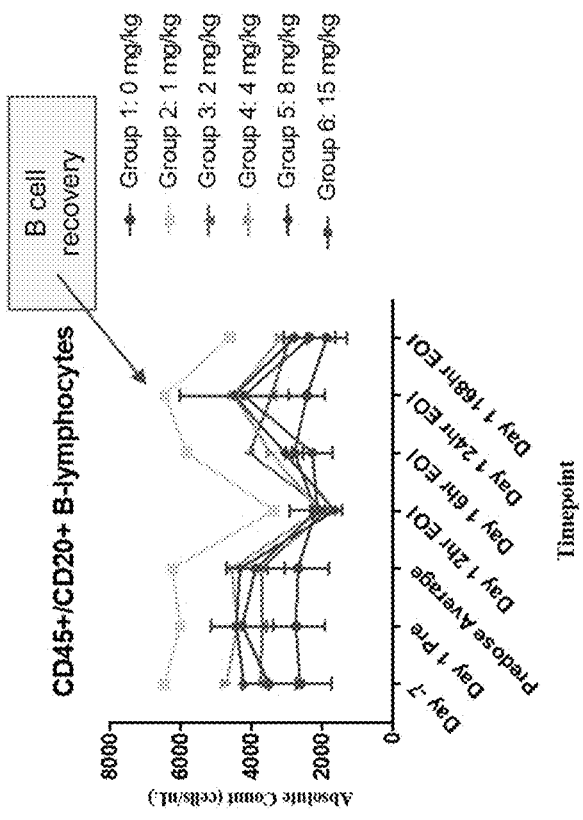

FIG. 23B is a graph showing the percent of cells that were gated as CD45+/CD3+T-lymphocytes in a flow cytometry assay in cynomolgus monkeys treated with a single dose of a LY6G6D TDB comprising the anti-LY6G6D 20A12.QNTv12 arm (two-cell) and the anti-CD3 38E4.v1 arm at the indicated dosages and in control (untreated) cynomolgus monkeys. A peak showing T cell recovery is labeled by an arrow.

Figure 23C:
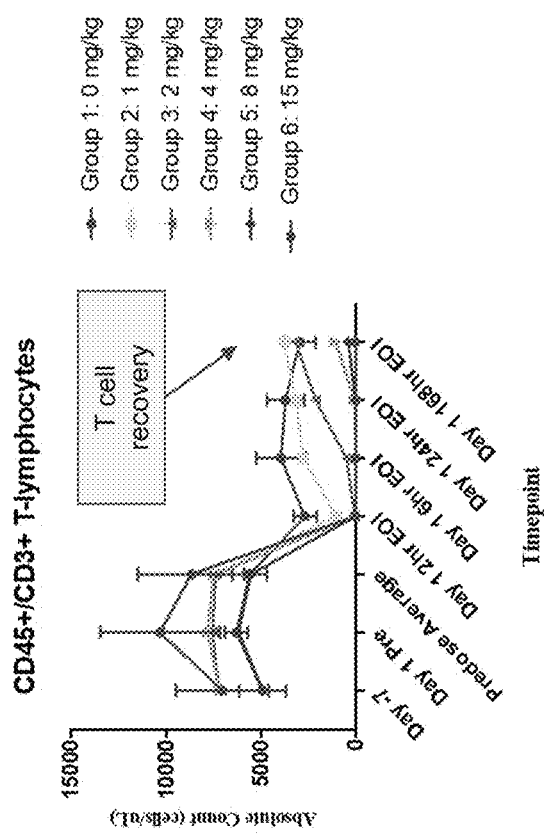

FIG. 23C is a graph showing the percent of cells that were gated as CD45+/CD20+B-lymphocytes in a flow cytometry assay in cynomolgus monkeys treated with a single dose of a LY6G6D TDB comprising the anti-LY6G6D 20A12.QNTv12 arm (two-cell) and the anti-CD3 38E4.v1 arm at the indicated dosages and in control (untreated) cynomolgus monkeys. A peak showing B cell recovery is labeled by an arrow.

Figure 23D:
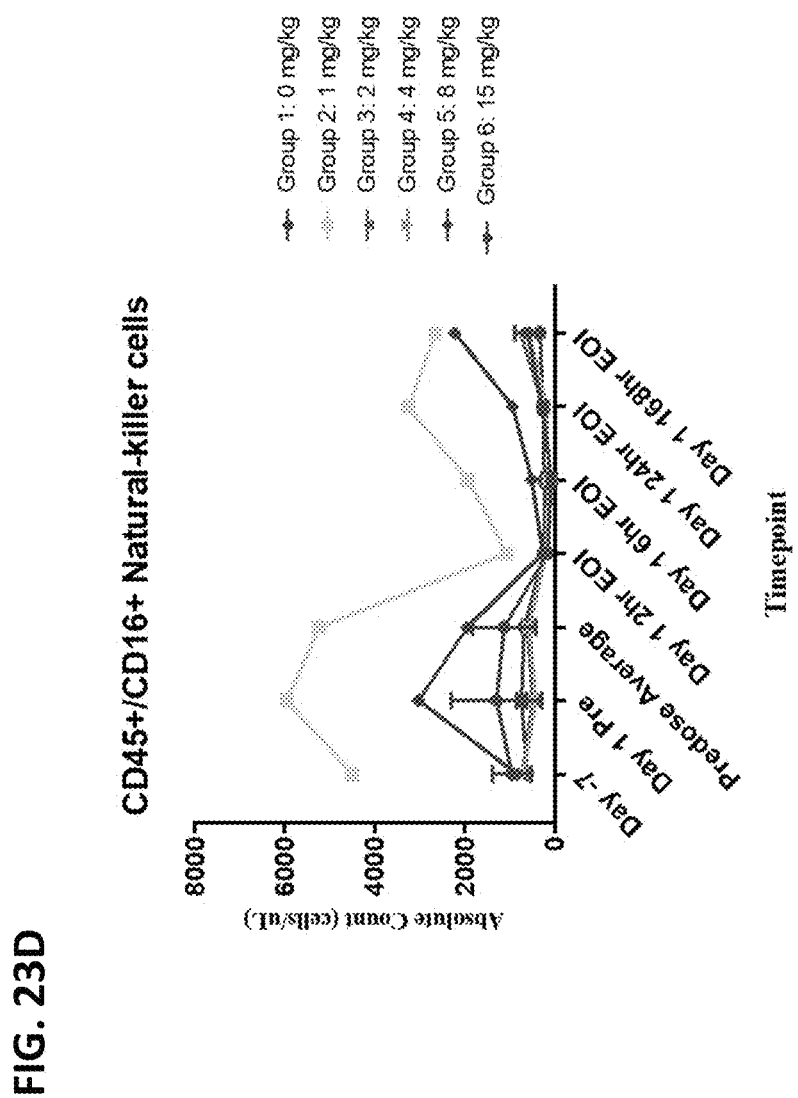

FIG. 23D is a graph showing the percent of cells that were gated as CD45+/CD16+ natural killer (NK) cells in a flow cytometry assay in cynomolgus monkeys treated with a single dose of a LY6G6D TDB comprising the anti-LY6G6D 20A12.QNTv12 arm (two-cell) and the anti-CD3 38E4.v1 arm at the indicated dosages and in control (untreated) cynomolgus monkeys.

Figure 24A:
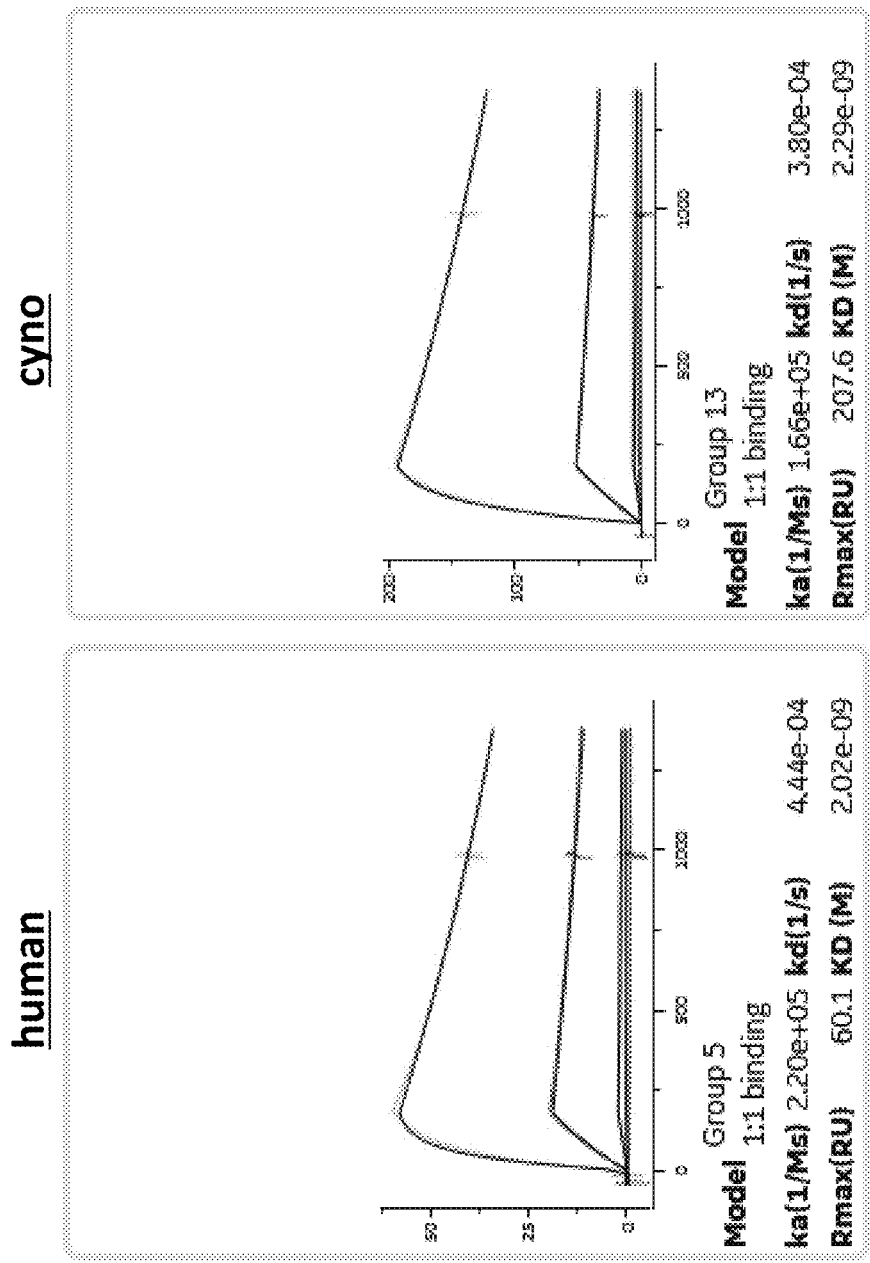

FIG. 24A is a pair of graphs showing binding of a LY6G6D TDB comprising the anti-LY6G6D 20A12.QNTv12 arm (two-cell) and the anti-CD3 38E4.v1 arm against a human (left panel) and cyno (right panel) Ly6G6D polypeptide as measured using a BIAcore assay. Ly6G6D-Fc was directly immobilized on the chip, and the TDB was flowed through at 37° C.

FIG. 24B is a pair of graphs showing binding of a LY6G6D TDB comprising the anti-LY6G6D 20A12.QNTv12 arm (two-cell) and the anti-CD3 40G5c arm against a human (left panel) and cyno (right panel) Ly6G6D polypeptide as measured using a BIAcore assay. Ly6G6D-Fc was directly immobilized on the chip, and the TDB was flowed through at 37° C.

Figure 24C:
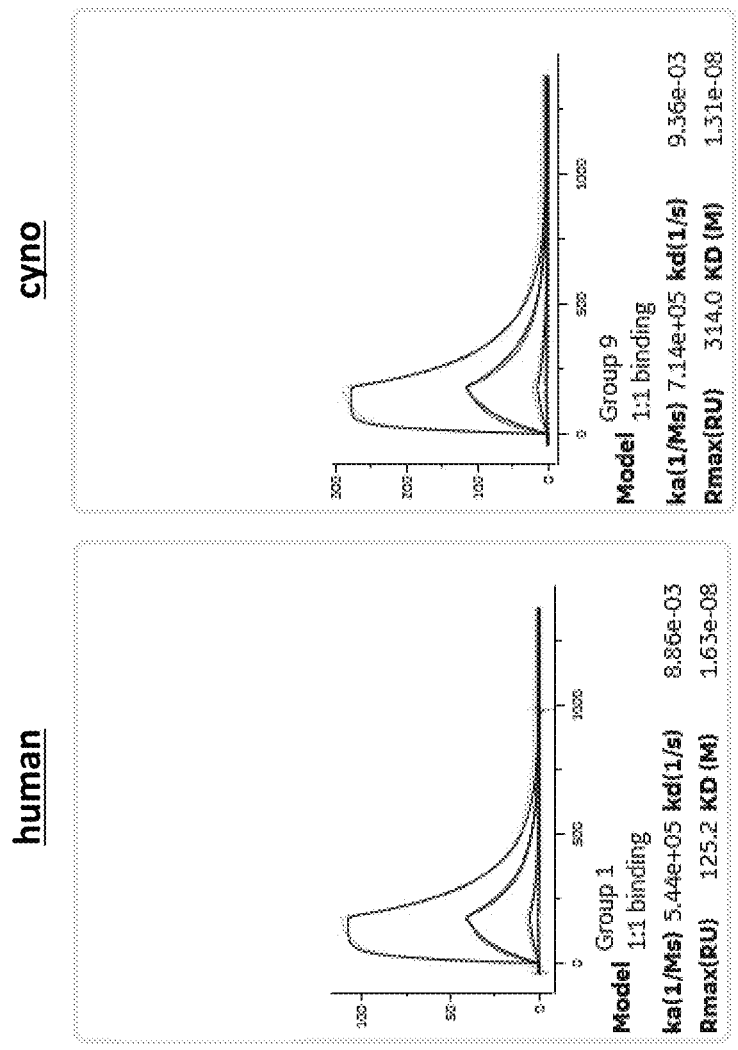

FIG. 24C is a pair of graphs showing binding of a LY6G6D TDB comprising the anti-LY6G6D 1G4 arm and the anti-CD3 38E4.v1 arm against a human (left panel) and cyno (right panel) Ly6G6D polypeptide as measured using a BIAcore assay. Ly6G6D-Fc was directly immobilized on the chip, and the TDB was flowed through at 37° C.

Figure 24D:
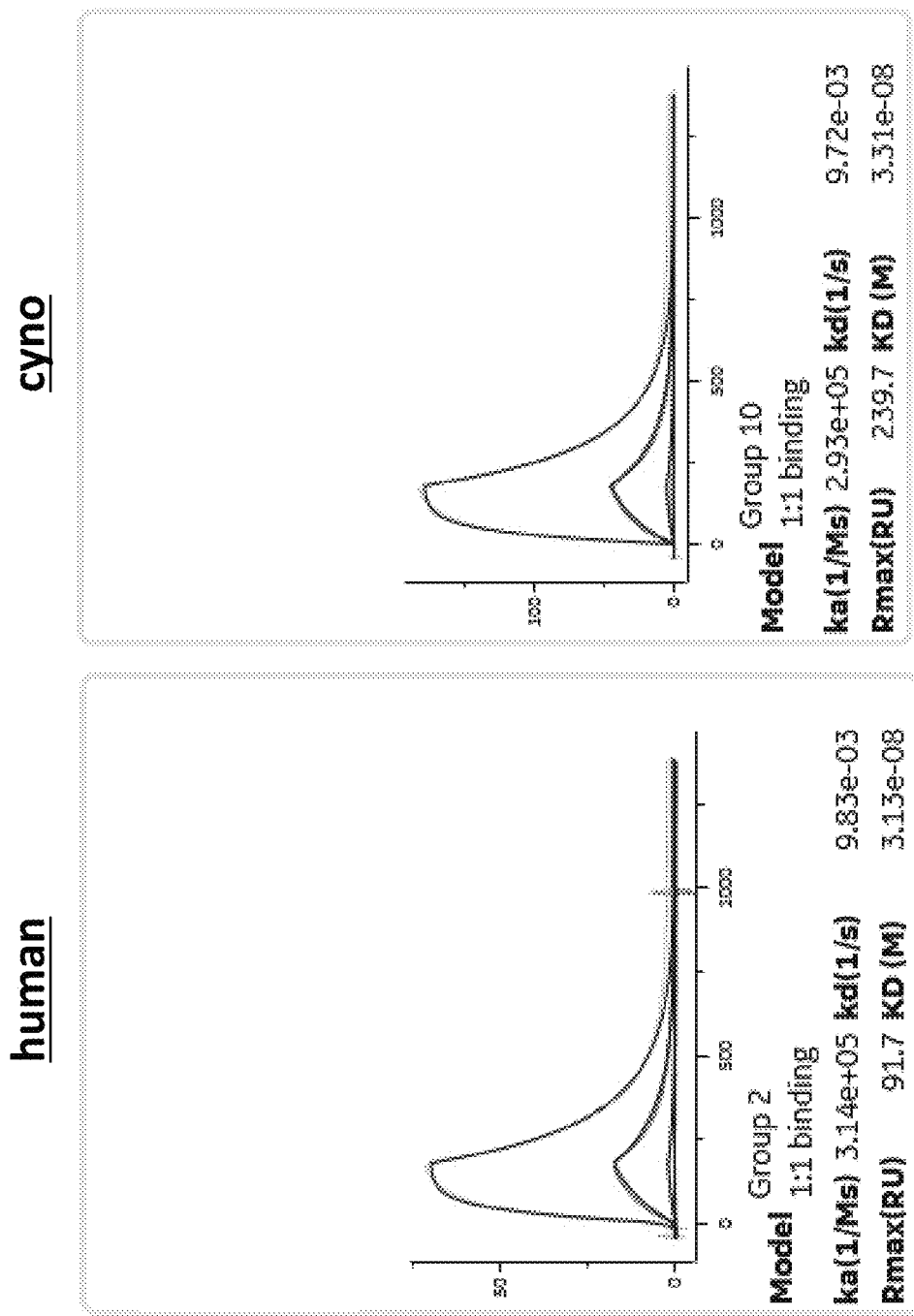

FIG. 24D is a pair of graphs showing binding of a LY6G6D TDB comprising the anti-LY6G6D 1G4 arm and the anti-CD3 40G5c arm against a human (left panel) and cyno (right panel) Ly6G6D polypeptide as measured using a BIAcore assay. Ly6G6D-Fc was directly immobilized on the chip, and the TDB was flowed through at 37° C.

Figure 25:
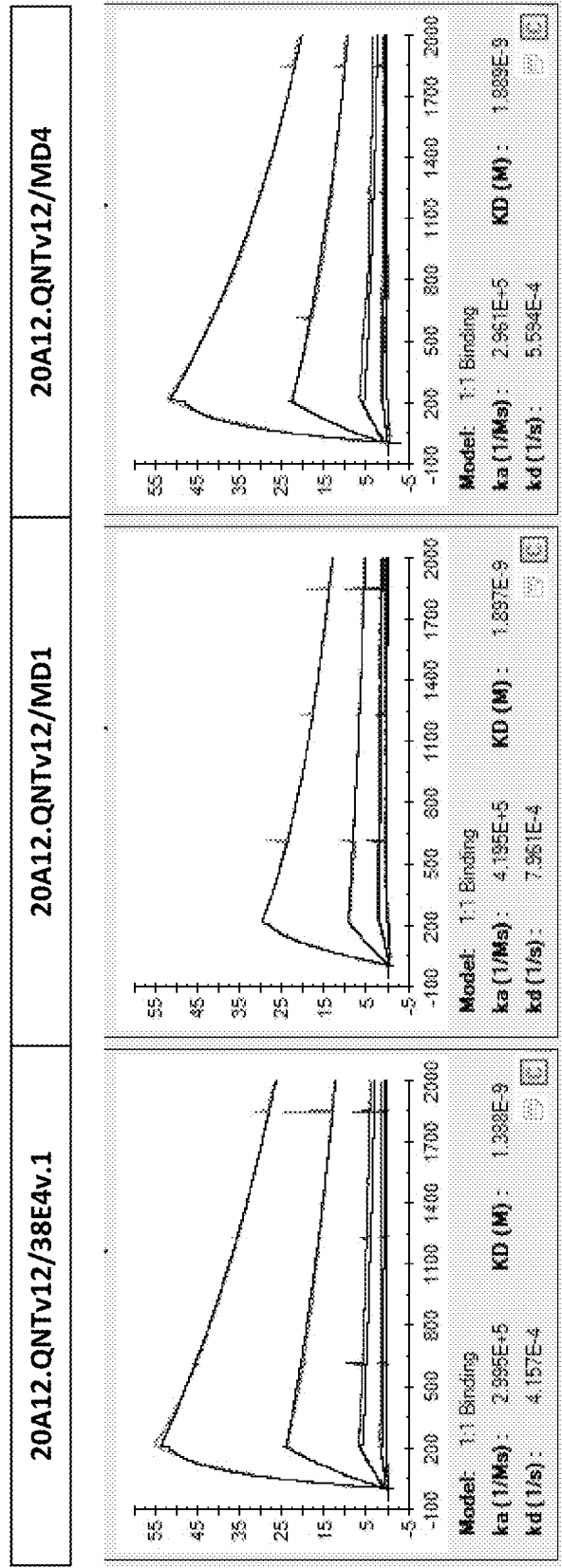

FIG. 25 is a set of graphs showing binding of a LY6G6D TDB comprising the anti-LY6G6D 20A12.QNTv12 arm (two-cell) and the anti-CD3 arm 38E4.v1 (left panel), the anti-LY6G6D 20A12.QNTv12 arm (one-cell) and the anti-CD3 arm 38E4.v1 MD1 (center panel), or the anti-LY6G6D 20A12.QNTv12 arm (one-cell) and the anti-CD3 arm 38E4.v1 MD4 (right panel) against a human Ly6G6D polypeptide as measured using a BIAcore assay. Ly6G6D-Fc was directly immobilized on the chip, and the TDB was flowed through at 37° C.

Figure 26A:
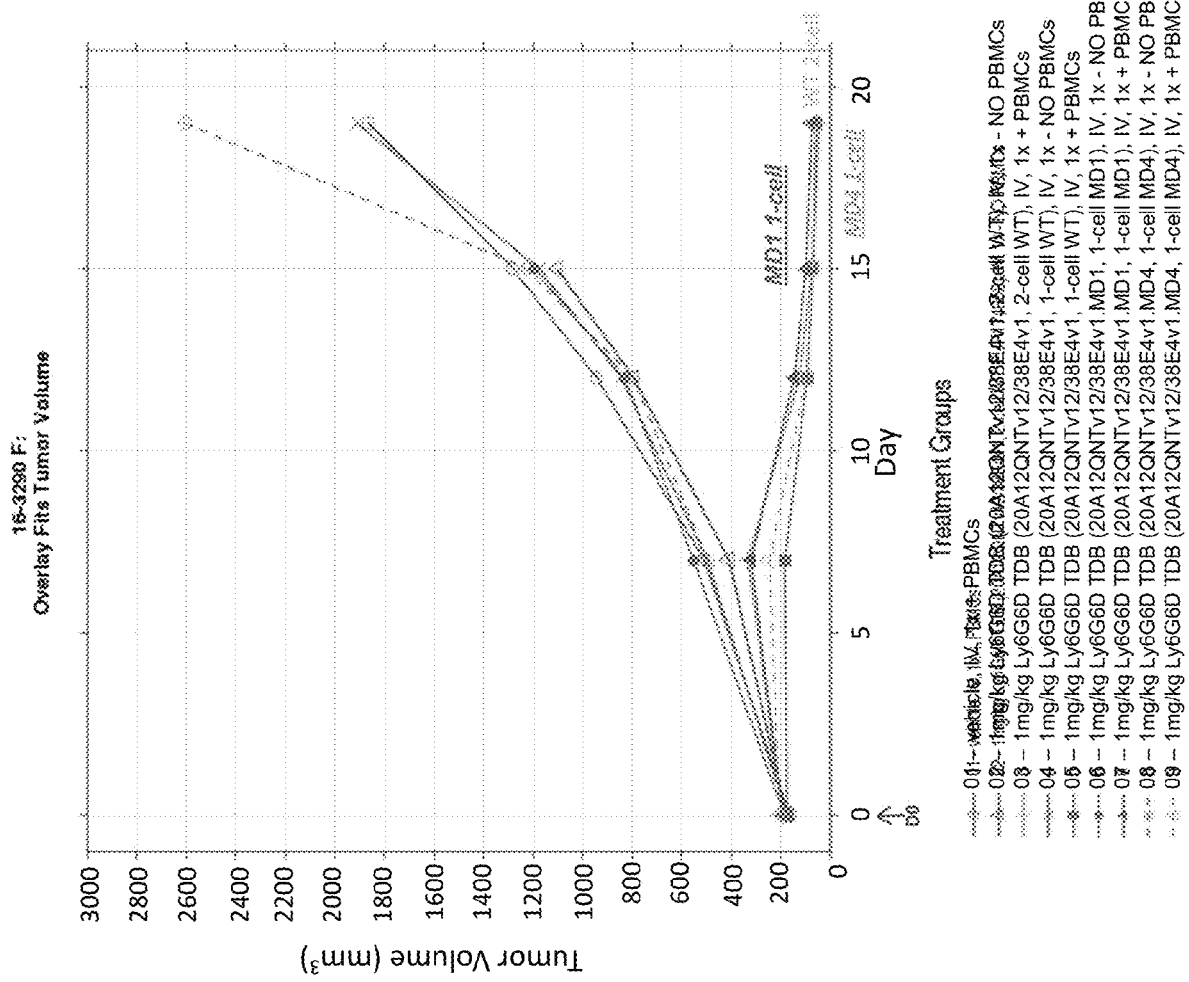

FIG. 26A is a graph showing tumor volume (mm²) of xenograft HT55 tumors in NSG™ mice following treatment with a LY6G6D TDB assembled using a one-cell system comprising the anti-LY6G6D 20A12.QNTv12 arm (one-cell) and an anti-CD3 arm 38E4v1 MD1, 38E4v1 MD4, or 38E4v1 (WT) and by a LY6G6D TDB assembled using a two-cell system and comprising the anti-LY6G6D 20A12.QNTv12 arm (two-cell) and the anti-CD3 38E4v1 (WT) arm. Treatments comprising the delivery vehicle and PMBCs or comprising the TDB and not comprising PMBCs are provided as controls.

Figure 26B:
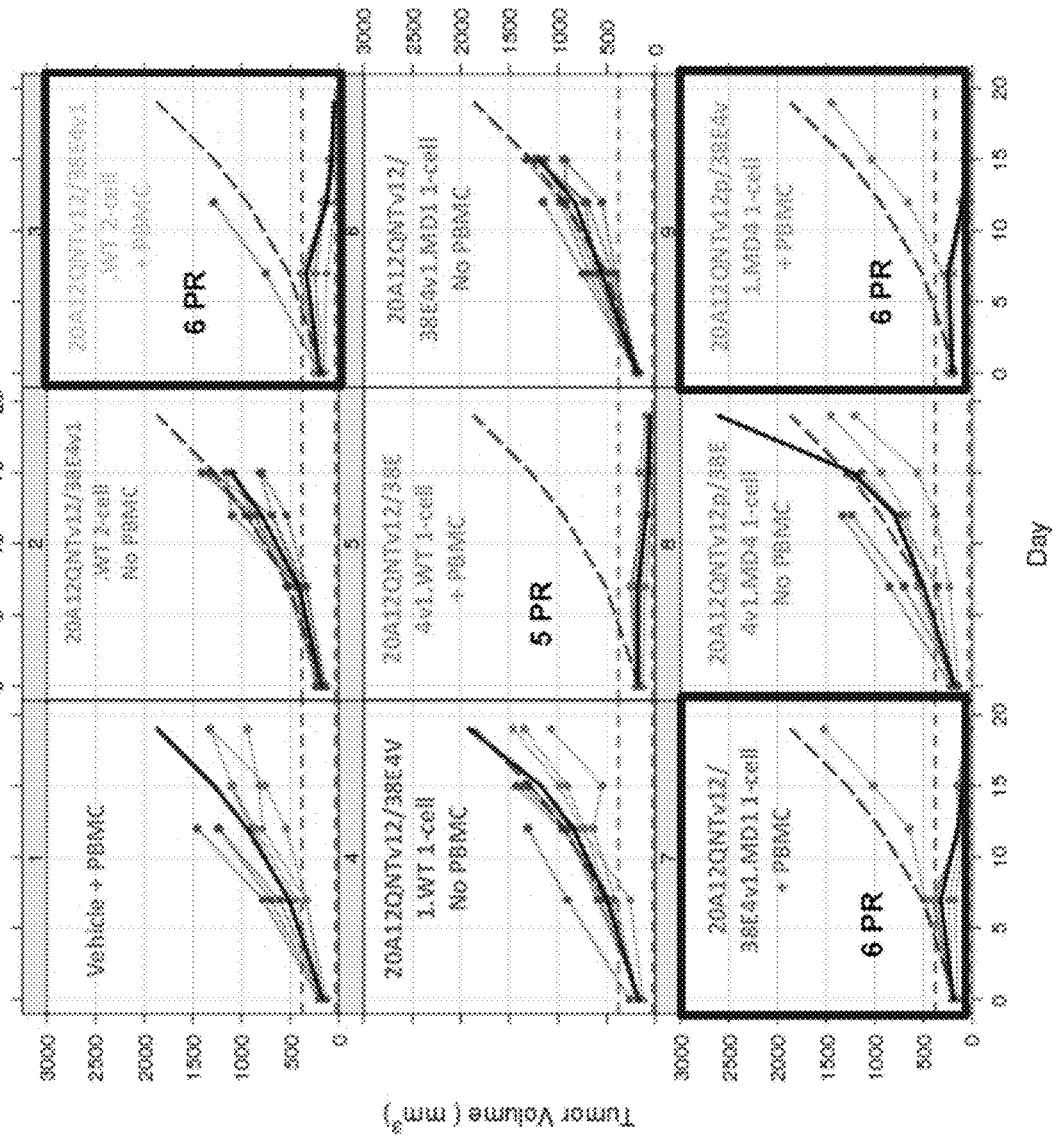

FIG. 26B is a set of graphs showing raw data for the tumor volume assay shown in FIG. 26A.

Figure 27:
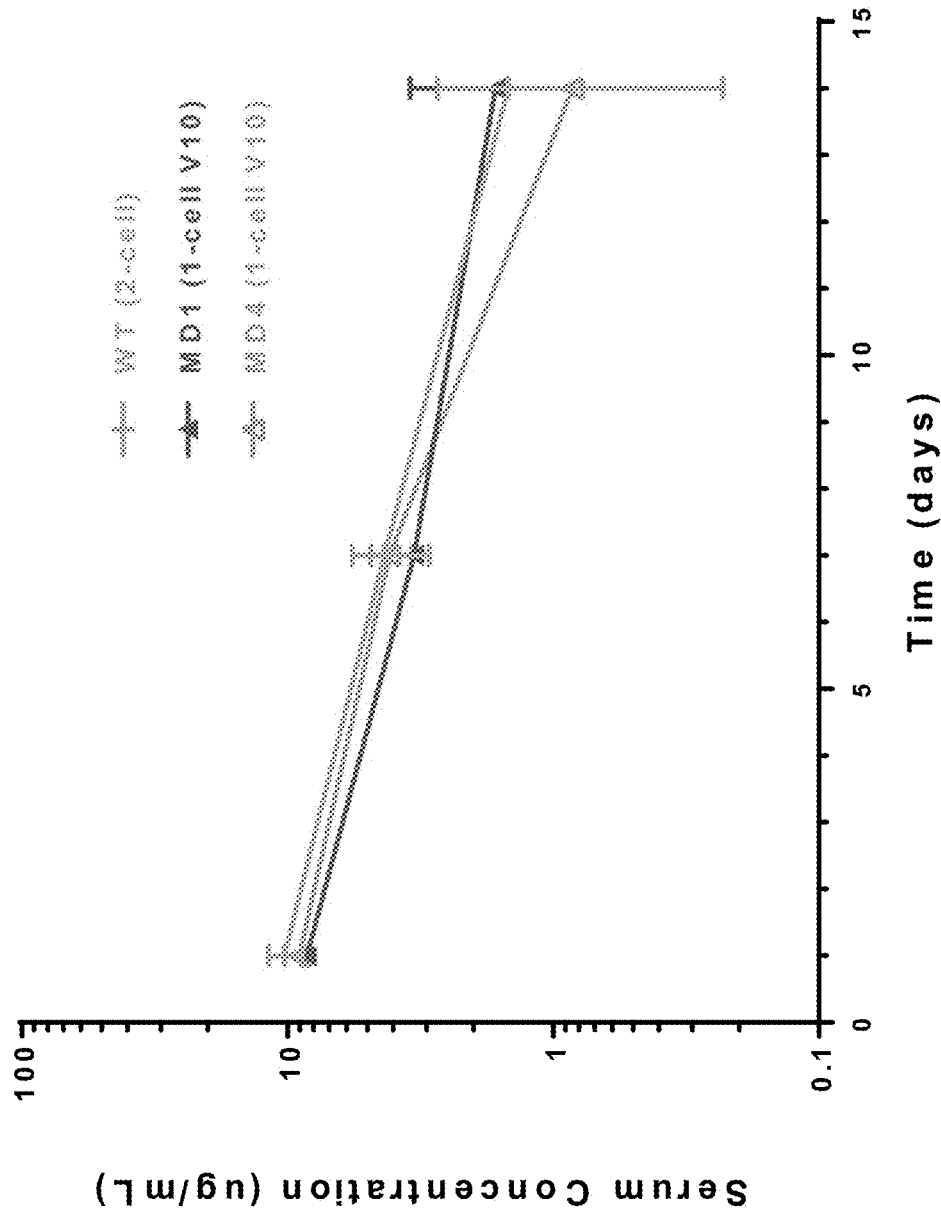

FIG. 27 is a graph showing serum concentration (in µg/mL) of a LY6G6D TDB assembled using a two-cell system and comprising the anti-LY6G6D 20A12.QNTv12 arm (two-cell) and the anti-CD3 38E4v1 (WT) arm and LY6G6D TDBs assembled using a one-cell system comprising the anti-LY6G6D 20A12.QNTv12 arm (one-cell) and an anti-CD3 38E4v1 MD1 or 38E4v1 MD4 arm.

Figure 28:
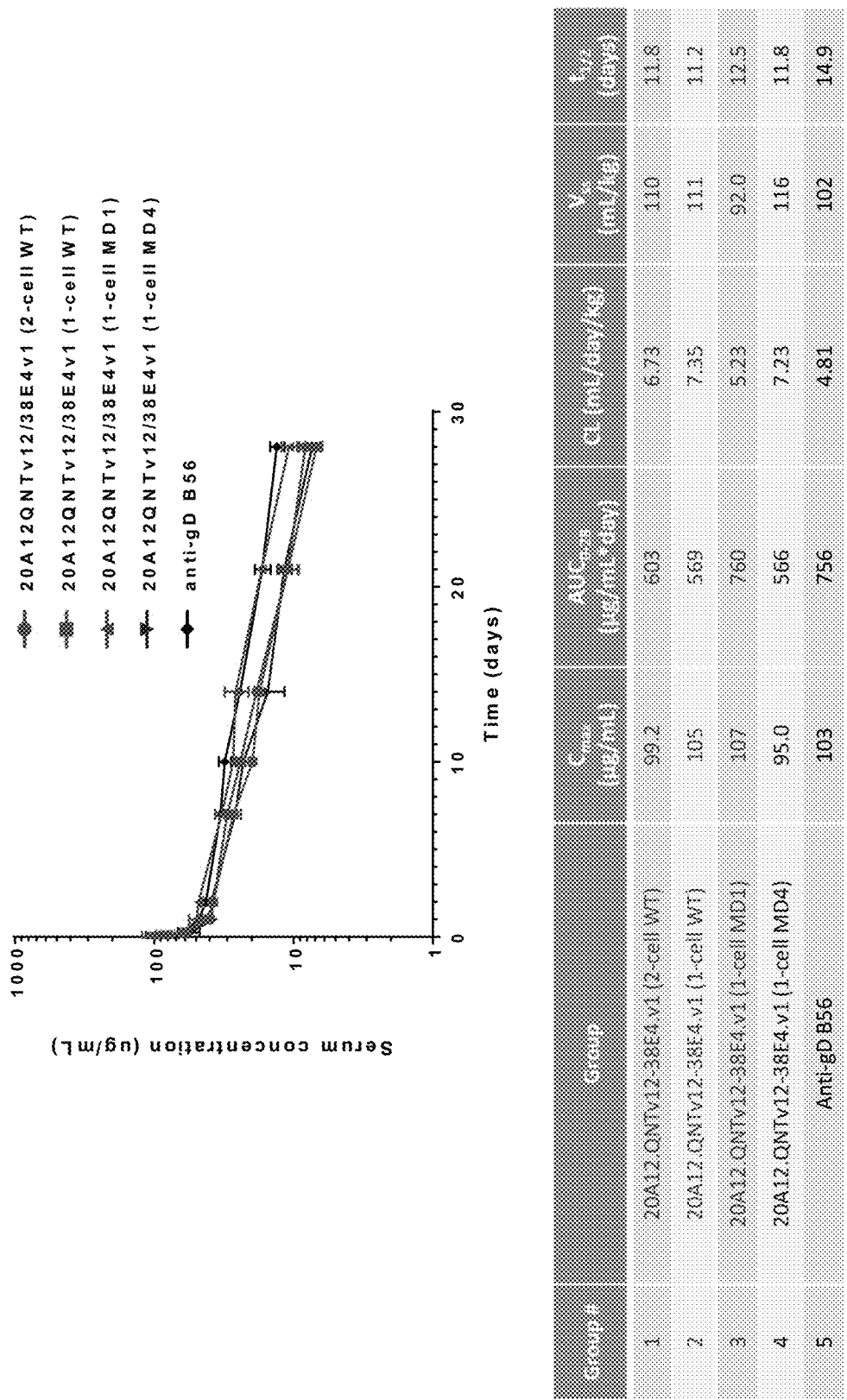

FIG. 28 is a graph and a table showing serum concentration (in µg/mL) of a LY6G6D TDB assembled using a one-cell system comprising the anti-LY6G6D 20A12.QNTv12 arm (one-cell) and an anti-CD3 38E4v1 MD1 or 38E4v1 MD4 arm and a LY6G6D TDB assembled using a two-cell system and comprising the anti-LY6G6D 20A12.QNTv12 arm (two-cell) and the anti-CD3 38E4v1 (WT) arm.

Figure 29A:
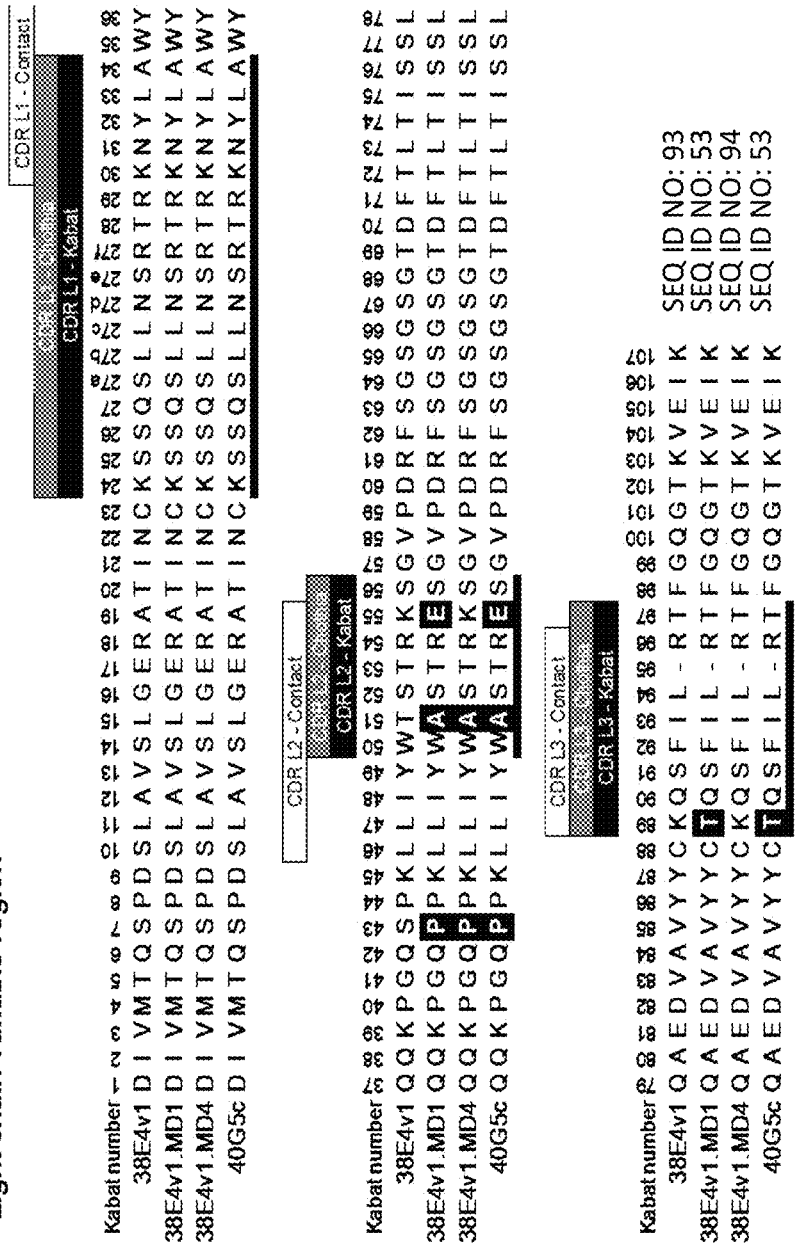

FIG. 29A is a sequence alignment showing the amino acid sequences of the VL of anti-CD3 clones 38E4v1, 40G5c, 38E4v1 MD1 (MD1), and 38E4v1 MD4 (MD4). The complementarity-determining regions (CDRs) CDR L1, CDR L2, and CDR L3 are indicated according to the contact, Chothia, and Kabat definitions. CDR sequences according to the Kabat definition are underlined.

FIG. 29B is a sequence alignment showing the amino acid sequences of the VH of anti-CD3 clones 38E4v1, 40G5c, 38E4v1 MD1 (MD1), and 38E4v1 MD4 (MD4). The complementarity-determining regions (CDRs) CDR L1, CDR L2, and CDR L3 are indicated according to the contact, Chothia, and Kabat definitions. CDR sequences according to the Kabat definition are underlined.

Figure 29C:
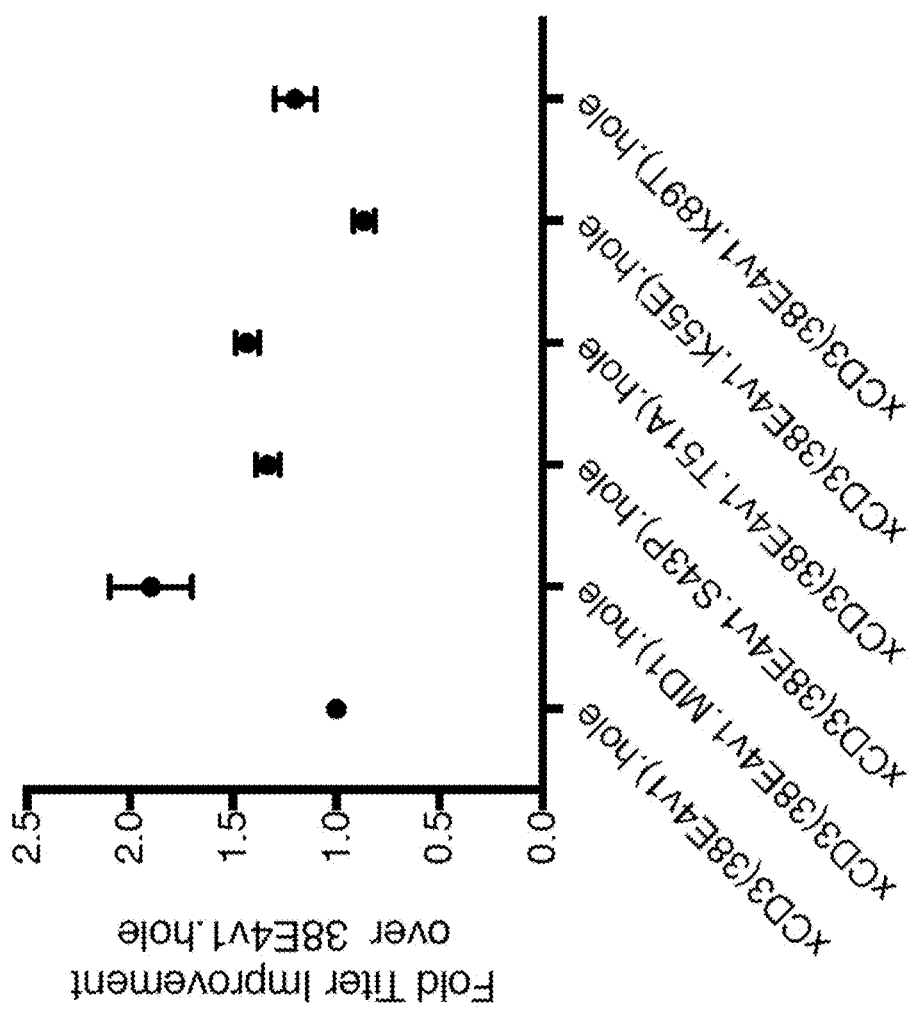

FIG. 29C is a graph showing the results of a transient transfection production assay including the anti-CD3 38E4v1, MD1, 38E4v1.S43P, 38E4v1.T51A, 38E4v1.K55E, and 38E4v1.K89T arms.

Figure 29D:
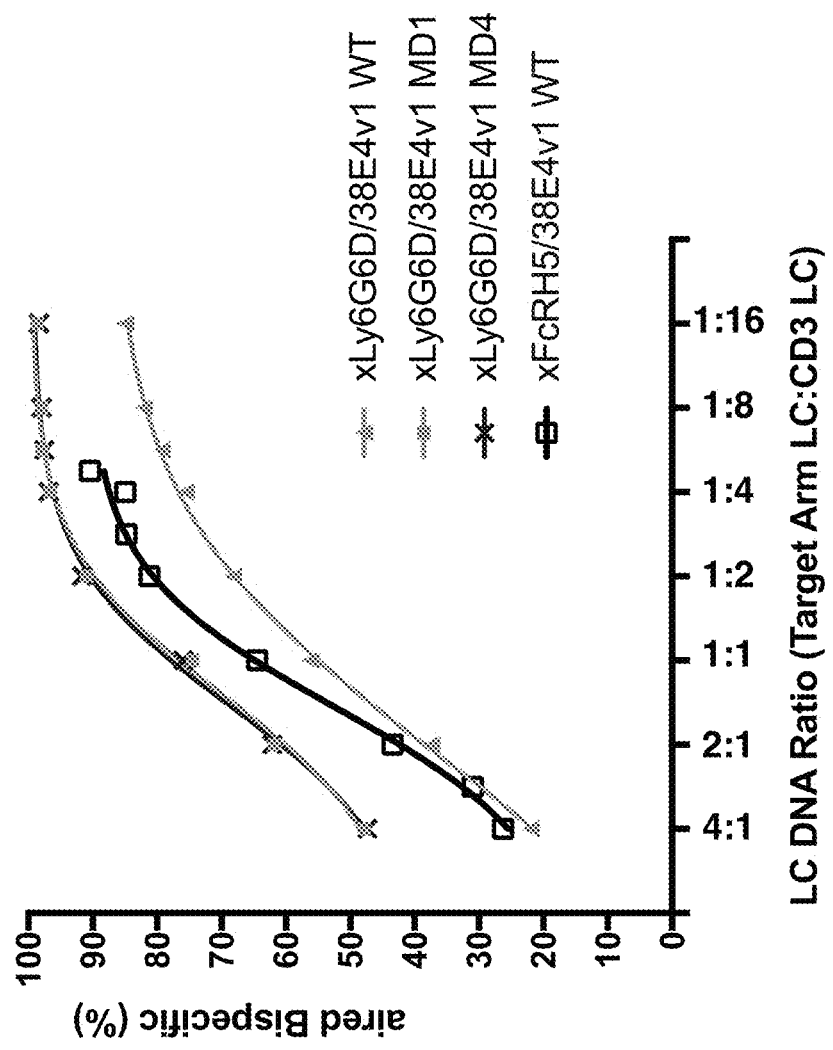

FIG. 29D is a graph showing the percent of properly paired bispecific antibodies produced for LY6G6D TDBs comprising an anti-LY6G6D arm or an anti-FcRH5 arm and an anti-CD3 arm 38E4v1 (WT), MD1, or variant 38E4v1 arms having single amino acid substitutions (indicated in parentheses) at varying ratios of target arm light chain (LC) DNA to anti-CD3 arm DNA (target arm LC:CD3 LC).

Figure 29E:
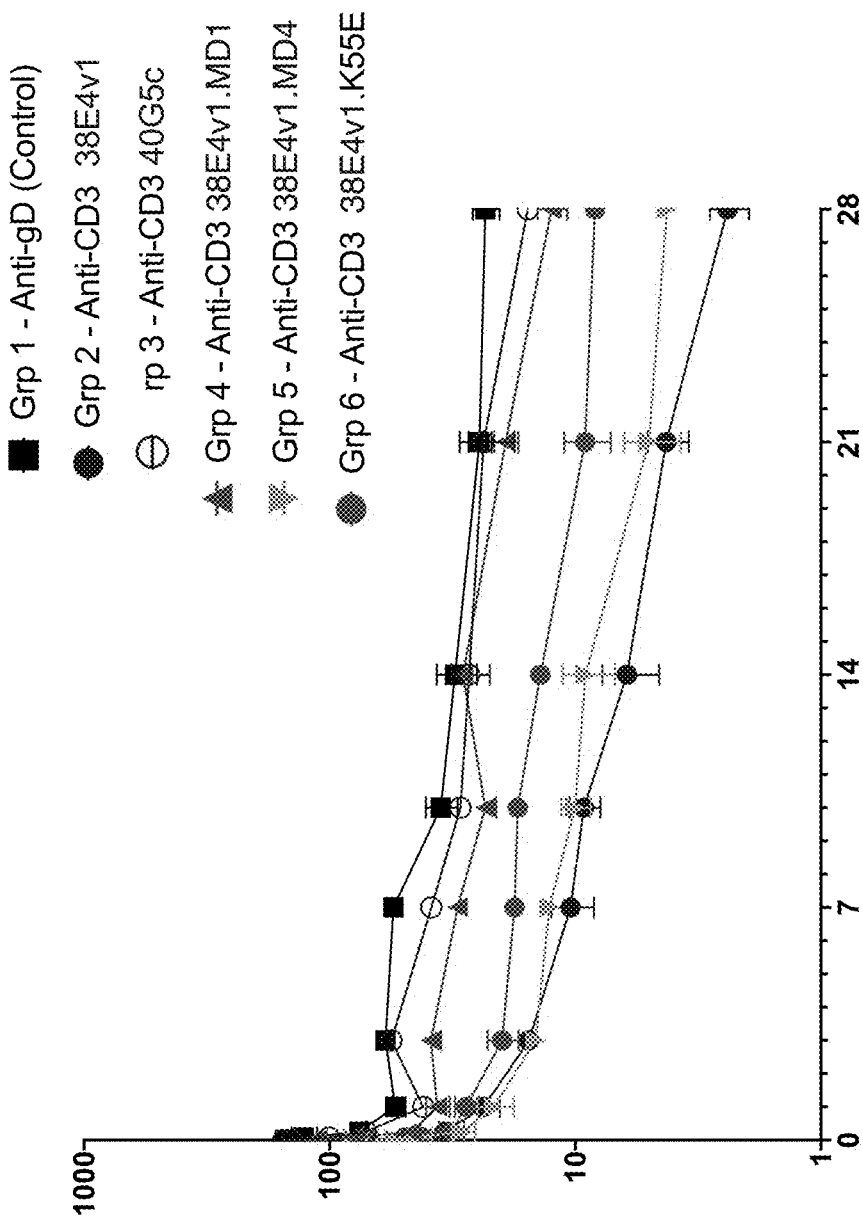

FIG. 29E is a graph showing serum concentration (in µg/mL) of following administration of a single 5 mg/kg dose of a monospecific, bivalent anti-CD3 antibody comprising the anti-CD3 arm 38E4v1, 40G5c, MD1, MD4, or 38E4v1 K55E to CB-17 SCID mice (n=3 per time point). An anti-gD antibody is shown as a control. Individual data points (symbols) are shown together with mean values connected (solid lines).

FIG. 29F is a sequence alignment showing the amino acid sequences of the VL of anti-CD3 clones 38E4v1, 40G5c, MD1, and MD4 comprising a Q38E amino acid substitution mutation (boxed) in framework region (FR) 2. This light chain variable region sequence is particularly useful for single-cell manufacturing of TDBs. The complementarity-determining regions (CDRs) CDR L1, CDR L2, and CDR L3 are indicated according to the contact, Chothia, and Kabat definitions. CDR sequences according to the Kabat definition are underlined.

FIG. 29G is a sequence alignment showing the amino acid sequences of the VH of anti-CD3 clones 38E4v1, 40G5c, MD1, and MD4 comprising a Q39K amino acid substitution mutation (boxed) in framework region (FR) 2. This heavy chain variable region sequence is particularly useful for single-cell manufacturing of TDBs. The complementarity-determining regions (CDRs) CDR L1, CDR L2, and CDR L3 are indicated according to the contact, Chothia, and Kabat definitions. CDR sequences according to the Kabat definition are underlined.

Figure 30:
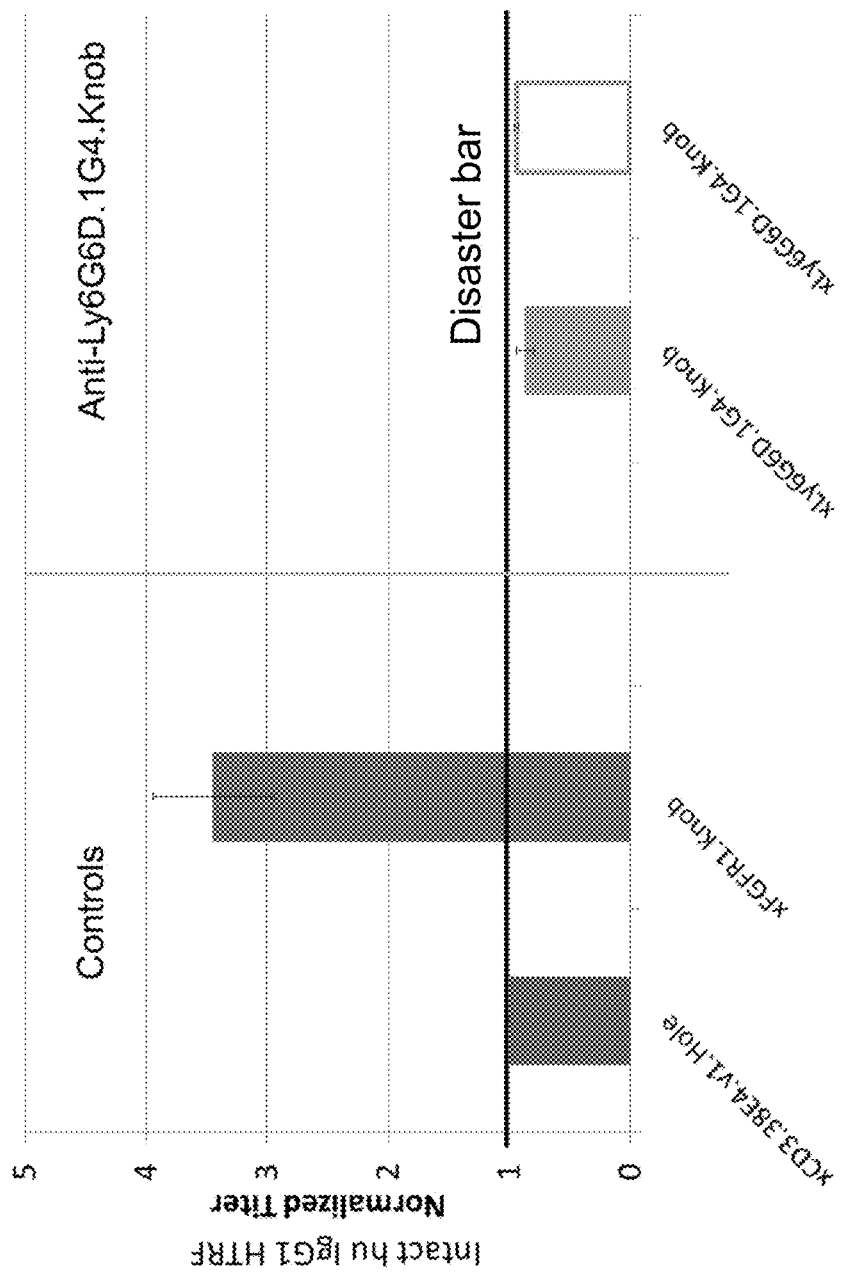

FIG. 30 is a graph showing the results of a transient transfection production assay for two manufacturing replicates of the anti-LY6G6D 1G4 arm. The anti-CD3 arm 38E4v1 and an anti-GFR1 arm are provided as controls.

Figure 31A:
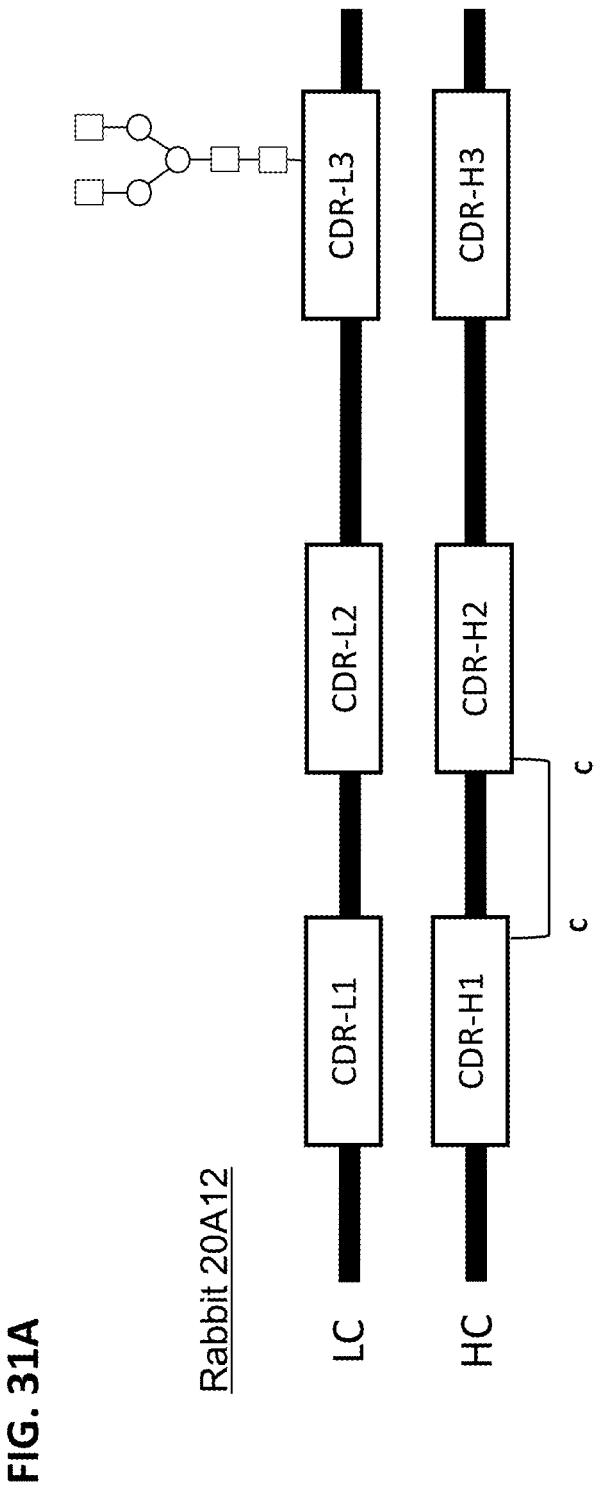

FIG. 31A is a diagram of the light chain (LC) and heavy chain (HC) of the rabbit clone 20A12 showing a glycosylation site at the CDR-L3 and a disulfide bond between two cysteine residues of the CDR-H1 and the CDR-L2.

Figure 31B:
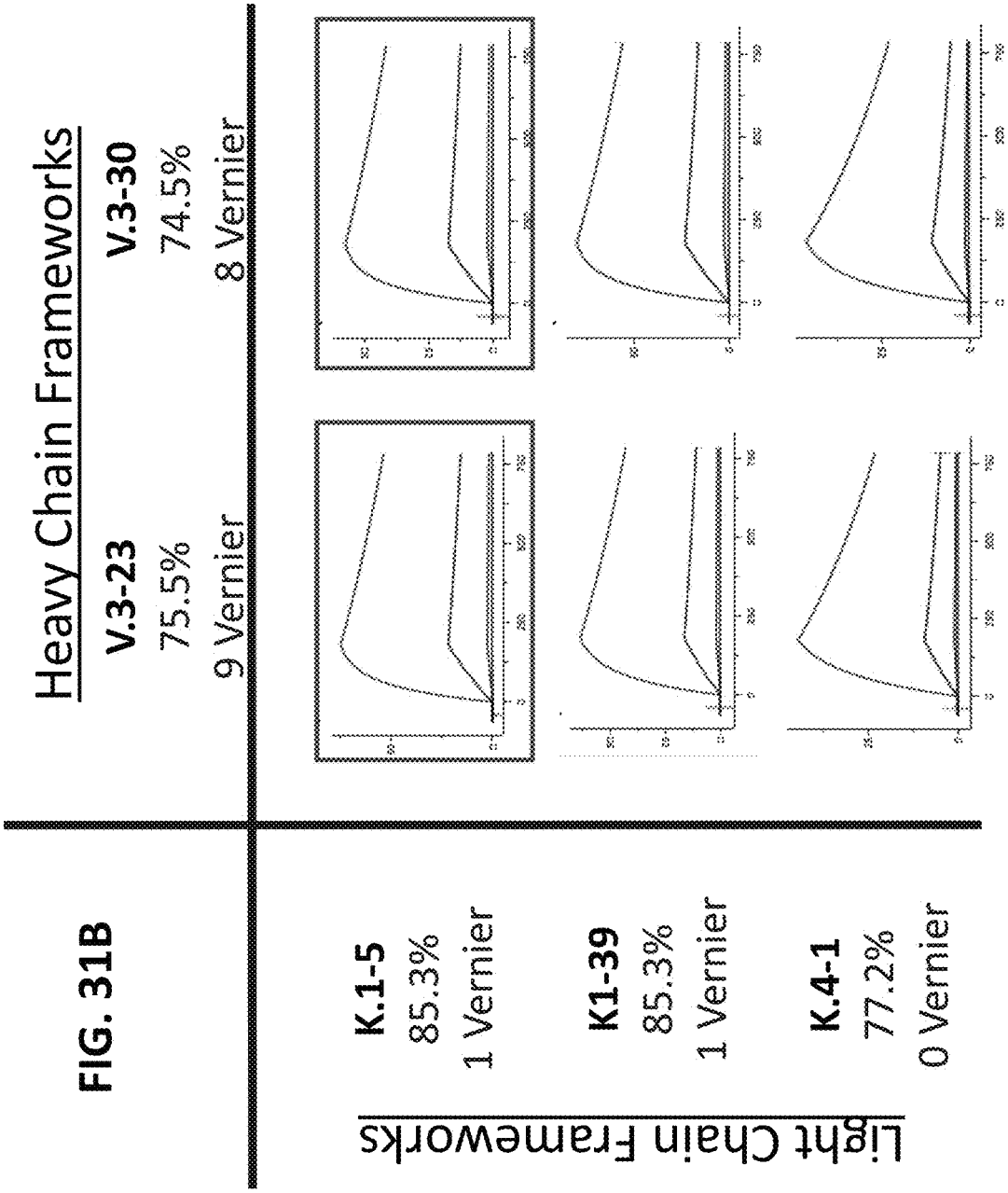

FIG. 31B is a set of graphs showing binding of variants of the anti-LY6G6D arm 20A12 comprising the rabbit 20A12 CDRs and the human light chain framework regions of hIGKV.1-5, hIGKV.1-39, and hIGKV.4-1, and the human heavy chain framework regions of hIGHV.3-23 and hIGHV.3-30 as measured using a BIAcore assay. The percent identity of the human germline sequence to the rb.20A12 sequence and the number of Vernier positions in each variant are shown.

FIG. 31C is a table showing the percent identity of various human VL germline sequences to the rb.20A12 sequence; the number of Vernier positions in each human germline sequence; and the prevalence of the germline sequence in humans.

FIG. 31D is a table showing the percent identity of various human VH germline sequences to the rb.20A12 sequence; the number of Vernier positions in each human germline sequence; and the prevalence of the germline sequence in humans.

Figure 32A:
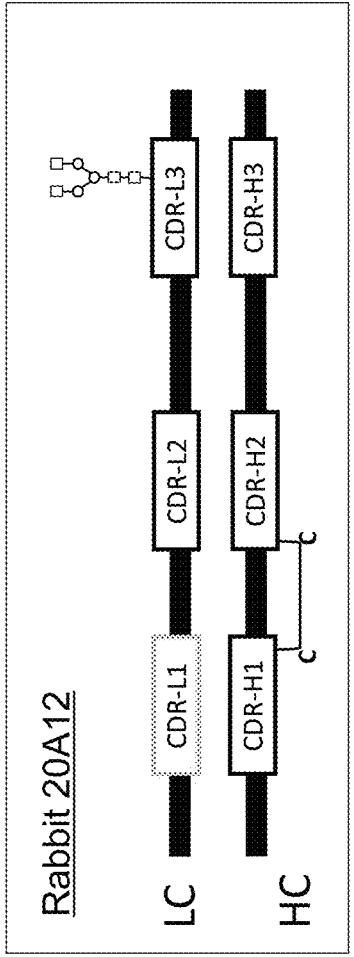

FIG. 32A is a diagram of the light chain (LC) and heavy chain (HC) of the rabbit clone 20A12 showing a glycosylation site at the CDR-L3 and a disulfide bond between two cysteine residues of the CDR-H1 and the CDR-L2.

Figure 32B:
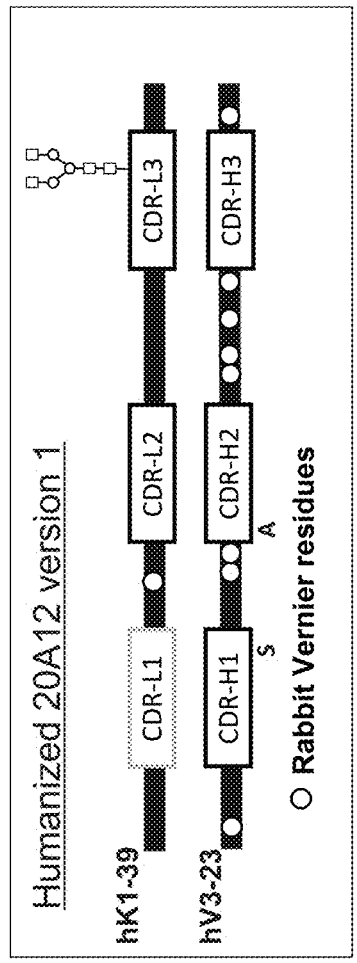

FIG. 32B is a diagram of the LC and HC of the humanized 20A12 variant 20A12.v1 showing a glycosylation site at the CDR-L3 and C35S amino acid substitution mutations that eliminate a disulfide bond between two cysteine residues of the CDR-H1 and the CDR-L2. 20A12.v1 comprises the VH framework regions of hIGHV.3-23 and the VL framework regions of hIGKV.1-39. The human framework regions have been modified at nine positions (circles) to comprise Vernier residues derived from the 20A12 rabbit sequence.

Figure 32C:
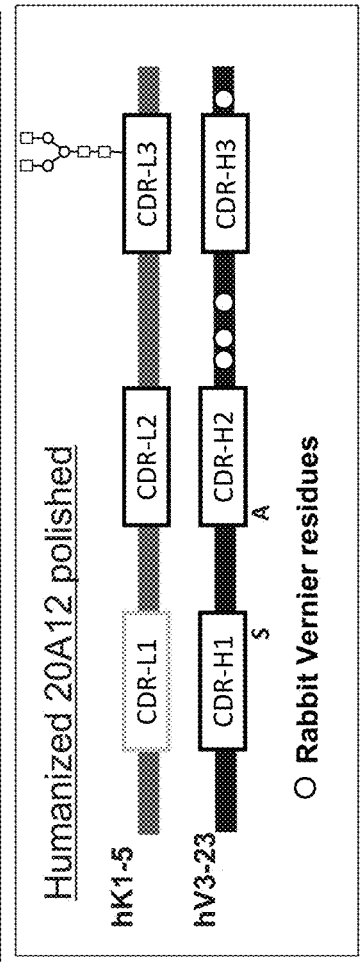

FIG. 32C is a diagram of the LC and HC of the polished humanized 20A12 variant showing a glycosylation site at the CDR-L3 and C35S and C50A amino acid substitution mutations that eliminate a disulfide bond between two cysteine residues of the CDR-H1 and the CDR-L2. The polished 20A12 variant comprises the VH framework regions of hIGHV.3-23 and the VL framework regions of hIGKV.1-5. The human framework regions have been modified at four positions (circles) to comprise Vernier residues derived from the 20A12 rabbit sequence.

FIG. 32D is a pair of diagrams and a table showing KD for rb.20A12 and various humanized variants thereof. The center column indicates amino acid substitution mutations relative to the human framework region heavy chain (H) sequences of hIGHV.3-23 and human framework region light chain (L) sequences that revert the amino acid position to a rabbit Vernier residue.

FIG. 33A is a table showing the percent identity of various human VL germline sequences to the rb.6E10 sequence; the number of Vernier positions in each human germline sequence; and the prevalence of the germline sequence in humans.

FIG. 33B is a table showing the percent identity of various human VH germline sequences to the rb.6E10 sequence; the number of Vernier positions in each human germline sequence; and the prevalence of the germline sequence in humans.

FIG. 34A is a set of graphs showing binding of rb.20A12 and a variety of chimeric Fabs having rb.20A12 variable domains and human constant regions to a Ly6G6D polypeptide, as measured using a BIAcore assay. Each of the chimeric Fabs comprises amino acid mutations at each of C35 of CDR-H1 and C50 of CDR-H2), as follows: C35S-C50A (SA), C35S-C50S (SS), C35I-C50A (IA), C35I-C50S (IS), and C35I-C50I (II). KD for each chimeric Fab is indicated.

Figure 34B:
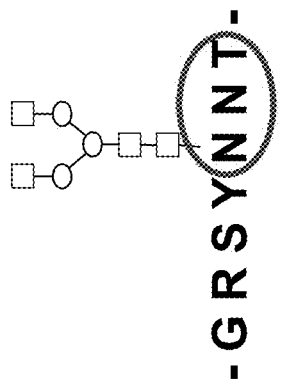

FIG. 34B is a sequence diagram showing a glycosylation site at the CDR-L3 of rb.20A12 having the sequence NNT and a table showing KD of variants of the polished humanized 20A12 light chain sequence described above having amino acid substitution mutations at the glycosylation site, as measured using a BIAcore assay for binding to LY6G6D.

FIG. 34C is a set of graphs showing binding of Fab variants of rabbit 20A12, rabbit 20A12 comprising C35I and C50A (IA) mutations, and the polished humanized 20A12 having a QNT amino acid substitution mutations at the glycosylation site of FIG. 34B to LY6G6D, as measured using a BIAcore assay. Ly6G6D-Fc was captured on a Protein A chip, and the Fab was flowed through at 37° C.

Figure 34D:
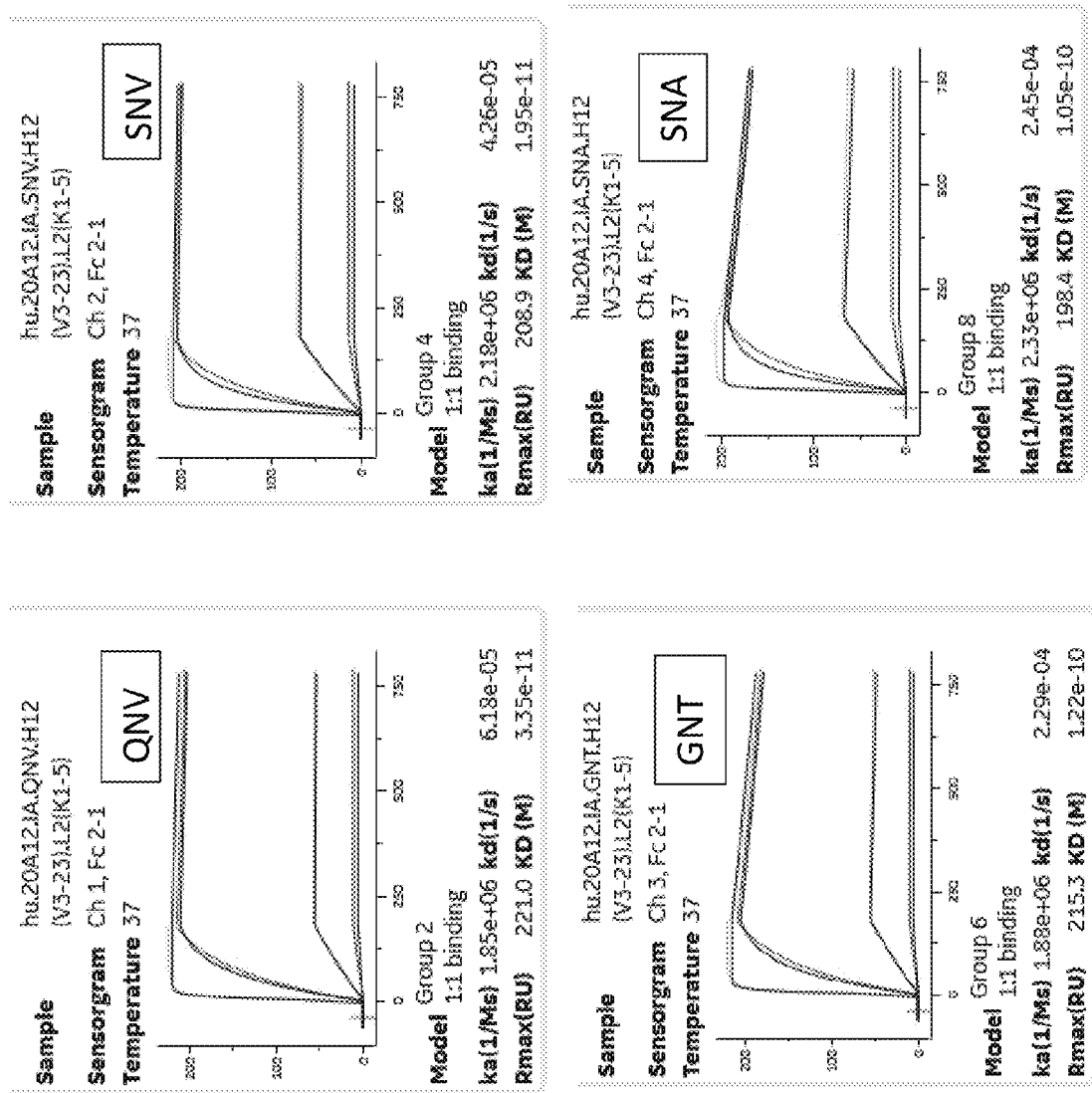

FIG. 34D is a set of graphs showing binding of Fab variants of the polished humanized 20A12 light chain sequence having QNV, SNV, GNT, and SNA amino acid substitution mutations at the glycosylation site of FIG. 34B to a Ly6G6D polypeptide, as measured using a BIAcore assay. Ly6G6D-Fc was captured on a Protein A chip, and the Fab was flowed through at 37° C.

FIG. 35A is a diagram showing the rabbit 20A12 of FIG. 32A and a graph showing binding of the diagrammed antibody to LY6G6D, as measured using a BIAcore assay.

FIG. 35B is a diagram showing the polished humanized 20A12 variant 20A12.QNTv12 and a graph showing binding of the diagrammed antibody to LY6G6D, as measured using a BIAcore assay.

Figure 36:
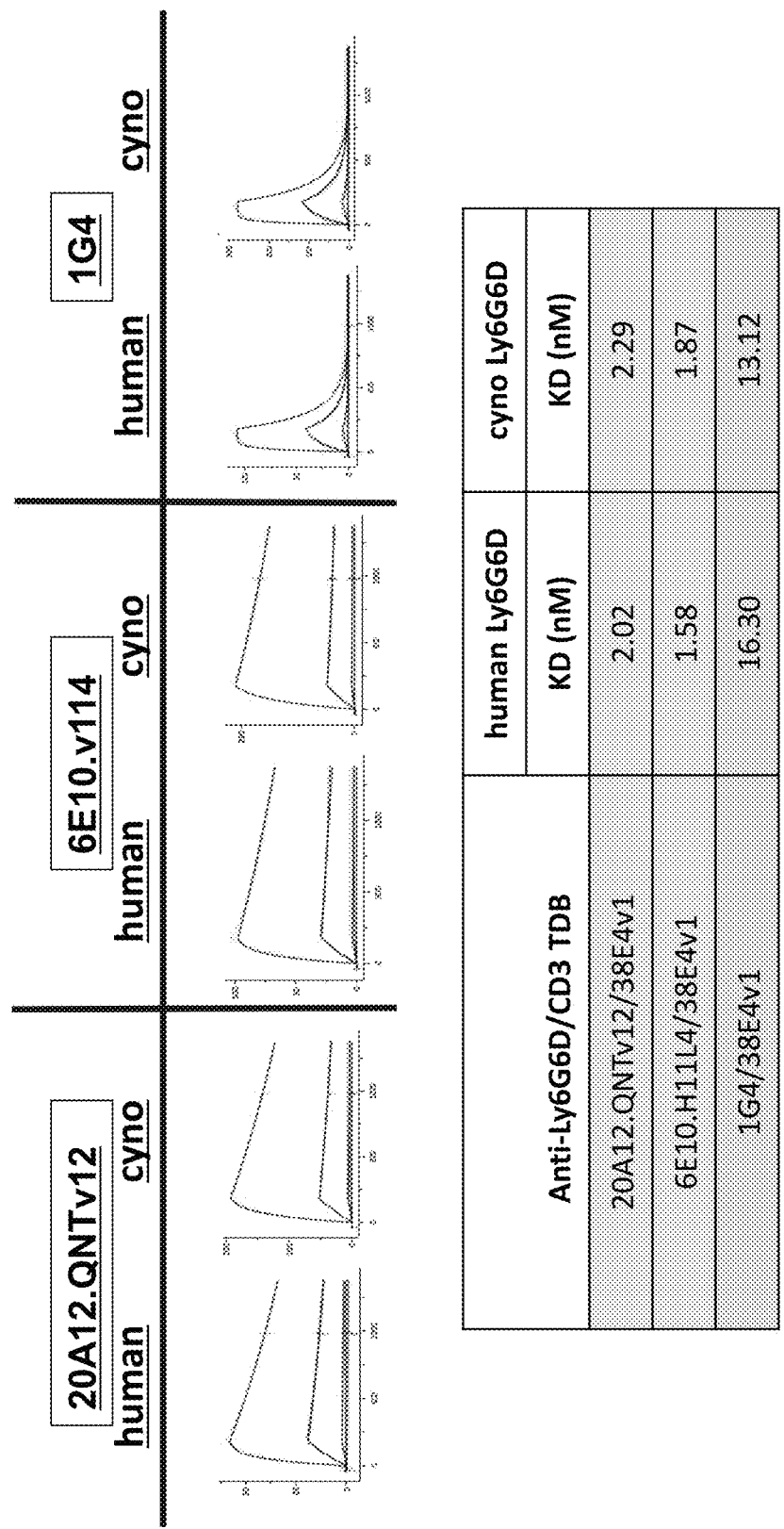

FIG. 36 is a set of graphs showing binding of 20A12.QNTv12, 6E10.v114, and 1G4 to human and cyno LY6G6D polypeptides and a table summarizing KD for each assay, as measured using a BIAcore assay. Ly6G6D-Fc was directly immobilized on the chip, and the TDB was flowed through at 37° C.

Figure 37:
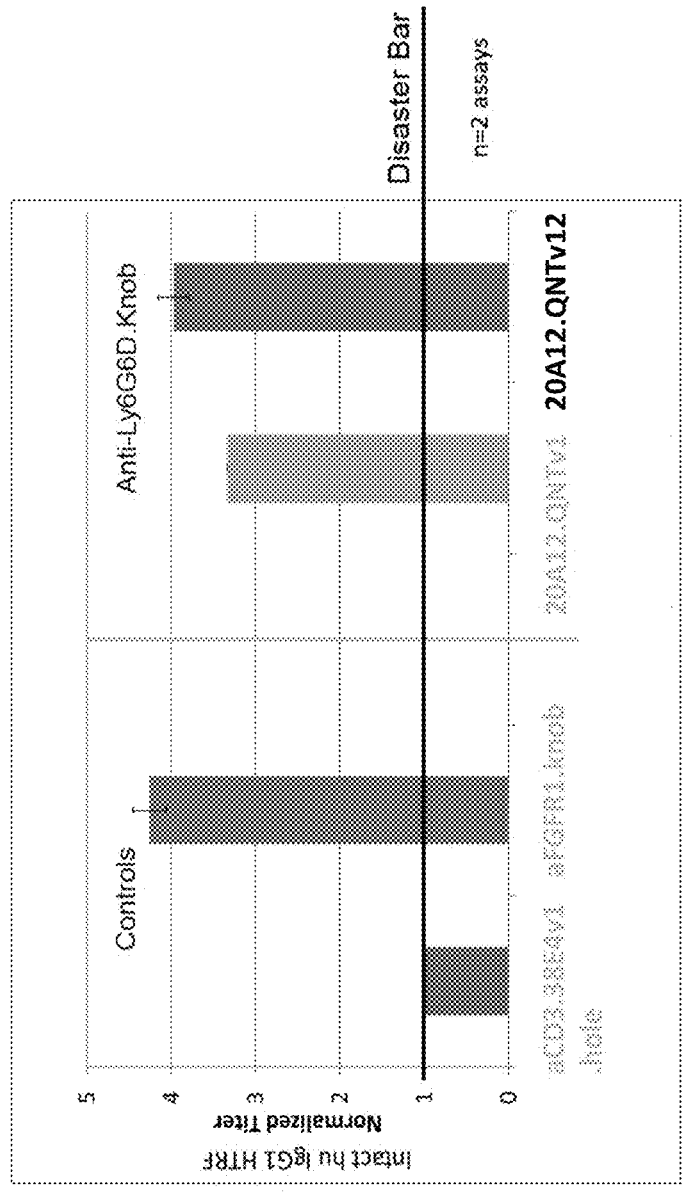

FIG. 37 is a graph showing the results of a transient transfection production assay for the anti-LY6G6D 20A12.QNTv.1 and 20A12.QNTv12 arms. The anti-CD3 arm 38E4v1 and an anti-FGFR1 arm are provided as controls.

Figure 38:
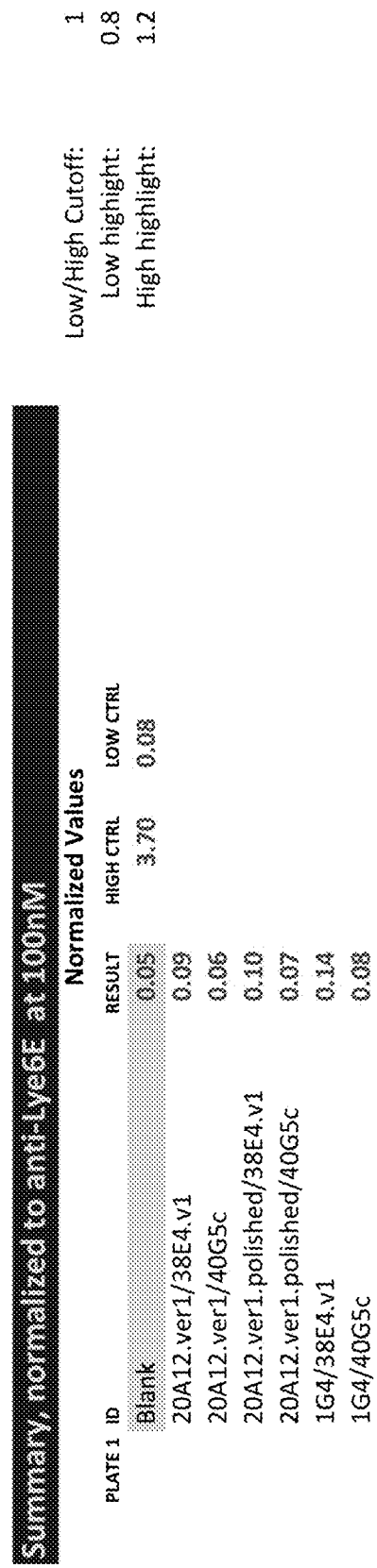

FIG. 38 is a table showing the results of a baculovirus (BV) ELISA assay for non-specific clearance for the anti-LY6G6D 20A12.QNTv12 (20A12.ver1.polished) arm.

Figure 39:

FIG. 39 is a table showing the results of molecule assessment (MA) analyses of TDBs comprising the anti-LY6G6D 20A12.QNTv12 arm and the anti-CD3 38E4v1 or 40G5c arm. Green coloring indicates assays for which no apparent issues were identified.

Figure 40A:
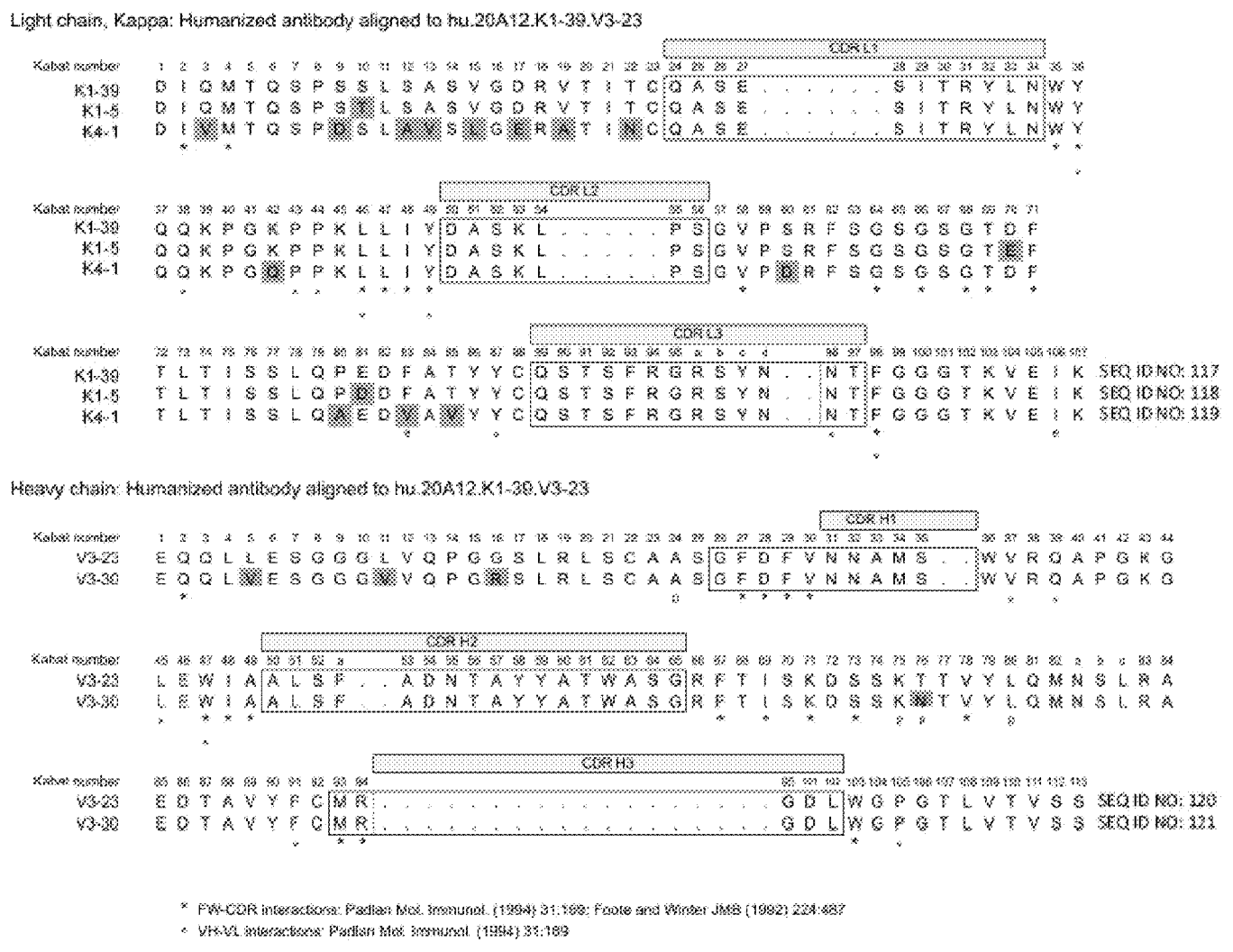

FIG. 40A is a sequence alignment showing the amino acid sequences of humanized variants of 20A12 comprising the CDRs of rb.20A12 and the VH framework regions of the human germline sequence hIGHV.3-23 or hIGHV.3-30 and the VL framework regions of the human germline sequence hIGHV.1-5, hIGKV.1-39, or hIGKV.4-1, each having rabbit Vernier residues. The complementarity-determining regions (CDRs) CDR L1, CDR L2, and CDR L3 are indicated. Residues that differ among the sequences are highlighted.

Figure 40B:
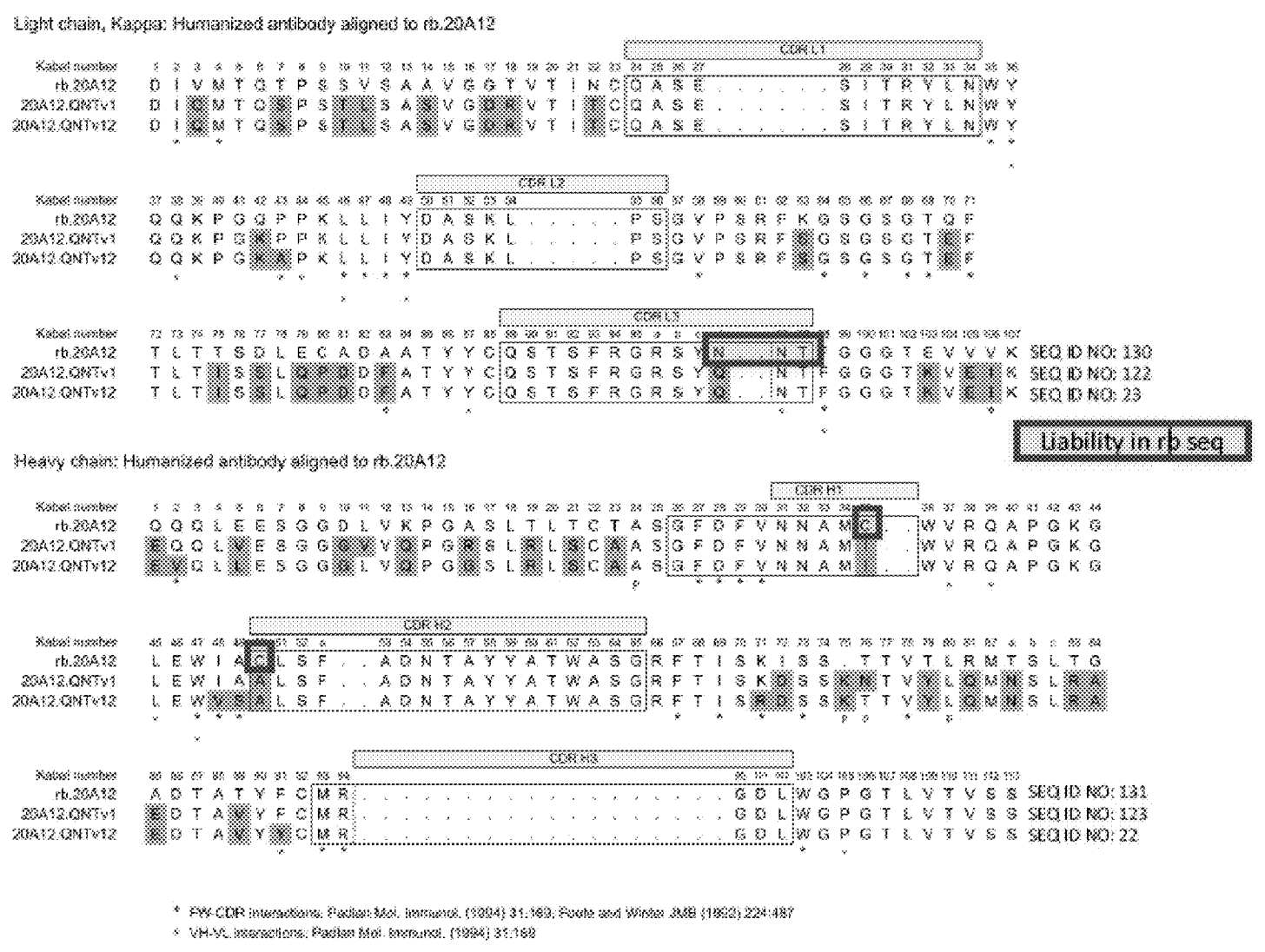

FIG. 40B is a sequence alignment showing the amino acid sequences of rb.20A12 and the humanized variants 20A12.QNTv.1 and 20A12.QNTv12. The complementarity-determining regions (CDRs) CDR L1, CDR L2, and CDR L3 are indicated. Residues that differ among the sequences are highlighted.

Figure 40C:
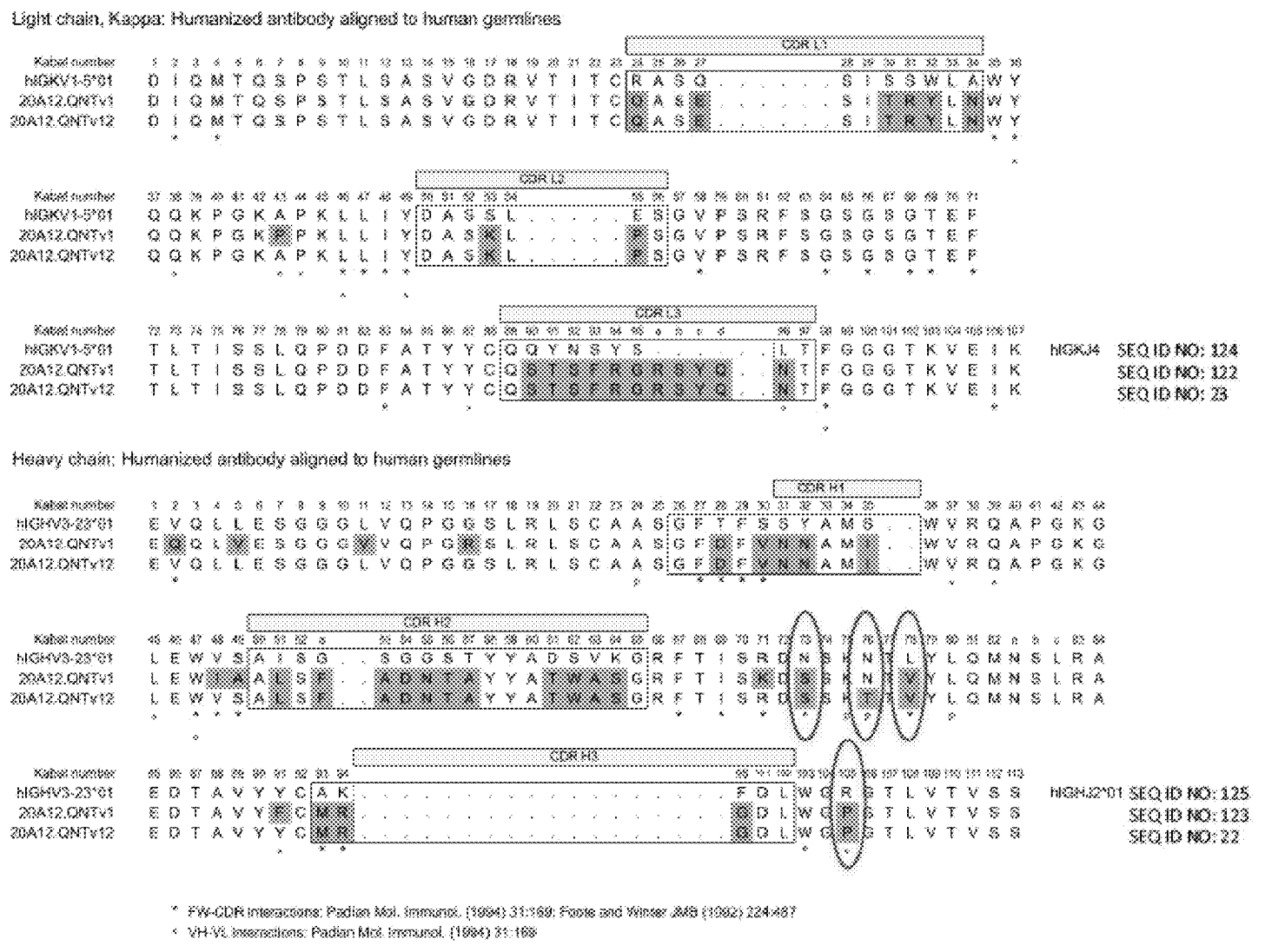

FIG. 40C is a sequence alignment showing the amino acid sequences of VH of the human germline sequence hIGHV.3-23, the VL of the human germline sequence hIGHV.1-5, and the VH and VL of the humanized 20A12 variants 20A12.QNTv.1 and 20A12.QNTv12. Rabbit Vernier residues present in 20A12.QNTv.1 and 20A12.QNTv12 are indicated by ovals. The complementarity-determining regions (CDRs) CDR L1, CDR L2, and CDR L3 are indicated. Residues that differ among the sequences are highlighted.

FIG. 41 is a table showing the results of molecule assessment (MA) analyses of the 6E10v1 Fab. Green coloring indicates assays for which no apparent issues were identified; red coloring indicates that issues were identified.

Figure 42:
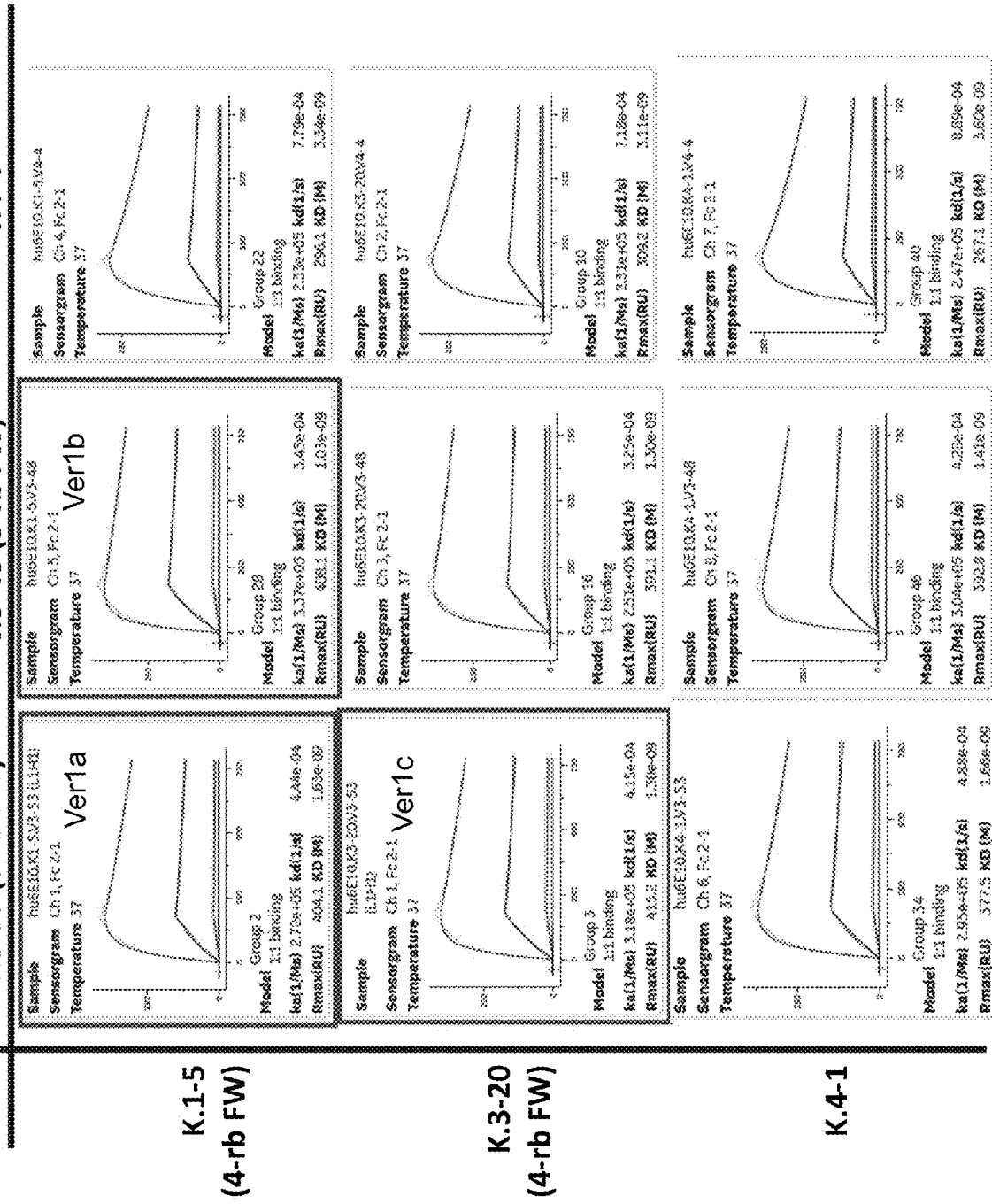

FIG. 42 is a set of graphs showing binding of variants of the anti-LY6G6D arm 6E10 comprising the rabbit 6E10 CDRs and the VH framework regions of the human germline sequence hIGHV.3-53, hIGHV.4-4, or hIGHV.3-48 and the VL framework regions of the human germline sequence hIGHV.1-5, hIGKV.3-20, or hIGKV.4-1, as measured using a BIAcore assay. The number of Vernier positions in each variant are shown.

Figure 43A:
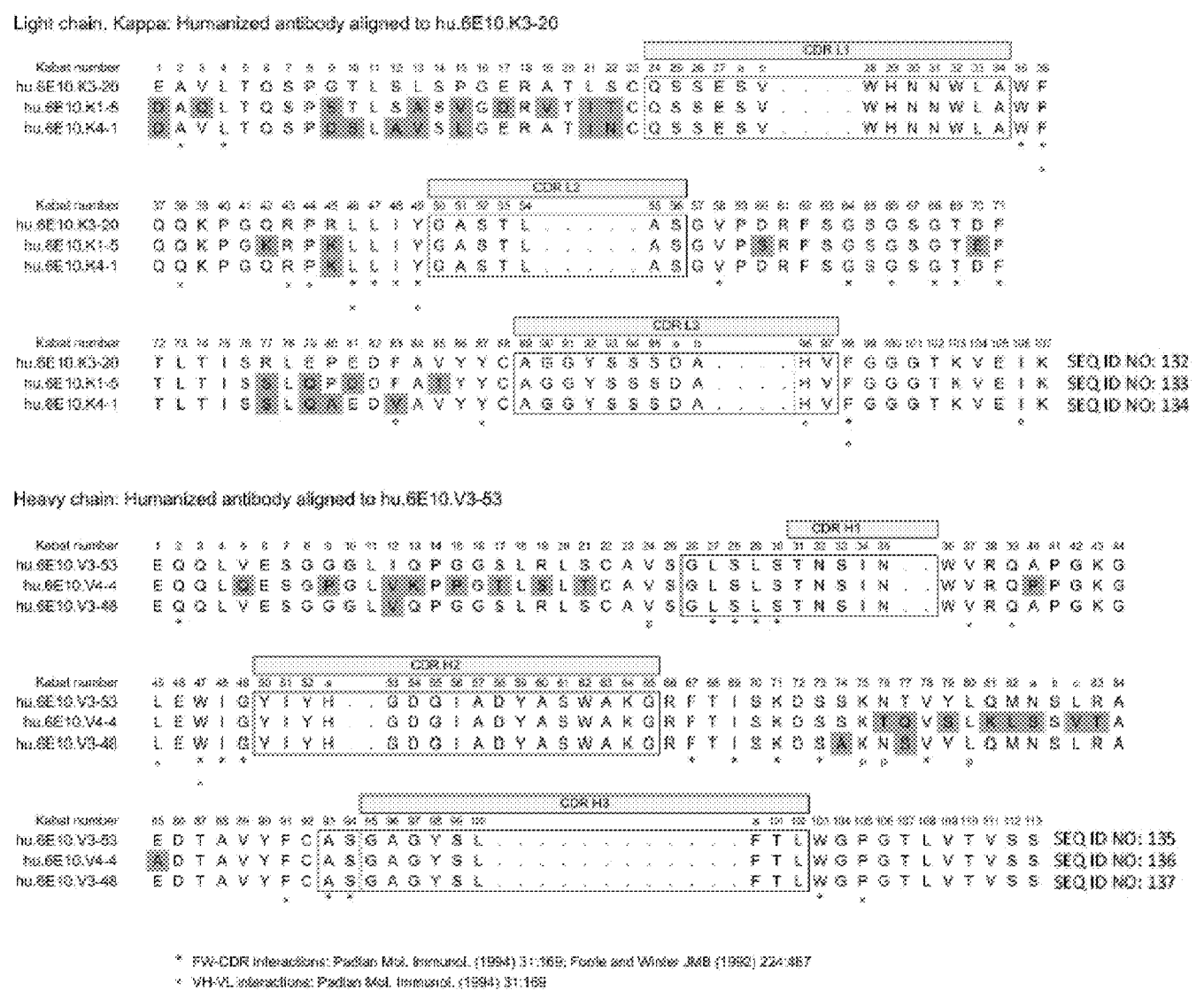

FIG. 43A is a sequence alignment showing the amino acid sequences of humanized variants of 6E10 comprising the CDRs of rb.6E10 and the VH framework regions of the human germline sequence hIGHV.3-53, hIGHV.4-4, or hIGHV.3-48 and the VL framework regions of the human germline sequence hIGHV.1-5, hIGKV.3-20, or hIGKV.4-1. The complementarity-determining regions (CDRs) CDR L1, CDR L2, and CDR L3 are indicated. Residues that differ among the sequences are highlighted.

Figure 43B:
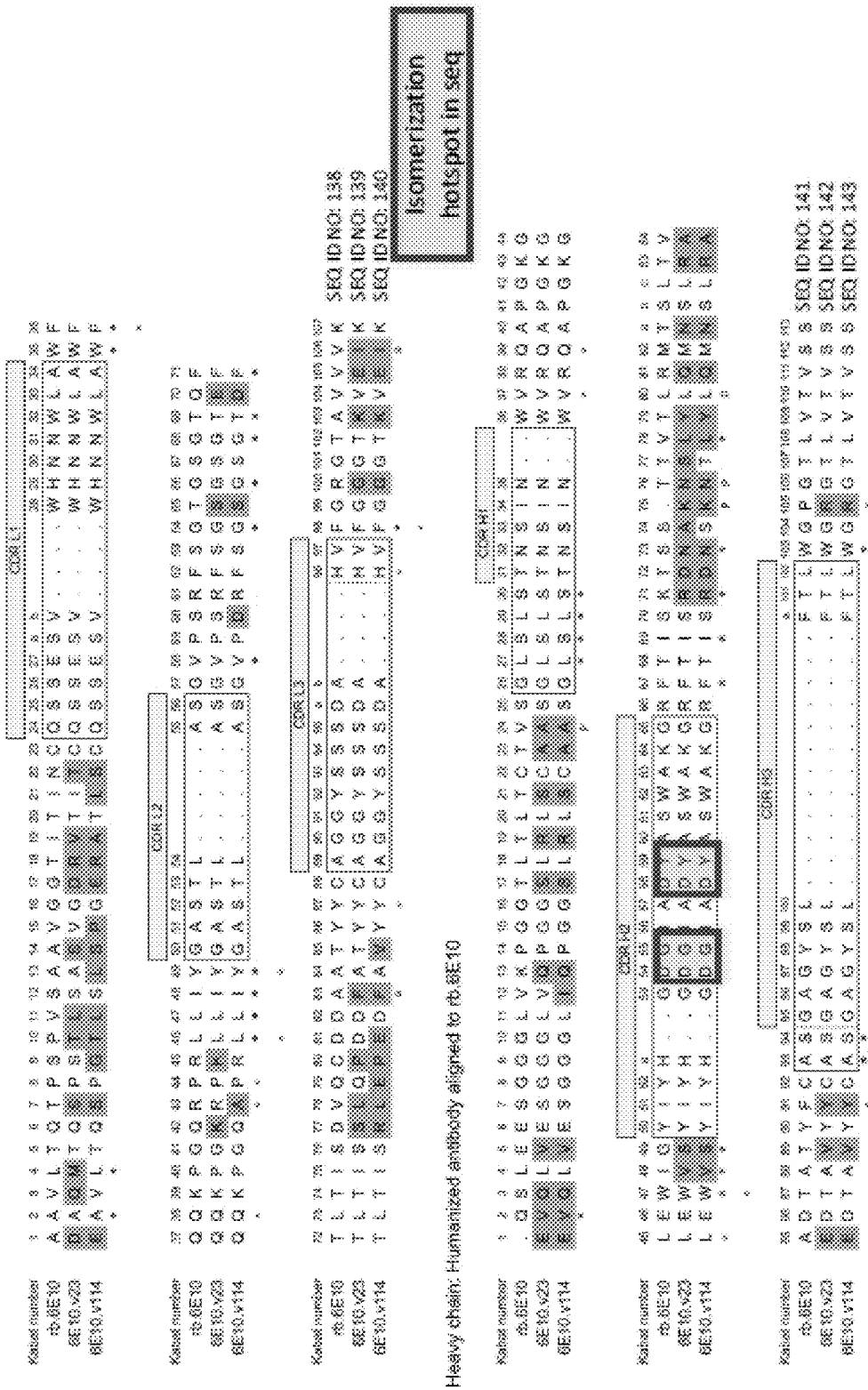

FIG. 43B is a sequence alignment showing the amino acid sequences of rb.6E10 and the humanized variants 6E10.v23 and 6E10.v114. The complementarity-determining regions (CDRs) CDR L1, CDR L2, and CDR L3 are indicated. Residues that differ among the sequences are highlighted.

Figure 43C:
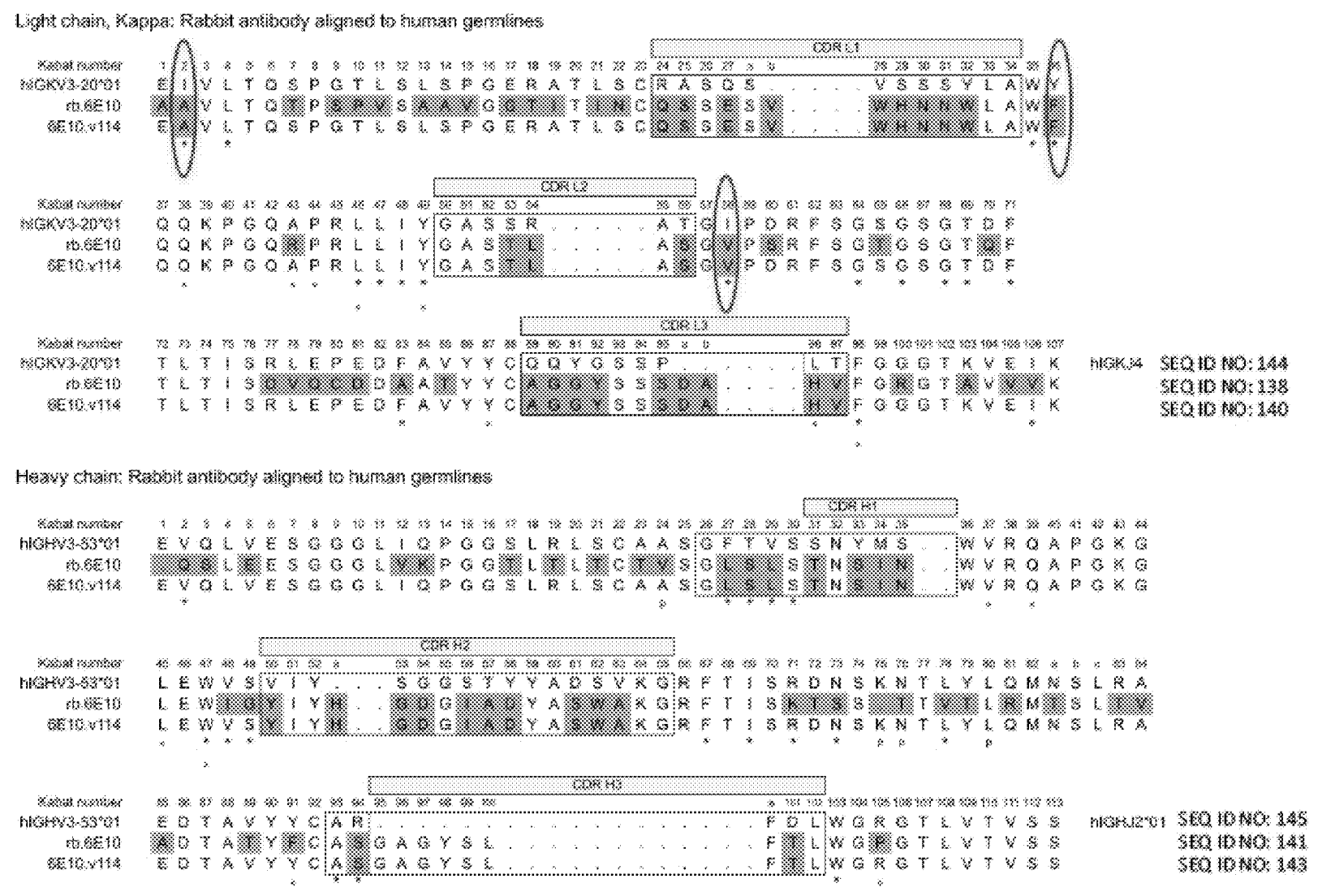

FIG. 43C is a sequence alignment showing the amino acid sequences of VH of the human germline sequence hIGHV.3-53*01, the VL of the human germline sequence hIGHV.3-20*01, and the VH and VL of rb.6E10 and the humanized 6E10 variant 6E10.v114. Rabbit Vernier residues present in rb.6E10 and 6E10.v114 are indicated by ovals. The complementarity-determining regions (CDRs) CDR L1, CDR L2, and CDR L3 are indicated. Residues that differ among the sequences are highlighted.

Figure 43D:
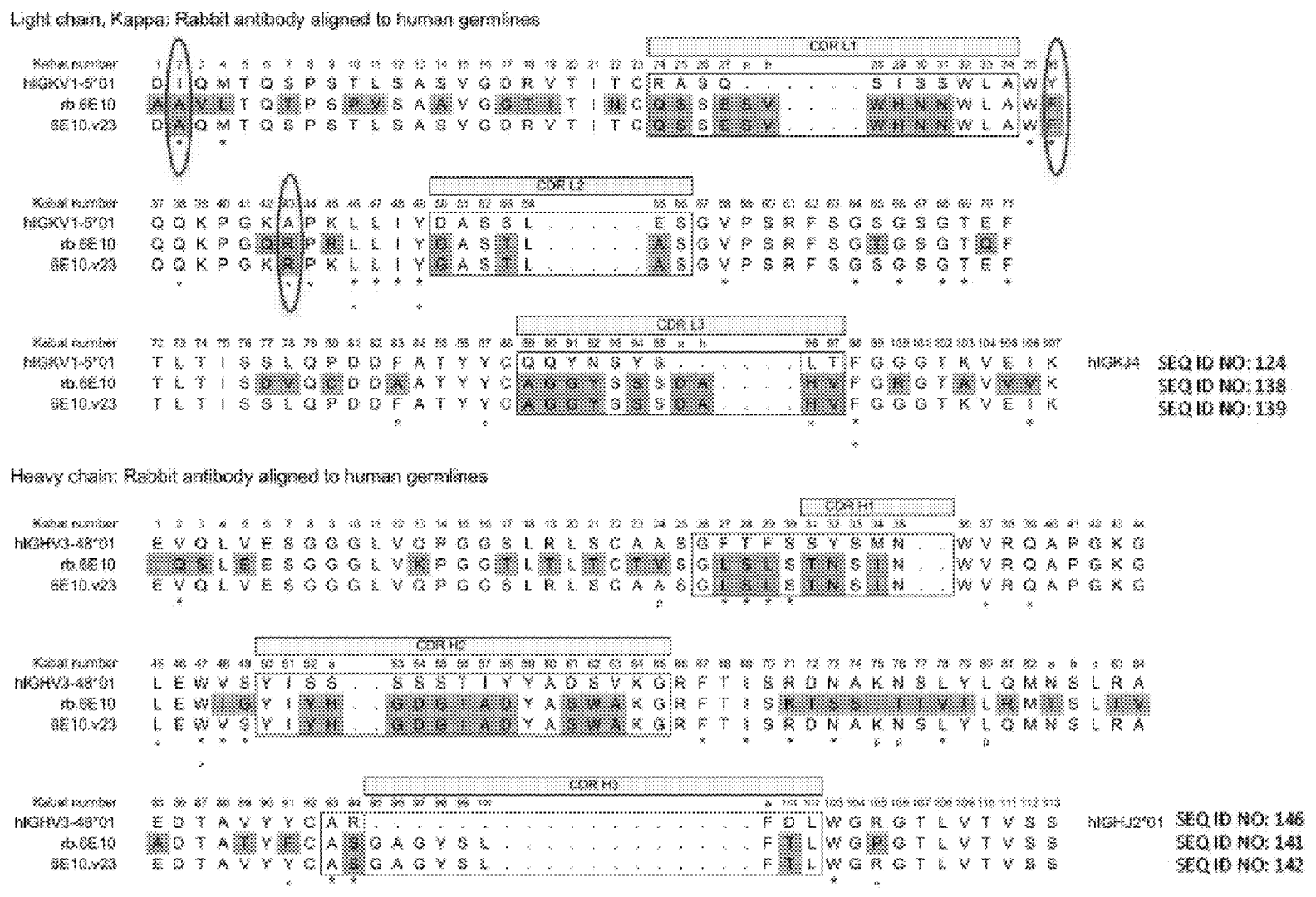

FIG. 43D is a sequence alignment showing the amino acid sequences of VH of the human germline sequence hIGHV.3-48*01, the VL of the human germline sequence hIGHV.1-5*01, and the VH and VL of rb.6E10 and the humanized 6E10 variant 6E10.v23. Rabbit Vernier residues present in rb.6E10 and 6E10.v23 are indicated by ovals. The complementarity-determining regions (CDRs) CDR L1, CDR L2, and CDR L3 are indicated. Residues that differ among the sequences are highlighted.

DETAILED DESCRIPTION OF THE INVENTION

I. Definitions

The term "about" as used herein refers to the usual error range for the respective value readily known to the skilled person in this technical field. Reference to "about" a value or parameter herein includes (and describes) aspects that are directed to that value or parameter per se.

It is understood that aspects of the invention described herein include "comprising," "consisting," and "consisting essentially of" aspects.

The term "Ly6G6D" or "lymphocyte antigen 6 complex, locus G61," as used herein, refers to any native Ly6G6D from any vertebrate source, including mammals such as primates (e.g. humans) and rodents (e.g., mice and rats), unless otherwise indicated, and encompasses "full-length," unprocessed Ly6G6D, as well as any form of Ly6G6D that results from processing in the cell. The term also encompasses naturally occurring variants of Ly6G6D, including, for example, splice variants or allelic variants. Ly6G6D is also referred to as G6D, Ly6-D, C6orf23, megakaryocyte-enhanced gene transcript 1 (MEGT1), and NG25 and is disclosed in U.S. Pat. No. 7,951,546, which is incorporated by reference herein in its entirety, as TAT201, with an amino acid sequence of SEQ ID NO: 75 and a nucleotide sequence, DNA234441, of SEQ ID NO: 76. Ly6G6D includes, for example, human Ly6G6D protein (NCBI RefSeq No. NP_067079.2), which is 133 amino acids in length.

The terms "anti-LY6G6D antibody" and "an antibody that binds to LY6G6D" refer to an antibody that is capable of binding LY6G6D with sufficient affinity such that the antibody is useful as a diagnostic and/or therapeutic agent in targeting LY6G6D. In one embodiment, the extent of binding of an anti-LY6G6D antibody to an unrelated, non-LY6G6D protein is less than about 10% of the binding of the antibody to LY6G6D as measured, e.g., by a radioimmunoassay (RIA). In certain embodiments, an antibody that binds to LY6G6D has a dissociation constant ($K_D$) of ≤1 µM, ≤250 nM, ≤100 nM, ≤15 nM, ≤10 nM, ≤6 nM, ≤4 nM, ≤2 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$M to $10^{-13}$ M). In certain embodiments, an anti-LY6G6D antibody binds to an epitope of LY6G6D that is conserved among LY6G6D from different species.

The term "cluster of differentiation 3" or "CD3," as used herein, refers to any native CD3 from any vertebrate source, including mammals such as primates (e.g. humans) and rodents (e.g., mice and rats), unless otherwise indicated, including, for example, CD3ε, CD3γ, CD3α, and CD3β chains. The term encompasses "full-length," unprocessed CD3 (e.g., unprocessed or unmodified CD3ε or CD3γ), as well as any form of CD3 that results from processing in the cell. The term also encompasses naturally occurring variants of CD3, including, for example, splice variants or allelic variants. CD3 includes, for example, human CD3ε protein (NCBI RefSeq No. NP_000724), which is 207 amino acids in length, and human CD3γ protein (NCBI RefSeq No. NP_000064), which is 182 amino acids in length.

The terms "anti-CD3 antibody" and "an antibody that binds to CD3" refer to an antibody that is capable of binding CD3 with sufficient affinity such that the antibody is useful as a diagnostic and/or therapeutic agent in targeting CD3. In one embodiment, the extent of binding of an anti-CD3 antibody to an unrelated, non-CD3 protein is less than about 10% of the binding of the antibody to CD3 as measured, e.g., by a radioimmunoassay (RIA). In certain embodiments, an antibody that binds to CD3 has a dissociation constant ($K_D$) of ≤1 µM, ≤250 nM, ≤100 nM, ≤15 nM, ≤10 nM, ≤5 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$M to $10^{-13}$ M). In certain embodiments, an anti-CD3 antibody binds to an epitope of CD3 that is conserved among CD3 from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments (e.g., bis-Fabs) so long as they exhibit the desired antigen-binding activity.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Specific illustrative and exemplary aspects for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "full-length antibody," "intact antibody," and "whole antibody" are used herein interchangeably to refer to an antibody having a structure substantially similar to a native antibody structure or having heavy chains that contain an Fc region as defined herein.

An "antibody fragment" refers to a molecule other than an intact antibody that comprises a portion of an intact antibody that binds the antigen to which the intact antibody binds. Examples of antibody fragments include but are not limited to bis-Fabs; Fv; Fab; Fab, Fab'-SH; F(ab')2; diabodies; linear antibodies; single-chain antibody molecules (e.g., scFv, ScFab); and multispecific antibodies formed from antibody fragments.

A "single-domain antibody" refers to an antibody fragment comprising all or a portion of the heavy chain variable domain or all or a portion of the light chain variable domain of an antibody. In certain aspects, a single-domain antibody is a human single-domain antibody (see, e.g., U.S. Pat. No. 6,248,516 B1). Examples of single-domain antibodies include but are not limited to a VHH.

A "Fab" fragment is an antigen-binding fragment generated by papain digestion of antibodies and consists of an entire L chain along with the variable region domain of the H chain (VH), and the first constant domain of one heavy chain (CH1). Papain digestion of antibodies produces two identical Fab fragments. Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having an additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Fv" consists of a dimer of one heavy- and one light-chain variable region domain in tight, noncovalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although often at a lower affinity than the entire binding site.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all Lys447 residues removed, antibody populations with no Lys447 residues removed, and antibody populations having a mixture of antibodies with and without the Lys447 residue.

A "functional Fc region" possesses an "effector function" of a native sequence Fc region. Exemplary "effector functions" include C1q binding; CDC; Fc receptor binding; ADCC; phagocytosis; down regulation of cell surface receptors (e.g., B cell receptor; BCR), etc. Such effector functions generally require the Fc region to be combined with a binding domain (e.g., an antibody variable domain) and can be assessed using various assays as disclosed, for example, in definitions herein.

A "native sequence Fc region" comprises an amino acid sequence identical to the amino acid sequence of an Fc region found in nature. Native sequence human Fc regions include a native sequence human IgG I Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, preferably at least about 90% homology therewith, or preferably at least about 95% homology therewith.

"Fc complex" as used herein refers to CH3 domains of two Fc regions interacting together to form a dimer or, as in certain aspects, two Fc regions interact to form a dimer, wherein the cysteine residues in the hinge regions and/or the CH3 domains interact through bonds and/or forces (e.g., Van der Waals, hydrophobic forces, hydrogen bonds, electrostatic forces, or disulfide bonds).

"Fc component" as used herein refers to a hinge region, a CH2 domain or a CH3 domain of an Fc region.

"Hinge region" is generally defined as stretching from about residue 216 to 230 of an IgG (EU numbering), from about residue 226 to 243 of an IgG (Kabat numbering), or from about residue 1 to 15 of an IgG (IMGT unique numbering).

The "lower hinge region" of an Fc region is normally defined as the stretch of residues immediately C-terminal to the hinge region, i.e., residues 233 to 239 of the Fc region (EU numbering).

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and preferably at least about 90% homology therewith, more preferably at least about 95% homology therewith.

"Fc receptor" or "FcR" describes a receptor that binds to the Fc region of an antibody. A preferred FcR is a native sequence human FcR. Moreover, a preferred FcR is one that binds an IgG antibody (a gamma receptor) and includes receptors of the FcγRI, FcγRII, and FcγRII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daëron, Annu. Rev. Immunol. 15:203-234 (1997)). FcRs are reviewed in Ravetch and Kinet, Annu. Rev. Immunol. 9:457-492 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

The term "knob-into-hole" or "KnH" technology as mentioned herein refers to the technology directing the pairing of two polypeptides together in vitro or in vivo by introducing a protuberance (knob) into one polypeptide and a cavity (hole) into the other polypeptide at an interface in which they interact. For example, KnHs have been introduced in the Fc:Fc interaction interfaces, CL:CH1 interfaces or VH/VL interfaces of antibodies (e.g., US2007/0178552, WO 96/027011, WO 98/050431 and Zhu et al. (1997) Protein Science 6:781-788). This is especially useful in driving the pairing of two different heavy chains together during the manufacture of multispecific antibodies. For example, multispecific antibodies having KnH in their Fc regions can further comprise single variable domains linked to each Fc region, or further comprise different heavy chain variable domains that pair with identical, similar, or different light chain variable domains. KnH technology can also be used to pair two different receptor extracellular domains together or any other polypeptide sequences that comprise different target recognition sequences.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The "CH1 region" or "CH1 domain" comprises the stretch of residues from about residue 118 to residue 215 of an IgG (EU numbering), from about residue 114 to 223 of an IgG (Kabat numbering), or from about residue 1.4 to residue 121 of an IgG (IMGT unique numbering) (Lefranc M-P, Giudicelli V, Duroux P, Jabado-Michaloud J, Folch G, Aouinti S, Carillon E, Duvergey H, Houles A, Paysan-Lafosse T, Hadi-Saljoqi S, Sasorith S, Lefranc G, Kossida S. IMGT®, the international ImMunoGeneTics information System® 25 years on. Nucleic Acids Res. 2015 January; 43 (Database issue):D413-22). The IL-15 polypeptide or IL-15Ra polypeptide may be covalently connected directly to the first residue of the CH1 domain, or alternatively may be covalently connected to a residue at a position C-terminal to the first residue of CH1. In alternative aspects, the IL-15 polypeptide or IL-15Ra polypeptide may be covalently connected to CH1 through a linker as defined herein.

The "CH2 domain" of a human IgG Fc region usually extends from about residues 244 to about 360 of an IgG (Kabat numbering), from about residues 231 to about 340 of an IgG (EU numbering), or from about residues 1.6 to about 125 of an IgG (IGMT unique numbering). The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, Molec. Immunol. 22: 161-206 (1985).

The "CH3 domain" comprises the stretch of residues C-terminal to a CH2 domain in an Fc region (i.e., from about amino acid residue 361 to about amino acid residue 478 of an IgG (Kabat numbering), from about amino acid residue 341 to about amino acid residue 447 of an IgG (EU numbering), or from about amino acid residue 1.4 to about amino acid residue 130 of an IgG (IGMT unique numbering)).

The "CL domain" or "constant light domain" comprises the stretch of residues C-terminal to a light-chain variable domain (VL). The light chain of an antibody may be a kappa (κ) ("Cκ") or lambda (λ) ("Cλ") light chain region. The Cκ region generally extends from about residue 108 to residue 214 of an IgG (Kabat or EU numbering) or from about residue 1.4 to residue 126 of an IgG (IMGT unique numbering). The Cλ residue generally extends from about residue 107a to residue 215 (Kabat numbering) or from about residue 1.5 to residue 127 (IMGT unique numbering) (Lefranc M-P, Giudicelli V, Duroux P, Jabado-Michaloud J, Folch G, Aouinti S, Carillon E, Duvergey H, Houles A, Paysan-Lafosse T, Hadi-Saljoqi S, Sasorith S, Lefranc G, Kossida S. IMGT®, the international ImMunoGeneTics information System® 25 years on. Nucleic Acids Res. 2015 January; 43 (Database issue):D413-22).

The light chain (LC) from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated α, δ, γ, ε, and μ, respectively. The γ and α classes are further divided into subclasses on the basis of relatively minor differences in CH sequence and function, e.g., humans express the following subclasses: IgG1, IgG2, IgG3, IgG4, IgA1, and IgA2.

As used herein the term "charged region" refers to a location of a polypeptide (e.g., an antibody) that includes one or more (e.g., 1, 2, 3, 4, 5, 6, 7, 8, 9, or 10) basic or acidic amino acids that are capable of forming a charge pair with a cognate charged region having one or more (e.g., 1, 2, 3, 4, 5, 6, 7, 8, 9, or 10) or basic or acidic amino acids, when the charged region and its cognate charged region have opposite overall relative charge.

As used herein the term "charge pair" refers to the bond that is formed between two charged regions of opposite overall charge.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. Human antibodies can be produced using various techniques known in the art, including phage-display libraries. Hoogenboom and Winter. *J. Mol. Biol.* 227:381, 1991; Marks et al. *J. Mol. Biol.* 222:581, 1991. Also available for the preparation of human monoclonal antibodies are methods described in Cole et al. *Monoclonal Antibodies and Cancer Therapy*, Alan R. Liss, p. 77 (1985); Boerner et al. *J. Immunol.*, 147(1):86-95, 1991. See also van Dijk and van de Winkel. *Curr. Opin. Pharmacol.* 5:368-74, 2001. Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al. *Proc. Natl. Acad. Sci. USA*. 103:3557-3562, 2006 regarding human antibodies generated via a human B-cell hybridoma technology.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al. *Sequences of Proteins of Immunological Interest*, Fifth Edition, NIH Publication 91-3242, Bethesda Md. (1991), vols. 1-3. In one aspect, for the VL, the subgroup is subgroup kappa I as in Kabat et al. supra. In one aspect, for the VH, the subgroup is subgroup III as in Kabat et al. supra.

A "humanized" antibody refers to a chimeric antibody comprising amino acid residues from non-human HVRs and amino acid residues from human FRs. In certain aspects, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. In certain aspects in which all or substantially all of the FRs of a humanized antibody correspond to those of a human antibody, any of the FRs of the humanized antibody may contain one or more amino acid residues (e.g., one or more Vernier position residues of FRs) from non-human FR(s). A humanized antibody optionally may comprise at least a portion of an antibody constant region derived from a human antibody.

A "humanized form" of an antibody, e.g., a non-human antibody, refers to an antibody that has undergone humanization.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed. W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al. *J. Immunol.* 150:880-887, 1993; Clarkson et al. *Nature* 352:624-628, 1991.

The term "hypervariable region" or "HVR" as used herein refers to each of the regions of an antibody variable domain which are hypervariable in sequence ("complementarity determining regions" or "CDRs"). Generally, antibodies comprise six CDRs: three in the VH (CDR-H1, CDR-H2, CDR-H3), and three in the VL (CDR-L1, CDR-L2, CDR-L3). Exemplary CDRs herein include:

(a) CDRs occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917, 1987);

(b) CDRs occurring at amino acid residues 24-34 (L1), 50-56 (L2), 89-97 (L3), 31-35b (H1), 50-65 (H2), and 95-102 (H3) (Kabat et al. *Sequences of Proteins of Immunological Interest*, 5th Ed. Public Health Service, National Institutes of Health, Bethesda, Md. (1991)); and (c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745, 1996).

Unless otherwise indicated, HVR residues and other residues in the variable domain (e.g., FR residues) are numbered herein according to Kabat et al. supra.

"Single-chain Fv" also abbreviated as "sFv" or "scFv" are antibody fragments that comprise the VH and VL antibody domains connected into a single polypeptide chain. Preferably, the scFv polypeptide further comprises a polypeptide linker between the VH and VL domains, which enables the scFv to form the desired structure for antigen binding. For a review of scFv, see Pluckthun, The Pharmacology of Monoclonal Antibodies, vol. 113, Rosenburg and Moore eds., Springer-Verlag, New York, pp. 269-315 (1994); Malmborg et al., J. Immunol. Methods 183:7-13, 1995.

By "targeting domain" is meant a part of a compound or a molecule that specifically binds to a target epitope, antigen, ligand, or receptor. Targeting domains include but are not limited to antibodies (e.g., monoclonal, polyclonal, recombinant, humanized, and chimeric antibodies), antibody fragments or portions thereof (e.g., bis-Fab fragments, Fab fragments, F(ab')$_2$, scFab, scFv antibodies, SMIP, single-domain antibodies, diabodies, minibodies, scFv-Fc, affibodies, nanobodies, and VH and/or VL domains of antibodies), receptors, ligands, aptamers, peptide targeting domains (e.g., cysteine knot proteins (CKP)), and other molecules having an identified binding partner. A targeting domain may target, block, agonize, or antagonize the antigen to which it binds.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "multispecific antibody" is used in the broadest sense and specifically covers an antibody that has polyepitopic specificity. In one aspect, the multispecific antibody binds to two different targets (e.g., bispecific antibody). Such multispecific antibodies include, but are not limited to, an antibody comprising a heavy chain variable domain (VH) and a light chain variable domain (VL), where the VH/VL unit has polyepitopic specificity, antibodies having two or more VL and VH domains with each VH/VL unit binding to a different epitope, antibodies having two or more single variable domains with each single variable domain binding to a different epitope, full-length antibodies, antibody fragments such as Fab, Fv, dsFv, scFv, diabodies, bispecific diabodies and triabodies, antibody fragments that have been linked covalently or non-covalently. "Polyepitopic specificity" refers to the ability to specifically bind to two or more different epitopes on the same or different target(s). "Monospecific" refers to the ability to bind only one antigen. In one aspect, the monospecific biepitopic antibody binds two different epitopes on the same target/antigen. In one aspect, the monospecific polyepitopic antibody binds to multiple different epitopes of the same target/antigen. According to one aspect, the multispecific antibody is an IgG antibody that binds to each epitope with an affinity of 5 µM to 0.001 pM, 3 µM to 0.001 pM, 1 µM to 0.001 pM, 0.5 µM to 0.001 pM, or 0.1 µM to 0.001 pM.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

As used herein, the term "immunoadhesin" designates molecules which combine the binding specificity of a heterologous protein (an "adhesin") with the effector functions of immunoglobulin constant domains. Structurally, the immunoadhesins comprise a fusion of an amino acid sequence with a desired binding specificity, which amino acid sequence is other than the antigen recognition and binding site of an antibody (i.e., is "heterologous" compared to a constant region of an antibody), and an immunoglobulin constant domain sequence (e.g., CH2 and/or CH3 sequence of an IgG). The adhesin and immunoglobulin constant domains may optionally be separated by an amino acid spacer. Exemplary adhesin sequences include contiguous amino acid sequences that comprise a portion of a receptor or a ligand that binds to a protein of interest. Adhesin sequences can also be sequences that bind a protein of interest, but are not receptor or ligand sequences (e.g., adhesin sequences in peptibodies). Such polypeptide sequences can be selected or identified by various methods, include phage display techniques and high throughput sorting methods. The immunoglobulin constant domain sequence in the immunoadhesin can be obtained from any immunoglobulin, such as IgG1, IgG2, IgG3, or IgG4 subtypes, IgA (including IgA1 and IgA2), IgE, IgD, or IgM.

"Chemotherapeutic agent" includes chemical compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (Angew Chem. Intl. Ed. Engl. 1994 33:183-186); dynemicin, including dynemicin A; bisphosphonates, such as clodronate; an esperamicin;

as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMF®); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) antiandrogens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgG1 λ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. Eur. J. Cancer 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6. 3 and E7.6. 3 and described in U.S. Pat. No. 6,235,883; MDX-447 (Medarex Inc); and mAb 806 or humanized mAb 806 (Johns et al., J. Biol. Chem. 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl], dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl)methoxy]phenyl]-6[5[[[2methylsulfonyl) ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724, 714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804, 396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and flupred-nidene acetate; immune selective anti-inflammatory peptides (ImSAIDs) such as phenylalanine-glutamine-glycine (FEG) and its D-isomeric form (feG) (IMULAN BioTherapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (Enbrel), infliximab (Remicade), adalimumab (Humira), certolizumab pegol (Cimzia), golimumab (Simponi), interleukin 1 (IL-1) blockers such as anakinra (Kineret), T cell costimulation blockers such as abatacept (Orencia), interleukin 6 (IL-6) blockers such as tocilizumab (ACTEMERA®); interleukin 13 (IL-13) blockers such as lebrikizumab; interferon alpha (IFN) blockers such as Rontalizumab; beta 7 integrin blockers such as rhuMAb Beta7; IgE pathway blockers such as Anti-M1 prime; Secreted homotrimeric LTa3 and membrane bound heterotrimer LTa1/β2 blockers such as anti-lymphotoxin alpha (LTa); radioactive isotopes (e.g., $At^{211}$, $I^{131}$, $I^{125}$, $Y^{90}$, $Re^{186}$, $Re^{188}$, $sm^{153}$, $Bi^{212}$, $P^{32}$, $Pb^{212}$, and radioactive isotopes of Lu); miscellaneous investigational agents such as thioplatin, PS-341, phenylbutyrate, ET-18-OCH3, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifarnib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal anti-inflammatory drugs with analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $sm^{153}$, $Bi^{212}$, $P^{32}$, $Pb^{212}$, and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

A "disorder" is any condition that would benefit from treatment including, but not limited to, chronic and acute disorders or diseases including those pathological conditions which predispose a mammal to the disorder in question. In one aspect, the disorder is a cancer, e.g., a colorectal cancer.

The terms "cell proliferative disorder" and "proliferative disorder" refer to disorders that are associated with some degree of abnormal cell proliferation. In one aspect, the cell proliferative disorder is cancer. In one aspect, the cell proliferative disorder is a tumor.

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder," and "tumor" are not mutually exclusive as referred to herein. The terms "cancer" and "cancerous" refer to or describe the physiological condition in mammals that is typically characterized by unregulated cell growth/proliferation. Aspects of cancer include solid tumor cancers and non-solid tumor cancers. Solid cancer tumors include, but are not limited to a colorectal cancer, a melanoma, a breast cancer, a lung cancer, a head and neck cancer, a bladder cancer, a kidney cancer, an ovarian cancer, a pancreatic cancer, or a prostate cancer, or metastatic forms thereof. The cancer may by a LY6G6D-positive cancer.

In some aspects, the cancer is a colorectal cancer. As used herein, the term "colorectal cancer," "CRC," "colon cancer," or "bowel cancer" refers to a cancer that develops from the large intestine, e.g., the colon or rectum. In some aspects, a CRC is a left-sided tumor, i.e., a tumor occurring in the distal colon (e.g., the distal third of the transverse colon, the splenic flexure the descending colon, the sigmoid colon, or the rectum). In other aspects, a CRC is a right-sided tumor, i.e., a tumor occurring in the proximal colon (e.g., the proximal two-thirds of the transverse colon, the ascending colon, and the cecum). Right-sided tumors may be associated with decreased OS. In some aspects, the CRC is metastatic. In some aspects, the CRC has a microsatellite instability status of "microsatellite stable" ("MSS") or "microsatellite instability low" ("MSI-L"). In other aspects, the CRC has a microsatellite instability status of "microsatellite instability high" ("MSI-H"). In some aspects, the CRC is a LY6G6D-positive (LY6G6D+) CRC.

As used herein, "microsatellite instability status" or "MSI status" refers to a characterization of microsatellite stability in a tumor tissue of a patient. The tumor tissue of a patient may be characterized as "microsatellite instability high" ("MSI-H"), "microsatellite instability low" ("MSI-L"), or "microsatellite stable" ("MSS"). MSI status may be assessed, for example, by using a PCR-based approach such as the MSI Analysis System (Promega, Madison, Wis.), which is comprised of 5 pseudomonomorphic mononucleotide repeats (BAT-25, BAT-26, NR-21, NR-24, and MONO-27) to detect MSI and 2 pentanucleotide loci (PentaC and PendaD) to confirm identity between normal and tumor samples. The size in bases for each microsatellite locus can be determined, e.g., by gel electrophoresis, and a tumor may be designated MSI-H if two or more mononucleotide loci vary in length compared to the germline DNA. See, e.g., Le et al. *NEJM* 372:2509-2520, 2015.

In some aspects, the stage of a CRC is assessed according to the American Joint Committee on Cancer (AJCC)/Union for International Cancer Control (UICC) TNM Classification of Malignant Tumors (TNM) classification system. In the TNM system, cancers are designated the letter T (tumor size), N (palpable nodes), and/or M (metastases). T1, T2, T3, and T4 describe the increasing size of the primary lesion. T1, T2, T3, and T4 may additionally be classified as a or b (e.g., T4a or T4b) to provide further information about the status, e.g., local advancement, of the cancer. N0, N1, N2, N3 indicates progressively advancing node involvement; and M0 and M1 reflect the absence or presence of distant metastases. In some aspects, the CRC of an individual is a stage I, stage II, or stage III CRC, e.g., a stage I, stage II, or stage III colon carcinoma. In some aspects, an individual does not have a stage IV CRC. In some aspects, an individual does not have a metastatic CRC. In some aspects, the CRC of an individual in a reference population is a stage I, stage II, stage III, or stage IV CRC, e.g., a stage I, stage II, stage III, or stage IV colon carcinoma.

In some aspects, the cancer is a breast cancer. Further aspects of breast cancer include a hormone receptor-positive (HR+) breast cancer, e.g., an estrogen receptor-positive (ER+) breast cancer, a progesterone receptor-positive (PR+) breast cancer, or an ER+/PR+ breast cancer. Other aspects of breast cancer include a HER2-positive (HER2+) breast cancer. Yet other aspects of breast cancer include a triple-negative breast cancer (TNBC). In some aspects, the breast cancer is an early breast cancer. In some aspects, the cancer is a lung cancer. Further aspects of lung cancer include an epidermal growth factor receptor-positive (EGFR+) lung cancer. Other aspects of lung cancer include an epidermal growth factor receptor-negative (EGFR−) lung cancer. Yet other aspects of lung cancer include a non-small cell lung cancer, e.g., a squamous lung cancer or a non-squamous lung cancer. Other aspects of lung cancer include a small cell lung cancer. In some aspects, the cancer is a head and neck cancer. Further aspects of head and neck cancer include a squamous cell carcinoma of the head & neck (SCCHN). In some aspects, the cancer is a bladder cancer. Further aspects of bladder cancer include a urothelial bladder cancer (UBC), a muscle invasive bladder cancer (MIBC), or a non-muscle invasive bladder cancer (NMIBC). In some aspects, the cancer is a kidney cancer. Further aspects of kidney cancer include a renal cell carcinoma (RCC). In some aspects, the cancer is a liver cancer. Further aspects of liver cancer include a hepatocellular carcinoma. In some aspects, the cancer is a prostate cancer. Further aspects of prostate cancer include a castration-resistant prostate cancer (CRPC). In some aspects, the cancer is a metastatic form of a solid tumor. In some aspects, the metastatic form of a solid tumor is a metastatic form of a melanoma, a breast cancer, a colorectal cancer, a lung cancer, a head and neck cancer, a bladder cancer, a kidney cancer, an ovarian cancer, a pancreatic cancer, or a prostate cancer. In some aspects, the cancer is a non-solid tumor cancer. Non-solid tumor cancers include, but are not limited to hematological cancers, e.g., a B-cell lymphoma. Further aspects of B-cell lymphoma include, e.g., a chronic lymphocytic leukemia (CLL), a diffuse large B-cell lymphoma (DLBCL), a follicular lymphoma, myelodysplastic syndrome (MDS), a non-Hodgkin lymphoma (NHL), an acute lymphoblastic leukemia (ALL), a multiple myeloma, an acute myeloid leukemia (AML), or a mycosis fungoides (MF).

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g., B cell receptor); and B cell activation.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) that are bound to their cognate antigen. To assess complement activation, a CDC assay, e.g., as described in Gazzano-Santoro et al., J. Immunol. Methods 202:163 (1996), can be performed.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxic agents. The antibodies "arm" the cytotoxic cells and are absolutely required for such killing. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet. *Annu. Rev. Immunol.* 9:457-92, 1991. To assess ADCC activity of a molecule of interest, an in vitro ADCC assay, such as that described in U.S. Pat. No. 5,500,362 or 5,821,337 can be performed. Useful effector cells for such assays include peripheral blood mononuclear cells (PBMC) and Natural Killer (NK) cells. Alternatively, or additionally, ADCC activity of the molecule of interest can be assessed in vivo, e.g., in an animal model such as that disclosed in Clynes et al. *Proc. Natl. Acad. Sci. USA.* 95:652-656, 1998.

"Complex" or "complexed" as used herein refers to the association of two or more molecules that interact with each other through bonds and/or forces (e.g., Van der Waals, hydrophobic, hydrophilic forces) that are not peptide bonds. In one aspect, the complex is heteromultimeric. It should be understood that the term "protein complex" or "polypeptide complex" as used herein includes complexes that have a non-protein entity conjugated to a protein in the protein complex (e.g., including, but not limited to, chemical molecules such as a toxin or a detection agent).

As used herein, "delaying progression" of a disorder or disease means to defer, hinder, slow, retard, stabilize, and/or postpone development of the disease or disorder (e.g., a cell proliferative disorder, e.g., cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

An "effective amount" of a compound, for example, an anti-LY6G6D antibody of the invention or a composition (e.g., pharmaceutical composition) thereof, is at least the minimum amount required to achieve the desired therapeutic or prophylactic result, such as a measurable improvement or prevention of a particular disorder (e.g., a cell proliferative disorder, e.g., cancer). An effective amount herein may vary according to factors such as the disease state, age, sex, and weight of the patient, and the ability of the antibody to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications, and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent or desirably stop) cancer cell infiltration into peripheral organs; inhibit (i.e., slow to some extent and desirably stop) tumor metastasis; inhibiting to some extent tumor growth; and/or relieving to some extent one or more of the symptoms associated with the disorder. An effective amount can be administered in one or more administrations. For purposes of this invention, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

The term "epitope" refers to the particular site on an antigen molecule to which an antibody binds. In some aspects, the particular site on an antigen molecule to which an antibody binds is determined by hydroxyl radical footprinting. In some aspects, the particular site on an antigen molecule to which an antibody binds is determined by crystallography.

A "growth inhibitory agent" when used herein refers to a compound or composition which inhibits growth of a cell either in vitro or in vivo. In one aspect, growth inhibitory agent is growth inhibitory antibody that prevents or reduces proliferation of a cell expressing an antigen to which the antibody binds. In another aspect, the growth inhibitory agent may be one which significantly reduces the percentage of cells in S phase. Aspects of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., The Molecular Basis of Cancer, Chapter 1, entitled "Cell cycle regulation, oncogenes, and antineoplastic drugs" by Murakami et al. (W. B. Saunders, Philadelphia, 1995), e.g., p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

An "immunoconjugate" is an antibody conjugated to one or more heterologous molecule(s), including but not limited to a cytotoxic agent.

The term "immunomodulatory agent" refers to a class of molecules that modifies the immune system response or the functioning of the immune system. Immunomodulatory agents include, but are not limited to, PD-1 axis binding antagonists, T cell-dependent bispecific antibodies, and mRNA-based personalized cancer vaccines, as well as thalidomide (α-N-phthalimido-glutarimide) and its analogues, OTEZLA® (apremilast), REVLIMID® (lenalidomide) and ACTI-MID™ (pomalidomide), and pharmaceutically acceptable salts or acids thereof.

A "subject" or an "individual" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain aspects, the subject or individual is a human.

An "isolated" protein or peptide is one which has been separated from a component of its natural environment. In some aspects, a protein or peptide is purified to greater than 95% or 99% purity as determined by, for example, electrophoresis (e.g., SDS-PAGE, isoelectric focusing (IEF), capillary electrophoresis) or chromatography (e.g., ion exchange or reverse phase HPLC).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "PD-1 axis binding antagonist" refers to a molecule that inhibits the interaction of a PD-1 axis binding partner with either one or more of its binding partner, so as to remove T cell dysfunction resulting from signaling on the PD-1 signaling axis—with a result being to restore or enhance T cell function (e.g., proliferation, cytokine production, target cell killing). As used herein, a PD-1 axis binding antagonist includes a PD-1 binding antagonist, a PD-L1 binding antagonist and a PD-L2 binding antagonist.

The term "PD-1 binding antagonist" refers to a molecule that decreases, blocks, inhibits, abrogates or interferes with signal transduction resulting from the interaction of PD-1 with one or more of its binding partners, such as PD-L1, PD-L2. In some aspects, the PD-1 binding antagonist is a molecule that inhibits the binding of PD-1 to one or more of its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one aspect, a PD-1 binding antagonist reduces the negative co-stimulatory signal mediated by or through cell surface proteins expressed on T lymphocytes mediated signaling through PD-1 so as render a dysfunctional T cell less dysfunctional (e.g., enhancing effector responses to antigen recognition). In some aspects, the PD-1 binding antagonist is an anti-PD-1 antibody. In a specific aspect, a PD-1 binding antagonist is MDX-1106 (nivolumab). In another specific aspect, a PD-1 binding antagonist is MK-3475 (pembrolizumab). In another specific aspect, a PD-1 binding antagonist is AMP-224. In another specific aspect, a PD-1 binding antagonist is MED1-0680. In another specific aspect, a PD-1 binding antagonist is PDR001. In another specific aspect, a PD-1 binding antagonist is REGN2810. In another specific aspect, a PD-1 binding antagonist is BGB-108.

The term "PD-L1 binding antagonist" refers to a molecule that decreases, blocks, inhibits, abrogates or interferes with signal transduction resulting from the interaction of PD-L1 with either one or more of its binding partners, such as PD-1, B7-1. In some aspects, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some aspects, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one aspect, a PD-L1 binding antagonist reduces the negative co-stimulatory signal mediated by or through cell surface proteins expressed on T lymphocytes mediated signaling through PD-L1 so as to render a dysfunctional T cell less dysfunctional (e.g., enhancing effector responses to antigen recognition). In some aspects, a PD-L1 binding antagonist is an anti-PD-L1 antibody. In still another specific aspect, an anti-PD-L1 antibody is MPDL3280A (atezolizumab, marketed as TECENTRIQ™ with a WHO Drug Information (International Nonproprietary Names for Pharmaceutical Substances), Recommended INN: List 74, Vol. 29, No. 3, 2015 (see page 387)). In a specific aspect, an anti-PD-L1 antibody is YW243.55.570. In another specific aspect, an anti-PD-L1 antibody is MDX-1105. In another specific aspect, an anti PD-L1 antibody is MSB0015718C. In still another specific aspect, an anti-PD-L1 antibody is MED14736.

The term "PD-L2 binding antagonist" refers to a molecule that decreases, blocks, inhibits, abrogates or interferes with signal transduction resulting from the interaction of PD-L2 with either one or more of its binding partners, such as PD-1. In some aspects, a PD-L2 binding antagonist is a molecule that inhibits the binding of PD-L2 to one or more of its binding partners. In a specific aspect, the PD-L2 binding antagonist inhibits binding of PD-L2 to PD-1. In some aspects, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one aspect, a PD-L2 binding antagonist reduces the negative co-stimulatory signal mediated by or through cell surface proteins expressed on T lymphocytes mediated signaling through PD-L2 so as render a dysfunctional T cell less dysfunctional (e.g., enhancing effector responses to antigen recognition). In some aspects, a PD-L2 binding antagonist is an immunoadhesin.

The term "protein," as used herein, refers to any native protein from any vertebrate source, including mammals such as primates (e.g., humans) and rodents (e.g., mice and rats), unless otherwise indicated. The term encompasses "full-length," unprocessed protein as well as any form of the protein that results from processing in the cell. The term also encompasses naturally occurring variants of the protein, e.g., splice variants or allelic variants.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full-length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one-time administration and typical dosages range from 10 to 200 units (Grays) per day.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some aspects, antibodies of the invention (e.g., anti-LY6G6D antibodies of the invention) are used to delay development of a disease or to slow the progression of a disease.

By "reduce" or "inhibit" is meant the ability to cause an overall decrease, for example, of 20% or greater, of 50% or greater, or of 75%, 85%, 90%, 95%, or greater. In certain aspects, reduce or inhibit can refer to the effector function of an antibody that is mediated by the antibody Fc region, such effector functions specifically including complement-dependent cytotoxicity (CDC), antibody-dependent cellular cytotoxicity (ADCC), and antibody-dependent cellular phagocytosis (ADCP).

According to the invention, the term "vaccine" relates to a pharmaceutical preparation (pharmaceutical composition) or product that upon administration induces an immune response, in particular a cellular immune response, which recognizes and attacks a pathogen or a diseased cell such as a cancer cell. A vaccine may be used for the prevention or treatment of a disease. A vaccine may be a cancer vaccine. A "cancer vaccine" as used herein is a composition that stimulates an immune response in a subject against a cancer. Cancer vaccines typically consist of a source of cancer-associated material or cells (antigen) that may be autologous (from self) or allogenic (from others) to the subject, along with other components (e.g., adjuvants) to further stimulate and boost the immune response against the antigen. Cancer vaccines can result in stimulating the immune system of the subject to produce antibodies to one or several specific antigens, and/or to produce killer T cells to attack cancer cells that have those antigens.

The term "personalized cancer vaccine" ("PCV") refers to a cancer vaccine that is adapted to the needs or special circumstances of an individual cancer patient. In some aspects, the PCV stimulates an immune response against one or more cancer-specific somatic mutations present in cancer cells of the patient, as described, for example, in PCT Pub. Nos. WO2014/082729 and WO2012/159754. The cancer-specific somatic mutation may be present in any cancer cell of a patient, e.g., a tumor cell, e.g., a circulating tumor cell. In some aspects, the cancer-specific somatic mutation is discovered using next-generation sequencing. In some aspects, a polypeptide comprising the cancer-specific somatic mutation or a nucleic acid (e.g., an RNA, e.g., an in vitro transcribed RNA) encoding a polypeptide comprising the cancer-specific somatic mutation is administered to the patient to stimulate the patient's immune response.

As used herein, "administering" is meant a method of giving a dosage of a compound (e.g., an anti-LY6G6D antibody of the invention) to a subject. In some aspects, the compositions utilized in the methods herein are administered intravenously. The compositions utilized in the methods described herein can be administered, for example, intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, in cremes, or in lipid compositions. The method of administration can vary depending on various factors (e.g., the compound or composition being administered and the severity of the condition, disease, or disorder being treated).

II. Compositions and Methods

In one aspect, the invention is based, in part, on anti-lymphocyte antigen 6 complex, locus G61 (anti-LY6G6D) antibodies. In certain embodiments, the anti-LY6G6D antibodies are multispecific (e.g., bispecific) and bind, in addition to LY6G6D or a fragment thereof, a second biological molecule, e.g., a surface antigen of a T cell, e.g., cluster of differentiation 3 (CD3). Antibodies of the invention are useful, for example, for treating or delaying the progression of a cell proliferative disorder, e.g., cancer, e.g., a colorectal cancer (CRC) (e.g., a LY6G6D-positive CRC) or for enhancing immune function in a subject having such a disorder.

A. Exemplary Anti-LY6G6D Antibodies

In one aspect, the invention provides isolated antibodies that bind to LY6G6D. In some aspects the anti-LY6G6D antibody binds to a human LY6G6D polypeptide (SEQ ID NO: 75) or a cynomolgus monkey (cyno) LY6G6D polypeptide (SEQ ID NO: 77). In some aspects, the anti-LY6G6D antibody binds to an epitope comprising, or within, amino acids 93-104 (SEQ ID NO: 87), 94-103 (SEQ ID NO: 78), or 99-101 (SEQ ID NO: 79) of LY6G6D (e.g., human LY6G6D). In some aspects, the anti-LY6G6D antibody binds to one, two, three, or all four of the residues Arg94, Leu101, Cys102, and Asn103 of LY6G6D. In some aspects, the anti-LY6G6D antibody binds to an epitope comprising residues Arg94, Asp95, Cys96, Tyr97, Leu98, Gly99, Asp100, Leu101, Cys102 and Asn103 of LY6G6D. In some aspects, the anti-LY6G6D antibody binds to an epitope consisting of residues Arg94, Asp95, Cys96, Tyr97, Leu98, Gly99, Asp100, Leu101, Cys102 and Asn103 of LY6G6D.

A LY6G6D epitope may be determined by the LY6G6D binding domain of the anti-LY6G6D antibody binding to peptide fragments of the epitope. A LY6G6D epitope may also be determined by alanine scanning mutagenesis. In one embodiment, a reduction in binding of a LY6G6D binding domain to mutated LY6G6D by 20%, 30%, 50%, 80% or more indicates the amino acid residue of LY6G6D mutated in an alanine scanning mutagenesis assay is an epitopic residue for the LY6G6D binding domain. Alternatively, a LY6G6D epitope may be determined by mass spectrometry. In some embodiments, the epitope is determined by crystallography (e.g., crystallography methods).

In some embodiments, a LY6G6D epitope may be determined by crystallography methods by combining an anti-LY6G6D antibody Fab, dissolved in a particular condition (e.g., 0.15 M NaCl, 25 mM tris, pH 7.5 at 10 mg/ml), with a molar excess (e.g., a 2-fold molar excess) of a LY6G6D peptide and initially screening a matrix of precipitants in a sitting or hanging drop vapor diffusion format. Optimized crystals may be grown, for example, from a 1:1 mixture with reservoir solution containing 70% v/v methyl-pentanediol, and 0.1 M HEPES buffer at pH 7.5. The reservoir may be used as a cryoprotectant. The crystals may be transferred to cryogenic temperature by sudden immersion into liquid nitrogen.

The diffraction data for crystals may be collected at a beam line. The recorded diffractions may be integrated and scaled using a program, such as HKL2000.

The structure may be phased by molecular replacement (MR), for example, using a program such as Phaser. For example, the MR search model is a Fab subunit derived from a crystal structure of HGFA/Fab complex (PDB code: 2R0L). The LY6G6D peptide is built into the structure based on a Fo-Fc map. The structure may be subsequently refined with programs REFMAC5 and PHENIX using the maximum likelihood target functions, anisotropic individual B-factor refinement method, and TLS refinement method, to achieve convergence.

In some aspects, the invention provides an anti-LY6G6D antibody having a binding domain comprising at least one, two, three, four, five, or six CDRs selected from (a) a CDR-H1 comprising the amino acid sequence of SEQ ID NO: 4; (b) a CDR-H2 comprising the amino acid sequence of SEQ ID NO: 5; (c) a CDR-H3 comprising the amino acid sequence of SEQ ID NO: 6; (d) a CDR-L1 comprising the amino acid sequence of SEQ ID NO: 1; (e) a CDR-L2 comprising the amino acid sequence of SEQ ID NO: 2; and (f) a CDR-L3 comprising the amino acid sequence of SEQ ID NO: 3 or any of SEQ ID NOs: 99-107.

In some aspects, the invention provides an anti-LY6G6D antibody having a binding domain comprising all six of (a) a CDR-H1 comprising the amino acid sequence of SEQ ID NO: 4 or SEQ ID NO: 111; (b) a CDR-H2 comprising the amino acid sequence of SEQ ID NO: 5, SEQ ID NO: 112, or SEQ ID NO: 113; (c) a CDR-H3 comprising the amino acid sequence of SEQ ID NO: 6; (d) a CDR-L1 comprising the amino acid sequence of SEQ ID NO: 1; (e) a CDR-L2 comprising the amino acid sequence of SEQ ID NO: 2; and (f) a CDR-L3 comprising the amino acid sequence of SEQ ID NO: 3 or any of SEQ ID NOs: 99-107.

In some aspects, the invention provides an anti-LY6G6D antibody having a binding domain comprising all six of (a) a CDR-H1 comprising the amino acid sequence of SEQ ID NO: 4; (b) a CDR-H2 comprising the amino acid sequence of SEQ ID NO: 5; (c) a CDR-H3 comprising the amino acid sequence of SEQ ID NO: 6; (d) a CDR-L1 comprising the amino acid sequence of SEQ ID NO: 1; (e) a CDR-L2 comprising the amino acid sequence of SEQ ID NO: 2; and (f) a CDR-L3 comprising the amino acid sequence of SEQ ID NO: 3.

In some aspects, the invention provides an anti-LY6G6D antibody having a binding domain comprising all six of (a) a CDR-H1 comprising the amino acid sequence of SEQ ID NO: 4; (b) a CDR-H2 comprising the amino acid sequence of SEQ ID NO: 5; (c) a CDR-H3 comprising the amino acid sequence of SEQ ID NO: 6; (d) a CDR-L1 comprising the amino acid sequence of SEQ ID NO: 1; (e) a CDR-L2 comprising the amino acid sequence of SEQ ID NO: 2; and (f) a CDR-L3 comprising the amino acid sequence of SEQ ID NO: 99.

In some aspects, the invention provides an anti-LY6G6D antibody having a binding domain comprising all six of (a) a CDR-H1 comprising the amino acid sequence of SEQ ID NO: 4; (b) a CDR-H2 comprising the amino acid sequence of SEQ ID NO: 5; (c) a CDR-H3 comprising the amino acid sequence of SEQ ID NO: 6; (d) a CDR-L1 comprising the amino acid sequence of SEQ ID NO: 1; (e) a CDR-L2 comprising the amino acid sequence of SEQ ID NO: 2; and (f) a CDR-L3 comprising the amino acid sequence of SEQ ID NO: 100.

In some aspects, the invention provides an anti-LY6G6D antibody having a binding domain comprising all six of (a) a CDR-H1 comprising the amino acid sequence of SEQ ID NO: 4; (b) a CDR-H2 comprising the amino acid sequence of SEQ ID NO: 5; (c) a CDR-H3 comprising the amino acid sequence of SEQ ID NO: 6; (d) a CDR-L1 comprising the amino acid sequence of SEQ ID NO: 1; (e) a CDR-L2 comprising the amino acid sequence of SEQ ID NO: 2; and (f) a CDR-L3 comprising the amino acid sequence of SEQ ID NO: 101.

In some aspects, the invention provides an anti-LY6G6D antibody having a binding domain comprising all six of (a) a CDR-H1 comprising the amino acid sequence of SEQ ID NO: 4; (b) a CDR-H2 comprising the amino acid sequence of SEQ ID NO: 5; (c) a CDR-H3 comprising the amino acid sequence of SEQ ID NO: 6; (d) a CDR-L1 comprising the amino acid sequence of SEQ ID NO: 1; (e) a CDR-L2 comprising the amino acid sequence of SEQ ID NO: 2; and (f) a CDR-L3 comprising the amino acid sequence of SEQ ID NO: 102.

In some aspects, the invention provides an anti-LY6G6D antibody having a binding domain comprising all six of (a) a CDR-H1 comprising the amino acid sequence of SEQ ID NO: 4; (b) a CDR-H2 comprising the amino acid sequence of SEQ ID NO: 5; (c) a CDR-H3 comprising the amino acid sequence of SEQ ID NO: 6; (d) a CDR-L1 comprising the amino acid sequence of SEQ ID NO: 1; (e) a CDR-L2 comprising the amino acid sequence of SEQ ID NO: 2; and (f) a CDR-L3 comprising the amino acid sequence of SEQ ID NO: 103.

In some aspects, the invention provides an anti-LY6G6D antibody having a binding domain comprising all six of (a) a CDR-H1 comprising the amino acid sequence of SEQ ID NO: 4; (b) a CDR-H2 comprising the amino acid sequence of SEQ ID NO: 5; (c) a CDR-H3 comprising the amino acid sequence of SEQ ID NO: 6; (d) a CDR-L1 comprising the amino acid sequence of SEQ ID NO: 1; (e) a CDR-L2 comprising the amino acid sequence of SEQ ID NO: 2; and (f) a CDR-L3 comprising the amino acid sequence of SEQ ID NO: 104.

In some aspects, the invention provides an anti-LY6G6D antibody having a binding domain comprising all six of (a) a CDR-H1 comprising the amino acid sequence of SEQ ID NO: 4; (b) a CDR-H2 comprising the amino acid sequence of SEQ ID NO: 5; (c) a CDR-H3 comprising the amino acid sequence of SEQ ID NO: 6; (d) a CDR-L1 comprising the amino acid sequence of SEQ ID NO: 1; (e) a CDR-L2 comprising the amino acid sequence of SEQ ID NO: 2; and (f) a CDR-L3 comprising the amino acid sequence of SEQ ID NO: 105.

In some aspects, the invention provides an anti-LY6G6D antibody having a binding domain comprising all six of (a)

a CDR-H1 comprising the amino acid sequence of SEQ ID NO: 4; (b) a CDR-H2 comprising the amino acid sequence of SEQ ID NO: 5; (c) a CDR-H3 comprising the amino acid sequence of SEQ ID NO: 6; (d) a CDR-L1 comprising the amino acid sequence of SEQ ID NO: 1; (e) a CDR-L2 comprising the amino acid sequence of SEQ ID NO: 2; and (f) a CDR-L3 comprising the amino acid sequence of SEQ ID NO: 106.

In some aspects, the invention provides an anti-LY6G6D antibody having a binding domain comprising all six of (a) a CDR-H1 comprising the amino acid sequence of SEQ ID NO: 4; (b) a CDR-H2 comprising the amino acid sequence of SEQ ID NO: 5; (c) a CDR-H3 comprising the amino acid sequence of SEQ ID NO: 6; (d) a CDR-L1 comprising the amino acid sequence of SEQ ID NO: 1; (e) a CDR-L2 comprising the amino acid sequence of SEQ ID NO: 2; and (f) a CDR-L3 comprising the amino acid sequence of SEQ ID NO: 107.

In some aspects, the invention provides an anti-LY6G6D antibody having a binding domain comprising all six of (a) a CDR-H1 comprising the amino acid sequence of SEQ ID NO: 111; (b) a CDR-H2 comprising the amino acid sequence of SEQ ID NO: 5; (c) a CDR-H3 comprising the amino acid sequence of SEQ ID NO: 6; (d) a CDR-L1 comprising the amino acid sequence of SEQ ID NO: 1; (e) a CDR-L2 comprising the amino acid sequence of SEQ ID NO: 2; and (f) a CDR-L3 comprising the amino acid sequence of SEQ ID NO: 3.

In some aspects, the invention provides an anti-LY6G6D antibody having a binding domain comprising all six of (a) a CDR-H1 comprising the amino acid sequence of SEQ ID NO: 4; (b) a CDR-H2 comprising the amino acid sequence of SEQ ID NO: 112; (c) a CDR-H3 comprising the amino acid sequence of SEQ ID NO: 6; (d) a CDR-L1 comprising the amino acid sequence of SEQ ID NO: 1; (e) a CDR-L2 comprising the amino acid sequence of SEQ ID NO: 2; and (f) a CDR-L3 comprising the amino acid sequence of SEQ ID NO: 3.

In some aspects, the invention provides an anti-LY6G6D antibody having a binding domain comprising all six of (a) a CDR-H1 comprising the amino acid sequence of SEQ ID NO: 4; (b) a CDR-H2 comprising the amino acid sequence of SEQ ID NO: 113; (c) a CDR-H3 comprising the amino acid sequence of SEQ ID NO: 6; (d) a CDR-L1 comprising the amino acid sequence of SEQ ID NO: 1; (e) a CDR-L2 comprising the amino acid sequence of SEQ ID NO: 2; and (f) a CDR-L3 comprising the amino acid sequence of SEQ ID NO: 3.

In some aspects, the anti-LY6G6D antibody may have a VH domain comprising an amino acid sequence having at least 90% sequence identity (e.g., at least 91%, 92%, 93%, 94%, 95%, 96%, 97%, 98%, or 99% sequence identity) to, or comprising the sequence of, SEQ ID NO: 10 and/or a VL domain comprising an amino acid sequence having at least 90% sequence identity (e.g., at least 91%, 92%, 93%, 94%, 95%, 96%, 97%, 98%, or 99% sequence identity) to, or comprising the sequence of, SEQ ID NO: 11. In a particular instance, the anti-LY6G6D antibody can be 20A12.QNTv12 (including one-cell and two-cell manufacturing variants), or a derivative or clonal relative thereof. In some aspects, the anti-LY6G6D antibody has a VH domain comprising the amino acid sequence of SEQ ID NO: 59 or a VL domain comprising the amino acid sequence of SEQ ID NO: 60. In some aspects, the anti-LY6G6D antibody has a VH domain comprising the amino acid sequence of SEQ ID NO: 59 and a VL domain comprising the amino acid sequence of SEQ ID NO: 60 In some aspects, the anti-LY6G6D antibody may comprise at least one (e.g., 1, 2, 3, or 4) of (a) an FR-H1 comprising the amino acid sequence of SEQ ID NO: 34; (b) an FR-H2 comprising the amino acid sequence of SEQ ID NO: 35; (c) an FR-H3 comprising the amino acid sequence of SEQ ID NO: 36; and (d) an FR-H4 comprising the amino acid sequence of SEQ ID NO: 37. In some aspects, the anti-LY6G6D antibody may comprise at least one (e.g., 1, 2, 3, or 4) of (a) an FR-L1 comprising the amino acid sequence of SEQ ID NO: 38; (b) an FR-L2 comprising the amino acid sequence of SEQ ID NO: 39; (c) an FR-L3 comprising the amino acid sequence of SEQ ID NO: 40; and (d) an FR-L4 comprising the amino acid sequence of SEQ ID NO: 41.

In some aspects, the anti-LY6G6D antibody comprises all four of (a) an FR-H1 comprising the amino acid sequence of SEQ ID NO: 34; (b) an FR-H2 comprising the amino acid sequence of SEQ ID NO: 35; (c) an FR-H3 comprising the amino acid sequence of SEQ ID NO: 36; and (d) an FR-H4 comprising the amino acid sequence of SEQ ID NO: 37, and/or comprises all four of (a) an FR-L1 comprising the amino acid sequence of SEQ ID NO: 38; (b) an FR-L2 comprising the amino acid sequence of SEQ ID NO: 39; (c) an FR-L3 comprising the amino acid sequence of SEQ ID NO: 40; and (d) an FR-L4 comprising the amino acid sequence of SEQ ID NO: 41. In some aspects, the anti-LY6G6D antibody may have a VH domain comprising the amino acid sequence of SEQ ID NO: 10 and/or a VL domain comprising the amino acid sequence of SEQ ID NO: 11.

In some aspects, the anti-LY6G6D antibody may comprise at least one (e.g., 1, 2, 3, or 4) of (a) an FR-H1 comprising the amino acid sequence of SEQ ID NO: 34; (b) an FR-H2 comprising the amino acid sequence of SEQ ID NO: 58; (c) an FR-H3 comprising the amino acid sequence of SEQ ID NO: 36; and (d) an FR-H4 comprising the amino acid sequence of SEQ ID NO: 37. In some aspects, the anti-LY6G6D antibody may comprise at least one (e.g., 1, 2, 3, or 4) of (a) an FR-L1 comprising the amino acid sequence of SEQ ID NO: 38; (b) an FR-L2 comprising the amino acid sequence of SEQ ID NO: 61; (c) an FR-L3 comprising the amino acid sequence of SEQ ID NO: 40; and (d) an FR-L4 comprising the amino acid sequence of SEQ ID NO: 41.

In some aspects, the anti-LY6G6D antibody comprises all four of (a) an FR-H1 comprising the amino acid sequence of SEQ ID NO: 34; (b) an FR-H2 comprising the amino acid sequence of SEQ ID NO: 58; (c) an FR-H3 comprising the amino acid sequence of SEQ ID NO: 36; and (d) an FR-H4 comprising the amino acid sequence of SEQ ID NO: 37 and/or comprises all four of (a) an FR-L1 comprising the amino acid sequence of SEQ ID NO: 38; (b) an FR-L2 comprising the amino acid sequence of SEQ ID NO: 61; (c) an FR-L3 comprising the amino acid sequence of SEQ ID NO: 40; and (d) an FR-L4 comprising the amino acid sequence of SEQ ID NO: 41. In some aspects, the anti-LY6G6D antibody may have a VH domain comprising the amino acid sequence of SEQ ID NO: 59 and/or a VL domain comprising the amino acid sequence of SEQ ID NO: 60.

In any of the above aspects, the anti-LY6G6D antibody may be humanized. In one embodiment, the anti-LY6G6D antibody comprises CDRs as in any of the above embodiments, and further comprises an acceptor human framework, e.g., a human immunoglobulin framework or a human consensus framework.

In a further aspect of the invention, the anti-LY6G6D antibody according to any of the above embodiments is a monoclonal antibody. In some aspects, the anti-LY6G6D antibody is a chimeric or human antibody. In one aspect, the anti-LY6G6D antibody is an antibody fragment, for example, a Fv, Fab, Fab', scFv, diabody, or F(ab')$_2$ fragment.

In another aspect, the antibody is a full-length antibody, e.g., an intact IgG antibody (e.g., an intact IgG1 antibody) or other antibody class or isotype as defined herein.

In a further aspect, an anti-LY6G6D antibody according to any of the above embodiments may incorporate any of the features, singly or in combination, as described in Sections 1-8 below.

B. Exemplary Anti-CD3 Antibodies

In another aspect, the invention provides isolated antibodies that bind to cluster of differentiation 3 (CD3) (e.g., CD3ε and/or CD3γ) and have the following six CDR sequences: (a) a CDR-H1 comprising the amino acid sequence of SEQ ID NO: 15; (b) a CDR-H2 comprising the amino acid sequence of SEQ ID NO: 16; (c) a CDR-H3 comprising the amino acid sequence of SEQ ID NO: 17; (d) a CDR-L1 comprising the amino acid sequence of SEQ ID NO: 12; (e) a CDR-L2 comprising the amino acid sequence of SEQ ID NO: 13 or SEQ ID NO: 50; and (f) a CDR-L3 comprising the amino acid sequence of SEQ ID NO: 14 or SEQ ID NO: 51, a VL sequence comprising SEQ ID NO: 21, 55, 90, or 92, VL and VH sequences comprising SEQ ID NOs: 21 or 55 and 20, respectively, or VL and VH sequences comprising SEQ ID NOs: 90 or 92 and 89, respectively. In some instances, the anti-CD3 antibody binds to a human CD3 polypeptide or a cynomolgus monkey (cyno) CD3 polypeptide. In some instances, the human CD3 polypeptide or the cyno CD3 polypeptide is a human CD3ε polypeptide (SEQ ID NO: 80) or a cyno CD3ε polypeptide (SEQ ID NO: 81), respectively. In some instances, the human CD3 polypeptide or the cyno CD3 polypeptide is a human CD3γ polypeptide (SEQ ID NO: 82) or a cyno CD3γ polypeptide (SEQ ID NO: 83), respectively. In some instances, the anti-CD3 antibody binds to an epitope within a fragment of CD3 (e.g., human CD3ε) consisting of amino acids 1-26 (SEQ ID NO: 84) or 1-27 (SEQ ID NO: 85) of human CD3ε.

In some aspects, the invention provides an anti-CD3 antibody having a binding domain comprising all six of (a) a CDR-H1 comprising the amino acid sequence of SEQ ID NO: 15; (b) a CDR-H2 comprising the amino acid sequence of SEQ ID NO: 16; (c) a CDR-H3 comprising the amino acid sequence of SEQ ID NO: 17; (d) a CDR-L1 comprising the amino acid sequence of SEQ ID NO: 12; (e) a CDR-L2 comprising the amino acid sequence of SEQ ID NO: 13; and (f) a CDR-L3 comprising the amino acid sequence of SEQ ID NO: 14.

In some aspects, the invention provides an anti-CD3 antibody having a binding domain comprising all six of (a) a CDR-H1 comprising the amino acid sequence of SEQ ID NO: 15; (b) a CDR-H2 comprising the amino acid sequence of SEQ ID NO: 16; (c) a CDR-H3 comprising the amino acid sequence of SEQ ID NO: 17; (d) a CDR-L1 comprising the amino acid sequence of SEQ ID NO: 12; (e) a CDR-L2 comprising the amino acid sequence of SEQ ID NO: 50; and (f) a CDR-L3 comprising the amino acid sequence of SEQ ID NO: 51.

In some instances, the anti-CD3 antibody may have a VH domain comprising an amino acid sequence having the sequence of SEQ ID NO: 20 or 89 and a VL domain comprising an amino acid sequence having the sequence of SEQ ID NO: 21 or 90. In a particular instance, the anti-CD3 antibody can be 38E4.v1 MD1, or a derivative or clonal relative thereof.

In some instances, the anti-CD3 antibody may have a VH domain comprising an amino acid sequence having the sequence of SEQ ID NO: 20 or 89 and a VL domain comprising an amino acid sequence having the sequence of SEQ ID NO: 55 or 92. In a particular instance, the anti-CD3 antibody can be 38E4.v1 MD4 or a derivative or clonal relative thereof.

In some aspects, the anti-CD3 antibody may comprise at least one (e.g., 1, 2, 3, or 4) of (a) an FR-H1 comprising the amino acid sequence of SEQ ID NO: 42; (b) an FR-H2 comprising the amino acid sequence of SEQ ID NO: 43 or SEQ ID NO: 62; (c) an FR-H3 comprising the amino acid sequence of SEQ ID NO: 44; and (d) an FR-H4 comprising the amino acid sequence of SEQ ID NO: 45 and/or at least one (e.g., 1, 2, 3, or 4) of (a) an FR-L1 comprising the amino acid sequence of SEQ ID NO: 46; (b) an FR-L2 comprising the amino acid sequence of SEQ ID NO: 47 or SEQ ID NO: 63; (c) an FR-L3 comprising the amino acid sequence of SEQ ID NO: 48; and (d) an FR-L4 comprising the amino acid sequence of SEQ ID NO: 49.

In some aspects, the anti-CD3 antibody comprises all four of (a) an FR-H1 comprising the amino acid sequence of SEQ ID NO: 42; (b) an FR-H2 comprising the amino acid sequence of SEQ ID NO: 43; (c) an FR-H3 comprising the amino acid sequence of SEQ ID NO: 44; and (d) an FR-H4 comprising the amino acid sequence of SEQ ID NO: 45 and/or comprises all four of (a) an FR-L1 comprising the amino acid sequence of SEQ ID NO: 46; (b) an FR-L2 comprising the amino acid sequence of SEQ ID NO: 47; (c) an FR-L3 comprising the amino acid sequence of SEQ ID NO: 48; and (d) an FR-L4 comprising the amino acid sequence of SEQ ID NO: 49.

In some aspects, the anti-CD3 antibody comprises all four of (a) an FR-H1 comprising the amino acid sequence of SEQ ID NO: 42; (b) an FR-H2 comprising the amino acid sequence of SEQ ID NO: 62; (c) an FR-H3 comprising the amino acid sequence of SEQ ID NO: 44; and (d) an FR-H4 comprising the amino acid sequence of SEQ ID NO: 45 and/or comprises all four of (a) an FR-L1 comprising the amino acid sequence of SEQ ID NO: 46; (b) an FR-L2 comprising the amino acid sequence of SEQ ID NO: 63; (c) an FR-L3 comprising the amino acid sequence of SEQ ID NO: 48; and (d) an FR-L4 comprising the amino acid sequence of SEQ ID NO: 49.

In any of the above embodiments, an anti-CD3 antibody may be humanized. In one embodiment, an anti-CD3 antibody comprises CDRs as in any of the above embodiments, and further comprises an acceptor human framework, e.g., a human immunoglobulin framework or a human consensus framework. In another aspect, an anti-CD3 antibody is provided, wherein the antibody comprises a VH as in any of the embodiments provided above, and a VL as in any of the embodiments provided above, wherein one or both of the variable domain sequences include post-translational modifications.

In a further aspect, the invention provides an antibody that binds to the same epitope as an anti-CD3 antibody provided herein. For example, in certain embodiments, an antibody is provided that binds to the same epitope as an anti-CD3 antibody comprising a VH sequence of SEQ ID NO: 20 and a VL sequence of SEQ ID NO: 21 or an anti-CD3 antibody comprising a VH sequence of SEQ ID NO: 20 and a VL sequence of SEQ ID NO: 55. In certain embodiments, an antibody is provided that binds to an epitope within a fragment of CD3 (e.g., human CD3ε) consisting of amino acids 1-26 (SEQ ID NO: 84) or 1-27 (SEQ ID NO: 85) of human CD3ε.

In a further aspect of the invention, an anti-CD3 antibody according to any of the above embodiments is a monoclonal antibody. In other embodiments, the anti-CD3 antibody is a chimeric or human antibody. In one embodiment, an anti- CD3 antibody is an antibody fragment, for example, a Fv, Fab, Fab', scFv, diabody, or F(ab')$_2$ fragment. In another embodiment, the antibody is a full-length antibody, e.g., an intact IgG antibody (e.g., an intact IgG1 antibody) or other antibody class or isotype as defined herein.

In a further aspect, an anti-CD3 antibody according to any of the above embodiments may incorporate any of the features, singly or in combination, as described in Sections 1-8 below.

1. Antibody Affinity

In certain embodiments, an antibody provided herein has a dissociation constant ($K_D$) of ≤1 µM, ≤250 nM, ≤100 nM, ≤15 nM, ≤10 nM, ≤6 nM, ≤4 nM, ≤2 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M).

In one embodiment, $K_D$ is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, $K_D$ is measured using a BIACORE® surface plasmon resonance assay. For example, an assay using a BIACORE®-2000 or a BIACORE®-3000 (BIAcore, Inc., Piscataway, N.J.) is performed at 37° C. with immobilized antigen CM5 chips at ~10 response units (RU). In one embodiment, carboxymethylated dextran biosensor chips (CM5, BIACORE, Inc.) are activated with N-ethyl-N' (3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 37° C. at a flow rate of approximately 25 µl/min. Association rates ($k_{on}$, or $k_a$) and dissociation rates ($k_{off}$, or $k_d$) are calculated using a simple one-to-one Langmuir binding model (BIACORE® Evaluation Software version 3.2) by simultaneously fitting the association and dissociation sensorgrams. The equilibrium dissociation constant ($K_D$) is calculated as the ratio $k_{off}/k_{on}$. See, for example, Chen et al., *J. Mol. Biol.* 293:865-881 (1999). If the on-rate exceeds $10^6$M$^{-1}$5$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 37° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

In some embodiments, an anti-LY6G6D antibody provided herein binds a human LY6G6D polypeptide with a $K_D$ of between about 1 nM and 500 nM at 37° C. as measured using a BIAcore assay, e.g., binds a human LY6G6D with a $K_D$ of ≤1 µM, ≤250 nM, ≤100 nM, ≤40 nM, ≤30 nM, ≤15 nM, ≤10 nM, ≤6 nM, ≤4 nM, ≤2 nM, ≤1 nM, ≤0.1 nM, ≤0.01 nM, or ≤0.001 nM. In some embodiments, an anti-LY6G6D antibody provided herein binds a human LY6G6D polypeptide with a $K_D$ of between about 100 nM and 0.01 nM; between about 50 nM and 5 nM; between about 40 nM and 10 nM; between about 35 nM and 15 nM; or between about 30 nM and 20 nM.

In some embodiments, an anti-CD3 antibody provided herein binds a human CD3 polypeptide with a $K_D$ of between about 100 pM and 10 nM at 37° C. as measured using a BIAcore assay, e.g., binds a human CD3 with a $K_D$ of ≤1 µM, ≤250 nM, ≤100 nM, ≤40 nM, ≤30 nM, ≤15 nM, ≤10 nM, ≤5 nM, ≤2 nM, ≤1 nM, ≤0.1 nM, ≤0.01 nM, or ≤0.001 nM. In some embodiments, an anti-CD3 antibody provided herein binds a human CD3 polypeptide with a $K_D$ of between about 100 nM and 0.01 nM; between about 50 nM and 5 nM; between about 40 nM and 10 nM; between about 35 nM and 15 nM; or between about 30 nM and 20 nM.

2. Antibody Fragments

In certain embodiments, an antibody provided herein (e.g., an anti-LY6G6D antibody or an anti-CD3 antibody) is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al. *Nat. Med.* 9:129-134 (2003); and Hollinger et al. *Proc. Natl. Acad. Sci. USA* 90: 6444-6448 (1993). Triabodies and tetrabodies are also described in Hudson et al. *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein (e.g., an anti-LY6G6D antibody or an anti-CD3 antibody) is a chimeric antibody. Certain chimeric antibodies are described, e.g., in U.S. Pat. No. 4,816,567; and Morrison et al. *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs (or portions thereof), for example, are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein (e.g., an anti-LY6G6D antibody or an anti-CD3 antibody) is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications*, pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention (e.g., anti-LY6G6D antibodies or anti-CD3 antibodies) may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci.*

*USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In any one of the above aspects, the anti-LY6G6D or anti-CD3 antibody provided herein is a multispecific antibody, for example, a bispecific antibody. Multispecific antibodies are antibodies (e.g., monoclonal antibodies) that have binding specificities for at least two different sites. In some aspects, bispecific antibodies may bind to two different epitopes of LY6G6D. In some aspects, one of the binding specificities is for LY6G6D and the other is for any other antigen (e.g., a second biological molecule, e.g., a surface antigen of a T cell, e.g., CD3). In some aspects, one of the binding specificities is for CD3 and the other is for any other antigen (e.g., a second biological molecule, e.g., a cell surface antigen, e.g., a tumor antigen). In some aspects, one of the binding specificities is for LY6G6D and the other is for CD3.

In some aspects, the anti-LY6G6D antibody comprises (a) a LY6G6D binding domain comprising a heavy chain polypeptide (H1) comprising a heavy chain variable (VH) domain (VH1) and a light chain polypeptide (L1) comprising a light chain variable (VL) domain (VL1) and (b) a CD3 binding domain comprising a heavy chain polypeptide (H2) comprising a heavy chain variable (VH) domain (VH2) and a light chain polypeptide (L2) comprising a light chain variable (VL) domain (VL2).

In some aspects, an anti-CD3 antibody having a first binding domain comprising (a) a CDR-H1 comprising the amino acid sequence of SEQ ID NO: 15; (b) a CDR-H2 comprising the amino acid sequence of SEQ ID NO: 16; (c) a CDR-H3 comprising the amino acid sequence of SEQ ID NO: 17; (d) a CDR-L1 comprising the amino acid sequence of SEQ ID NO: 12; (e) a CDR-L2 comprising the amino acid sequence of SEQ ID NO: 13 or SEQ ID NO: 50; and (f) a CDR-L3 comprising the amino acid sequence of SEQ ID NO: 14 or SEQ ID NO: 51, such as 38E4.v1 MD1 or 38E4.v1 MD4, may have a second binding domain that binds to a cell surface antigen (e.g., a tumor antigen, e.g., LY6G6D) on a target cell other than an immune effector cell.

In some aspects, the cell surface antigen may be expressed in low copy number on the target cell. For example, in some aspects, the cell surface antigen is expressed or present at less than 35,000 copies per target cell. In some embodiments, the low copy number cell surface antigen is present between 100 and 35,000 copies per target cell; between 100 and 30,000 copies per target cell; between 100 and 25,000 copies per target cell; between 100 and 20,000 copies per target cell; between 100 and 15,000 copies per target cell; between 100 and 10,000 copies per target cell; between 100 and 5,000 copies per target cell; between 100 and 2,000 copies per target cell; between 100 and 1,000 copies per target cell; or between 100 and 500 copies per target cell. Copy number of the cell surface antigen can be determined, for example, using a standard Scatchard plot.

For example, in some aspects, an anti-LY6G6D antibody having a binding domain comprising all six of (a) a CDR-H1 comprising the amino acid sequence of SEQ ID NO: 4; (b) a CDR-H2 comprising the amino acid sequence of SEQ ID NO: 5; (c) a CDR-H3 comprising the amino acid sequence of SEQ ID NO: 6; (d) a CDR-L1 comprising the amino acid sequence of SEQ ID NO: 1; (e) a CDR-L2 comprising the amino acid sequence of SEQ ID NO: 2; and (f) a CDR-L3 comprising the amino acid sequence of SEQ ID NO: 3 may have a second binding domain that binds to CD3. In some aspects, the first binding domain that binds LY6G6D comprises at least one (e.g., 1, 2, 3, or 4) of heavy chain framework regions FR-H1, FR-H2, FR-H3, and FR-H4 comprising the sequences of SEQ ID NOs: 34-37, respectively, and/or at least one (e.g., 1, 2, 3, or 4) of the light chain framework regions FR-L1, FR-L2, FR-L3, and FR-L4 comprising the sequences of SEQ ID NOs: 38-41, respectively. In other aspects, the first binding domain that binds LY6G6D comprises at least one (e.g., 1, 2, 3, or 4) of heavy chain framework regions FR-H1, FR-H2, FR-H3, and FR-H4 comprising the sequences of SEQ ID NOs: 34, 58, 36, and 37, respectively, and/or at least one (e.g., 1, 2, 3, or 4) of the light chain framework regions FR-L1, FR-L2, FR-L3, and FR-L4 comprising the sequences of SEQ ID NOs: 38, 61, 40, and 41, respectively. In some aspects, the first binding domain that binds to LY6G6D may, for example, comprise (a) a VH1 domain comprising an amino acid sequence having at least 90% sequence identity (e.g., at least 91%, 92%, 93%, 94%, 95%, 96%, 97%, 98%, or 99% sequence identity) to, or having the sequence of, SEQ ID NO: 10, and (b) a VL1 domain comprising an amino acid sequence having at least 90% sequence identity (e.g., at least 91%, 92%, 93%, 94%, 95%, 96%, 97%, 98%, or 99% sequence identity) to, or having the sequence of, SEQ ID NO: 11 such as possessed by the anti-LY6G6D antibody 20A12.QNTv12 described herein. In some aspects, the first binding domain that binds to LY6G6D comprises (a) a VH1 domain comprising an amino acid sequence having the sequence of, SEQ ID NO: 59 and (b) a VL1 domain comprising an amino acid sequence having the sequence of SEQ ID NO: 60.

In some aspects of the above-described anti-LY6G6D antibody having a second binding domain that binds to CD3, the second domain binding to CD3 comprises at least one, two, three, four, five, or six CDRs selected from (a) a CDR-H1 comprising the amino acid sequence of SEQ ID NO: 15; (b) a CDR-H2 comprising the amino acid sequence of SEQ ID NO: 16; (c) a CDR-H3 comprising the amino acid sequence of SEQ ID NO: 17; (d) a CDR-L1 comprising the amino acid sequence of SEQ ID NO: 12; (e) a CDR-L2 comprising the amino acid sequence of SEQ ID NO: 13 or SEQ ID NO: 50; and (f) a CDR-L3 comprising the amino acid sequence of SEQ ID NO: 14 or SEQ ID NO: 51.

In some aspects, the second domain binding to CD3 comprises all six of (a) a CDR-H1 comprising the amino acid sequence of SEQ ID NO: 15; (b) a CDR-H2 comprising the amino acid sequence of SEQ ID NO: 16; (c) a CDR-H3 comprising the amino acid sequence of SEQ ID NO: 17; (d) a CDR-L1 comprising the amino acid sequence of SEQ ID NO: 12; (e) a CDR-L2 comprising the amino acid sequence of SEQ ID NO: 13; and (f) a CDR-L3 comprising the amino acid sequence of SEQ ID NO: 14.

In some aspects, the second domain binding to CD3 comprises a binding domain comprising all six of (a) a CDR-H1 comprising the amino acid sequence of SEQ ID NO: 15; (b) a CDR-H2 comprising the amino acid sequence of SEQ ID NO: 16; (c) a CDR-H3 comprising the amino acid sequence of SEQ ID NO: 17; (d) a CDR-L1 comprising the amino acid sequence of SEQ ID NO: 12; (e) a CDR-L2 comprising the amino acid sequence of SEQ ID NO: 50; and (f) a CDR-L3 comprising the amino acid sequence of SEQ ID NO: 51.

In some instances, the second domain binding to CD3 comprises a VH2 domain comprising an amino acid sequence having at least 90% sequence identity (e.g., at least 91%, 92%, 93%, 94%, 95%, 96%, 97%, 98%, or 99% sequence identity) to, or having the sequence of, SEQ ID NO: 20 and/or a VL2 domain comprising an amino acid sequence having at least 90% sequence identity (e.g., at least 91%, 92%, 93%, 94%, 95%, 96%, 97%, 98%, or 99% sequence identity) to, or having the sequence of, SEQ ID NO: 21. In a particular instance, the anti-CD3 antibody can be 38E4.v1 MD1, or a derivative or clonal relative thereof.

In some instances, the second domain binding to CD3 may have a VH2 domain comprising an amino acid sequence having at least 90% sequence identity (e.g., at least 91%, 92%, 93%, 94%, 95%, 96%, 97%, 98%, or 99% sequence identity) to, or having the sequence of, SEQ ID NO: 20 and/or a VL2 domain comprising an amino acid sequence having at least 90% sequence identity (e.g., at least 91%, 92%, 93%, 94%, 95%, 96%, 97%, 98%, or 99% sequence identity) to, or having the sequence of, SEQ ID NO: 55. In a particular instance, the anti-CD3 antibody can be 38E4.v1 MD4 or a derivative or clonal relative thereof.

In some aspects, the second domain binding to CD3 may comprise at least one (e.g., 1, 2, 3, or 4) of (a) an FR-H1 comprising the amino acid sequence of SEQ ID NO: 42; (b) an FR-H2 comprising the amino acid sequence of SEQ ID NO: 43 or SEQ ID NO: 62; (c) an FR-H3 comprising the amino acid sequence of SEQ ID NO: 44; and (d) an FR-H4 comprising the amino acid sequence of SEQ ID NO: 45 and/or at least one (e.g., 1, 2, 3, or 4) of (a) an FR-L1 comprising the amino acid sequence of SEQ ID NO: 46; (b) an FR-L2 comprising the amino acid sequence of SEQ ID NO: 47 or SEQ ID NO: 63; (c) an FR-L3 comprising the amino acid sequence of SEQ ID NO: 48; and (d) an FR-L4 comprising the amino acid sequence of SEQ ID NO: 49.

In some aspects, the anti-CD3 antibody comprises all four of (a) an FR-H1 comprising the amino acid sequence of SEQ ID NO: 42; (b) an FR-H2 comprising the amino acid sequence of SEQ ID NO: 43; (c) an FR-H3 comprising the amino acid sequence of SEQ ID NO: 44; and (d) an FR-H4 comprising the amino acid sequence of SEQ ID NO: 45 and/or comprises all four of (a) an FR-L1 comprising the amino acid sequence of SEQ ID NO: 46; (b) an FR-L2 comprising the amino acid sequence of SEQ ID NO: 47; (c) an FR-L3 comprising the amino acid sequence of SEQ ID NO: 48; and (d) an FR-L4 comprising the amino acid sequence of SEQ ID NO: 49. In some aspects, the anti-LY6G6D antibody may have a VH2 domain comprising the amino acid sequence of SEQ ID NO: 20 and/or a VL2 domain comprising the amino acid sequence of SEQ ID NO: 21. In other aspects, the anti-LY6G6D antibody may have a VH2 domain comprising the amino acid sequence of SEQ ID NO: 20 and/or a VL2 domain comprising the amino acid sequence of SEQ ID NO: 55.

In some aspects, the anti-CD3 antibody comprises all four of (a) an FR-H1 comprising the amino acid sequence of SEQ ID NO: 42; (b) an FR-H2 comprising the amino acid sequence of SEQ ID NO: 62; (c) an FR-H3 comprising the amino acid sequence of SEQ ID NO: 44; and (d) an FR-H4 comprising the amino acid sequence of SEQ ID NO: 45 and/or comprises all four of (a) an FR-L1 comprising the amino acid sequence of SEQ ID NO: 46; (b) an FR-L2 comprising the amino acid sequence of SEQ ID NO: 63; (c) an FR-L3 comprising the amino acid sequence of SEQ ID NO: 48; and (d) an FR-L4 comprising the amino acid sequence of SEQ ID NO: 49.

In some embodiments, a bispecific antibody may be used to localize a cytotoxic agent to a cell that expresses a tumor antigen, e.g., Ly6G6D. Bispecific antibodies may be prepared as full-length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). "Knob-in-hole" engineering of multispecific antibodies may be utilized to generate a first arm containing a knob and a second arm containing the hole into which the knob of the first arm may bind. The knob of the multispecific antibodies of the invention may be an anti-CD3 arm in one embodiment. Alternatively, the knob of the multispecific antibodies of the invention may be an anti-target/antigen arm in one embodiment. The hole of the multispecific antibodies of the invention may be an anti-CD3 arm in one embodiment. Alternatively, the hole of the multispecific antibodies of the invention may be an anti-target/antigen arm in one embodiment. Multispecific antibodies may also be engineered using immunoglobulin crossover (also known as Fab domain exchange or CrossMab format) technology (see, e.g., WO2009/080253; Schaefer et al., *Proc. Natl. Acad. Sci. USA*, 108:11187-11192 (2011)). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science*, 229: 81 (1985)); using leucine zippers to produce bi-specific antibodies (see, e.g., Kostelny et al., *J. Immunol.*, 148(5):1547-1553 (1992)); using "diabody" technology for making bispecific antibody fragments (see, e.g., Hollinger et al., *Proc. Natl. Acad. Sci. USA*, 90:6444-6448 (1993)); and using single-chain Fv (sFv) dimers (see, e.g. Gruber et al., *J. Immunol.*, 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibodies, or antibody fragments thereof, may also include a "Dual Acting FAb" or "DAF" comprising an antigen binding site that binds to CD3 as well as another, different antigen (e.g., a second biological molecule) (see, e.g., US 2008/0069820).

7. Antibody Variants

In some aspects, amino acid sequence variants of the anti-LY6G6D and/or anti-CD3 antibodies of the invention (e.g., bispecific anti-LY6G6D antibodies of the invention that bind to LY6G6D, e.g., with high affinity (e.g., 20A12.QNTv12), and a second biological molecule, e.g., CD3, such as TDB antibodies of the invention or variants thereof) are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen-binding.

a. Substitution, Insertion, and Deletion Variants

In certain embodiments, antibody variants having one or more amino acid substitutions are provided. Sites of interest for substitutional mutagenesis include the CDRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, for example, retained/improved antigen binding, decreased immunogenicity, or improved ADCC or CDC.

TABLE 1

Exemplary and Preferred Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more CDR residues are mutated and the variant antibodies displayed on phage and screened for a particular biological activity (e.g. binding affinity).

Alterations (e.g., substitutions) may be made in CDRs, e.g., to improve antibody affinity. Such alterations may be made in CDR "hotspots," i.e., residues encoded by codons that undergo mutation at high frequency during the somatic maturation process (see, e.g., Chowdhury, *Methods Mol. Biol.* 207:179-196 (2008)), and/or residues that contact an antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. Such alterations may, for example, be outside of antigen contacting residues in the CDRs. In certain embodiments of the variant VH and VL sequences provided above, each CDR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b. Glycosylation Variants

In certain embodiments, anti-LY6G6D and/or anti-CD3 antibodies of the invention (e.g., bispecific anti-LY6G6D antibodies of the invention that bind to LY6G6D, preferably with high affinity (e.g., 20A12.QNTv12), and a second biological molecule, e.g., CD3) can be altered to increase or decrease the extent to which the antibody is glycosylated. Addition or deletion of glycosylation sites to anti-LY6G6D antibody of the invention may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, anti-LY6G6D and/or anti-CD3 antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. Biotech. Bioeng. 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Anti-LY6G6D and/or anti-CD3 antibodies variants are further provided with bisected oligosaccharides, for example, in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c. Fc Region Variants

In certain embodiments, one or more amino acid modifications may be introduced into the Fc region of an anti-LY6G6D and/or anti-CD3 antibody of the invention (e.g., a bispecific anti-LY6G6D antibody of the invention that binds to LY6G6D, preferably with high affinity (e.g., 20A12.QNTv12), and a second biological molecule, e.g., CD3, thereby generating an Fc region variant (see e.g., US 2012/0251531). The Fc region variant may comprise a human Fc region sequence (e.g., a human IgG1, IgG2, IgG3 or IgG4 Fc region) comprising an amino acid modification (e.g., a substitution) at one or more amino acid positions.

In certain embodiments, the invention contemplates an anti-LY6G6D and/or an anti-CD3 antibody variant that possesses some but not all effector functions, which make it a desirable candidate for applications in which the half-life of the antibody in vivo is important, yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and Cyto-Tox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al. *J. Immunol. Methods* 202: 163 (1996); Cragg, M. S. et al. *Blood.* 101:1045-1052 (2003); and Cragg, M. S. and M. J. Glennie *Blood.* 103: 2738-2743 (2004)). FcRn binding and in vivo clearance/half life determinations can also be performed using methods known in the art (see, e.g., Petkova, S. B. et al. *Int'l. Immunol.* 18(12):1759-1769 (2006)).

Antibodies with reduced effector function include those with substitution of one or more of Fc region residues 238, 265, 269, 270, 297, 327 and 329 (U.S. Pat. Nos. 6,737,056 and 8,219,149). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. Nos. 7,332,581 and 8,219,149).

In certain embodiments, the proline at position 329 of a wild-type human Fc region in the antibody is substituted with glycine or arginine or an amino acid residue large enough to destroy the proline sandwich within the Fc/Fc.gamma. receptor interface that is formed between the proline 329 of the Fc and tryptophan residues Trp 87 and Trp 110 of FcgRIII (Sondermann et al. *Nature.* 406, 267-273, 2000). In certain embodiments, the antibody comprises at least one further amino acid substitution. In one embodiment, the further amino acid substitution is S228P, E233P, L234A, L235A, L235E, N297A, N297D, or P331S, and still in another embodiment the at least one further amino acid substitution is L234A and L235A of the human IgG1 Fc region or S228P and L235E of the human IgG4 Fc region (see e.g., US 2012/0251531), and still in another embodiment the at least one further amino acid substitution is L234A and L235A and P329G of the human IgG1 Fc region.

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lifes and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

In some aspects, the anti-LY6G6D and/or anti-CD3 antibody (e.g., bispecific anti-LY6G6D antibody) comprises an Fc region comprising an N297G mutation. In some embodiments, the anti-LY6G6D antibody comprising the N297G mutation comprises an anti-LY6G6D arm comprising a first binding domain comprising the following six CDRs: (a) a CDR-H1 comprising the amino acid sequence of SEQ ID NO: 4; (b) a CDR-H2 comprising the amino acid sequence of SEQ ID NO: 5; (c) a CDR-H3 comprising the amino acid sequence of SEQ ID NO: 6; (d) a CDR-L1 comprising the amino acid sequence of SEQ ID NO: 1; (e) a CDR-L2 comprising the amino acid sequence of SEQ ID NO: 2; and (f) a CDR-L3 comprising the amino acid sequence of SEQ ID NO: 3; and an anti-CD3 arm.

In some embodiments, the anti-LY6G6D antibody comprising the N297G mutation comprises an anti-CD3 arm comprising a first binding domain comprising (a) a VH domain comprising an amino acid sequence of SEQ ID NO: 10 and (b) a VL domain comprising an amino acid sequence of SEQ ID NO: 11, and an anti-CD3 arm. In other embodiments, the anti-LY6G6D antibody comprising the N297G mutation comprises an anti-CD3 arm comprising a first binding domain comprising (a) a VH domain comprising an amino acid sequence of SEQ ID NO: 59 and (b) a VL domain comprising an amino acid sequence of SEQ ID NO: 60, and an anti-CD3 arm.

In some embodiments, the anti-LY6G6D antibody comprising the N297G mutation comprises one or more heavy chain constant domains, wherein the one or more heavy chain constant domains are selected from a first CH1 ($CH1_1$) domain, a first CH2 ($CH2_1$) domain, a first CH3 ($CH3_1$) domain, a second CH1 ($CH1_2$) domain, second CH2 ($CH2_2$) domain, and a second CH3 ($CH3_2$) domain. In some aspects, at least one of the one or more heavy chain constant domains is paired with another heavy chain constant domain. In some aspects, the $CH3_1$ and $CH3_2$ domains each comprise a protuberance or cavity, and wherein the protuberance or cavity in the $CH3_1$ domain is positionable in the cavity or protuberance, respectively, in the $CH3_2$ domain. In some aspects, the $CH3_1$ and $CH3_2$ domains meet at an interface between said protuberance and cavity. In some aspects, the $CH2_1$ and $CH2_2$ domains each comprise a protuberance or cavity, and wherein the protuberance or cavity in the $CH2_1$ domain is positionable in the cavity or protuberance, respectively, in the $CH2_2$ domain. In other instances, the $CH2_1$ and $CH2_2$ domains meet at an interface between said protuberance and cavity. In some aspects, the anti-LY6G6D antibody is an IgG1 antibody.

In some embodiments, the anti-CD3 antibody comprising the N297G mutation comprises an anti-LY6G6D arm comprising a first binding domain comprising (a) a VH domain comprising an amino acid sequence of SEQ ID NO: 10 or SEQ ID NO: 59 and (b) a VL domain comprising an amino acid sequence of SEQ ID NO: 11 or SEQ ID NO; 60, and an anti-CD3 arm, wherein (a) the anti-LY6G6D arm comprises T366S, L368A, Y407V, and N297G substitution mutations and (b) the anti-CD3 arm comprises T366W and N297G substitution mutations.

In other embodiments, the anti-CD3 antibody comprising the N297G mutation comprises an anti-LY6G6D arm comprising a first binding domain comprising (a) a VH domain comprising an amino acid sequence of SEQ ID NO: 10 or SEQ ID NO: 59 and (b) a VL domain comprising an amino acid sequence of SEQ ID NO: 11 or SEQ ID NO; 60, and an anti-CD3 arm, wherein (a) the anti-LY6G6D arm comprises T366W and N297G substitution mutations and (b) the anti-CD3 arm comprises T366S, L368A, Y407V, and N297G mutations.

d. Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, for example, in U.S. Pat. No. 7,521,541.

e. Antibody Derivatives

In certain embodiments, an anti-LY6G6D antibody of the invention (e.g., bispecific anti-LY6G6D antibody of the invention that binds to LY6G6D, preferably with high affinity (e.g., 20A12.QNTv12), and a second biological molecule, e.g., CD3) provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc. In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

8. Charged Regions

In some aspects, the binding domain that binds LY6G6D or CD3 comprises a VH1 comprising a charged region ($CR_1$) and a VL1 comprising a charged region ($CR_2$), wherein the $CR_1$ in the VH1 forms a charge pair with the $CR_2$ in the VL1. In some aspects, the $CR_1$ comprises a basic amino acid residue and the $CR_2$ comprises an acidic amino acid residue. In some aspects, the $CR_1$ comprises a Q39K substitution mutation (Kabat numbering). In some aspects, the $CR_1$ consists of the Q39K substitution mutation. In some aspects, the $CR_2$ comprises a Q38E substitution mutation (Kabat numbering). In some aspects, the $CR_2$ consists of the Q38E substitution mutation. In some aspects, the second binding domain that binds CD3 comprises a VH2 comprising a charged region ($CR_3$) and a VL2 comprising a charged region ($CR_4$), wherein the $CR_4$ in the VL2 forms a charge pair with the $CR_3$ in the VH2. In some aspects, the $CR_4$ comprises a basic amino acid residue and the $CR_3$ comprises an acidic amino acid residue. In some aspects, the $CR_4$ comprises a Q38K substitution mutation (Kabat numbering). In some aspects, the $CR_4$ consists of the Q38K substitution mutation. In some aspects, the $CR_3$ comprises a Q39E substitution mutation (Kabat numbering). In some aspects, the $CR_3$ consists of the Q39E substitution mutation. In some aspects, the VL1 domain is linked to a light chain constant domain (CL1) domain and the VH1 is linked to a first heavy chain constant domain (CH1), wherein the CL1 comprises a charged region ($CR_5$) and the CH1 comprises a charged region ($CR_6$), and wherein the $CR_5$ in the CL1 forms a charge pair with the $CR_6$ in the $CH1_1$. In some aspects, the $CR_5$ comprises a basic amino acid residue and the $CR_6$ comprises an acidic residue. In some aspects, the $CR_5$ comprises a V133K substitution mutation (EU numbering). In some aspects, the $CR_5$ consists of the V133K substitution mutation. In some aspects, the $CR_6$ comprises a S183E substitution mutation (EU numbering). In some aspects, the $CR_6$ consists of the S183E substitution mutation.

In other aspects, the VL2 domain is linked to a CL domain (CL2) and the VH2 is linked to a CH1 domain ($CH1_2$), wherein the CL2 comprises a charged region ($CR_7$) and the $CH1_2$ comprises a charged region ($CR_8$), and wherein the $CR_8$ in the $CH1_2$ forms a charge pair with the $CR_7$ in the CL2. In some aspects, the $CR_8$ comprises a basic amino acid residue and the $CR_7$ comprises an acidic amino acid residue. In some aspects, the $CR_8$ comprises a S183K substitution mutation (EU numbering). In some aspects, the $CR_8$ consists of the S183K substitution mutation. In some aspects, the $CR_7$ comprises a V133E substitution mutation (EU numbering). In some aspects, the $CR_7$ consists of the V133E substitution mutation.

In other aspects, the VL2 domain is linked to a CL domain (CL2) and the VH2 is linked to a CH1 domain ($CH1_2$), wherein (a) the CL2 comprises one or more mutations at amino acid residues F116, L135, S174, S176, and/or T178 (EU numbering) and (b) the $CH1_2$ comprises one or more mutations at amino acid residues A141, F170, S181, S183, and/or V185 (EU numbering). In some aspects, the CL2 comprises one or more of the following substitution mutations: F116A, L135V, S174A, S176F, and/or T178V. In some aspects, the CL2 comprises the following substitution mutations: F116A, L135V, S174A, S176F, and T178V. In some aspects, the $CH1_2$ comprises one or more of the following substitution mutations: A141I, F170S, S181M, S183A, and/or V185A. In some aspects, the $CH1_2$ comprises the following substitution mutations: A141I, F170S, S181 M, S183A, and V185A.

In other aspects, the binding domain that binds LY6G6D or CD3 comprises a VH domain (VH1) comprising a charged region ($CR_1$) and a VL domain (VL1) comprising a charged region ($CR_2$), wherein the $CR_2$ in the $VL_1$ forms a charge pair with the $CR_1$ in the VH1. In some aspects, the $CR_2$ comprises a basic amino acid residue and the $CR_1$ comprises an acidic amino acid residue. In some aspects, the $CR_2$ comprises a Q38K substitution mutation (Kabat numbering). In some aspects, the $CR_2$ consists of the Q38K substitution mutation. In some aspects, the $CR_1$ comprises a Q39E substitution mutation (Kabat numbering). In some aspects, the $CR_1$ consists of the Q39E substitution mutation. In some aspects, the second binding domain that binds CD3 comprises a VH domain (VH2) comprising a charged region ($CR_3$) and a VL domain (VL2) comprising a charged region ($CR_4$), wherein the $CR_3$ in the VH2 forms a charge pair with the $CR_4$ in the VL2. In some aspects, the $CR_3$ comprises a basic amino acid residue and the $CR_4$ comprises an acidic amino acid residue. In some aspects, the $CR_3$ comprises a Q39K substitution mutation (Kabat numbering). In some aspects, the $CR_3$ consists of the Q39K substitution mutation. In some aspects, the $CR_4$ comprises a Q38E substitution mutation (Kabat numbering). In some aspects, the $CR_4$ consists of the Q38E substitution mutation. In some aspects, the VL1 domain is linked to a light chain constant domain (CL1) and the VH1 is linked to a first heavy chain constant domain ($CH1_1$), wherein the CL1 comprises a charged region ($CR_5$) and the $CH1_1$ comprises a charged region ($CR_6$), and wherein the $CR_6$ in the $CH1_1$ forms a charge pair with the $CR_5$ in the CL1. In some aspects, the $CR_6$ comprises a basic amino acid residue and the $CR_5$ comprises an acidic amino acid residue. In some aspects, the $CR_6$ comprises a S183K substitution mutation (EU numbering). In some aspects, the $CR_6$ consists of the S183K substitution mutation. In some aspects, the $CR_5$ comprises a V133E substitution mutation (EU numbering). In some aspects, the $CR_5$ consists of the V133E substitution mutation.

In other aspects, the VL2 domain is linked to a CL domain (CL2) and the VH2 is linked to a CH1 domain ($CH1_2$), wherein the CL2 comprises a charged region ($CR_7$) and the $CH1_2$ comprises a charged region ($CR_8$), and wherein the $CR_7$ in the CL2 forms a charged pair with the $CR_8$ in the $CH1_2$. In some aspects, the $CR_7$ comprises a basic amino acid residue and the $CR_8$ comprises an acidic residue. In some aspects, the $CR_7$ comprises a V133K substitution mutation (EU numbering). In some aspects, the $CR_7$ consists of the V133K substitution mutation. In some aspects, the $CR_8$ comprises a S183E substitution mutation (EU numbering). In some aspects, the $CR_8$ consists of the S183E substitution mutation.

In other aspects, the VL2 domain is linked to a CL domain (CL2) and the VH2 is linked to a CH1 domain ($CH1_2$), wherein (a) the CL2 comprises one or more mutations at amino acid residues F116, L135, S174, S176, and/or T178 (EU numbering) and (b) the $CH1_2$ comprises one or more mutations at amino acid residues A141, F170, S181, S183, and/or V185 (EU numbering). In some aspects, the CL2 comprises one or more of the following substitution mutations: F116A, L135V, S174A, S176F, and/or T178V. In some aspects, the CL2 comprises the following substitution mutations: F116A, L135V, S174A, S176F, and T178V. In some aspects, the $CH1_2$ comprises one or more of the following substitution mutations: A141I, F170S, S181M, S183A, and/or V185A. In some aspects, the $CH1_2$ comprises the following substitution mutations: A141I, F170S, S181 M, S183A, and V185A. In some aspects, the anti-FcRH5 antibody comprises one or more heavy chain constant domains, wherein the one or more heavy chain constant domains are selected from a first CH2 domain ($CH2_1$), a first CH3 domain ($CH3_1$), a second CH2 domain ($CH2_2$), and a second CH3 domain ($CH3_2$). In some aspects, at least one of the one or more heavy chain constant domains is paired with another heavy chain constant domain. In some aspects, the $CH3_1$ and the $CH3_2$ each comprise a protuberance ($P_1$) or a cavity ($C_1$), and wherein the $P_1$ or the $C_1$ in the $CH3_1$ is positionable in the $C_1$ or the $P_1$, respectively, in the $CH3_2$. In some aspects, the $CH3_1$ and the $CH3_2$ meet at an interface between the $P_1$ and the $C_1$. In some aspects, the $CH2_1$ and the $CH2_2$ each comprise ($P_2$) or a cavity ($C_2$), and wherein the P2 or the C2 in the $CH2_1$ is positionable in the C2 or the $P_2$, respectively, in the $CH2_2$. In some aspects, the $CH2_1$ and the $CH2_2$ meet at an interface between the P2 and the C2.

B. Recombinant Methods and Compositions

Anti-LY6G6D antibodies of the invention (e.g., bispecific anti-LY6G6D antibodies of the invention that bind to LY6G6D, preferably with high affinity (e.g., 20A12.QNTv12), and a second biological molecule, e.g., CD3) and/or anti-CD3 antibodies of the invention (e.g., 38E4v1 MD1 (MD1) and 38E4v1 MD4 (MD4)) may be produced using recombinant methods and compositions, for example, as described in U.S. Pat. No. 4,816,567. In one embodiment, an isolated nucleic acid encoding an anti-LY6G6D antibody described herein is provided. Such nucleic acid may encode an amino acid sequence comprising the VL and/or an amino acid sequence comprising the VH of the antibody (e.g., the light and/or heavy chains of the antibody). In another embodiment, an isolated nucleic acid encoding an anti-CD3 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-LY6G6D antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-LY6G6D antibody and/or an anti-CD3 antibody, a nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

1. Two-Cell Methods for Manufacturing Bispecific Antibodies

In some aspects, an antibody of the invention (e.g., a LY6G6D TDB, e.g., a LY6G6D TDB having an anti-CD3 arm and an anti-Ly6G6D arm (e.g., 20A12.QNTv12)) is manufactured using a method comprising two host cell lines. In some aspects, a first arm of the antibody (e.g., a first arm comprising a hole region) is produced in a first host cell line, and a second arm of the antibody (e.g., a second arm comprising a knob region) is produced in a second host cell line. The arms of the antibody are purified from the host cell lines and assembled in vitro.

2. One-Cell Methods for Manufacturing Bispecific Antibodies

In some aspects, an antibody of the invention (e.g., a LY6G6D TDB, e.g., a LY6G6D TDB having an anti-CD3 arm (e.g., 38E4.v1 MD1 or 38E4.v1 MD4) and an anti-Ly6G6D arm (e.g., 20A12.QNTv12)), is manufactured using a method comprising a single host cell line. In some aspects, a first arm of the antibody (e.g., a first arm comprising a hole region) and a second arm of the antibody (e.g., a second arm comprising a knob region) are produced in and purified from a single host cell line. Preferably, the first arm and the second arm are expressed at comparable levels in the host cell, e.g., are both expressed at a high level in the host cell. Similar levels of expression increase the likelihood of efficient TDB production and decrease the likelihood of light chain (LC) mispairing of TDB components. The first arm and second arm of the antibody may each further comprise amino acid substitution mutations introducing charge pairs, as described in Section IIB (8) herein. The charge pairs promote the pairing of heavy and light chain cognate pairs of each arm of the bispecific antibody, thereby minimizing mispairing.

3. Host Cells

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

C. Assays

Anti-LY6G6D antibodies of the invention (e.g., bispecific anti-LY6G6D antibodies of the invention that bind to LY6G6D, preferably with high affinity (e.g., 20A12.QNTv12), and a second biological molecule, e.g., CD3, such as TDB antibodies of the invention or variants thereof) provided herein may be identified, screened for, or characterized for their physical/chemical properties and/or biological activities by various assays known in the art.

1. Binding Assays and Other Assays

In one aspect, an anti-LY6G6D or anti-CD3 antibody of the invention is tested for its antigen binding activity, for example, by known methods such as ELISA, Western blot, etc.

In another aspect, competition assays may be used to identify an antibody that competes with an anti-LY6G6D antibody of the invention for binding to LY6G6D or to identify an antibody that competes with an anti-CD3 antibody of the invention for binding to CD3.

In an exemplary competition assay, immobilized LY6G6D is incubated in a solution comprising a first labeled antibody that binds to LY6G6D and a second unlabeled antibody that is being tested for its ability to compete with the first antibody for binding to LY6G6D. The second antibody may be present in a hybridoma supernatant. As a control, immobilized LY6G6D is incubated in a solution comprising the first labeled antibody but not the second unlabeled antibody. After incubation under conditions permissive for binding of the first antibody to LY6G6D, excess unbound antibody is removed, and the amount of label associated with immobilized LY6G6D is measured. If the amount of label associated with immobilized LY6G6D is substantially reduced in the test sample relative to the control sample, then that indicates that the second antibody is competing with the first antibody for binding to LY6G6D. See, e.g., Harlow and Lane (1988) *Antibodies: A Laboratory Manual*. Ch.14 (Cold Spring Harbor Laboratory, Cold Spring Harbor, NY). Another exemplary competition assay comprises immobilized CD3 and a first labeled antibody that binds to CD3, wherein the assay is performed as described above.

2. Activity Assays

In one aspect, assays are provided for identifying anti-LY6G6D antibodies thereof having biological activity. Biological activity may include, for example, binding to LY6G6D (e.g., LY6G6D on the surface of a tumor), or a peptide fragment thereof, either in vivo, in vitro, or ex vivo. In the case of a multispecific (e.g., bispecific) anti-LY6G6D antibody of the invention (e.g., a TDB antibody having one anti-LY6G6D arm, e.g., 20A12.QNTv12, and one arm that recognizes a second biological molecule, e.g., a cell surface antigen, e.g., CD3), biological activity may also include, for example, effector cell activation (e.g., T cell (e.g., CD8+ and/or CD4+ T cell) activation), effector cell population expansion (i.e., an increase in T cell count), target cell population reduction (i.e., a decrease in the population of cells expressing LY6G6D on their cell surfaces), and/or target cell killing. Antibodies having such biological activity in vivo and/or in vitro are provided. In certain embodiments, an antibody of the invention is tested for such biological activity, as described in detail in the Examples herein.

Further, cells may be washed in RPMI medium containing 10% FBS, supplemented with GlutaMax, penicillin & streptomycin, and ~0.2 million suspended cells added to a 96-well U-bottom plate. Cells may be cultured in RPM11640 supplemented with 10% FBS at 37° C. in a humidified standard cell culture incubator. For BJAB cell killing assays, 20,000 BJAB cells may be incubated with effector cells, either as huPBMCs or purified T cells, as indicated ratios per assay, in the presence of various concentrations of TDB antibodies for 24 hours.

D. Immunoconjugates

The invention also provides immunoconjugates comprising an anti-LY6G6D antibody and/or an anti-CD3 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an anti-LY6G6D antibody and/or an anti-CD3 antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an anti-LY6G6D antibody and/or an anti-CD3 antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or 1123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Methods and Compositions for Diagnostics and Detection

In certain embodiments, any of the anti-LY6G6D and/or anti-CD3 antibodies of the invention (e.g., bispecific anti-LY6G6D antibodies of the invention that bind to LY6G6D, preferably with high affinity (e.g., 20A12.QNTv12), and a second biological molecule, e.g., CD3) is useful for detecting the presence of LY6G6D and/or CD3 in a biological sample. The term "detecting" as used herein encompasses quantitative or qualitative detection. In certain embodiments, a biological sample comprises a cell or tissue.

In one embodiment, an anti-LY6G6D antibody for use in a method of diagnosis or detection is provided. In a further aspect, a method of detecting the presence of LY6G6D in a biological sample is provided. In certain embodiments, the method comprises contacting the biological sample with an anti-LY6G6D antibody as described herein under conditions permissive for binding of the anti-LY6G6D antibody to LY6G6D, and detecting whether a complex is formed between the anti-LY6G6D antibody and LY6G6D. Such method may be an in vitro or in vivo method.

In another embodiment, an anti-CD3 antibody for use in a method of diagnosis or detection is provided. In a further aspect, a method of detecting the presence of CD3 in a biological sample is provided. In certain embodiments, the method comprises contacting the biological sample with an anti-CD3 antibody as described herein under conditions permissive for binding of the anti-CD3 antibody to CD3, and detecting whether a complex is formed between the anti-CD3 antibody and CD3. Such method may be an in vitro or in vivo method.

In certain embodiments, labeled anti-LY6G6D and/or anti-CD3 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-LY6G6D antibody and/or anti-CD3 antibody of the invention (e.g., bispecific anti-LY6G6D antibodies of the invention that bind to LY6G6D, preferably with high affinity (e.g., 20A12.QNTv12), and a second biological molecule, e.g., CD3) are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide an additional therapeutic agent (e.g., a chemotherapeutic agent, a cytotoxic agent, a growth inhibitory agent, and/or an anti-hormonal agent, such as those recited herein above). Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, for example, films, or microcapsules.

The formulations to be used for in vivo administration are generally sterile. Sterility may be readily accomplished, e.g., by filtration through sterile filtration membranes.

G. Therapeutic Methods and Compositions

Any of the anti-LY6G6D antibodies and/or anti-CD3 antibodies of the invention (e.g., bispecific anti-LY6G6D antibodies of the invention that bind to LY6G6D, preferably with high affinity (e.g., 20A12.QNTv12), and a second biological molecule, e.g., CD3, preferably with high affinity, e.g., LY6G6D TDBs having an anti-Ly6G6D arm, such as 20A12.QNTv12, and an anti-CD3 arm, such as 38E4.v1 MD1 or 38E4.v1 MD4) may be used in therapeutic methods.

In one aspect, an anti-LY6G6D antibody for use as a medicament is provided. In further aspects, an anti-LY6G6D antibody, e.g., a LY6G6D TDB having an anti-CD3 arm (e.g., 38E4.v1 MD1 or 38E4.v1 MD4) and an anti-Ly6G6D arm (e.g., 20A12.QNTv12) for use in treating or delaying progression of a cell proliferative disorder (e.g., a cancer, e.g., a colorectal cancer) is provided. In some embodiments, the cancer is a LY6G6D-positive cancer (e.g., a LY6G6D-positive colorectal cancer). In certain embodiments, an anti-LY6G6D antibody for use in a method of treatment is provided. In certain embodiments, the invention provides an anti-LY6G6D antibody (e.g., a LY6G6D TDB having an anti-CD3 arm (e.g., 38E4.v1 MD1 or 38E4.v1 MD4) and an anti-Ly6G6D arm (e.g., 20A12.QNTv12)) for use in a method of treating an individual having a cell proliferative disorder comprising administering to the individual an effective amount of the anti-LY6G6D antibody. In one such embodiment, the method further comprises administering to the individual an effective amount of at least one additional therapeutic agent, for example, as described below. In further embodiments, the invention provides an anti-LY6G6D antibody (e.g., a LY6G6D TDB having an anti-CD3 arm (e.g., 38E4.v1 MD1 or 38E4.v1 MD4) and an anti-Ly6G6D arm (e.g., 20A12.QNTv12)) for use in enhancing immune function in an individual having a cell proliferative disorder.

In certain embodiments, the invention provides an anti-LY6G6D antibody for use in a method of enhancing immune function in an individual having a cell proliferative disorder comprising administering to the individual an effective of the anti-LY6G6D antibody, (e.g., a bispecific anti-LY6G6D antibody of the invention that binds to a second biological molecule, e.g., CD3), (e.g., to activate effector cells (e.g., T cells, e.g., CD8+ and/or CD4+ T cells), expand (increase) an effector cell population, reduce a target cell (e.g., a cell expressing a second biological molecule recognized by an anti-LY6G6D antibody of the invention, such as a bispecific TDB antibody of the invention) population, and/or kill a target cell (e.g., target tumor cell). An "individual" according to any of the above embodiments may be a human.

In a further aspect, the invention provides for the use of an anti-LY6G6D antibody in the manufacture or preparation of a medicament. In one embodiment, the medicament is for treatment of a cell proliferative disorder (e.g., a cancer, e.g., a colorectal cancer). In some embodiments, the cancer is a LY6G6D-positive cancer (e.g., a LY6G6D-positive colorectal cancer). In a further embodiment, the medicament is for use in a method of treating a cell proliferative disorder comprising administering to an individual having a cell proliferative disorder an effective amount of the medicament. In one such embodiment, the method further comprises administering to the individual an effective amount of at least one additional therapeutic agent, for example, as described below. In a further embodiment, the medicament is for activating effector cells (e.g., T cells, e.g., CD8+ and/or CD4+ T cells), expanding (increasing) an effector cell population, reducing a target cell population (e.g., a population of cells expressing LY6G6D), and/or killing target cells (e.g., target tumor cells) in the individual. In a further embodiment, the medicament is for use in a method of enhancing immune function in an individual having a cell proliferative disorder comprising administering to the individual an amount effective of the medicament to activate effector cells (e.g., T cells, e.g., CD8+ and/or CD4+ T cells), expand (increase) an effector cell population, reduce a target cell population (e.g., a population of cells expressing LY6G6D), and/or kill a target cell (e.g., target tumor cell). An "individual" according to any of the above embodiments may be a human.

In a further aspect, the invention provides a method for treating a cell proliferative disorder (e.g., a cancer, e.g., a colorectal cancer). In some embodiments, the cancer is a LY6G6D-positive cancer (e.g., a LY6G6D-positive colorectal cancer). In one embodiment, the method comprises administering to an individual having such a cell proliferative disorder an effective amount of an anti-LY6G6D antibody, e.g., a LY6G6D TDB having an anti-CD3 arm (e.g., 38E4.v1 MD1 or 38E4.v1 MD4) and an anti-Ly6G6D arm (e.g., 20A12.QNTv12). In one such embodiment, the method further comprises administering to the individual an effective amount of at least one additional therapeutic agent, for example, as described below. An "individual" according to any of the above embodiments may be a human.

In a further aspect, the invention provides a method for enhancing immune function in an individual having a cell proliferative disorder. In one embodiment, the method comprises administering to the individual an effective amount of an anti-LY6G6D antibody (e.g., a LY6G6D TDB having an anti-CD3 arm (e.g., 38E4.v1 MD1 or 38E4.v1 MD4) and an anti-Ly6G6D arm (e.g., 20A12.QNTv12)) to activate effector cells (e.g., T cells, e.g., CD8+ and/or CD4+ T cells), expand (increase) an effector cell population, reduce a target cell population (e.g., a population of cells expressing LY6G6D), and/or kill a target cell (e.g., target tumor cell). In one embodiment, an "individual" is a human.

In a further aspect, the invention provides a method for treating a colorectal cancer, esophageal cancer, stomach cancer, small intestine cancer, large intestine cancer, or an adenocarcinoma (e.g., colorectal adenocarcinoma, gastric adenocarcinoma, or pancreatic adenocarcinoma), which may be metastatic adenocarcinoma (e.g., metastatic colorectal adenocarcinoma, metastatic gastric adenocarcinoma, or metastatic pancreatic adenocarcinoma), by administering an effective amount of an anti-LY6G6D antibody of the invention, such as a bispecific TDB antibody of the invention, such as an anti-Ly6G6D targeting TDB, such as a Ly6G6D TDB having a high-affinity anti-CD3 arm, such as 38E4.v1 MD1 or 38E4.v1 MD4, and an anti-Ly6G6D arm, such as 20A12.QNTv12. In some aspects, the cancer has a microsatellite instability status of "microsatellite stable" ("MSS") or "microsatellite instability low" ("MSI-L"). In other aspects, the cancer has a microsatellite instability status of "microsatellite instability high" ("MSI-H"). In some aspects, the cancer is LY6G6D-positive.

In some aspects, the invention provides a method for treating a colorectal cancer, e.g., a colorectal cancer having a microsatellite instability status of "microsatellite stable" ("MSS") or "microsatellite instability low" ("MSI-L"), by administering an effective amount of an anti-LY6G6D antibody of the invention, such as a bispecific TDB antibody of the invention, such as an anti-Ly6G6D targeting TDB, such as a Ly6G6D TDB having a high-affinity anti-CD3 arm, such as 38E4.v1 MD1 or 38E4.v1 MD4, and an anti-Ly6G6D arm, such as 20A12.QNTv12.

In a further aspect, the invention provides pharmaceutical formulations comprising any of the anti-LY6G6D antibodies provided herein (e.g., LY6G6D TDBs having an anti-CD3 arm (e.g., 38E4.v1 MD1 or 38E4.v1 MD4) and an anti-Ly6G6D arm (e.g., 20A12.QNTv12)), e.g., for use in any of the above therapeutic methods. In one embodiment, a pharmaceutical formulation comprises any of the anti-LY6G6D antibodies provided herein and a pharmaceutically acceptable carrier. In another embodiment, a pharmaceutical formulation comprises any of the anti-LY6G6D antibodies provided herein and at least one additional therapeutic agent, for example, as described herein.

An antibody of the invention (and/or any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. In some embodiments, the antibody is administered by intravenous administration. In other embodiments, the antibody is administered by subcutaneous administration. In some embodiments, an anti-LY6G6D antibody administered by subcutaneous injection exhibits a less toxic response in a patient than the same anti-LY6G6D antibody administered by intravenous injection. Dosing can be by any suitable route, for example, by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with, one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (e.g., an anti-LY6G6D antibody, e.g., a LY6G6D TDB having an anti-CD3 arm (e.g., 38E4.v1 MD1 or 38E4.v1 MD4) and an anti-Ly6G6D arm (e.g., 20A12.QNTv12)) (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

As a general proposition, the therapeutically effective amount of the anti-LY6G6D antibody (e.g., LY6G6D TDB having an anti-CD3 arm (e.g., 38E4.v1 MD1 or 38E4.v1 MD4) and an anti-Ly6G6D arm (e.g., 20A12.QNTv12)) administered to human will be in the range of about 0.01 to about 100 mg/kg of patient body weight whether by one or more administrations. In some embodiments, the antibody used is about 0.01 to about 45 mg/kg, about 0.01 to about 40 mg/kg, about 0.01 to about 35 mg/kg, about 0.01 to about 30 mg/kg, about 0.01 to about 25 mg/kg, about 0.01 to about 20 mg/kg, about 0.01 to about 15 mg/kg, about 0.01 to about 10 mg/kg, about 0.01 to about 5 mg/kg, or about 0.01 to about 1 mg/kg administered daily, for example. In one embodiment, an anti-LY6G6D antibody described herein is administered to a human at a dose of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg or about 1400 mg on day 1 of 21-day cycles. The dose may be administered as a single dose or as multiple doses (e.g., 2 or 3 doses), such as infusions. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg, or 10 mg/kg (or any combination thereof) may be administered to the patient. Such doses may be administered intermittently, for example, every week or every three weeks (e.g., such that the patient receives from about two to about twenty, or, for example, about six doses of the anti-LY6G6D antibody). An initial higher loading dose, followed by one or more lower doses may be administered. The progress of this therapy is easily monitored by conventional techniques and assays.

H. Additional Therapeutic Agents

Antibodies of the invention can be used either alone or in combination with other agents in a therapy. For instance, an antibody of the invention may be co-administered with at least one additional therapeutic agent. In certain embodiments, an additional therapeutic agent is a chemotherapeutic agent, growth inhibitory agent, cytotoxic agent, agent used in radiation therapy, anti-angiogenesis agent, apoptotic agent, anti-tubulin agent, or other agent, such as a epidermal growth factor receptor (EGFR) antagonist (e.g., a tyrosine kinase inhibitor), HER1/EGFR inhibitor (e.g., erlotinib (TARCEVA™), platelet derived growth factor inhibitor (e.g., GLEEVEC™ (Imatinib Mesylate)), a COX-2 inhibitor (e.g., celecoxib), interferon, cytokine, antibody other than the anti-CD3 antibody of the invention, such as an antibody that bind to one or more of the following targets ErbB2, ErbB3, ErbB4, PDGFR-beta, BlyS, APRIL, BCMA VEGF, or VEGF receptor(s), TRAIL/Apo2, PD-1, PD-L1, PD-L2, or another bioactive or organic chemical agent.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-LY6G6D antibody and administration of an additional therapeutic agent occur within about one month, or within about one, two or three weeks, or within about one, two, three, four, five, or six days, of each other. Anti-LY6G6D antibodies of the invention (e.g., a bispecific anti-LY6G6D antibody of the invention that binds to a second biological molecule, e.g., CD3) can also be used in combination with radiation therapy. In some embodiments, the additional therapy may be surgery, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy. In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is surgery. In some embodiments, the additional therapy is a combination of radiation therapy and surgery.

In some embodiments, a Ly6G6D TDB (e.g., a LY6G6D TDB having an anti-CD3 arm (e.g., 38E4.v1 MD1 or 38E4.v1 MD4) and an anti-Ly6G6D arm (e.g., 20A12.QNTv12)) is co-administered (concurrently, as a single or multiple compositions (e.g., formulations)) with one or more additional therapeutic agents, such as any one, two, three, four, five, six, seven, eight, nine, ten, or all eleven of the following: FOLFOX (oxaliplatin (ELOXATIN™) combined with 5-fluorouracil and leucovorin), capecitabine (XELODA®), 5-fluorouracil (5-FU), CapeOx (XELOX; capecitabine with oxaliplatin), leucovorin (folinic acid), bevacizumab (AVASTIN®), cetuximab (ERBITUX®), panitumumab (VECTIBIX®), regorafenib (STIVARGA®), irinotecan (CPT-11; CAMPTOSAR®), and FLOX (5-fluorouracil with oxaliplatin). In other embodiments, a Ly6G6D TDB is administered before one or more additional therapeutic agents, such as any one, two, three, four, five, six, seven, eight, nine, ten, or all eleven of the following: FOLFOX (oxaliplatin (ELOXATIN™) combined with 5-fluorouracil and leucovorin), capecitabine (XELODA®), 5-fluorouracil (5-FU), CapeOx (XELOX; capecitabine with oxaliplatin), leucovorin (folinic acid), bevacizumab (AVASTIN®), cetuximab (ERBITUX®), panitumumab (VECTIBIX®), regorafenib (STIVARGA®), irinotecan (CPT-11; CAMPTOSAR®), and FLOX (5-fluorouracil with oxaliplatin). In other embodiments, a Ly6G6D TDB is administered after one or more additional therapeutic agents, such as any one, two, three, four, five, six, seven, eight, nine, ten, or all eleven of the following: FOLFOX (oxaliplatin (ELOXATIN™) combined with 5-fluorouracil and leucovorin), capecitabine (XELODA®), 5-fluorouracil (5-FU), CapeOx (XELOX; capecitabine with oxaliplatin), leucovorin (folinic acid), bevacizumab (AVASTIN®), cetuximab (ERBITUX®), panitumumab (VECTIBIX®), regorafenib (STIVARGA®), irinotecan (CPT-11; CAMPTOSAR®), and FLOX (5-fluorouracil with oxaliplatin).

i. Growth Inhibitory Agents

In some aspects, the additional therapeutic agent is a growth inhibitory agent. Exemplary growth inhibitory agents include agents that block cell cycle progression at a place other than S phase, e.g., agents that induce G1 arrest (e.g., DNA alkylating agents such as tamoxifen, prednisone, dacarbazine, mechlorethamine, cisplatin, methotrexate, 5-fluorouracil, or ara-C) or M-phase arrest (e.g., vincristine, vinblastine, taxanes (e.g., paclitaxel and docetaxel), doxorubicin, epirubicin, daunorubicin, etoposide, or bleomycin).

ii. Radiation Therapies

In some aspects, the additional therapeutic agent is a radiation therapy. Radiation therapies include the use of directed gamma rays or beta rays to induce sufficient damage to a cell so as to limit its ability to function normally or to destroy the cell altogether. Typical treatments are given as a one-time administration and typical dosages range from 10 to 200 units (Grays (Gy)) per day.

iii. Cytotoxic Agents

In some aspects, the additional therapeutic agent is a cytotoxic agent, e.g., a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $sm^{153}$, $Bi^{212}$, $P^{32}$, $Pb^{212}$, and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and antitumor or anticancer agents.

iv. Immunomodulatory Agents

In some aspects, the additional therapeutic agent is an immunomodulatory agent, e.g., a PD-L1 axis binding antagonist, which may be a PD-1 binding antagonist, a PD-L1 binding antagonist, or a PD-L2 binding antagonist. PD-1 (programmed death 1) is also referred to in the art as "programmed cell death 1," "PDCD1," "CD279," and "SLEB2." An exemplary human PD-1 is shown in UniProtKB/Swiss-Prot Accession No. Q15116. PD-L1 (programmed death ligand 1) is also referred to in the art as "programmed cell death 1 ligand 1," "PDCD1LG1," "CD274," "B7-H," and "PDL1." An exemplary human PD-L1 is shown in UniProtKB/Swiss-Prot Accession No. Q9NZQ7.1. PD-L2 (programmed death ligand 2) is also referred to in the art as "programmed cell death 1 ligand 2," "PDCD1LG2," "CD273," "B7-DC," "Btdc," and "PDL2." An exemplary human PD-L2 is shown in UniProtKB/Swiss-Prot Accession No. Q9BQ51. In some instances, PD-1, PD-L1, and PD-L2 are human PD-1, PD-L1, and PD-L2.

In some aspects, the PD-1 binding antagonist is a molecule that inhibits the binding of PD-1 to its ligand binding partners. In a specific aspect, the PD-1 ligand binding partners are PD-L1 and/or PD-L2. In another instance, a PD-L1 binding antagonist is a molecule that inhibits the binding of PD-L1 to its binding ligands. In a specific aspect, PD-L1 binding partners are PD-1 and/or B7-1. In another instance, a PD-L2 binding antagonist is a molecule that inhibits the binding of PD-L2 to its ligand binding partners. In a specific aspect, the PD-L2 binding ligand partner is PD-1. The antagonist may be an antibody, an antigen binding fragment thereof, an immunoadhesin, a fusion protein, or oligopeptide.

In some aspects, the PD-1 binding antagonist is an anti-PD-1 antibody (e.g., a human antibody, a humanized antibody, or a chimeric antibody).

In some aspects, the PD-L1 binding antagonist is an anti-PD-L1 antibody, for example, as described below. In some aspects, the anti-PD-L1 antibody is capable of inhibiting binding between PD-L1 and PD-1 and/or between PD-L1 and B7-1. In some aspects, the anti-PD-L1 antibody is a monoclonal antibody. In some aspects, the anti-PD-L1 antibody is an antibody fragment selected from the group consisting of Fab, Fab'-SH, Fv, scFv, and $(Fab')_2$ fragments. In some aspects, the anti-PD-L1 antibody is a humanized antibody. In some aspects, the anti-PD-L1 antibody is a human antibody.

In some aspects, the immune checkpoint inhibitor is an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof. In some aspects, the immune checkpoint inhibitor is an antagonist directed against TIGIT (e.g., an anti-TIGIT antibody).

In some aspects, the additional therapeutic agent is 5-fluorouracil (5-FU); irinotecan; capecitabine; oxaliplatin; cetuximab; bevacizumab; panitumumab; aflibercept, regorafenib; ramucirumab, TAS-102 (trifluridine and tipiracil); pembrolizumab; nivolumab; nivolumab and ipilimumab; vemurafenib; FOLFOXIRI and bevacizumab an anti-EGFR therapy in combination with a BRAF and/or MEK inhibitor, optionally including a cytotoxic agent; FOLFOX/FOLFIRI and an anti-EGFR therapy; or FOLFOX/FOLFIRI/ FOLFOXIRI and bevacizumab.

1. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXAMPLES

The following are examples of methods and compositions of the invention. It is understood that various other aspects may be practiced, given the general description provided above, and the examples are not intended to limit the scope of the claims.

Example 1. LY6G6D is a Surface Marker of Colorectal Cancer Cells and has Limited Expression in Normal Tissues Expression of lymphocyte antigen 6 family member G6D (LY6G6D) (SEQ ID NO: 75) in human normal and tumor tissues was assessed using The Cancer Genome Atlas (TCGA) (Grossman et al., *New England Journal of Medicine*, 375(12): 1109-1112) and Genotype-Tissue Expression Project (GTEx) data (Pierson et al., *PLoS Comput Biol*, 11, e1004220, 2015) and immunohistochemistry (IHC).

A. Expression of LY6G6D

Figure 1A:
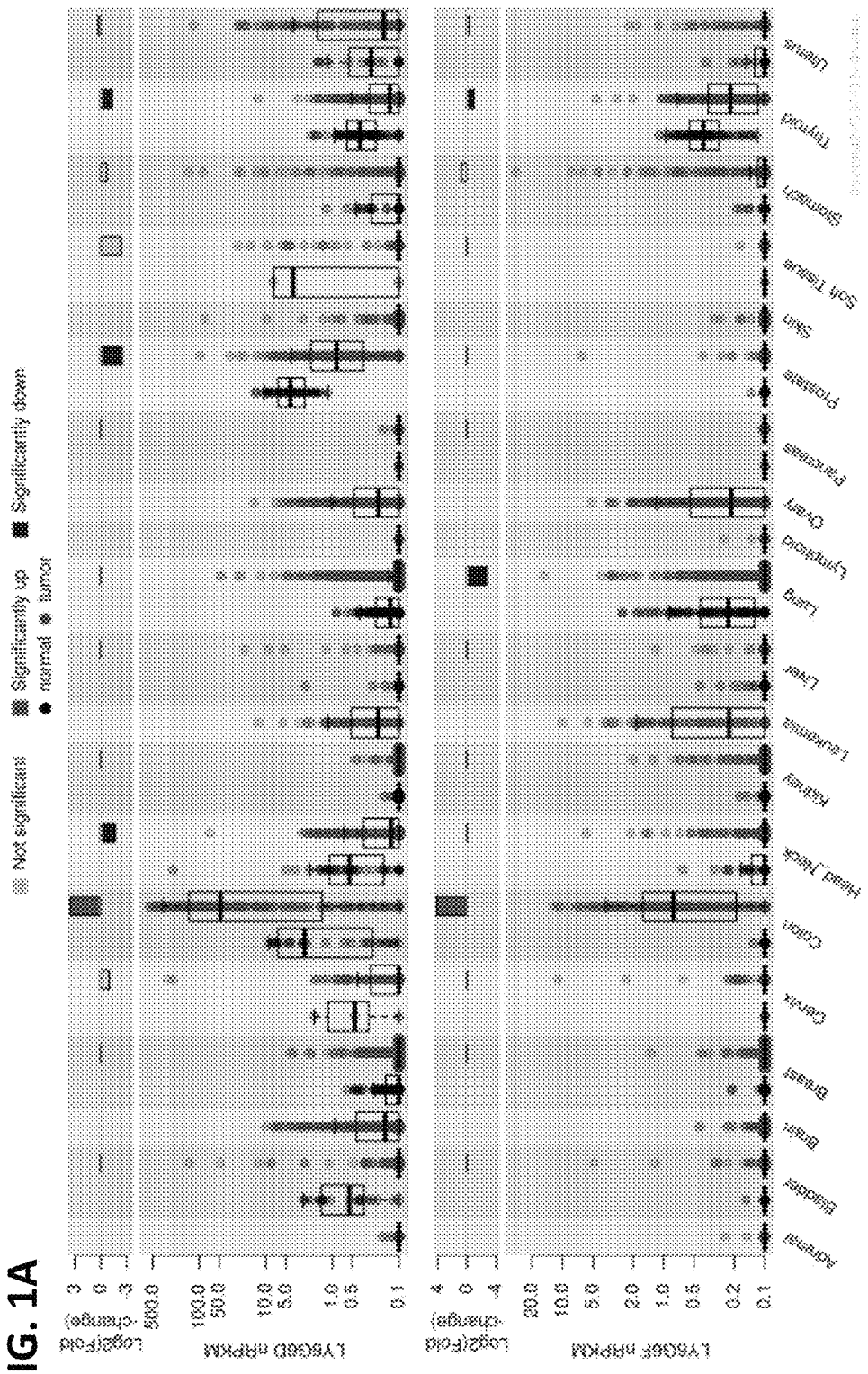
FIG. 1A is a plot showing expression of LY6G6D and LY6G6F in normal (black) and tumor (red) tissues in normalized reads per kilobase million (nRPKM) in The Cancer Genome Atlas (TCGA). LY6G6D is significantly overexpressed in colon tumor tissue.
Figure 1B:
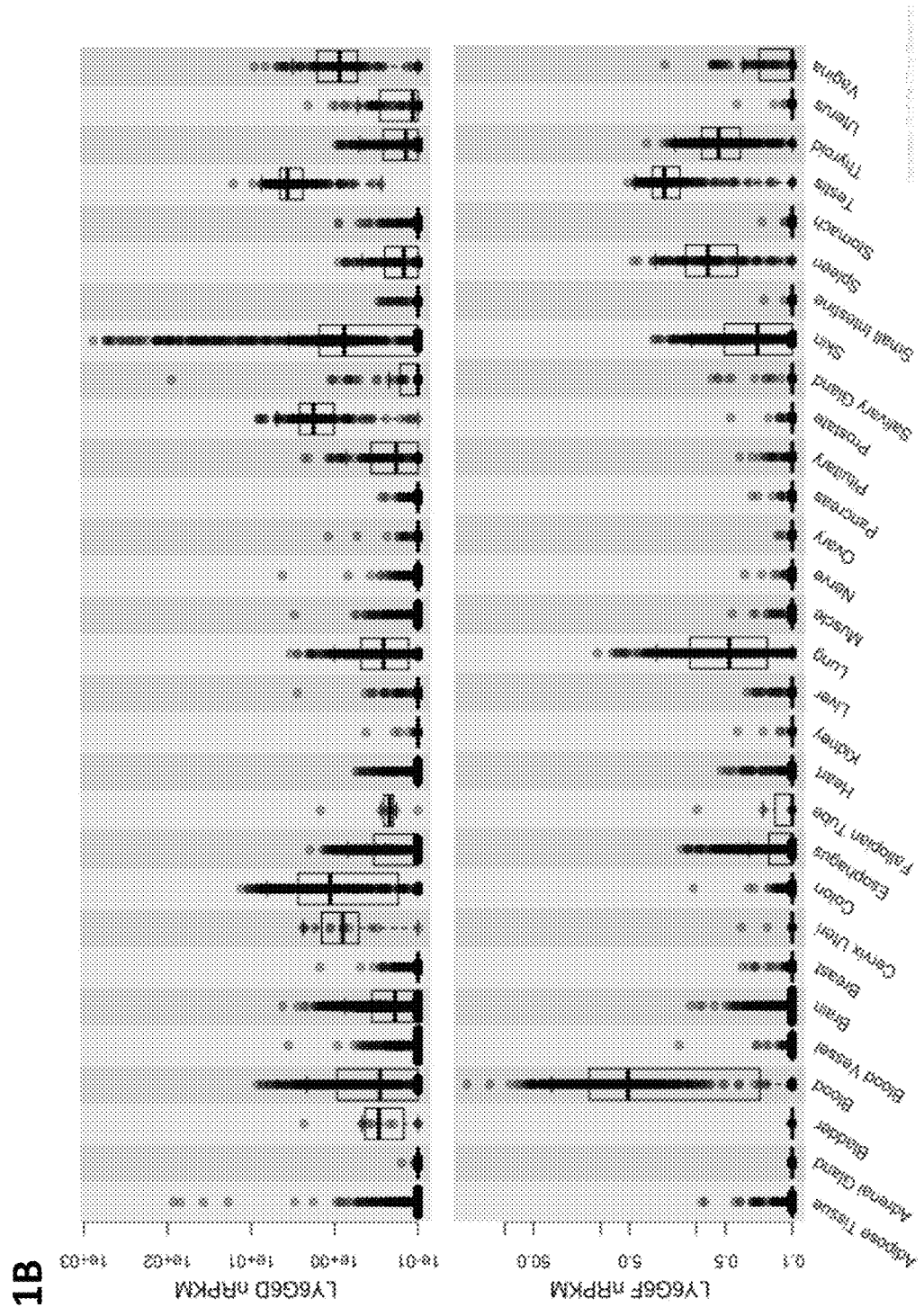
FIG. 1B is a plot showing expression of LY6G6D and LY6G6F in normal tissues in nRPKM in public GTEx Project data.

FIG. 1A shows expression of LY6G6D and lymphocyte antigen 6 family member G6F (LY6G6F) in normal and tumor tissues in human tissues in TCGA data. In tumor tissues, the indication with highest expression of LY6G6D is colon, and LY6G6D is significantly overexpressed only in colon tumor tissue. Normal colon tissues show some expression of LY6G6D as well, albeit at much lower levels. Noteworthy expression (>1 nRPKM) of LY6G6F is mostly found in colon tumor tissue. FIG. 1B shows expression of LY6G6D and LY6G6F in normal tissues in public GTEx Project data. LY6G6D is most highly expressed in prostate, testis, cervix and vagina tissue, and considerable expression is found in normal colon tissue and a subset of skin samples. LY6G6F is most highly expressed in the blood, followed by testis, spleen, thyroid and lung tissue.

B. Expression of LY6G6D in MSS and MSI-L CRCs

Figure 1C:
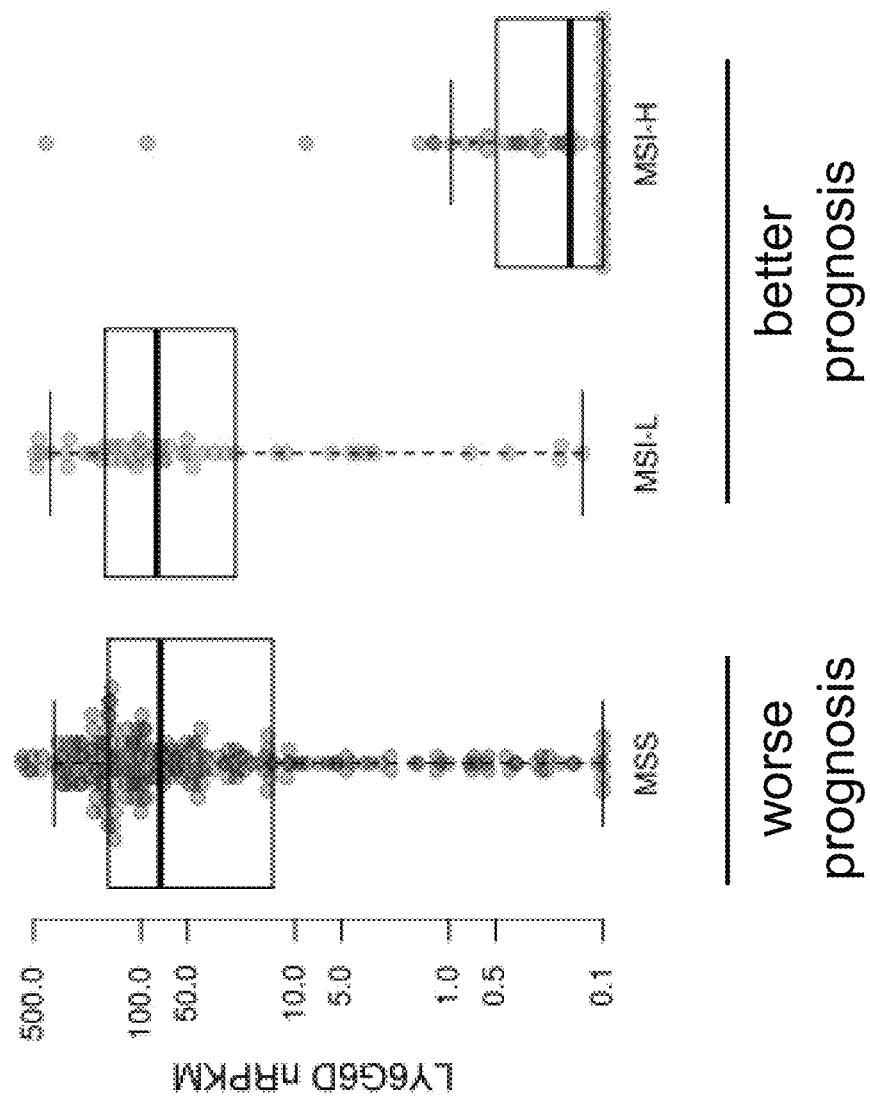
FIG. 1C is a set of box plots showing expression of LY6G6D in nRPKM in colorectal cancers (CRCs) having a microsatellite instability (MSI) status of microsatellite stable (MSS), microsatellite instability low (MSI-L), or microsatellite instability high (MSI-H). The association between MSI status of a CRC and prognosis is indicated.

LY6G6D is most highly expressed in colorectal cancers (CRCs) having a microsatellite instability (MSI) status of microsatellite stable (MSS), microsatellite instability low (MSI-L), or microsatellite instability high (MSI-H); MSS CRCs are associated with worse prognosis (FIG. 1C).

C. IHC Staining of LY6G6D

Human CRC tumors were stained for LY6G6D. About 20% of primary CRC cases were identified as LY6G6D-positive by IHC. 141 Tissue MicroArray (TMA) primary colon tumors were assessed. 21 tumors showed weak (1+) IHC staining (14%), 5 showed moderate (2+) staining, and 4 showed strong (3+) staining (6-7% combined) (FIG. 2A). FIGS. 2B-2D show weak (1+), moderate (2+), and strong (3+) IHC staining for LY6G6D in primary colon tumor tissue.

Figure 3B:
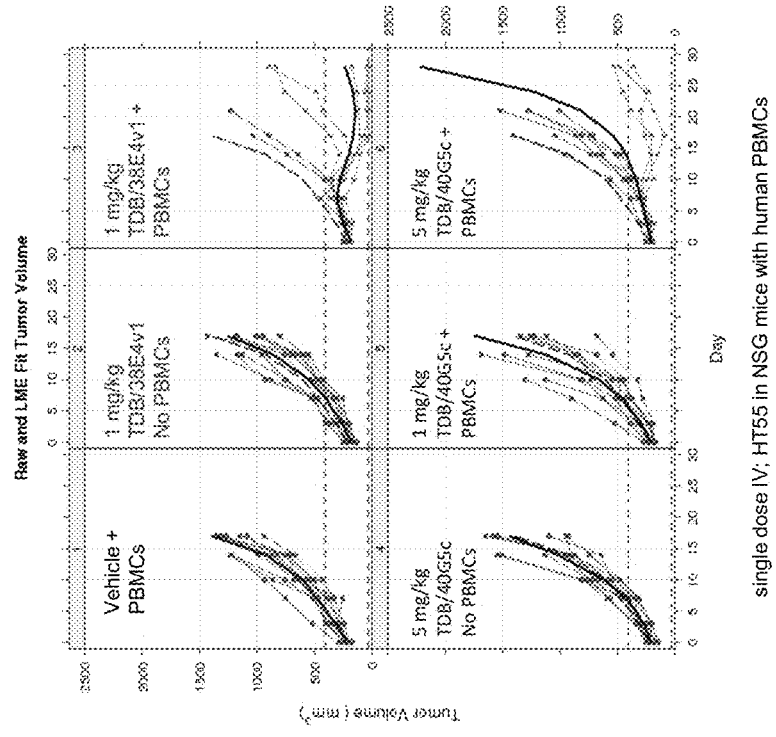
FIG. 3B is a set of graphs showing tumor volume (mm$^2$) of xenograft HT55 tumors in NSG™ mice following treatment with a LY6G6D TDB comprising an anti-LY6G6D 1G4 arm and an anti-CD3 40G5c or 38E4v1 arm. Mice were humanized with healthy donor PBMCs. Treatments comprising the delivery vehicle and PMBCs or comprising the LY6G6D TDB and not comprising PMBCs are provided as controls.

Example 2. Manufacturing Liabilities in Anti-LY6G6D 1G4 Arm, Anti-LY6G6D Clone Generation, Epitope Mapping, and Humanization A. Manufacturing Liabilities in Anti-LY6G6D 1G4 Arm Anti-LY6G6D TDBs comprising the chimeric anti-LY6G6D 1G4 arm and an anti-CD3 38E4.v1 arm demonstrated in vitro killing of HT55 cells (human colon carcinoma cell line) (FIG. 3A) and in vivo activity against xenograft LS1034 and HT55 tumors in NSG™ mice (FIG. 3B). 1G4 is a mouse hybridoma antibody; chimeric 1G4 (ch1G4) is a mouse/human chimeric antibody in which the mouse variable domains (VH and VL) of 1G4 were genetically fused to, respectively, human heavy chain constant domains (CH1, CH2, and CH3) having an N297G amino acid substitution mutation in CH2 and comprising a "hole" region" and a human light chain constant domain (CL). A humanized version of the 1G4 arm was generated and showed in vitro and in vivo efficacy (FIGS. 3C and 3D).

A molecule assessment (MA) liability was identified for amino acid residue W50 of the humanized 1G4 light chain (LC) CDR2 (WASTRIS; SEQ ID NO: 110). Briefly, humanized IG4 was tested for stress under chemical conditions with AAPH (2,2-azobis(2-amidinopropane) dihydrochloride), a small molecule known to generate free radicals (see, e.g., Ji et al., *J. Pharm. Sci.* 98(12):4485-4500, 2009), as well as under thermal conditions at varying pH (a two-week thermal stress test at 40° C., pH 5.5). The light chain residue W50 was identified as having increased oxidation (72.0% oxidation) following AAPH stress.

The thermal stress assay mimics stability over the shelf life of the product. Samples were buffer exchanged into 20 mM His Acetate, 240 mM sucrose, pH 5.5 and diluted to a concentration of 1 mg/mL. One mL of each sample was stressed at 40° C. for 2 weeks, and a second was stored at −70° C. as a control. Both samples were then digested using trypsin to create peptides that could be analyzed using liquid chromatography (LC)-mass spectrometry (MS) analysis. For each peptide in the sample, retention time (as measured using liquid chromatography) and high-resolution accurate mass and peptide ion fragmentation information (amino acid sequence information) were acquired. Extracted ion chromatograms (XIC) were generated for peptides of interest (e.g., native and modified peptide ions) from the data sets at a window of +/−10 ppm, and peaks were integrated to determine area. Relative percentages of modification were calculated for each sample by taking the (area of the modified peptide) divided by (area of the modified peptide plus the area of the native peptide) multiplied by 100.)

Figure 3A:
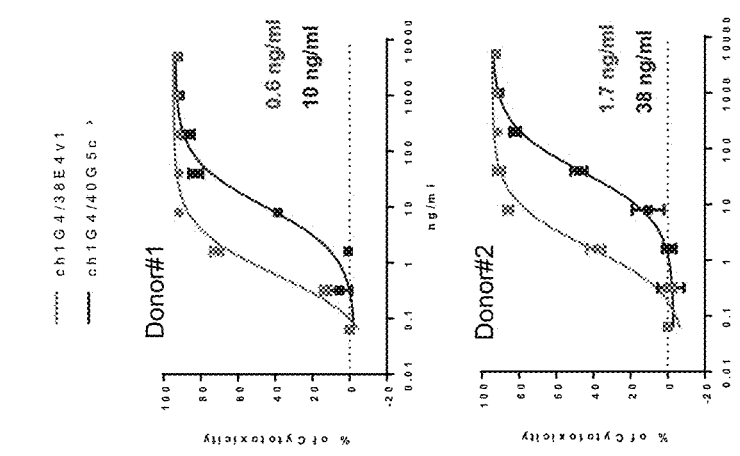
FIG. 3A is a pair of graphs showing in vitro killing of HT55 cells (human colon carcinoma cell line) supplemented with 10× human PBMCs from Donor #1 or Donor #2 by a LY6G6D T cell-dependent bispecific antibody (TDB) comprising an anti-LY6G6D 1G4 arm and an anti-CD3 38E4v1 or 40G5c arm. EC50 values for each TDB are listed.

Additionally, the 1G4 arm failed a transient transfection assay for production (FIG. 3O). W50 was replaced with all 18 alternative amino acids (excluding Cys), but binding affinity appeared to be impacted by the replacement. Finally, as shown in FIG. 3A, the 1G4 arm is effective only when paired with the high-affinity 38E4.v1 arm, but not when paired with the low-affinity 40G5c. A new discovery campaign for anti-LY6G6D antibodies was thus undertaken.

B. Generation of Rabbit Anti-huLY6G6D mAbs

Anti-human LY6G6D (huLY6G6D) monoclonal antibodies (mAbs) were generated in rabbits. New Zealand White rabbits were immunized with human Ly6G6D, and single B cells were isolated from the immunized rabbits using a modified protocol of Offner et al. *PLoS ONE*, 9(2), 2014. This modified workflow included direct FACS sorting of IgG+ huLy6G6D+ B cells into single wells. The B cell culture supernatants were assayed by ELISA for binding to human Ly6G6D and an irrelevant control protein. Ly6G6D-specific B cells were lysed and immediately frozen at −80° C. for storage until molecular cloning. The variable regions (VH and VL) of each rabbit B cell monoclonal antibody were cloned into expression vectors from extracted mRNA as previously described (Offner et al. *PloS ONE*, 9(2), 2014). Individual recombinant rabbit antibodies were expressed in Expi293 cells and subsequently purified with protein A. Purified anti-Ly6G6D antibodies were then subjected to functional activity assays and kinetic screening. About 280 anti-Ly6G6D ELISA+ clones were generated. 96 clones were subsequently binned into four distinct epitope-binning groups, as described below.

Figure 4A:
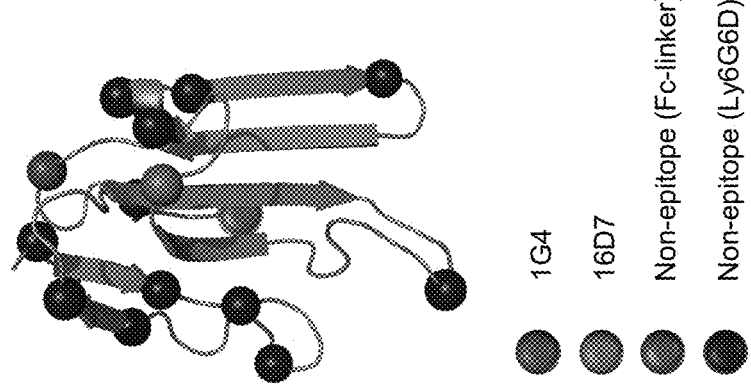
FIG. 4A is a ribbon diagram showing the location of engineered glycosylation sites (red, pink, green, and blue circles) in a structural homology model of the LY6G6D polypeptide. Glycosylation sites are color-coded based on their effect on antibody binding. Glycosylation at the site marked by the red circle disrupted the binding of 1G4.
Figure 4B:
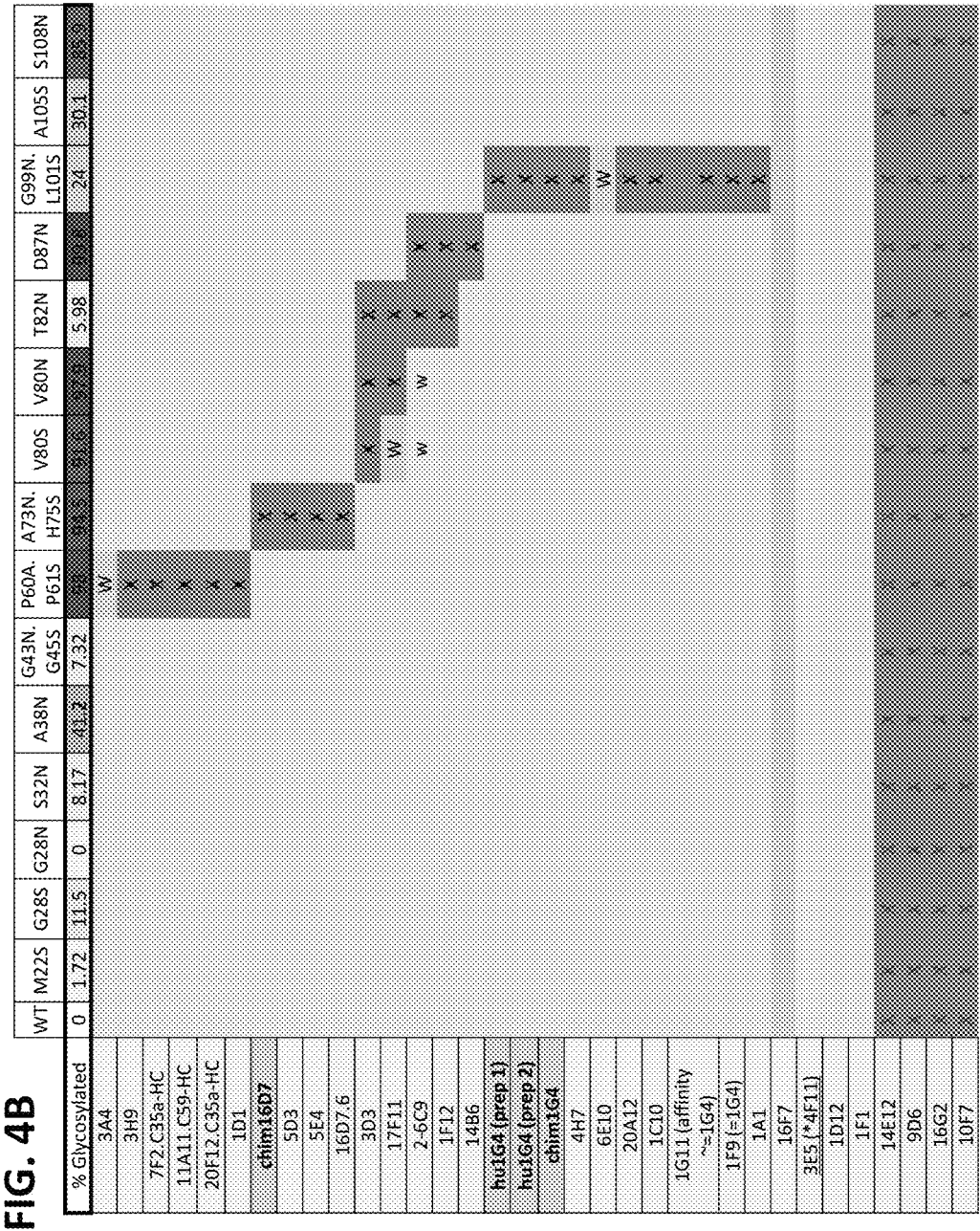

C. Kinetic Analysis and Anti-LY6G6D Epitope Binning Using Glycoengineered LY6G6D An array-based SPR imaging system (Carterra®, USA) was used for kinetics testing and epitope binning of a panel of 96 rabbit anti-huLY6G6D monoclonal antibodies, including 1G4. For epitope binning, LY6G6D polypeptides were engineered to introduce glycosylation sites throughout the surface of the molecule (FIGS. 4A and 4B). Sites were chosen for ease of adding the glycosylation site with minimal disruption from the natural sequence. Candidate anti-LY6G6D antibodies were tested for interaction with the glycoengineered LY6G6D polypeptides (FIG. 4B). Purified antibodies were diluted at 10 µg/ml in 10 mM sodium acetate buffer, pH 4.5. Using amine coupling, antibodies were directly immobilized onto a SPR sensorprism CMD 200M chip (XanTec Bioanalytics, Germany) using a SPRi-Continuous Flow Microspotter™ (Carterra®, USA) to create an array of 96 antibodies. For analysis, the IBIS MX96 SPRi (Carterra®, USA) was used to evaluate analytes binding to the immobilized ligands. For kinetic analyses, human Ly6G6D were injected for 3 minutes from 0 to 300 nM at 3-fold dilution, followed by a dissociation period of 10 minutes. For epitope binning, each glycosylation mutant of human Ly6G6D was first injected for 4 minutes at 50 nM, followed by a second 4-minute injection of the individual monoclonal antibody at 10 µg/ml. The surface was regenerated with 10 mM glycine, pH 1.5 between cycles. The experiment was performed at 25° C. in a running buffer of HBS-T buffer (0.01M HEPES pH 7.4, 0.15M NaCl, 0.05% surfactant P20). The kinetic data were processed using Scrubber 2.0 (BioLogic Software), and the epitope binning data were processed using the Wasatch binning software tool (Carterra®, USA).

Figure 4C:
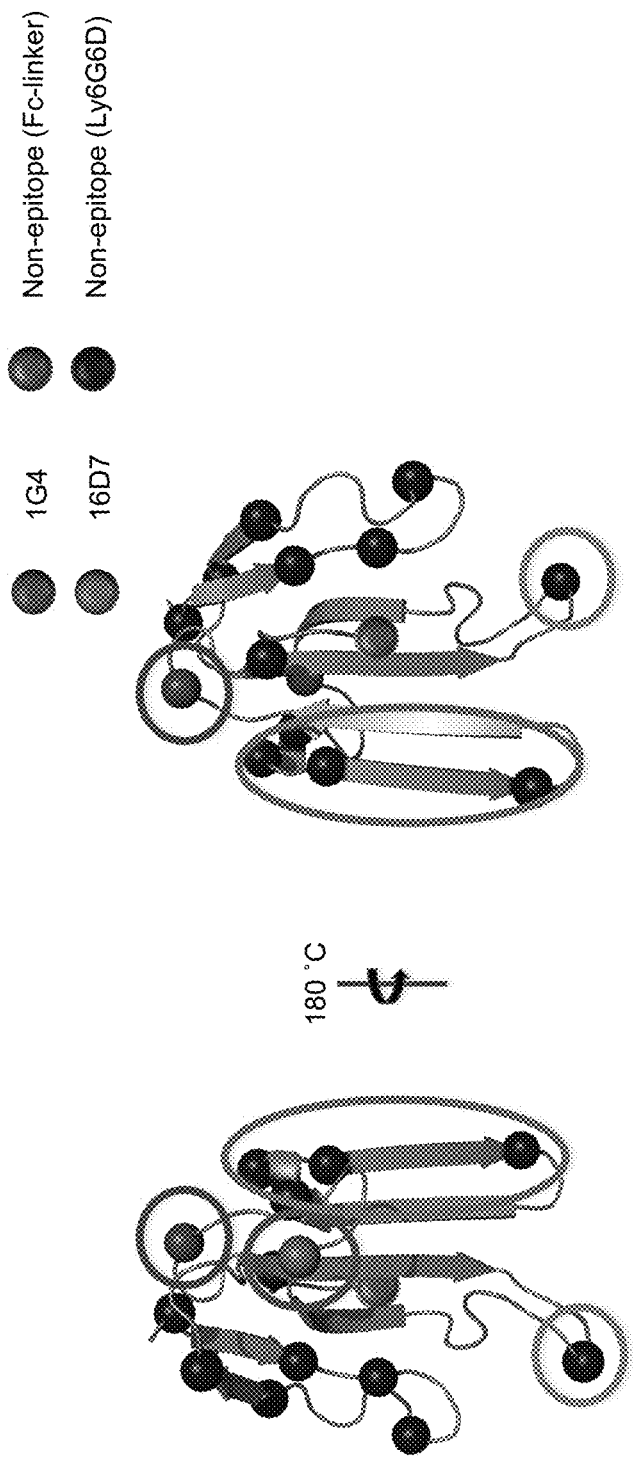
Figure 4D:
Figure 4E:
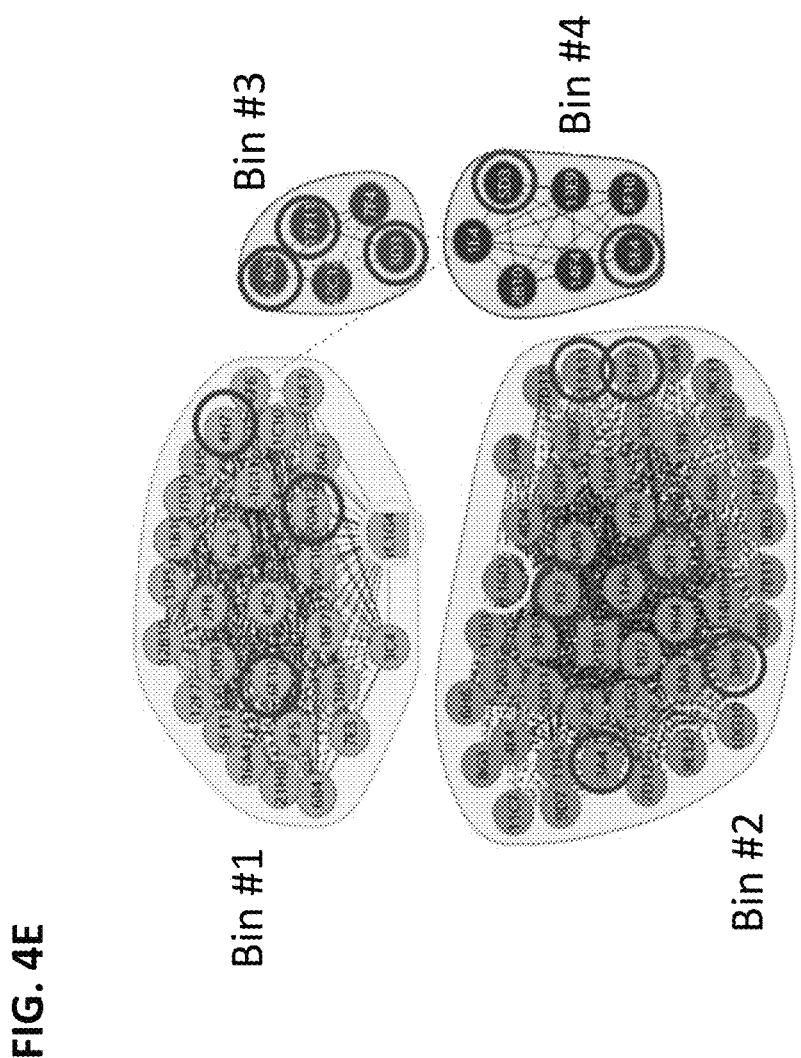

Binding of 1G4 and the rabbit anti-LY6G6D antibody 20A12 to the LY6G6D polypeptide was disrupted in the glycoengineered LY6G6D polypeptide having G99N.L101S amino acid substitution mutations (FIG. 4B). Binding of other rabbit anti-LY6G6D antibodies was variously disrupted by P60A.P61S, A73N.H75S, V80S, V80N, T82N, or D87N amino acid substitution mutations (FIG. 4B). Rabbit antibody clones and 1G4 were placed into four distinct epitope bins based on the results of the glycoengineering assay (FIG. 4E): Bin 1 includes three groups of sequences and includes 1G4, 20A12, 6E10, and 4H7; Bin 4 includes six groups of sequences and includes f.16D7; and Bins 3 and 4 each include three groups of sequences. The amino acid residues affected by glycosylation mutations are color-coded and the Bins 1, 2, 3, and 4 are indicated by underlining in FIG. 4D (SEQ ID NO: 88). The anti-LY6G6D antibodies 1G4 and 16D7 bind epitopes on opposite sides of the antigen, as shown in FIG. 4C.

D. Cell-Based Cytotoxicity Assay

To evaluate the ability of the new panel of rabbit antibodies to target a Ly6G6D-positive tumor cell line, bispecific T cell-dependent antibodies (TDBs) comprising an anti-CD3 40G5c arm paired with different rabbit anti-LY6G6D arms were made. Representative rabbit antibodies from each epitope bin (Bin 1, 2, 3 and 4) were reformatted into half-antibodies having an Fc region comprising a "knob" region, chimeric rabbit variable domains, and human constant domains having N297G and T366W mutations. After purification, the "knob" anti-LY6G6D arms were annealed with an anti-CD3 40G5c arm having an Fc region comprising a "hole" region and were assayed for binding to, and in vitro killing of, HT55 cells (FIGS. 4F, 4G, and 13A-13E). The rabbit antibodies from Bin 1 (e.g., 20A12 and 6E10), the bin that included 1G4, were found to be the most effective at both binding and killing of HT55 cells.

E. Kinetic Analysis

Figure 4F:
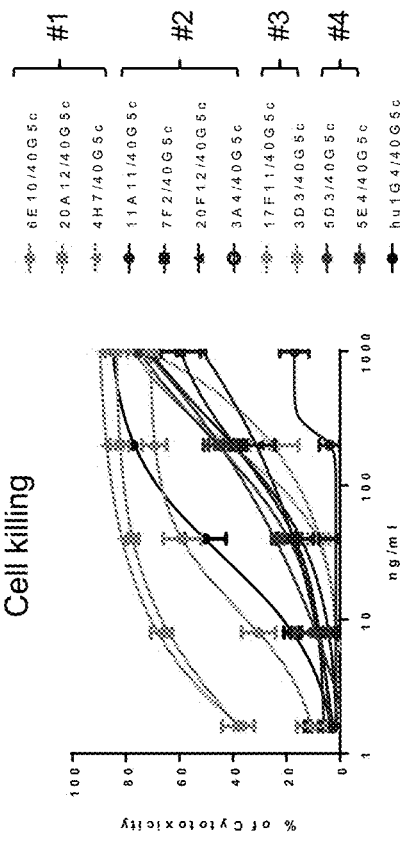
Figure 4G:
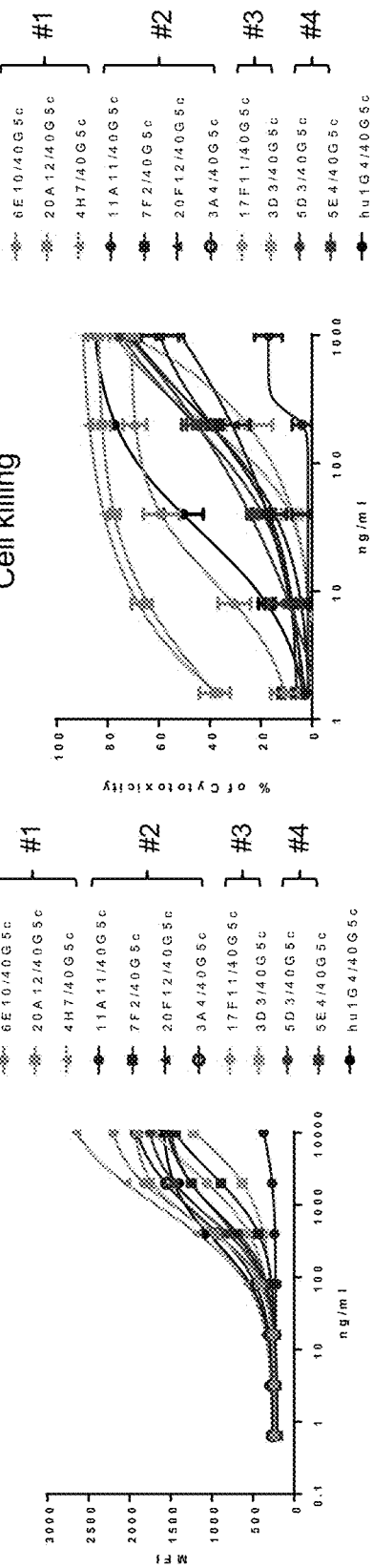
Figure 4H:
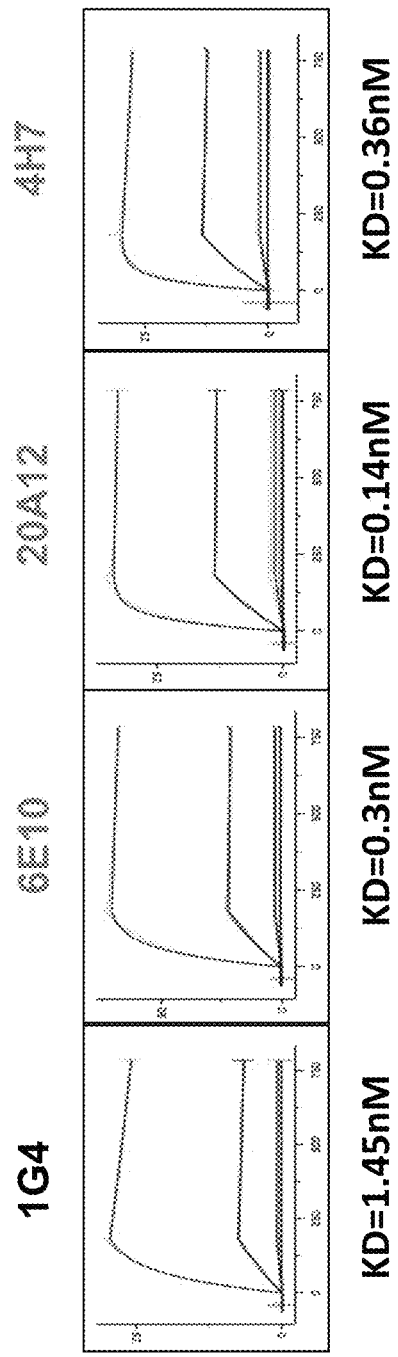

The binding affinity of anti-LY6G6D rabbit antibodies to LY6G6D was determined using a BIAcore™ T200 machine (GE Healthcare Life Sciences). Briefly, BIAcore™ research-grade CM5 chips were activated with 1-ethyl-3-(3-dimethylaminopropyl) carbodiimide (EDC) and N-hydroxysuccinimide (NHS) reagents according to the suppliers instructions. For kinetics measurements, Ly6G6D protein was coupled to the chips to achieve approximately 100 response units (RU) in each flow cell. Unreacted coupling groups were blocked with 1M ethanolamine. Rabbit antibodies were expressed as chimera antigen-binding fragments (Fabs) with rabbit variable domains and human constant domains. Ten-fold serial dilutions of Fabs were injected in HBS-P buffer at 37° C. with a flow rate of 30 µL/min. Association rates (ka) and dissociation rates (kd) were calculated using a 1:1 Langmuir binding model (BIAcore™ T200 Evaluation Software version 2.0). The equilibrium dissociation constant ($K_D$) was calculated as the ratio kd/ka (FIG. 4H).

F. Humanization of Rabbit Antibodies

The Bin 1 rabbit monoclonal antibodies 20A12 and 6E10 were humanized as described below. Residue numbers are according to Kabat et al., Sequences of proteins of immunological interest, 5th Ed., Public Health Service, National Institutes of Health, Bethesda, Md. (1991).

Humanization of 20A12

One challenge in the humanization of rabbit antibodies is that the differences between rabbit and human sequences are greater than those between rodent and human sequences. Multiple frameworks were thus applied for the humanization of 20A12.

The hypervariable regions from each of the rabbit antibodies, namely positions 24-34 (L1), 50-56 (L2), and 89-97 (L3) in the VL domain and positions 26-35 (H1), 50-65 (H2) and 95-102 (H3) in the VH domain, were each grafted into two human acceptor frameworks. Variants of the rb.20A12 light chain were generated based on the human light chain germline sequences hIGHV.1-5, hIGKV.1-39, and hIGKV.4-1, and variants of the rb.20A12 heavy chain were generated based on the human heavy chain germline sequences hIGHV.3-23 and hIGHV.3-30 (FIGS. 31B, 31C, and 40A). These germline sequences were selected based on their high serum prevalence and high sequence identity to rb.20A12 (FIGS. 31C and 31D). The VL CDR KV1-5*01 and the VH CDR HV3-23*01 were selected for further analysis. The 20A12 sequence comprising fully human framework regions is shown as L2H10 in FIG. 32D.

Humanized 20A12 variants were assessed as Fabs. The human germline frameworks (VL and VH) were modified at all presumptive rabbit Vernier positions such that each Vernier position comprised the amino acid present in the rabbit antibody sequence (i.e., rb20A12). Rabbit Vernier positions were identified based on known rodent Vernier positions. The variant in which all heavy chain and light chain Vernier positions have been reverted to the rabbit amino acid is referred to as L1H1 (hu20A12.L1H1) in FIG. 32D. The variant in which all heavy chain and light chain rabbit Vernier positions comprise the human amino acid is referred to as L2H10. To assess whether each rabbit Vernier position affects the binding affinity of the antibody or huLY6G6D, rabbit Vernier positions were individually reverted to the amino acid of the corresponding human sequence, i.e., KV1-5*01 or HV3-23*01. One light chain variant, L2, and eight additional heavy chain variants, H2-H9, were made. L2 comprises a P43A amino acid substitution mutation relative to the KV1-5*01 sequence. H2-H9 comprise, respectively, Q2V, I48V, A49S, K71R, S73N, V78L, F91Y, and P105R amino acid substitution mutations relative to the HV3-23*01 sequence. Binding affinity of the variant antibodies was compared to that of the parental clone comprising fully human framework sequences (L2H10) using a BIAcore assay (FIG. 32D). The rabbit heavy chain residues S73, T76, V78, and P105 were determined to be the key rabbit Vernier residues based on binding affinity evaluation of the variant antibodies described above.

FIG. 32C shows a polished version of humanized 20A12 comprising the rabbit heavy chain residues S73, T76, V78, and P105, and human residues at all other rabbit Vernier positions. The polished humanized 20A12 was also modified to comprise C35S or C35I and C50A amino acid substitutions, as described below. The S73, V78, and P105 rabbit Vernier residues, the additional rabbit Vernier residue T76, and the C35S and C50A amino acid substitutions were also grafted onto the human germline HV3-30*1 to generate an additional humanized, polished version of rb.20A12.

About 20-40% of rabbit antibodies contain extra cysteine residues. For example, the rabbit 20A12 clone contains a cysteine pair in CDR-H1 and CDR-H2 (C35 at CDR-H1 and C50 at CDR-H2) (FIG. 31A; FIG. 40B). Cysteines at these two positions are commonly found and are believed to form a disulfide bond. In order the remove this cysteine pair, which could be a liability in development, C35 and C50 of rb.20A12 were simultaneously mutated to C35S-C50A, C35S-C50S, C35I-C50A, C35I-C50S, C35I-C50I, and C35G-C50T, and variants were assessed for binding to LY6G6D. Each of the variants were assessed in the form of chimeric Fabs with rabbit variable domains and human constant regions. The variant rb20A12.IA (C35I-C50A) was found to retain most of the affinity of the parent ($K_D$ 0.86 nM) (FIGS. 34A and 34C). The C35I-C50A mutations were thus included in the polished humanized 20A12 heavy chain sequence described above.

Additionally, the rabbit 20A12 light chain sequence contains a glycosylation motif (NNT) in CDR3 (FIG. 32A and FIG. 40B), and this site was confirmed to be glycosylated. A series of variants were made in the rabbit/human chimera backbone in order to remove this glycosylation site: NNT was replaced with QNT, QNV, SNA, SNV, ANT, GNT, NNV, or NNA (FIG. 34B). The QNT, QNV, SNV, GNT, and SNA substitutions were incorporated into the polished humanized 20A12 light chain sequence described above and were assayed for binding to LY6G6D (FIGS. 34B-34D).

20A12.QNTv12

The 20A12.QNTv12 variant was selected as the humanized rb.20A12 antibody. 20A12.QNTv12 comprises the VL framework regions of KV1-5*01; the VH framework regions of CDR HV3-23*01, modified with the amino acid substitutions S73, T76, V78, and P105 (derived from rabbit Vernier positions); and the CDRs of rb.20A12, with the replacement of the cysteine residues in CDR-H1 and CDR-H2 with I and A, respectively, and an NNT to QNT mutation at the glycosylation site in CDR-L3 (FIGS. 32A, 40B, and 40C). $K_D$ is 0.23 nM for rb.20A12 and 0.14 nM for 20A12.QNTv12.

Binding to LY6G6D

The humanized rb.20A12 variant 20A12.QNTv12, the humanized rb.6E10 variant 6E10.v114, and the anti-LY6G6D 1G4 arm were paired with the anti-CD3 38E4v1 or 40G5c arm as TDBs and tested for affinity to human and cynomolgus LY6G6D in a BIAcore® assay. Rabbit 20A12, rabbit 6E10, and humanized 20A12.QNTv12 and 20A12.SNVv12 were additionally assayed for binding as antigen-binding fragments (Fabs). LY6G6D-Fc was directly immobilized on a chip, and TDBs were flowed through at 37° C., except for the rb6E10 Fab, which was assayed at 25° C. Results are shown in Table 2 below.

TABLE 2

Binding properties of 20A12 and 6E10 Fab and TDB variants

| Sample | ka (1/Ms) | kd (1/s) | KD (M) |
|---|---|---|---|
| rb20A12 Fab | 4.12E+05 | 1.76E−04 | 4.26E−10 |
| hu20A12.QNTv12 fab | 1.67E+06 | 2.27E−04 | 1.36E−10 |
| hu20A12.SNVv12 fab | 2.18E+06 | 4.26E−05 | 1.95E−11 |
| hu20A12.QNTv12/38E4v1 TDB | 2.20E+05 | 4.44E−04 | 2.02E−09 |
| hu20A12.QNTv12/40G5c TDB | 8.06E+04 | 4.53E−04 | 5.62E−09 |
| rb6E10 Fab (@25° C.) | 2.00E+05 | 6.37E−05 | 3.18E−10 |
| hu6E10.v114/38E4v1 TDB | 1.98E+05 | 3.12E−04 | 1.58E−09 |
| hu6E10.v114/40G5c TDB | 1.01E+05 | 2.92E−04 | 2.89E−09 |

Transient Transfection Production Assay

Two humanized rb.20A12 variants, 20A12.QNTv1 and 20A12.QNTv12, were assessed in a transient transfection production assay. One day after transfection into Chinese hamster ovary (CHO) cells, growth medium was exchanged for a proprietary production medium. Supernatants were collected one day after adding the production medium and were evaluated for antibody titer using an Fc-binding ELISA, Production yield was normalized against 38E4v1. aFGFR1.knob is provided as a control. Both 20A12.QNTv.1 and 20A12.QNTv12 had acceptable yield (FIG. 37).

20A12.v1, 20A12.v1.polished (20A12.QNTv12), and 1G4 all showed favorable results in a BV ELISA assay (an in vitro test for risk of atypical clearance; Hotzel et al., MAbs, 4: 753-760, 2012) when paired with either the 38E4v1 or the 40G5c anti-CD3 arm (FIG. 38). Results were normalized to anti-Lye6E, an antibody used as a control for high binding signal in the BV ELISA assay.

LY6G6D TDBs comprising anti-LY6G6D arm 20A12.QNTv12 and the anti-CD3 arm 38E4v1 or 40G5c were assessed for molecule assessment liabilities using thermal stress and AAPH oxidation stress tests. No liabilities were identified (FIG. 39).

The humanized rb.20A12 variant 20A12.QNTv12, the humanized rb.6E10 variant 6E10.v114, and the anti-LY6G6D 1G4 arm were paired with the anti-CD3 38E4v1 arm as TDBs and tested for affinity to human and cynomolgus LY6G6D in a BIAcore® assay. LY6G6D-Fc was directly immobilized on a chip, and TDBs were flowed through at 37° C. $K_D$ for the TDBs comprising the 1G4 arm was substantially higher than that of either the 20A12.QNTv12 arm or the 6E10.v114 arm for both human and cyno LY6G6D (FIG. 36).

Humanization of Rb.6E10

Multiple frameworks were applied for the humanization of 6E10. The rb6E10 VL CDRs were grafted into the human germline sequences KV1-5*01 and KV3-20*01, and VH CDRs were grafted into the human germline sequences HV3-53*01 and HV3-48*01 (FIG. 43A). These germline sequences were selected based on their high serum prevalence and high sequence identity to rb.6E10 (FIGS. 33A and 33B). As described above for 20A12, all VL and VH Vernier positions from rabbit antibodies were grafted into their respective human germline frameworks. The grafts with all rabbit amino acids at Vernier positions are referred to as version 1 (hu.6E10.v1a for KV1-5/HV3-53; hu.6E10.v1 b for KV1-5/HV3-48; and hu.6E10.v1c for K3-20/HV3-53). Five additional light chain variants were made for each germline (KV1-5: L2-L6 and KV3-20: L2-L6), and ten additional heavy chain variants (H2-H11) were made for HV3-53. For the KV1-5 light chain, Ala2, Phe36, and Arg43 (L3) were determined to be the key rabbit Vernier residues based on binding affinity evaluation of the variant antibodies described above (data not shown). Similarly, for the KV3-20 light chain, Ala2, Phe36 and Val58 (L4) were determined to be the key rabbit Vernier residues. For the heavy chain, the CDR graft into HV3-53*01 (H11) was found to be sufficient to maintain the affinity toward huLy6G6D; no rabbit Vernier positions were included. An additional CDR graft was made in germline HV3-48*01 (3-48H2). The heavy chain H11 was paired with KV3-20.L4 as 6E10v114. The heavy chain HV3-48.H2 was paired with KV1-5.L3 as 6E10v23 (FIGS. 43A-43D).

The results of a molecule assessment (MA) assay for the 6E10v1 variant are shown in FIG. 41. D(54)G and D(58)Y in CDR-H2 were found to be unstable, having a 30.2% increase in isomerization over two weeks.

Example 3. Sequence and Crystal Structure of the Anti-LY6G6D Antibody Hu.20A12.QNTv12

As described in Example 2, the humanized rabbit antibody 20A12.QNTv12, which has an overlapping epitope with 1G4 (Example 2), was identified as a potent anti-LY6G6D antibody. 20A12.QNTv12 exhibited a high binding affinity against human Ly6G6D as a TDB at 37° C. ($K_D$ about 2 nM, vs. about 16 nM for 1G4), comparable binding affinity to human and cynomolgus monkey LY6G6D, and favorable results in a BV ELISA assay, an expression test, and molecule assessment (MA) thermal and oxidation tests. The amino acid sequence of 20A12.QNTv12, including variants modified to comprise charge pairs for one-cell manufacturing, and the crystal structure of 20A12.QNTv12 bound to LY6G6D are described below.

A. Amino Acid Sequences of 20A12.QNTv12

Figure 5C:
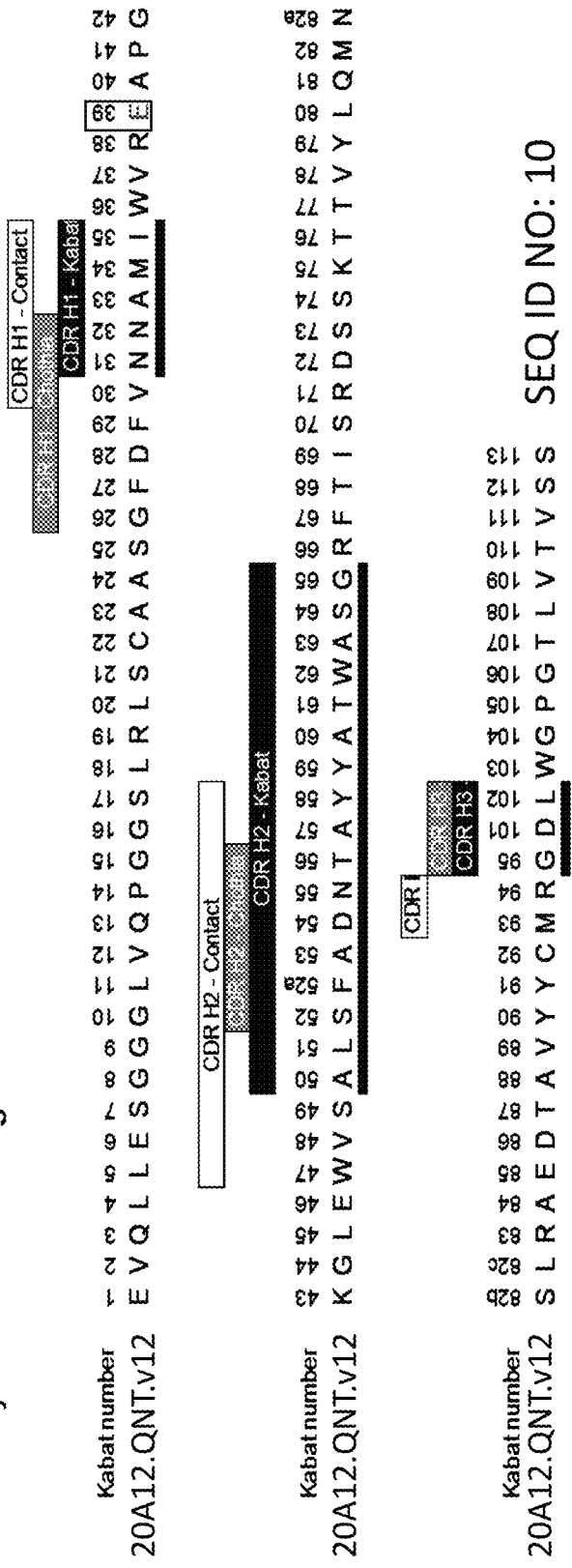
Figure 6B:
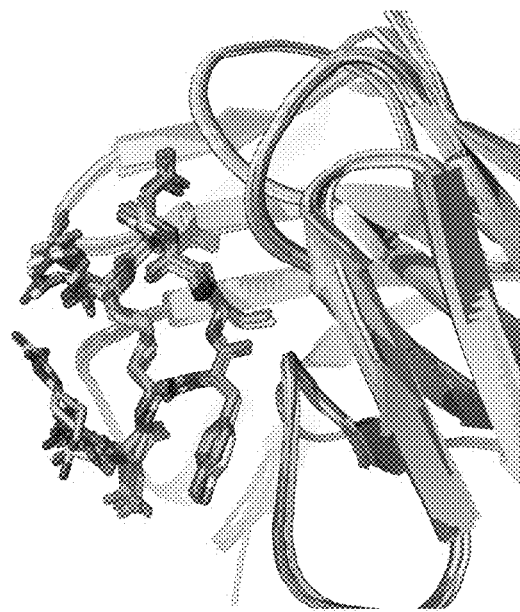
Figure 6A:
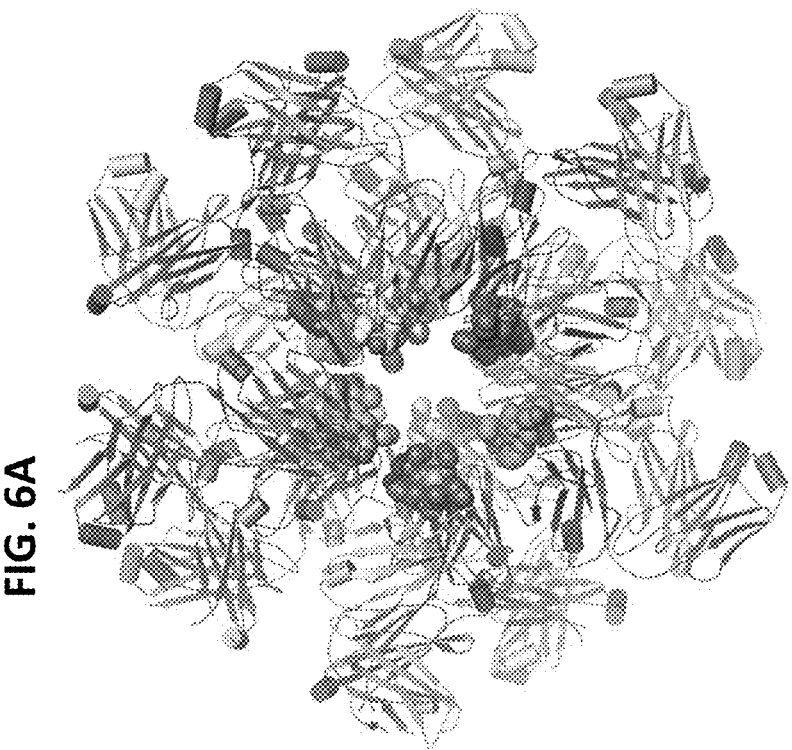
Figure 6D:
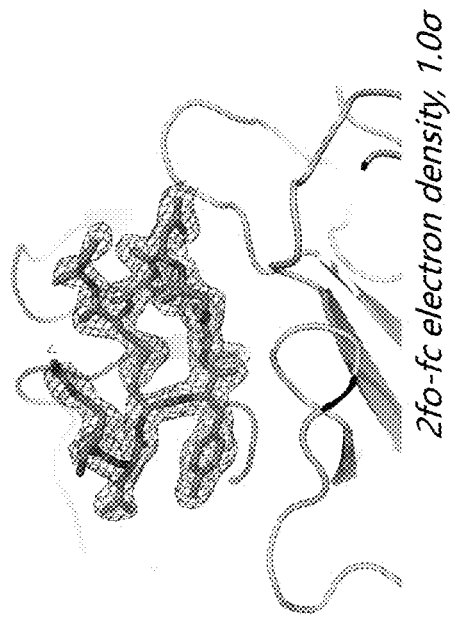
Figure 6C:
Figure 6F:
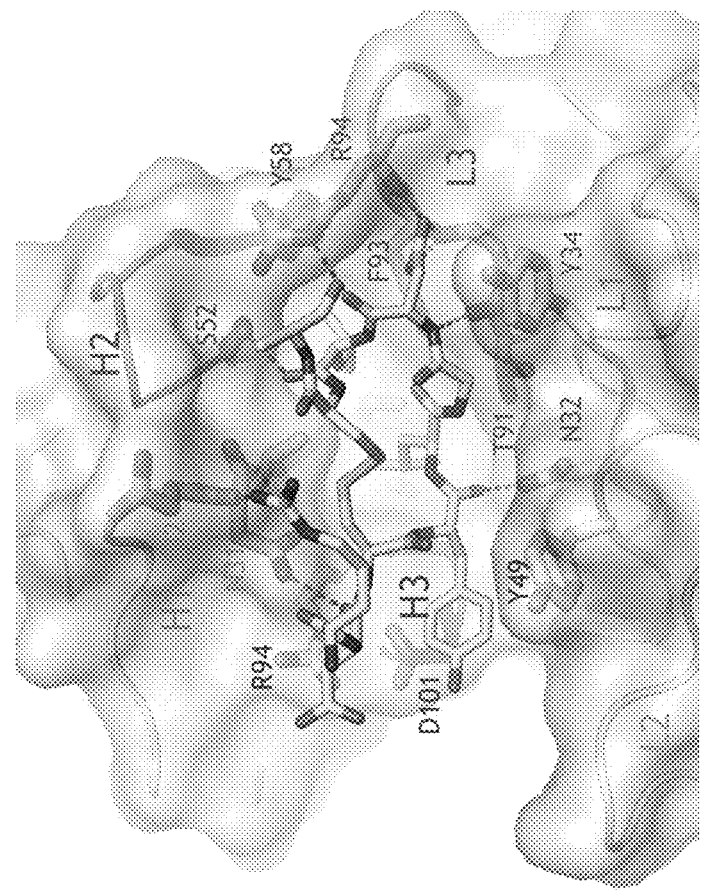
Figure 6E:
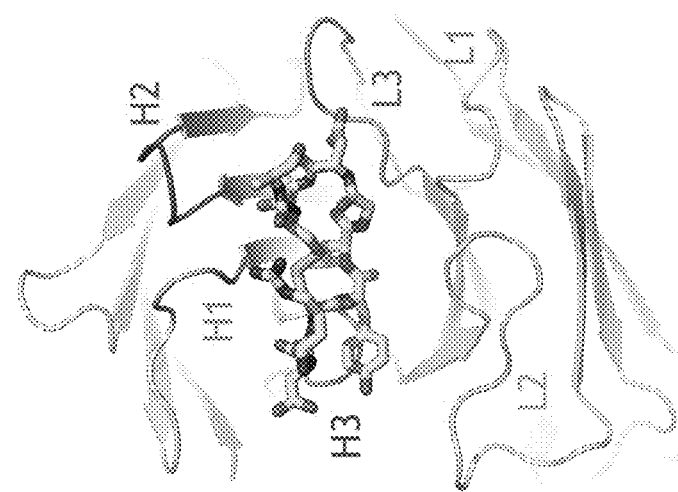

The amino acid sequences of the heavy chain variable region and light chain variable regions of 20A12.QNTv12 are shown in FIGS. 5A and 5B (SEQ ID NOs: 22 and 23). The amino acid sequences of the heavy chain variable region and light chain variable regions of variants of 20A12.QNTv12 modified to comprise charge pairs for one-cell manufacturing are shown in FIGS. 5C and 5D (SEQ ID NOs: 10 and 11).

B. Crystal Structures of 20A12.QNTv12 Antibody Bound to LY6G6D

To determine the crystal structure of 20A12.QNTv12 bound to LY6G6D, a polypeptide comprising amino acids 93-104 of LY6G6D (SEQ ID NO: 78) was co-crystallized with the fragment antigen-binding region (Fab) of the 20A12.QNTv12 antibody (FIGS. 6A-6F). The crystal structure of the 20A12.QNTv12-LY6G6D complex was resolved to 2.2 Å, R/$R_{free}$ 19.9/24.3%; P1 spacegroup: 82, 138, 139, 68, 75, 90. Ten 20A12.QNTv12 Fabs were tested. LY6G6D residues 94-103 were resolved bound to all ten copies. The Ly6G6D 94-103 polypeptide formed a dimer in a crystal structure of the anti-LY6G6D 1G4, and was bound as a monomer to 20A12.QNTv12.

C. Crystal Structure of 20A12.QNTv12 vs. 1G4

In addition, a polypeptide comprising amino acids 93-104 of LY6G6D (SEQ ID NO: 87) was co-crystallized with the fragment antigen-binding region (Fab) of the 20A12.QNTv12 antibody (SEQ ID NOs: 96-97) or the Fab of 1G4 (SEQ ID NOs: 94 and 95). The peptide backbone conformations were similar between the 1G4 and 20A12.QNTv12 structures due to disulfide staple, whereas the side chains showed significant conformational mobility (FIGS. 7A and 7B). 20A12.QNTv12 and 1G4 were found to bind different residues of the LY6G6D peptide, as shown in FIGS. 7C-7F and Tables 3 and 4.

FIGS. 7C and 7D show the interaction of 20A12.QNTv12 with LY6G6D. Residues in 20A12.QNTv12 that interact with LY6G6D are labeled in FIG. 7D. Table 3 summarizes interface residues in the 20A12.QNTv12 Fab: LY6G6D complex. The epitope of the 20A12.QNTv12 Fab on human LY6G6D consists of residues Arg94, Asp95, Cys96, Tyr97, Leu98, Gly99, Asp100, Leu101, Cys102 and Asn103 (RDCYLGDLCN). Each of these residues is positioned within 5 Å of the Fab. The 20A12.QNTv12 Fab utilizes the heavy chain residues Asn31, Asn32, Ala33, and Met34 from CDRH1, Ser52 from CDRH2, and Arg98, Gly99, and Asp100 from CDRH3 and the light chain residues Thr91, Ser92, Phe93 and Arg94 from CDRL3 to interact with LY6G6D.

TABLE 3

Summary of interface residues in the 20A12.QNTv12 Fab: LY6G6D complex

| Interface residues in 20A12.QNTv12 Fab Heavy Chain (SEQ ID NO: 96) | Interface residues in LY6G6D (SEQ ID NO: 87) | Interface residues in 20A12.QNTv12 Fab Light Chain (SEQ ID NO: 97) |
|---|---|---|
| Asn 31 | Arg 94 | Thr 91 |
| Asn 32 | Asp 95 | Ser 92 |
| Ala 33 | Cys 96 | Phe 93 |
| Met 34 | Tyr 97 | Arg 94 |

TABLE 3-continued

Summary of interface residues in the
20A12.QNTv12 Fab: LY6G6D complex

| Interface residues in 20A12.QNTv12 Fab Heavy Chain (SEQ ID NO: 96) | Interface residues in LY6G6D (SEQ ID NO: 87) | Interface residues in 20A12.QNTv12 Fab Light Chain (SEQ ID NO: 97) |
|---|---|---|
| Ser 52 | Leu 98 | |
| Arg 98 | Gly 99 | |
| Gly 99 | Asp 100 | |
| Asp 100 | Leu 101 | |
| | Cys 102 | |
| | Asn 103 | |

FIGS. 7E and 7F show the interaction of 1G4 with LY6G6D. Residues in 1G4 that interact with LY6G6D are labeled in FIG. 7F. Table 4 summarizes interface residues in the 1G4 Fab: LY6G6D complex. The epitope of the 1G4 Fab on human LY6G6D consists of residues His93, Asp95, Cys96, Tyr97, Leu98, Gly99 and Asp100; each of these residues is positioned within 5 Å of the Fab. Unlike 20A12.QNTv12, 1G4 was not found to interact with LY6G6D residues Arg94, Leu101, Cys102, or Asn103. Therefore, LY6G6D residues Arg94, Leu101, Cys102, and Asn103 are epitopic residues that are uniquely bound by 20A12.QNTv12.

The 1G4 Fab utilizes the heavy chain residues Thr31, Tyr3, and Val33 from CDRH1 and Arg99 and Asn100 from CDRH3 and the light chain residues Ser97, Tyr98, Ser99 and Ala100 from CDRL3 to interact with LY6G6D.

TABLE 4

Summary of interface residues in the 1G4 Fab: LY6G6D complex

| Interface residues in 1G4 Fab Heavy Chain (SEQ ID NO: 147) | Interface residues in LY6G6D (SEQ ID NO: 87) | Interface residues in 1G4 Fab Light Chain (SEQ ID NO: 95) |
|---|---|---|
| Thr 31 | His 93 | Ser 97 |
| Tyr 32 | Asp 95 | Tyr 98 |
| Val 33 | Cys 96 | Ser 99 |
| Arg 99 | Tyr 97 | Ala 100 |
| Asn 100 | Leu 98 | |
| | Gly 99 | |
| | Asp 100 | |

Example 4. In Vitro TDB Activity Assays

Cytotoxicity, Cell Binding, T Cell Activation, and Cell Killing

LY6G6D TDBs (e.g., LY6G6D TDBs having an anti-LY6G6D arm 20A12.QNTv12, or a variant thereof) paired with either the anti-CD3 arm 38E4v1 or 40G5c were tested for in vitro activity using HT55 cells (human colon carcinoma cell line), which endogenously express a medium level of LY6G6D (FIGS. 9A-9C, 10A-10D, and 11F-11H). 40G5c and 38E4v1 are humanized hybridoma antibodies obtained from mice immunized with a KLH (keyhole limpet hemocyanin) conjugated peptide spanning the N-terminal 27 amino acids of human CD3ε. 40G5c has been previously observed to have relatively low affinity for CD3, whereas 38E4v1 has been observed to have high affinity (U.S. Pub. No. 2015-0166661).

Human peripheral blood mononuclear cells (PBMCs) were isolated from whole blood of healthy donors by Ficoll gradient and were used as effector cells. Co-cultures of human PBMCs and HT55 cells (E:T=10:1) were incubated in the presence of various concentrations of the LY6G6D TDB. Target cell killing and T-cell activation were measured after 72 hours of incubation. Target cell killing was quantified as Percent Cytotoxicity by measuring the intensity of luminescence (RLU) in a CellTiter-GLO® assay.

The percentage of target-cell killing was calculated using the following equation:

% of target cell killing={(RLU in non-treated well−RLU in TDB-treated well)/(RLU in non-treated well)}×100.

Activation of CD4+ T cell and CD8+ T cells was measured using fluorescence activated cell sorting (FACS). For CD8+ T cells, surface expression of CD69 and CD25 was detected, and the percentage of CD8+ T cells that were CD69+CD25+ were reported as CD8+ T-cell activation.

The LY6G6D TDB comprising the anti-LY6G6D 20A12.QNTv12 arm and the anti-CD3 38E4v1 arm was potent in inducing T-cell activation (FIGS. 9B, 9C, 10B, 10C, 11G, and 11I) and target-cell killing (FIGS. 9A, 10A, 10D, 11D-11F and 11H) in vitro against HT55 in a dose-dependent manner. When paired with the high-affinity anti-CD3 arm 38E4v1, 20A12.QNTv12 had comparable in vitro cell killing potency to 1G4. When the 20A12.QNTv12 arm was paired with the low-affinity anti-CD3 arm 40G5c, cell killing potency was lower than for the 38E4v1 arm; however, the TDB comprising the 20A12.QNTv12 and 40G5c arms had greater cell killing potency than the TDB comprising the 1G4 and 40G5c arms. (FIGS. 11D and 11E). Rabbit 20A12 also showed a higher binding affinity to HT55 cells than 1G4 (FIG. 4F).

In an assay using PMBCs from ten healthy human donors, average cell killing EC50 by a TDB comprising the anti-LY6G6D 20A12.QNTv12 arm and the anti-CD3 38E4v1 arm was about 1.04 ng/ml (7 pM); average CD8+ T cell activation EC50 was about 87 ng/ml (583 pM) (FIGS. 11F-11H). Cell killing and CD8+ T cell activation were also tested in Colo320DM (human Dukes' type C, colorectal adenocarcinoma cell line) and LS1034 (human Dukes' type C, colorectal adenocarcinoma cell line) cells (FIG. 11A), which express different levels of LY6G6D (FIGS. 11B and 11I).

Example 5. In Vivo TDB Activity and Clearance Assays

A. Tumor Volume

Candidate LY6G6D TDBs comprising the anti-LY6G6D 20A12.QNTv12 arm and an anti-CD3 40G5c or 38E4.v1 arm were tested for in vivo activity against xenograft LS1034 and HT55 tumors in NSG™ mice (FIGS. 16A-16C 17A-17C). Mice were humanized with healthy donor peripheral blood mononuclear cells (PBMCs). Treatments comprising the delivery vehicle and PMBCs or comprising the TDB and not comprising PMBCs were provided as controls. Serum concentration of TDBs was measured using a Generic Immunoglobulin Pharmacokinetic (GRIP) ELISA assay (Yang et al., J. Immunol. Methods, 8-20, 2008) following administration of a single dose of the TDB.

In vivo efficacy of LY6G6D TDBs comprising the anti-LY6G6D 20A12.QNTv12 arm and an anti-CD3 40G5c or 38E4.v1 arm against LS1034 tumors (LY6G6D IHC score 3+) and HT55 tumors (LY6G6D IHC score 2+) was established. For the LS1034 and HT55 tumor models, greater efficacy was observed for the TDB comprising the high-affinity anti-CD3 38E4.v1 arm (1 mg/kg, single dose, IV, D0) (FIGS. 16A and 17A). Efficacy and PK were dose-dependent for the LY6G6D TDB comprising 38E4.v1, and a small difference in serum PK between the LY6G6D TDB comprising 38E4v1 and the LY6G6D TDB comprising 40G5c was observed (FIGS. 16A-16C and 17A-17C). In vivo efficacy of LY6G6D TDBs comprising the anti-LY6G6D 20A12.QNTv12 arm and an anti-CD3 38E4.v1 arm was also tested against Colo320DM tumors (FIG. 11J).

B. Clearance in SCID Mice

Clearance of LY6G6D TDBs comprising the anti-LY6G6D arm 20A12.QNTv12 and an anti-CD3 40G5c or 38E4.v1 arm was measured in severe combined immunodeficient (SCID) mice following intravenous administration of a single 5 mg/kg dose of the antibody using a GRIP ELISA assay (FIG. 18). The clearance rate (7.67 mL/day/kg) was comparable to other TDBs paired with the 38E4v1 anti-CD3 arm. Clearance rates ranged from 8.6 to 16 mL/kg/day. The TDB comprising 20A12.QNTv12 and 38E4v1 had acceptable pharmacokinetics (PK) in SCID mice and showed less than two-fold difference in systemic CL compared to the control antibody anti-gD 5B6. No PK liability (atypical PK) was apparent for the LY6G6D TDB comprising 20A12.QNTv12 and 38E4v1 arms in non-binding species. All dosing solutions were recovered within ±20% of the nominal dose.

Example 6. Cynomolgus Monkey Safety Assay

A. Toxicity Study in Cynomolgus Monkey

A toxicity study for a LY6G6D TDB comprising the anti-LY6G6D 20A12.QNTv12 arm and the anti-CD3 38E4.v1 arm was performed in cynomolgus monkeys (cyno). The study had an adaptive design with iterative and staggered dose groups (FIG. 19). Group 2 was treated with a single dose (1 mg/kg) IV infusion of the LY6G6D TDB on day 1 (D1). Groups 3, 4, and 5 were treated with a single dose (2, 4, and 8 mg/kg, respectively) IV infusion, and group 6 was treated with a single dose (15 mg/kg) IV infusion. Terminal necropsy was performed on D8 for histopathology evaluation (FIG. 19). Objectives of the study were to de-risk the LY6G6D target in healthy animals and to test dose ranges. PK/PD and standard toxicity endpoints were included based on previous TDB experience.

Intravenous PK was assessed for all treatment groups using a GRIP ELISA assay. Results showed greater than dose proportional systemic exposure (dose normalized $AUC_{0-7}$). Clearance (CL) decreased with increase in dose of the TDB (4 mg/kg and above), suggesting saturation of target-mediated drug disposition (TMDD) at these doses (CD3 mediated, in peripheral blood) (FIG. 20A; Table 5). PK at the 1 mg/kg dose was comparable to historical data for other TDBs in cyno, e.g., a gD/38E4v1 TDB, which showed a CL of about 20 mL/kg/day (FIGS. 20A and 20B). Dosing solutions were recovered within ±20% of the nominal value

TABLE 5

Intravenous PK for cynomolgus monkeys treated with TDBs

| Dose | Animal # | $C_{max}$ (ug/mL) | $AUC_{0-7}$ (day*ug/mL) | $AUC_{0-7}$/Dose (day*kg*ug/mL/mg) | CL (mL/day/kg) | $t_{1/2}$ (days) |
|---|---|---|---|---|---|---|
| 1 mg/kg | 2001 | 23.5 | 35.1 | 35.1 | 25.9 | 2.24 |
| 2 mg/kg | 3001 | 45.4 | 83.5 | 41.8 | 20.4 | 2.68 |
| 4 mg/kg | 4001 | 115 | 246 | 61.5 | 12.8 | 3.20 |
| 8 mg/kg | 5001 | 211 | 452 | 56.5 | 12.3 | 4.27 |
| 15 mg/kg | 6001 | 344 | 926 | 61.7 | 12.5 | 3.40 |
| 15 mg/kg | 6003 | 364 | 940 | 62.7 | 10.9 | 4.42 |

Single dose IV treatment with a LY6G6D TDB comprising the anti-LY6G6D arm 20A12.QNTv12 and the anti-CD3 38E4.v1 arm was well-tolerated at doses up to 15 mg/kg. Clinical observations included no veterinary treatment and no effect on mortality, body weight, or food consumption. At the 15 mg/kg dose, vomitus (moderate) was observed in Animal No. 6001, and pale face and tremors (slight) were noted in Animal No. 6003 at 4-5 hours post-dose only. Clinical Pathology showed no evidence of inflammation or liver injury and mild C-reactive protein (CRP) elevation (FIG. 22B). Anatomic Pathology found perivascular/vascular mononuclear infiltrates in the brain of one animal at the 15 mg/kg dose (Animal No. 6003, with noted slight tremors) (FIG. 21).

Concentration of the cytokines G-CSF, IL-1Ra, MCP-1, TNF-α, IL-13, IL-8 and C-reactive protein (CRP) was measured following treatment (FIGS. 22A and 22B). Some cytokines showed a mild increase in concentration at doses≥1 mg/kg. No dose-response relationship was apparent. A mild increase in MCP-1 at was observed at ≥4 mg/kg (FIG. 22A). All changes had returned to baseline at 24 hours after treatment.

Counts of CD3+/CD4+/CD5+CD25 expressing T-helper (Th) lymphocytes, CD3+/CD8+/CD5+CD25 expressing T-cytotoxic (Tc) lymphocytes, CD45+/CD3+T-lymphocytes, CD45+/CD20+B-lymphocytes, and CD45+/CD16+ natural-killer cells were measured by flow cytometry (FIGS. 23A-23D). Measurements were taken at 7 days before treatment (Day −7) and on the day of treatment (Day 1 Pre) and were averaged to provide a predose average. After the end of infusion, measurements were taken at 2 hours, 6 hours, 24 hours, and 168 hours. Peaks showing mild T cell activation (FIG. 23A), T cell recovery (FIG. 23B), and B cell recovery (FIG. 23C) were observed.

Example 7. BIAcore Assays for Affinity

TDBs comprising the anti-LY6G6D 20A12.QNTv12 arm and the anti-CD3 38E4.v1 arm (FIG. 24A) or 40G5C arm (FIG. 24B) were assayed for affinity for a human and cyno Ly6G6D polypeptide using a BIAcore assay. Ly6G6D-Fc was directly immobilized on the chip, and the TDB was flowed through at 37° C. Similar assays were performed for TDBs comprising the anti-LY6G6D 1G4 arm and the anti-CD3 38E4.v1 arm (FIG. 24C) or 40G5C arm (FIG. 24D). Results of these assays are provided in Table 6.

TABLE 6

BIAcore analyses of TDBs against human and cyno LY6G6D-Fc

|  | Human Ly6G6D | | | | Cyno Ly6G6D | | | |
| --- | --- | --- | --- | --- | --- | --- | --- | --- |
|  | Ka (1/Ms) | Kd (1/s) | $K_D$ (M) | Rmax | Ka (1/Ms) | Kd (1/s) | $K_D$ (M) | Rmax |
| 20A12.QNTv12/ 38E4v1 | 2.20E+05 | 44.4E−04 | 2.02E−09 | 60.085 | 1.66E+05 | 3.80E−04 | 2.29E−09 | 208 |
| 20A12.QNTv12/ 40G5c | 8.06E+04 | 4.56E−04 | 5.62E−09 | 52.603 | 8.43E+04 | 4.13E−04 | 4.91E−09 | 171 |
| 1G4/38E4v1 | 5.44E+05 | 8.86E−03 | 1.63E−08 | 125.15 | 7.14E+05 | 9.36E−03 | 1.31E−08 | 314 |
| 1G4/40G5c | 3.14E+05 | 9.83E−03 | 3.13E−08 | 91.745 | 2.93E+05 | 9.71E−03 | 3.31E−08 | 240 |

A LY6G6D TDB manufactured using the two-cell system and comprising the anti-LY6G6D 20A12.QNTv12 arm and the anti-CD3 38E4.v1 arm had high binding affinity against human and cyno LY6G6D polypeptides and the human and cyno extracellular domain (ECD) of CD3 (Table 7).

TABLE 7

BIAcore analyses of TDBs against human and cyno LY6G6D-Fc and CD3 ECD

| Molecule | Target | Biacore $K_D$ nM |
| --- | --- | --- |
| 20A12.QNTv12 | huLY6G6D | 2.02 |
|  | cyLY6G6D | 2.29 |
|  | huCD3 | 20 |
|  | CyCD3 | 15 |

TDBs comprising the anti-LY6G6D arm 20A12.QNTv12 and the anti-CD3 38E4.v1 (left panel; produced using a two-cell-manufacturing system), 38E4.v1 MD1 (center panel; produced using a one-cell-manufacturing system), or 38E4.v1 MD4 arm (right panel; produced using a one-cell-manufacturing system) were assayed for affinity for a human Ly6G6D polypeptide (FIG. 25) using a BIAcore assay. Results of these assays are provided in Table 8.

TABLE 8

BIAcore analyses of TDBs against human and cyno LY6G6D-Fc

| Sample | Ligand | Rmax (RU) | ka (1/Ms) | kd (1/s) | KD (nM) |
| --- | --- | --- | --- | --- | --- |
| 20A12.QNTv12/38E4v1 | hu Ly6G6D | 57.9 | 2.99E+05 | 4.16E−04 | 1.39 |
|  | cyno Ly6G6D | 57.2 | 2.31E+05 | 4.44E−04 | 1.92 |
| 20A12.QNTv12.MD1/38E4v1 | hu Ly6G6D | 33.3 | 4.20E+05 | 7.96E−04 | 1.90 |
|  | cyno Ly6G6D | 34.9 | 1.41E+05 | 5.12E−04 | 3.63 |
| 20A12.QNTv12.MD4/38E4v1 | hu Ly6G6D | 56.2 | 2.96E+05 | 5.59E−04 | 1.89 |
|  | cyno Ly6G6D | 54.6 | 2.19E+05 | 5.74E−04 | 2.62 | anti-CD3 38E4v1 arm is relatively poorly expressed, whereas the anti-LY6G6D arm 20A12.QNTv12 is highly expressed (FIG. 37). In a transient transfection assay to assess TDB assembly, the LY6G6D TDB comprising a 38E4v1 arm and a 20A12.QNTv12 arm did not reach>80% correct pairing even when the ratios of DNAs encoding the respective arms were modified to a ratio of 1:16 (FIG. 29D).

Two variants of the anti-CD3 38E4v1 arm, 38E4v1 MD1 (MD1) and 38E4v1 MD4 (MD4), were developed to have improved expression over 38E4v1 and thus enable improved manufacturing of a one-cell format LY6G6D TDB (e.g., a one-cell format LY6G6D TDB having an anti-LY6G6D arm 20A12.QNTv12). MD1 and MD4 were found to have favorable bispecific to LC-mispair impurity ratio (i.e., high purity of correctly formed LY6G6D TDBs) and comparable in vitro potency, in vivo potency, and PK to wild-type 38E4v1.

TDBs manufactured using the one-cell system were additionally modified to comprise amino acid substitution mutations introducing charge pairs, as shown in FIG. 8D or 8E, and as described herein.

B. One-Cell Variant of 20A12.QNTv12

To facilitate manufacturing in a one-cell system, the heavy chain and light chain sequences of the 20A12.QNTv12 arm were modified to comprise amino acid substitution mutations introducing charge pairs (FIGS. 5C, 5D, and 8A-8E).

C. Generation of 38E4v1 Expression Variants MD1 and MD4

To create expression-improved variants of 38E4v1 suitable for manufacturing in a one-cell system, the VL sequence of 38E4v1 was modified with residues from 40G5c, an anti-CD3 antibody having better expression than 38E4v1, as described below. The two 38E4v1 variants 38E4v1 MD1 (MD1) and 38E4v1 MD4 (MD4) have favorable bispecific to LC-mispair impurity ratio and comparable in vitro potency, in vivo potency, and PK to wild-type (WT) 38E4v1 in mice.

Variants of the 38E4v1 light chain variable region (VL) comprising one or more amino acid substitutions derived Example 8. Development of MD1 and MD4 Anti-CD3 Arms for One-Cell Manufacturing A. One-Cell and Two-Cell Manufacturing Systems Anti-LY6G6D antibodies (e.g., 20A12.QNTv12) were manufactured as LY6G6D T cell-dependent bispecific antibodies (LY6G6D TDBs) having a first arm with anti-LY6G6D specificity and a second arm with anti-CD3 specificity, as shown in FIG. 8A. TDBs were manufactured using either a two-cell system (FIG. 8B) or a one-cell system (FIG. 8C). For one-cell manufacturing, it is important that the first arm and the second arm are expressed at comparable levels in the host cell: large differences in the level of expression increase the likelihood of light chain (LC) mispairing and decrease the likelihood of correct pairing of the TDB. The from the light chain sequence of the lower-affinity anti-CD3 antibody 40G5c were generated (FIG. 29A). 38E4v1 The MD1 VL contains four amino acid substitutions relative to the sequence of 38E4v1: S43P, T51A, K55E, and K89T (FIG. 29A). The MD4 VL contains only the S43P and T51A substitutions (FIG. 29A). Variants comprising only a S43P, T51A, K55E, or K89T amino acid substitution were also generated. All 38E4v1 variants comprised the heavy chain variable region (VH) sequence of 38E4v1 (FIG. 29B).

C. Transient Transfection Assay

The expression levels of 38E4v1, MD1, and variants comprising only S43P, T51A, K55E, or K89T amino acid substitutions relative to 38E4v1 were evaluated in a transient transfection assay in Chinese hamster ovary (CHO) 11-9 host cells.

One day after transfection, growth medium was exchanged for a production medium. Supernatants were collected one day after adding the production medium and were evaluated for antibody titer using an Fc-binding ELISA, Production yield was normalized against 38E4v1. The 38E4v1 light chain appears to limit the yield of antibody expression. Unexpectedly, replacing individual positions in the 38E4v1 light chain with residues from the lower-affinity anti-CD3 antibody 40G5c (S43P, T51A, or K89T) led to modest improvements in yields (FIG. 29C), and a more substantial increase in yield was observed when these changes were combined in the MD1 variant, which comprises all of the S43P, T51A, K55E, K89T amino acid substitutions (FIGS. 29A and 29C).

In a transient transfection assay for TDB assembly, the expression-improved 38E4v1 variants MD1 and MD4 reached 95% assembly of intact antibodies at a 1:4 ratio of target arm (anti-LY6G6D) light chain (LC) DNA to anti-CD3 arm DNA, whereas 38E4v1 did not reach>80% proper pairing even at a 1:16 LC DNA to anti-CD3 arm DNA ratio (FIG. 29D). The successful cell line development clone xFcRH5 is provided as a control. MD1 and MD4 thus allow for a high percentage of properly paired bispecific antibodies to be produced.

D. Binding Kinetics Assay

The binding kinetics of the 38E4v1 MD1 and MD4 arms showed affinity to human and cyno CD3 ligands comparable to that of the high-affinity wild-type anti-CD3 38E4v1 arm (WT) (Table 9). The MD1 and MD4 variants thus retained the high affinity of 38E4v1. Assays were performed using a BIAcore T200: 27mer human and cyno CD3 polypeptides were conjugated to biotin and were immobilized on a SA CM5 chip, and TDBs were flowed through at 100 µl/min at 37° C.

TABLE 9

BIAcore analyses of TDBs against human and cyno CD3

| Sample | Ligand | ka (1/Ms) | kd (1/s) | KD (M) | Rmax (RU) |
|---|---|---|---|---|---|
| WT two-cell | HuCD3e pept | 2.44E+06 | 4.29E-02 | 1.76E-08 | 27.8 |
|  | biotin | 2.22E+06 | 4.86E-02 | 2.19E-08 | 26.8 |
| WT two-cell | CyCD3e pept | 2.60E+06 | 3.37E-02 | 1.30E-08 | 32.6 |
|  | biotin | 2.21E+06 | 3.64E-02 | 1.65E-08 | 32.6 |
| WT one-cell | HuCD3e pept | 2.59E+06 | 5.16E-02 | 1.99E-08 | 29 |
|  | biotin | 2.34E+06 | 4.98E-02 | 2.13E-08 | 26.2 |
| WT one-cell | CyCD3e pept | 2.60E+06 | 3.99E-02 | 1.54E-08 | 34.8 |
|  | biotin | 2.65E+06 | 4.37E-02 | 1.65E-08 | 33 |
| MD1 one-cell | HuCD3e pept | 1.54E+06 | 5.04E-02 | 3.28E-08 | 25.2 |
|  | biotin | 1.41E+06 | 4.56E-02 | 3.24E-08 | 21.2 |
| MD1 one-cell | CyCD3e pept | 1.44E+06 | 3.83E-02 | 2.66E-08 | 31.9 |
|  | biotin | 1.47E+06 | 3.76E-02 | 2.56E-08 | 26.8 |

TABLE 9-continued

BIAcore analyses of TDBs against human and cyno CD3

| Sample | Ligand | ka (1/Ms) | kd (1/s) | KD (M) | Rmax (RU) |
|---|---|---|---|---|---|
| MD4 one-cell | HuCD3e pept | 2.89E+06 | 5.44E-02 | 1.88E-08 | 25.3 |
|  | biotin | 2.66E+06 | 4.95E-02 | 1.86E-08 | 26.1 |
| MD4 one-cell | CyCD3e pept | 3.09E+06 | 4.33E-02 | 1.40E-08 | 30.6 |
|  | biotin | 2.89E+06 | 4.26E-02 | 1.47E-08 | 33.4 |

E. Pharmacokinetics Assays

To assess the pharmacokinetics (PK) of the various anti-CD3 arms, PK profiles of 38E4v1, 40G5c, MD1, MD4, and 38E4v1.K55E were measured in CB-17 SCID mice following single dose administration of each variant. An anti-gD antibody was used as a control. The anti-gD antibody is a non-binding control IgG targeting the glycoprotein D epitope of herpes simplex virus. All antibodies were tested as monospecific, bivalent anti-CD3 antibodies having a human IgG1 isotype with an N297G mutation to attenuate FcγR-mediated effector function.

Six groups of female CB-17.SCID mice (n=12 per group; Charles River Laboratories, 251) were administered a single IV dose of each antibody at a dose of 5 mg/kg. Female mice were used for convenience. Historically, we have not observed any differences in PK studies that used male or female mice. Blood samples were collected via the femoral vein at selected time points (3 replicates for each time point) for up to 21 days. Total antibody concentrations in serum were determined by a GRIP ELISA (plate coated with anti-human IgG and detected with anti-human IgG) with the limit of detection of 15.6 ng/mL and used for PK evaluations. The dosing solution recoveries were 111%, 110%, 106%, 97.8%, 103% and 106% for anti-gD, 38E4v1, 40G5c, MD1, MD4, and 38E4v1.K55E, respectively. The dosing recoveries were within 20%; therefore, nominal doses were used for further analysis.

PK profiles were pooled from different mice at different time points. Nominal sample collection times and actual dose solution concentrations were used in data analysis. Non-compartmental analysis (NCA) parameters were estimated using Phoenix WinNonlin® 64 with sparse sampling and IV bolus input. Standard error values were provided. Mice were euthanized after being anesthetized with isoflurane (5% isoflurane with 2 L/min of $O_2$). All procedures were approved by and conformed to the guidelines and principles set by the Institutional Animal Care and Use Committee (IACUC) of Genentech and were performed in a facility accredited by Association for Assessment and Accreditation of Laboratory Animal Care International.

The anti-CD3 antibody variants do not cross react with mouse CD3; thus, the mouse PK profiles of TDBs comprising anti-CD3 antibody variants provided an opportunity to compare the PK and non-specific elimination rate of the variants in the absence of target binding. Serum concentration-time profiles of the anti-CD3 antibody variants were assessed, along with the anti-gD control (FIG. 29E). The PK data of each group were characterized by NCA (Table 10).

The anti-gD administered group had the highest exposure compared to the groups administered anti-CD3 antibody variants. The 40G5c administered group had slightly lower exposure based on its $AUC_{last}$ value compared to the anti-gD administered group and had the highest exposure compared to the rest of the anti-CD3 antibody variants. On the other hand, 38E4v1 had the lowest exposure based on its $AUC_{last}$ compared to the rest of the anti-CD3 antibody variants.

Among the three variants MD1, MD4, and K55E, MD1 had the highest exposure based on its $AUC_{last}$, and its PK profile was similar to the 40G5c administered group. The MD4 administered group had the lowest exposure based on its $AUC_{last}$ among the three variants, and its PK profile was similar to the 38E4v1 administered group. In addition, MD1 improved 38E4v1 exposure by ~3 fold based on $AUC_{inf}$ in mice. Furthermore, anti-gD, 40G5c and 38E4v1.MD1 administered groups had comparable $V_{ss}$ values, which were approximately 2-fold lower than $V_{ss}$ values of the 38E4v1, MD4, and K55E administered groups (Table 10).

TABLE 10

PK parameters of anti-CD3ε antibody variants

| Groups | n | Dose (mg/kg) | $C_{max}$ (μg/mL) | $AUC_{last}$ (μg/mL*day) | $AUC_{inf}$ (μg/mL*day) | CL (mL/day/kg) | $V_{ss}$ (mL/kg) | $t_{1/2}$ (days) |
|---|---|---|---|---|---|---|---|---|
| Anti-gD | 12 | 5 | 152 ± 1.30 | 1050 ± 25.1 | 2020 | 2.47 | 97.2 | 19 |
| anti-CD3.38E4v1 | 12 | 5 | 70.8 ± 1.64 | 245 ± 10.7 | 279 | 17.9 | 226 | 9.62 |
| anti-CD3.40G5c | 12 | 5 | 155 ± 4.47 | 884 ± 28.5 | 1300 | 3.85 | 95.6 | 18.4 |
| anti-CD3.38E4v1.MD1 | 12 | 5 | 117 ± 2.62 | 726 ± 15.8 | 938 | 5.33 | 101 | 11.7 |
| anti-CD3.38E4v1.MD4 | 12 | 5 | 78.7 ± 3.55 | 274 ± 10.2 | 354 | 14.1 | 256 | 13 |
| anti-CD3.38E4v1.K55E | 12 | 5 | 72.5 ± 1.26 | 413 ± 14.2 | 629 | 7.95 | 204 | 18 |

Standard error values are provided where applicable.
$C_{max}$ = Maximum observed serum concentration,
$AUC_{last}$ = Area under the serum-concentration time curve from time 0 to last measured time points, day 28.
$AUC_{inf}$ = Area under the serum-concentration time curve from time 0 extrapolated to infinity.
CL = Clearance.
$V_{ss}$ = Volume of distribution at steady state.
$t_{1/2}$ = terminal half-life.

Given the lower exposure of 38E4v1 compared to 40G5c, it was next assessed whether there were characteristics of the CD3 arm that could have contributed non-specifically to the observed lower exposure. We estimated the antibody variable region (Fv) charge and hydrophobicity of 38E4v1 and 40G5c using in silico Clearance Assessment Tool (iCAT), a sequence-based calculation tool that provides a theoretical risk assessment of antibody clearance in cynomolgus monkeys (Sharma et al., Proc Natl Acad Sci USA, 111: 18601-6, 2014). This assessment is based on parameters calculated from the Fv domain sequence. The iCAT score was evaluated for the anti-CD3 bivalent antibody. The calculated Fv charge of 38E4v1 was +7.6, which is outside the range for acceptable in vivo clearance (the acceptable range includes Fv charges≥0 and ≤+6.2), whereas the calculated Fv charge of 40G5c was within the acceptable range at +5.6. The calculated Fv charge for MD1 was +4.7, and for MD4 was +7.6. MD1 thus had an improved Fv charge compared to 38E4v1 and an acceptable theoretical risk for clearance in cynomolgus monkeys.

In addition, the anti-CD3 variants were tested using baculovirus (BV) ELISA. BV ELISA is an in vitro tool used for assessment of non-specific clearance (Hotzel et al., MAbs, 4: 753-760, 2012). This assessment is based on ELISA detection of non-specific binding to baculovirus particles, and can identify antibodies having increased risk for fast clearance. The BV ELISA score for 38E4v1 was 1.15, which was outside the range of predicting acceptable in vivo clearance (a BV ELISA score of >1.0 indicates high probability of fast clearance). In contrast, the BV ELISA score was 0.15 for MD1 and was 0.72 for MD4; thus, both MD1 and MD4 were within the acceptable range. Interestingly, while MD4 passed the BV ELISA test for further testing in vivo, the in vivo mouse PK data demonstrated that MD4 did not improve the exposure of 38E4v1 when compared to MD1.

Example 9. TDB Activity Assays for Antibodies Produced in One-Cell System

Candidate LY6G6D TDBs assembled using a one-cell system (FIGS. 8C-8E) and comprising the anti-LY6G6D 20A12.QNTv12 arm and an anti-CD3 38E4v1 MD1 (MD1), 38E4v1 MD4 (MD4), or 38E4v1 (WT) arm were tested for in vitro activity, in vivo activity, and affinity with a CD3 polypeptide. A TDB assembled using a two-cell system (FIG. 8B) and comprising the anti-LY6G6D 20A12.QNTv12 arm and the anti-CD3 38E4v1 arm was used as a control.

A. In Vitro Cytotoxicity, Cell Binding, and T Cell Activation

LY6G6D TDBs assembled using a one-cell system and comprising the anti-LY6G6D 20A12.QNTv12 arm and an anti-CD3 38E4v1 MD1, 38E4v1 MD4, or 38E4v1 arm (WT) were tested for in vitro activity in HT55 cells supplemented with PBMCs from a healthy donor, activation of CD4+ T cells, and activation of CD8+ T cells (FIGS. 14A-14C and 15A-15C). Killing was quantified as percent cytotoxicity in a CELLTITER-GLO® assay, and CD4+ T cell and CD8+ T cells were measured using fluorescence activated cell sorting (FACS), as described in Example 2. All TDB were dosed at 1 mg/kg. LY6G6D TDBs comprising the variant 38E4v1 arms were potent in inducing T-cell activation (FIGS. 14B, 14C, 15B, and 15C) and target-cell killing (FIGS. 14A and 15A) in vitro against HT55. The MD1 and MD4 variants thus retain the high in vitro potency of 38E4v1 while providing improved manufacturability in the one-cell system.

B. In Vivo Activity

LY6G6D TDBs comprising the anti-LY6G6D 20A12.QNTv12 arm and a variant 38E4v1 anti-CD3 arm assembled using a one-cell system were tested for in vivo activity against xenograft HT55 tumors in NSG™ mice (FIGS. 26A and 26B). Mice were humanized with healthy donor peripheral blood mononuclear cells (PBMCs). Treatments comprising the delivery vehicle and PMBCs or comprising the TDB and not comprising PMBCs were provided as controls. The one-cell variants comprising the anti-CD3

38E4v1 MD1 or 38E4v1 MD4 arm showed comparable tumor regression to the two-cell LY6G6D TDB.

Clearance of TDBs was measured in HT55 tumor model mice and in SCID mice following intravenous administration of a single dose of the antibody using a GRIP ELISA assay (FIGS. 27 and 28). PK of the one-cell variants comprising the anti-CD3 38E4v1 MD1 or 38E4v1 MD4 arm was comparable to that of the two-cell TDB. No PK liability (e.g., atypical PK) was identified for one-cell TDB variants. Dosing solutions were recovered within ±20% of nominal value.

C. Assays for Affinity to CD3

The candidate LY6G6D TDBs assembled using a one-cell system and comprising the anti-CD3 38E4v1 MD1 or 38E4v1 MD4 arm showed affinity to CD3 comparable to that of TDBs assembled using either a one-cell system or a two-cell system and comprising the anti-CD3 38E4v1 arm; MD1 and MD4, like 38E4v1, are thus high-affinity anti-CD3 arms (Table 11). Assays were performed using a BIAcore T200. 27mer human and cyno CD3 polypeptides were conjugated to biotin and were immobilized on a SA CM5 chip. LY6G6D TDBs were flowed through at 37° C.

TABLE 11

BIAcore analyses of TDBs against human and cyno CD3

| Variant | CD3 Affinity ($K_D$ in nM) | |
| --- | --- | --- |
| | Human | Cyno |
| two-cell WT | 19.8 | 14.8 |
| one-cell WT | 20.6 | 15.9 |
| one-cell MD1 | 32.6 | 26.1 |
| one-cell MD4 | 18.7 | 14.4 |

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A bispecific antibody that binds to lymphocyte antigen 6 family member G6D (LY6G6D) and cluster of differentiation 3 (CD3), wherein the bispecific antibody comprises: a LY6G6D binding domain comprising a heavy chain polypeptide (H1) and a light chain polypeptide (L1) and a CD3 binding domain comprising a heavy chain polypeptide (H2) and a light chain polypeptide (L2), wherein each H1 and H2 comprises a heavy chain variable domain (VH) and a heavy chain constant domain (CH1) and each L1 and L2 comprises a light chain variable domain (VL) and a light chain constant domain (CL), wherein:
   (a) the LY6G6D binding domain comprises the following six CDRs:
      (i) a CDR-H1 comprising the amino acid sequence of SEQ ID NO: 4;
      (ii) a CDR-H2 comprising the amino acid sequence of SEQ ID NO: 5;
      (iii) a CDR-H3 comprising the amino acid sequence of SEQ ID NO: 6;
      (iv) a CDR-L1 comprising the amino acid sequence of SEQ ID NO: 1;
      (v) a CDR-L2 comprising the amino acid sequence of SEQ ID NO: 2; and
      (vi) a CDR-L3 comprising the amino acid sequence of SEQ ID NO: 3; and
   (b) the CD3 binding domain comprises the following six CDRs:
      (i) a CDR-H1 comprising the amino acid sequence of SEQ ID NO: 15;
      (ii) a CDR-H2 comprising the amino acid sequence of SEQ ID NO: 16;
      (iii) a CDR-H3 comprising the amino acid sequence of SEQ ID NO: 17;
      (iv) a CDR-L1 comprising the amino acid sequence of SEQ ID NO: 12;
      (v) a CDR-L2 comprising the amino acid sequence of SEQ ID NO: 13; and
      (vi) a CDR-L3 comprising the amino acid sequence of SEQ ID NO: 14.

2. The bispecific antibody of claim 1, wherein:
   (a) the CH1 of H1 comprises an amino acid substitution at S183 (EU numbering) and the CL of L1 comprises an amino acid substitution at V133 (EU numbering) and/or the CH1 of H2 comprises an amino acid substitution at S183 (EU numbering) and the CL of L2 comprises an amino acid substitution at V133 (EU numbering); and
   (b) the VH of H1 comprises an amino acid substitution at position Q39 and the VL of L1 comprises an amino acid substitution at position Q38 and/or the VH of H2 comprises an amino acid substitution at position Q39 and the VL of L2 comprises an amino acid substitution at position Q38 (all Kabat numbering).

3. The bispecific antibody of claim 1, wherein:
   (a) H1 comprises the amino acid sequence of SEQ ID NO: 7;
   (b) L1 comprises the amino acid sequence of SEQ ID NO: 9;
   (c) H2 comprises the amino acid sequence of SEQ ID NO: 18; and
   (d) L2 comprises the amino acid sequence of SEQ ID NO: 19.

4. The bispecific antibody of claim 1, wherein:
   (a) H1 comprises the amino acid sequence of SEQ ID NO: 64;
   (b) L1 comprises the amino acid sequence of SEQ ID NO: 65;
   (c) H2 comprises the amino acid sequence of SEQ ID NO: 69; and
   (d) L2 comprises the amino acid sequence of SEQ ID NO: 70.

5. The bispecific antibody of claim 1, wherein:
   (a) H1 comprises the amino acid sequence of SEQ ID NO: 8;
   (b) L1 comprises the amino acid sequence of SEQ ID NO: 9;
   (c) H2 comprises the amino acid sequence of SEQ ID NO: 67; and
   (d) L2 comprises the amino acid sequence of SEQ ID NO: 19.

6. The bispecific antibody of claim 1, wherein:
   (a) H1 comprises the amino acid sequence of SEQ ID NO: 66;
   (b) L1 comprises the amino acid sequence of SEQ ID NO: 65;
   (c) H2 comprises the amino acid sequence of SEQ ID NO: 68; and
   (d) L2 comprises the amino acid sequence of SEQ ID NO: 70.

7. A bispecific antibody that binds to LY6G6D and CD3, wherein the bispecific antibody comprises: a LY6G6D binding domain comprising an H1 and an L1 and a CD3 binding domain comprising a heavy chain polypeptide (H2) and a light chain polypeptide (L2), wherein each H1 and H2 comprises a heavy chain variable domain (VH) and a heavy chain constant domain (CH1) and each L1 and L2 comprises a light chain variable domain (VL) and a light chain constant domain (CL), wherein:
   (a) the LY6G6D binding domain comprises the following six CDRs:
      (i) a CDR-H1 comprising the amino acid sequence of SEQ ID NO: 4;
      (ii) a CDR-H2 comprising the amino acid sequence of SEQ ID NO: 5;
      (iii) a CDR-H3 comprising the amino acid sequence of SEQ ID NO: 6;
      (iv) a CDR-H1 comprising the amino acid sequence of SEQ ID NO: 1;
      (v) a CDR-L2 comprising the amino acid sequence of SEQ ID NO: 2; and
      (vi) a CDR-L3 comprising the amino acid sequence of SEQ ID NO: 3; and
   (b) the CD3 binding domain comprises the following six CDRs:
      (i) a CDR-H1 comprising the amino acid sequence of SEQ ID NO: 15;
      (ii) a CDR-H2 comprising the amino acid sequence of SEQ ID NO: 16;
      (iii) a CDR-H3 comprising the amino acid sequence of SEQ ID NO: 17;
      (iv) a CDR-L1 comprising the amino acid sequence of SEQ ID NO: 12;
      (v) a CDR-L2 comprising the amino acid sequence of SEQ ID NO: 50; and
      (vi) a CDR-L3 comprising the amino acid sequence of SEQ ID NO: 51.

8. The bispecific antibody of claim 7, wherein:
   (a) the CH1 of H1 comprises an amino acid substitution at S183 (EU numbering) and the CL of L1 comprises an amino acid substitution at V133 (EU numbering) and/or the CH1 of H2 comprises an amino acid substitution at S183 (EU numbering) and the CL of L2 comprises an amino acid substitution at V133 (EU numbering); and (b) the VH of H1 comprises an amino acid substitution at position Q39 and the VL of L1 comprises an amino acid substitution at position Q38 and/or the VH of H2 comprises an amino acid substitution at position Q39 and the VL of L2 comprises an amino acid substitution at position Q38 (all Kabat numbering).

9. The bispecific antibody of claim 7, wherein:
(a) H1 comprises the amino acid sequence of SEQ ID NO: 7;
(b) L1 comprises the amino acid sequence of SEQ ID NO: 9;
(c) H2 comprises the amino acid sequence of SEQ ID NO: 18; and
(d) L2 comprises the amino acid sequence of SEQ ID NO: 57.

10. The bispecific antibody of claim 7, wherein:
(a) H1 comprises the amino acid sequence of SEQ ID NO: 64;
(b) L1 comprises the amino acid sequence of SEQ ID NO: 65;
(c) H2 comprises the amino acid sequence of SEQ ID NO: 69; and
(d) L2 comprises the amino acid sequence of SEQ ID NO: 73.

11. The bispecific antibody of claim 7, wherein:
(a) H1 comprises the amino acid sequence of SEQ ID NO: 8;
(b) L1 comprises the amino acid sequence of SEQ ID NO: 9;
(c) H2 comprises the amino acid sequence of SEQ ID NO: 67; and
(d) L2 comprises the amino acid sequence of SEQ ID NO: 57.

12. The bispecific antibody of claim 7, wherein:
(a) H1 comprises the amino acid sequence of SEQ ID NO: 66;
(b) L1 comprises the amino acid sequence of SEQ ID NO: 65;
(c) H2 comprises the amino acid sequence of SEQ ID NO: 68; and
(d) L2 comprises the amino acid sequence of SEQ ID NO: 73.

13. One or more isolated nucleic acids encoding the antibody of claim 1 or 7, or a portion thereof comprising a binding domain that binds to LY6G6D.

14. A composition comprising the antibody of claim 1 or 7.

15. The bispecific antibody of claim 1 or 7, wherein:
(a) the CH1 of H1 comprises an amino acid substitution at position S183 and the CL of L1 comprises an amino acid substitution at position V133 and/or the CH1 of H2 comprises an amino acid substitution at position S183 and the CL of L2 comprises an amino acid substitution at position V133 (all EU numbering), wherein the substituted residue at position S183 in the CH1 of H1 forms a charge pair with the substituted residue at position V133 in the CL of L1 and/or the substituted residue at position S183 in the CH1 of H2 forms a charge pair with the substituted residue at position V133 in the CL of L2; and
(b) the VH of H1 comprises an amino acid substitution at position Q39 and the VL of L1 comprises an amino acid substitution at position Q38 and/or the VH of H2 comprises an amino acid substitution at position Q39 and the VL of L2 comprises an amino acid substitution at position Q38 (all Kabat numbering), wherein the substituted residue at position Q39 in the VH of H1 forms a charge pair with the substituted residue at position Q38 in the VL of L1 and/or the substituted residue at position Q39 in the VH of H2 forms a charge pair with the substituted residue at position Q38 in the VL of L2.

16. The bispecific antibody of claim 15, wherein:
(a) the CH1 of H1 comprises a S183K mutation; the CL of L1 comprises a V133E mutation; the CH1 of H2 comprises a S183E mutation; and the CL of L2 comprises a V133K mutation (all EU numbering); and
(b) the VH of H1 comprises a Q39E mutation; the VL of L1 comprises a Q38K mutation; the VH of H2 comprises a Q39K mutation; and the VL of L2 comprises a Q38E mutation (all Kabat numbering).

17. The bispecific antibody of claim 15, wherein:
(a) the CH1 of H1 comprises a S183E mutation and the CL of L1 comprises a V133K mutation, and the CH1 of H2 comprises a S183K mutation and the CL of L2 comprises a V133E mutation (all EU numbering); and
(b) the VH of H1 comprises a Q39K mutation, the VL of L1 comprises a Q38E mutation, the VH of H2 comprises a Q39E mutation, and the VL of L2 comprises a Q38K mutation (all Kabat numbering).

18. The bispecific antibody of claim 1 or 7, wherein the amino acid at S43 (Kabat numbering) in the VL of L2 is replaced with proline.

19. The bispecific antibody of claim 1, wherein the VH of H1 comprises the amino acid sequence of SEQ ID NO: 10; the VL of L1 comprises the amino acid sequence of SEQ ID NO: 11; the VH of H2 comprises the amino acid sequence of SEQ ID NO: 20; and the VL of L2 comprises the amino acid sequence of SEQ ID NO: 21.

20. The bispecific antibody of claim 1, wherein the VH of H1 comprises the amino acid sequence of SEQ ID NO: 59; the VL of L1 comprises the amino acid sequence of SEQ ID NO: 60; the VH of H2 comprises the amino acid sequence of SEQ ID NO: 89; and the VL of L2 comprises the amino acid sequence of SEQ ID NO: 90.

21. The bispecific antibody of claim 7, wherein the VH of H1 comprises the amino acid sequence of SEQ ID NO: 10; the VL of L1 comprises the amino acid sequence of SEQ ID NO: 11; the VH of H2 comprises the amino acid sequence of SEQ ID NO: 20; and the VL of L2 comprises the amino acid sequence of SEQ ID NO: 55.

22. The bispecific antibody of claim 7, wherein the VH of H1 comprises the amino acid sequence of SEQ ID NO: 59; the VL of L1 comprises the amino acid sequence of SEQ ID NO: 60; the VH of H2 comprises the amino acid sequence of SEQ ID NO: 89; and the VL of L2 comprises the amino acid sequence of SEQ ID NO: 92.

23. The bispecific antibody of claim 1 or 7, wherein the bispecific antibody is a full-length antibody.

24. The bispecific antibody of claim 1 or 7, wherein a first CH3 domain ($CH3_1$) of an Fc region of the H1 and a second CH3 domain ($CH3_2$) of an Fc region of the H2 each comprise a protuberance or a cavity, and wherein the protuberance or cavity in the $CH3_1$ is positionable in the cavity or protuberance, respectively, in the $CH3_2$.

25. The bispecific antibody of claim 24, wherein the $CH3_1$ and the $CH3_2$ meet at an interface between the protuberance and cavity.

26. The bispecific antibody of claim 24, wherein the CH3₁ of the Fc region of the H1 comprises a protuberance and the CH3₂ of the Fc region of the H2 comprises a cavity.

27. The bispecific antibody of claim 24, wherein (a) the CH3₁ of the Fc region of the H1 comprises a protuberance comprising a T366W amino acid substitution mutation (EU numbering); (b) the CH3₂ of the Fc region of the H2 comprises a cavity comprising a T366S, L368A, or Y407V amino acid substitution mutation (EU numbering), or a combination thereof; or (c) both (a) and (b).

28. The bispecific antibody of claim 27, wherein (a) the CH3₁ of the Fc region of the H1 comprises a protuberance comprising a T366W amino acid substitution mutation (EU numbering); (b) the CH3₂ of the Fc region of the H2 comprises a cavity comprising T366S, L368A, and Y407V amino acid substitution mutations (EU numbering); or (c) both (a) and (b).

29. The bispecific antibody of claim 28, wherein (a) the CH3₁ of the Fc region of the H1 comprises a protuberance comprising a T366W amino acid substitution mutation (EU numbering) and (b) the CH3₂ of the Fc region of the H2 comprises a cavity comprising T366S, L368A, and Y407V amino acid substitution mutations (EU numbering).

30. The bispecific antibody of claim 24, wherein the CH3₁ of the Fc region of the H1 comprises a cavity and the CH3₂ of the Fc region of the H2 comprises a protuberance.

31. The bispecific antibody of claim 24, wherein (a) the CH3₁ of the Fc region of the H1 comprises a cavity comprising a T366S, L368A, or Y407V amino acid substitution mutation (EU numbering), or a combination thereof; (b) the CH3₂ of the Fc region of the H2 comprises a protuberance comprising a T366W amino acid substitution mutation (EU numbering); or (c) both (a) and (b).

32. The bispecific antibody of claim 31, wherein (a) the CH3₁ of the Fc region of the H1 comprises a cavity comprising T366S, L368A, and Y407V amino acid substitution mutations (EU numbering);
(b) the CH3₂ of the Fc region of the H2 comprises a protuberance comprising a T366W amino acid substitution mutation (EU numbering); or (c) both (a) and (b).

33. The bispecific antibody of claim 32, wherein (a) the CH3₁ of the Fc region of the H1 comprises a cavity comprising T366S, L368A, and Y407V amino acid substitution mutations (EU numbering) and (b) the CH3₂ of the Fc region of the H2 comprises a protuberance comprising a T3661W amino acid substitution mutation (EU numbering).

34. The bispecific antibody of claim 24, wherein the Fc regions are human IgG isotype Fc regions, or Fc region variants thereof.

35. The bispecific antibody of claim 34, wherein the Fc regions are human IgG isotype Fc region variants.

36. The bispecific antibody of claim 35, wherein the human IgG isotype Fc region variants each comprise a mutation at amino acid residue N297 (EU numbering) that results in the absence of glycosylation.

37. The bispecific antibody of claim 36, wherein the mutation at amino acid residue N297 is a substitution mutation.

38. The bispecific antibody of claim 36, wherein the mutation at amino acid residue N297 reduces effector function of the Fc reaion.

39. The bispecific antibody of claim 37, wherein the substitution mutation is an N297G or N297A mutation.

40. The bispecific antibody of claim 39, wherein the human IgG isotype Fc region variants each comprise the N297G mutation.

41. A bispecific antibody that binds to LY6G6D and CD3, wherein the bispecific antibody comprises: a LY6G6D binding domain comprising a heavy chain polypeptide (H1) and a light chain polypeptide (L1) and a CD3 binding domain comprising a heavy chain polypeptide (H2) and a light chain polypeptide (L2), wherein each H1 and H2 comprises a heavy chain variable domain (VH) and a heavy chain constant domain (CH1) and each L1 and L2 comprises a light chain variable domain (VL) and a light chain constant domain (CL), wherein:
the VH of H1 comprises the amino acid sequence of SEQ ID NO: 10; the VL of LA comprises the amino acid sequence of SEQ ID NO: 11; the VH of H2 comprises the amino acid sequence of SEQ ID NO: 20; and
the VL of L2 comprises the amino acid sequence of SEQ ID NO: 21.

42. A bispecific antibody that binds to LY6G6D and CD3, wherein the bispecific antibody comprises: a LY6G6D binding domain comprising a heavy chain polypeptide (H1) and a light chain polypeptide (L1) and a CD3 binding domain comprising a heavy chain polypeptide (H2) and a light chain polypeptide (L2), wherein each H1 and H2 comprises a heavy chain variable domain (VH) and a heavy chain constant domain (CH1) and each L1 and L2 comprises a light chain variable domain (VL) and a light chain constant domain (CL), wherein:
the VH of H1 comprises the amino acid sequence of SEQ ID NO: 59; the VL of L1 comprises the amino acid sequence of SEQ ID NO: 60; the VH of H2 comprises the amino acid sequence of SEQ ID NO: 89; and the VL of L2 comprises the amino acid sequence of SEQ ID NO: 90.

43. A bispecific antibody that binds to LY6G6D and CD3, wherein the bispecific antibody comprises: a LY6G6D binding domain comprising a heavy chain polypeptide (H1) and a light chain polypeptide (L1) and a CD3 binding domain comprising a heavy chain polypeptide (H2) and a light chain polypeptide (L2), wherein each H1 and H2 comprises a heavy chain variable domain (VH) and a heavy chain constant domain (CH1) and each L1 and L2 comprises a light chain variable domain (VL) and a light chain constant domain (CL), wherein:
the VH of H1 comprises the amino acid sequence of SEQ ID NO: 10; the VL of L1 comprises the amino acid sequence of SEQ ID NO: 11; the VH of H2 comprises the amino acid sequence of SEQ ID NO: 20; and the VL of L2 comprises the amino acid sequence of SEQ ID NO: 55.

44. A bispecific antibody that binds to LY6G6D and CD3, wherein the bispecific antibody comprises: a LY6G6D binding domain comprising a heavy chain polypeptide (H1) and a light chain polypeptide (L1) and a CD3 binding domain comprising a heavy chain polypeptide (H2) and a light chain polypeptide (L2), wherein each H1 and H2 comprises a heavy chain variable domain (VH) and a heavy chain constant domain (CH1) and each L1 and L2 comprises a light chain variable domain (VL) and a light chain constant domain (CL), wherein:
the VH of HI comprises the amino acid sequence of SEQ ID NO: 59; the VL of L1 comprises the amino acid sequence of SEQ ID NO: 60; the VH of H2 comprises the amino acid sequence of SEQ ID NO: 89; and the VL of L2 comprises the amino acid sequence of SEQ ID NO: 92.

* * * * *

SEQUENCE LISTING

```
<160> NUMBER OF SEQ ID NOS: 147

<210> SEQ ID NO 1
<211> LENGTH: 11
<212> TYPE: PRT
<213> ORGANISM: Artificial Sequence
<220> FEATURE:
<223> OTHER INFORMATION: Synthetic Construct

<400> SEQUENCE: 1

Gln Ala Ser Glu Ser Ile Thr Arg Tyr Leu Asn
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2

Asp Ala Ser Lys Leu Pro Ser
1               5

<210> SEQ ID NO 3
<211> LENGTH: 13
<212> TYPE: PRT
<213> ORGANISM: Artificial Sequence
<220> FEATURE:
<223> OTHER INFORMATION: Synthetic Construct

<400> SEQUENCE: 3

Gln Ser Thr Ser Phe Arg Gly Arg Ser Tyr Gln Asn Thr
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Synthetic Construct
```

```
<400> SEQUENCE: 4

Asn Asn Ala Met Ile
1               5

<210> SEQ ID NO 5
<211> LENGTH: 17
<212> TYPE: PRT
<213> ORGANISM: Artificial Sequence
<220> FEATURE:
<223> OTHER INFORMATION: Synthetic Construct

<400> SEQUENCE: 5

Ala Leu Ser Phe Ala Asp Asn Thr Ala Tyr Tyr Ala Thr Trp Ala Ser
1               5                   10                  15

Gly

<210> SEQ ID NO 6
<211> LENGTH: 3
<212> TYPE: PRT
<213> ORGANISM: Artificial Sequence
<220> FEATURE:
<223> OTHER INFORMATION: Synthetic Construct

<400> SEQUENCE: 6

Gly Asp Leu
1

<210> SEQ ID NO 7
<211> LENGTH: 442
<212> TYPE: PRT
<213> ORGANISM: Artificial Sequence
<220> FEATURE:
<223> OTHER INFORMATION: Synthetic Construct

<400> SEQUENCE: 7

Glu Val Gln Leu Leu Glu Ser Gly Gly Leu Val Gln Pro Gly Gly
1               5                   10                  15

Ser Leu Arg Leu Ser Cys Ala Ala Ser Gly Phe Asp Phe Val Asn Asn
                20                  25                  30

Ala Met Ile Trp Val Arg Glu Ala Pro Gly Lys Gly Leu Glu Trp Val
            35                  40                  45

Ser Ala Leu Ser Phe Ala Asp Asn Thr Ala Tyr Tyr Ala Thr Trp Ala
        50                  55                  60

Ser Gly Arg Phe Thr Ile Ser Arg Asp Ser Ser Lys Thr Thr Val Tyr
65                  70                  75                  80

Leu Gln Met Asn Ser Leu Arg Ala Glu Asp Thr Ala Val Tyr Tyr Cys
                85                  90                  95

Met Arg Gly Asp Leu Trp Gly Pro Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Lys Ser Val Val Thr Val Pro Ser Ser Ser Leu Gly Thr Gln Thr
            180                 185                 190
```

```
Tyr Ile Cys Asn Val Asn His Lys Pro Ser Asn Thr Lys Val Asp Lys
            195                 200                 205

Lys Val Glu Pro Lys Ser Cys Asp Lys Thr His Thr Cys Pro Pro Cys
210                 215                 220

Pro Ala Pro Glu Leu Leu Gly Pro Ser Val Phe Leu Phe Pro Pro
225                 230                 235                 240

Lys Pro Lys Asp Thr Leu Met Ile Ser Arg Thr Pro Glu Val Thr Cys
            245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
            275                 280                 285

Glu Gln Tyr Gly Ser Thr Tyr Arg Val Val Ser Val Leu Thr Val Leu
            290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Trp Cys Leu Val Lys Gly Phe Tyr
            355                 360                 365

Pro Ser Asp Ile Ala Val Glu Trp Glu Ser Asn Gly Gln Pro Glu Asn
            370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
            435                 440

<210> SEQ ID NO 8
<211> LENGTH: 442
<212> TYPE: PRT
<213> ORGANISM: Artificial Sequence
<220> FEATURE:
<223> OTHER INFORMATION: Synthetic Construct

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Val Asn Asn
                20                  25                  30

Ala Met Ile Trp Val Arg Glu Ala Pro Gly Lys Gly Leu Glu Trp Val
            35                  40                  45

Ser Ala Leu Ser Phe Ala Asp Asn Thr Ala Tyr Tyr Ala Thr Trp Ala
50                  55                  60

Ser Gly Arg Phe Thr Ile Ser Arg Asp Ser Ser Lys Thr Thr Val Tyr
65                  70                  75                  80

Leu Gln Met Asn Ser Leu Arg Ala Glu Asp Thr Ala Val Tyr Tyr Cys
                85                  90                  95

Met Arg Gly Asp Leu Trp Gly Pro Gly Thr Leu Val Thr Val Ser Ser
            100                 105                 110
```

Ala Ser Thr Lys Gly Pro Ser Val Phe Pro Leu Ala Pro Ser Ser Lys
            115                 120                 125

Ser Thr Ser Gly Gly Thr Ala Ala Leu Gly Cys Leu Val Lys Asp Tyr
        130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Lys Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Gly Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Ser Cys Ala Val Lys Gly Phe Tyr
        355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Val Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

<210> SEQ ID NO 9
<211> LENGTH: 218
<212> TYPE: PRT
<213> ORGANISM: Artificial Sequence
<220> FEATURE:
<223> OTHER INFORMATION: Synthetic Construct

<400> SEQUENCE: 9

Asp Ile Gln Met Thr Gln Ser Pro Ser Thr Leu Ser Ala Ser Val Gly
1               5                   10                  15

Asp Arg Val Thr Ile Thr Cys Gln Ala Ser Glu Ser Ile Thr Arg Tyr
            20                  25                  30

```
Leu Asn Trp Tyr Gln Lys Lys Pro Gly Lys Ala Pro Lys Leu Leu Ile
            35                  40                  45

Tyr Asp Ala Ser Lys Leu Pro Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Ser Thr Ser Phe Arg Gly Arg
                 85                  90                  95

Ser Tyr Gln Asn Thr Phe Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Glu Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
            210                 215

<210> SEQ ID NO 10
<211> LENGTH: 112
<212> TYPE: PRT
<213> ORGANISM: Artificial Sequence
<220> FEATURE:
<223> OTHER INFORMATION: Synthetic Construct

<400> SEQUENCE: 10

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Asp Phe Val Asn Asn
            20                  25                  30

Ala Met Ile Trp Val Arg Glu Ala Pro Gly Lys Gly Leu Glu Trp Val
            35                  40                  45

Ser Ala Leu Ser Phe Ala Asp Asn Thr Ala Tyr Tyr Ala Thr Trp Ala
 50                  55                  60

Ser Gly Arg Phe Thr Ile Ser Arg Asp Ser Ser Lys Thr Thr Val Tyr
 65                  70                  75                  80

Leu Gln Met Asn Ser Leu Arg Ala Glu Asp Thr Ala Val Tyr Tyr Cys
                 85                  90                  95

Met Arg Gly Asp Leu Trp Gly Pro Gly Thr Leu Val Thr Val Ser Ser
            100                 105                 110

<210> SEQ ID NO 11
<211> LENGTH: 111
<212> TYPE: PRT
<213> ORGANISM: Artificial Sequence
<220> FEATURE:
<223> OTHER INFORMATION: Synthetic Construct
```

<400> SEQUENCE: 11

Asp Ile Gln Met Thr Gln Ser Pro Ser Thr Leu Ser Ala Ser Val Gly
1               5                   10                  15

Asp Arg Val Thr Ile Thr Cys Gln Ala Ser Glu Ser Ile Thr Arg Tyr
            20                  25                  30

Leu Asn Trp Tyr Gln Lys Pro Gly Lys Ala Pro Lys Leu Leu Ile
        35                  40                  45

Tyr Asp Ala Ser Lys Leu Pro Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Ser Thr Ser Phe Arg Gly Arg
                85                  90                  95

Ser Tyr Gln Asn Thr Phe Gly Gly Gly Thr Lys Val Glu Ile Lys
            100                 105                 110

<210> SEQ ID NO 12
<211> LENGTH: 17
<212> TYPE: PRT
<213> ORGANISM: Artificial Sequence
<220> FEATURE:
<223> OTHER INFORMATION: Synthetic Construct

<400> SEQUENCE: 12

Lys Ser Ser Gln Ser Leu Leu Asn Ser Arg Thr Arg Lys Asn Tyr Leu
1               5                   10                  15

Ala

<210> SEQ ID NO 13
<211> LENGTH: 7
<212> TYPE: PRT
<213> ORGANISM: Artificial Sequence
<220> FEATURE:
<223> OTHER INFORMATION: Synthetic Construct

<400> SEQUENCE: 13

Trp Ala Ser Thr Arg Glu Ser
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic Construct

<400> SEQUENCE: 14

Thr Gln Ser Phe Ile Leu Arg Thr
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic Construct

<400> SEQUENCE: 15

Ser Tyr Tyr Ile His
1               5

```
<210> SEQ ID NO 16
<211> LENGTH: 17
<212> TYPE: PRT
<213> ORGANISM: Artificial Sequence
<220> FEATURE:
<223> OTHER INFORMATION: Synthetic Construct

<400> SEQUENCE: 16

Trp Ile Tyr Pro Glu Asn Asp Asn Thr Lys Tyr Asn Glu Lys Phe Lys
1               5                   10                  15

Asp

<210> SEQ ID NO 17
<211> LENGTH: 10
<212> TYPE: PRT
<213> ORGANISM: Artificial Sequence
<220> FEATURE:
<223> OTHER INFORMATION: Synthetic Construct

<400> SEQUENCE: 17

Asp Gly Tyr Ser Arg Tyr Tyr Phe Asp Tyr
1               5                   10

<210> SEQ ID NO 18
<211> LENGTH: 449
<212> TYPE: PRT
<213> ORGANISM: Artificial Sequence
<220> FEATURE:
<223> OTHER INFORMATION: Synthetic Construct

<400> SEQUENCE: 18

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Thr Ser Tyr
            20                  25                  30

Tyr Ile His Trp Val Arg Lys Ala Pro Gly Gln Gly Leu Glu Trp Ile
        35                  40                  45

Gly Trp Ile Tyr Pro Glu Asn Asp Asn Thr Lys Tyr Asn Glu Lys Phe
    50                  55                  60

Lys Asp Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Gly Tyr Ser Arg Tyr Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220
```

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gly Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Ser
        355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 19
<211> LENGTH: 219
<212> TYPE: PRT
<213> ORGANISM: Artificial Sequence
<220> FEATURE:
<223> OTHER INFORMATION: Synthetic Construct

<400> SEQUENCE: 19

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Glu Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

```
Gln Leu Lys Ser Gly Thr Ala Ser Val Lys Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 20
<211> LENGTH: 119
<212> TYPE: PRT
<213> ORGANISM: Artificial Sequence
<220> FEATURE:
<223> OTHER INFORMATION: Synthetic Construct

<400> SEQUENCE: 20

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Tyr Ile His Trp Val Arg Lys Ala Pro Gly Gln Gly Leu Glu Trp Ile
        35                  40                  45

Gly Trp Ile Tyr Pro Glu Asn Asp Asn Thr Lys Tyr Asn Glu Lys Phe
    50                  55                  60

Lys Asp Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Gly Tyr Ser Arg Tyr Tyr Phe Asp Tyr Trp Gly Gln Gly
            100                 105                 110

Thr Leu Val Thr Val Ser Ser
        115

<210> SEQ ID NO 21
<211> LENGTH: 112
<212> TYPE: PRT
<213> ORGANISM: Artificial Sequence
<220> FEATURE:
<223> OTHER INFORMATION: Synthetic Construct

<400> SEQUENCE: 21

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Glu Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80
```

```
Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
                100                 105                 110

<210> SEQ ID NO 22
<211> LENGTH: 112
<212> TYPE: PRT
<213> ORGANISM: Artificial Sequence
<220> FEATURE:
<223> OTHER INFORMATION: Synthetic Construct

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Val Asn Asn
                20                  25                  30

Ala Met Ile Trp Val Arg Gln Ala Pro Gly Lys Gly Leu Glu Trp Val
                35                  40                  45

Ser Ala Leu Ser Phe Ala Asp Asn Thr Ala Tyr Tyr Ala Thr Trp Ala
            50                  55                  60

Ser Gly Arg Phe Thr Ile Ser Arg Asp Ser Ser Lys Thr Thr Val Tyr
65              70                  75                  80

Leu Gln Met Asn Ser Leu Arg Ala Glu Asp Thr Ala Val Tyr Tyr Cys
                85                  90                  95

Met Arg Gly Asp Leu Trp Gly Pro Gly Thr Leu Val Thr Val Ser Ser
                100                 105                 110

<210> SEQ ID NO 23
<211> LENGTH: 111
<212> TYPE: PRT
<213> ORGANISM: Artificial Sequence
<220> FEATURE:
<223> OTHER INFORMATION: Synthetic Construct

<400> SEQUENCE: 23

Asp Ile Gln Met Thr Gln Ser Pro Ser Thr Leu Ser Ala Ser Val Gly
1               5                   10                  15

Asp Arg Val Thr Ile Thr Cys Gln Ala Ser Glu Ser Ile Thr Arg Tyr
                20                  25                  30

Leu Asn Trp Tyr Gln Gln Lys Pro Gly Lys Ala Pro Lys Leu Leu Ile
                35                  40                  45

Tyr Asp Ala Ser Lys Leu Pro Ser Gly Val Pro Ser Arg Phe Ser Gly
            50                  55                  60

Ser Gly Ser Gly Thr Glu Phe Thr Leu Thr Ile Ser Ser Leu Gln Pro
65              70                  75                  80

Asp Asp Phe Ala Thr Tyr Tyr Cys Gln Ser Ser Phe Arg Gly Arg
                85                  90                  95

Ser Tyr Gln Asn Thr Phe Gly Gly Gly Thr Lys Val Glu Ile Lys
                100                 105                 110

<210> SEQ ID NO 24
<211> LENGTH: 16
<212> TYPE: PRT
<213> ORGANISM: Artificial Sequence
<220> FEATURE:
<223> OTHER INFORMATION: Synthetic Construct
```

```
<400> SEQUENCE: 24

Lys Ser Ser Gln Ser Leu Leu Asp Ser Asp Gly Arg Thr Tyr Leu His
1               5                   10                  15

<210> SEQ ID NO 25
<211> LENGTH: 7
<212> TYPE: PRT
<213> ORGANISM: Artificial Sequence
<220> FEATURE:
<223> OTHER INFORMATION: Synthetic Construct

<400> SEQUENCE: 25

Leu Val Ser Asn Leu Asp Ser
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic Construct

<400> SEQUENCE: 26

Trp Gln Gly Thr His Leu Pro Phe Thr
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic Construct

<400> SEQUENCE: 27

Ser Tyr Trp Ile Gln
1               5

<210> SEQ ID NO 28
<211> LENGTH: 18
<212> TYPE: PRT
<213> ORGANISM: Artificial Sequence
<220> FEATURE:
<223> OTHER INFORMATION: Synthetic Construct

<400> SEQUENCE: 28

Glu Ile Leu Pro Gly Ser Asp Asn Thr Asn Tyr Asn Glu Lys Phe Lys
1               5                   10                  15

Gly Lys

<210> SEQ ID NO 29
<211> LENGTH: 4
<212> TYPE: PRT
<213> ORGANISM: Artificial Sequence
<220> FEATURE:
<223> OTHER INFORMATION: Synthetic Construct

<400> SEQUENCE: 29

Trp Phe Ala Tyr
1

<210> SEQ ID NO 30
<211> LENGTH: 443
<212> TYPE: PRT
<213> ORGANISM: Artificial Sequence
<220> FEATURE:
```

<223> OTHER INFORMATION: Synthetic Construct

<400> SEQUENCE: 30

```
Gln Val Gln Leu Gln Gln Ser Gly Ala Glu Leu Met Lys Pro Gly Ala
1               5                   10                  15

Ser Val Lys Ile Ser Cys Lys Ala Ser Gly Tyr Thr Phe Ser Ser Tyr
            20                  25                  30

Trp Ile Gln Trp Ile Lys Gln Arg Pro Gly His Gly Leu Glu Trp Ile
        35                  40                  45

Gly Glu Ile Leu Pro Gly Ser Asp Asn Thr Asn Tyr Asn Glu Lys Phe
    50                  55                  60

Lys Gly Lys Ala Thr Phe Thr Ala Asp Thr Ser Ser Thr Ala Tyr
65                  70                  75                  80

Met Gln Leu Ser Ser Leu Thr Ser Glu Asp Ser Ala Ile Tyr Tyr Cys
                85                  90                  95

Ala Lys Trp Phe Ala Tyr Trp Gly Gln Gly Thr Thr Val Thr Val Ser
            100                 105                 110

Ala Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Gly Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400
```

```
                Phe Leu Tyr Ser Lys Leu Thr Val Asp Lys Ser Arg Trp Gln Gln Gly
                                405                 410                 415

Asn Val Phe Ser Cys Ser Val Met His Glu Ala Leu His Asn His Tyr
                                420                 425                 430

Thr Gln Lys Ser Leu Ser Leu Ser Pro Gly Lys
                        435                 440

<210> SEQ ID NO 31
<211> LENGTH: 219
<212> TYPE: PRT
<213> ORGANISM: Artificial Sequence
<220> FEATURE:
<223> OTHER INFORMATION: Synthetic Construct

<400> SEQUENCE: 31

Asp Ile Val Met Thr Gln Thr Pro Leu Thr Leu Ser Val Thr Ile Gly
1               5                   10                  15

His Pro Ala Ser Ile Ser Cys Lys Ser Gln Ser Leu Leu Asp Ser
                20                  25                  30

Asp Gly Arg Thr Tyr Leu His Trp Leu Phe Gln Arg Pro Gly Gln Ser
            35                  40                  45

Pro Arg Arg Leu Ile Tyr Leu Val Ser Asn Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Leu Pro Phe Thr Phe Gly Ser Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 32
<211> LENGTH: 113
<212> TYPE: PRT
<213> ORGANISM: Artificial Sequence
<220> FEATURE:
<223> OTHER INFORMATION: Synthetic Construct

<400> SEQUENCE: 32

Gln Val Gln Leu Gln Gln Ser Gly Ala Glu Leu Met Lys Pro Gly Ala
1               5                   10                  15

Ser Val Lys Ile Ser Cys Lys Ala Ser Gly Tyr Thr Phe Ser Ser Tyr
                20                  25                  30

Trp Ile Gln Trp Ile Lys Gln Arg Pro Gly His Gly Leu Glu Trp Ile
            35                  40                  45
```

Gly Glu Ile Leu Pro Gly Ser Asp Asn Thr Asn Tyr Asn Glu Lys Phe
            50                  55                  60

Lys Gly Lys Ala Thr Phe Thr Ala Asp Thr Ser Ser Thr Ala Tyr
 65                  70                  75                  80

Met Gln Leu Ser Ser Leu Thr Ser Glu Asp Ser Ala Ile Tyr Tyr Cys
                85                  90                  95

Ala Lys Trp Phe Ala Tyr Trp Gly Gln Gly Thr Thr Val Thr Val Ser
                100                 105                 110

Ala

<210> SEQ ID NO 33
<211> LENGTH: 112
<212> TYPE: PRT
<213> ORGANISM: Artificial Sequence
<220> FEATURE:
<223> OTHER INFORMATION: Synthetic Construct

<400> SEQUENCE: 33

Asp Ile Val Met Thr Gln Thr Pro Leu Thr Leu Ser Val Thr Ile Gly
 1               5                  10                  15

His Pro Ala Ser Ile Ser Cys Lys Ser Ser Gln Ser Leu Leu Asp Ser
                20                  25                  30

Asp Gly Arg Thr Tyr Leu His Trp Leu Phe Gln Arg Pro Gly Gln Ser
            35                  40                  45

Pro Arg Arg Leu Ile Tyr Leu Val Ser Asn Leu Asp Ser Gly Val Pro
     50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Trp Gln Gly
                85                  90                  95

Thr His Leu Pro Phe Thr Phe Gly Ser Gly Thr Lys Val Glu Ile Lys
                100                 105                 110

<210> SEQ ID NO 34
<211> LENGTH: 30
<212> TYPE: PRT
<213> ORGANISM: Artificial Sequence
<220> FEATURE:
<223> OTHER INFORMATION: Synthetic Construct

<400> SEQUENCE: 34

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Asp Phe Val
                20                  25                  30

<210> SEQ ID NO 35
<211> LENGTH: 14
<212> TYPE: PRT
<213> ORGANISM: Artificial Sequence
<220> FEATURE:
<223> OTHER INFORMATION: Synthetic Construct

<400> SEQUENCE: 35

Trp Val Arg Glu Ala Pro Gly Lys Gly Leu Glu Trp Val Ser
 1               5                  10

<210> SEQ ID NO 36
<211> LENGTH: 32
<212> TYPE: PRT

```
<213> ORGANISM: Artificial Sequence
<220> FEATURE:
<223> OTHER INFORMATION: Synthetic Construct

<400> SEQUENCE: 36

Arg Phe Thr Ile Ser Arg Asp Ser Ser Lys Thr Thr Val Tyr Leu Gln
1               5                   10                  15
Met Asn Ser Leu Arg Ala Glu Asp Thr Ala Val Tyr Tyr Cys Met Arg
            20                  25                  30

<210> SEQ ID NO 37
<211> LENGTH: 11
<212> TYPE: PRT
<213> ORGANISM: Artificial Sequence
<220> FEATURE:
<223> OTHER INFORMATION: Synthetic Construct

<400> SEQUENCE: 37

Trp Gly Pro Gly Thr Leu Val Thr Val Ser Ser
1               5                   10

<210> SEQ ID NO 38
<211> LENGTH: 23
<212> TYPE: PRT
<213> ORGANISM: Artificial Sequence
<220> FEATURE:
<223> OTHER INFORMATION: Synthetic Construct

<400> SEQUENCE: 38

Asp Ile Gln Met Thr Gln Ser Pro Ser Thr Leu Ser Ala Ser Val Gly
1               5                   10                  15
Asp Arg Val Thr Ile Thr Cys
            20

<210> SEQ ID NO 39
<211> LENGTH: 15
<212> TYPE: PRT
<213> ORGANISM: Artificial Sequence
<220> FEATURE:
<223> OTHER INFORMATION: Synthetic Construct

<400> SEQUENCE: 39

Trp Tyr Gln Lys Lys Pro Gly Lys Ala Pro Lys Leu Leu Ile Tyr
1               5                   10                  15

<210> SEQ ID NO 40
<211> LENGTH: 32
<212> TYPE: PRT
<213> ORGANISM: Artificial Sequence
<220> FEATURE:
<223> OTHER INFORMATION: Synthetic Construct

<400> SEQUENCE: 40

Gly Val Pro Ser Arg Phe Ser Gly Ser Gly Ser Gly Thr Glu Phe Thr
1               5                   10                  15
Leu Thr Ile Ser Ser Leu Gln Pro Asp Asp Phe Ala Thr Tyr Tyr Cys
            20                  25                  30

<210> SEQ ID NO 41
<211> LENGTH: 10
<212> TYPE: PRT
<213> ORGANISM: Artificial Sequence
<220> FEATURE:
<223> OTHER INFORMATION: Synthetic Construct
```

<400> SEQUENCE: 41

Phe Gly Gly Gly Thr Lys Val Glu Ile Lys
1               5                   10

<210> SEQ ID NO 42
<211> LENGTH: 30
<212> TYPE: PRT
<213> ORGANISM: Artificial Sequence
<220> FEATURE:
<223> OTHER INFORMATION: Synthetic Construct

<400> SEQUENCE: 42

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr
            20                  25                  30

<210> SEQ ID NO 43
<211> LENGTH: 14
<212> TYPE: PRT
<213> ORGANISM: Artificial Sequence
<220> FEATURE:
<223> OTHER INFORMATION: Synthetic Construct

<400> SEQUENCE: 43

Trp Val Arg Glu Ala Pro Gly Gln Gly Leu Glu Trp Ile Gly
1               5                   10

<210> SEQ ID NO 44
<211> LENGTH: 32
<212> TYPE: PRT
<213> ORGANISM: Artificial Sequence
<220> FEATURE:
<223> OTHER INFORMATION: Synthetic Construct

<400> SEQUENCE: 44

Arg Val Thr Ile Thr Ala Asp Thr Ser Thr Ser Thr Ala Tyr Leu Glu
1               5                   10                  15

Leu Ser Ser Leu Arg Ser Glu Asp Thr Ala Val Tyr Tyr Cys Ala Arg
            20                  25                  30

<210> SEQ ID NO 45
<211> LENGTH: 11
<212> TYPE: PRT
<213> ORGANISM: Artificial Sequence
<220> FEATURE:
<223> OTHER INFORMATION: Synthetic Construct

<400> SEQUENCE: 45

Trp Gly Gln Gly Thr Leu Val Thr Val Ser Ser
1               5                   10

<210> SEQ ID NO 46
<211> LENGTH: 23
<212> TYPE: PRT
<213> ORGANISM: Artificial Sequence
<220> FEATURE:
<223> OTHER INFORMATION: Synthetic Construct

<400> SEQUENCE: 46

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 47
<211> LENGTH: 15
<212> TYPE: PRT
<213> ORGANISM: Artificial Sequence
<220> FEATURE:
<223> OTHER INFORMATION: Synthetic Construct

<400> SEQUENCE: 47

Trp Tyr Gln Gln Lys Pro Gly Gln Pro Pro Lys Leu Leu Ile Tyr
1               5                   10                  15

<210> SEQ ID NO 48
<211> LENGTH: 32
<212> TYPE: PRT
<213> ORGANISM: Artificial Sequence
<220> FEATURE:
<223> OTHER INFORMATION: Synthetic Construct

<400> SEQUENCE: 48

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 49
<211> LENGTH: 10
<212> TYPE: PRT
<213> ORGANISM: Artificial Sequence
<220> FEATURE:
<223> OTHER INFORMATION: Synthetic Construct

<400> SEQUENCE: 49

Phe Gly Gln Gly Thr Lys Val Glu Ile Lys
1               5                   10

<210> SEQ ID NO 50
<211> LENGTH: 7
<212> TYPE: PRT
<213> ORGANISM: Artificial Sequence
<220> FEATURE:
<223> OTHER INFORMATION: Synthetic Construct

<400> SEQUENCE: 50

Trp Ala Ser Thr Arg Lys Ser
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic Construct

<400> SEQUENCE: 51

Lys Gln Ser Phe Ile Leu Arg Thr Phe
1               5

<210> SEQ ID NO 52
<211> LENGTH: 119
<212> TYPE: PRT
<213> ORGANISM: Artificial Sequence
<220> FEATURE:
<223> OTHER INFORMATION: Synthetic Construct

<400> SEQUENCE: 52

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Tyr Ile His Trp Val Arg Gln Ala Pro Gly Gln Gly Leu Glu Trp Ile
        35                  40                  45

Gly Trp Ile Tyr Pro Glu Asn Asp Asn Thr Lys Tyr Asn Glu Lys Phe
50                  55                  60

Lys Asp Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Gly Tyr Ser Arg Tyr Tyr Phe Asp Tyr Trp Gly Gln Gly
                100                 105                 110

Thr Leu Val Thr Val Ser Ser
            115

<210> SEQ ID NO 53
<211> LENGTH: 112
<212> TYPE: PRT
<213> ORGANISM: Artificial Sequence
<220> FEATURE:
<223> OTHER INFORMATION: Synthetic Construct

<400> SEQUENCE: 53

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
                100                 105                 110

<210> SEQ ID NO 54

<400> SEQUENCE: 54

000

<210> SEQ ID NO 55
<211> LENGTH: 112
<212> TYPE: PRT
<213> ORGANISM: Artificial Sequence
<220> FEATURE:
<223> OTHER INFORMATION: Synthetic Construct

<400> SEQUENCE: 55

Asp Ile Val Met Thr Gln Ser Pro Asp Ser Leu Ala Val Ser Leu Gly
1               5                   10                  15

```
Glu Arg Ala Thr Ile Asn Cys Lys Ser Ser Gln Ser Leu Leu Asn Ser
                20                  25                  30

Arg Thr Arg Lys Asn Tyr Leu Ala Trp Tyr Gln Glu Lys Pro Gly Gln
            35                  40                  45

Pro Pro Lys Leu Leu Ile Tyr Trp Ala Ser Thr Arg Lys Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Val Glu Ile Lys
                100                 105                 110
```

<210> SEQ ID NO 56

<400> SEQUENCE: 56

000

<210> SEQ ID NO 57
<211> LENGTH: 219
<212> TYPE: PRT
<213> ORGANISM: Artificial Sequence
<220> FEATURE:
<223> OTHER INFORMATION: Synthetic Construct

<400> SEQUENCE: 57

```
Asp Ile Val Met Thr Gln Ser Pro Asp Ser Leu Ala Val Ser Leu Gly
 1               5                   10                  15

Glu Arg Ala Thr Ile Asn Cys Lys Ser Ser Gln Ser Leu Leu Asn Ser
                20                  25                  30

Arg Thr Arg Lys Asn Tyr Leu Ala Trp Tyr Gln Glu Lys Pro Gly Gln
            35                  40                  45

Pro Pro Lys Leu Leu Ile Tyr Trp Ala Ser Thr Arg Lys Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Lys Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
210                 215
```

<210> SEQ ID NO 58
<211> LENGTH: 14
<212> TYPE: PRT
<213> ORGANISM: Artificial Sequence
<220> FEATURE:
<223> OTHER INFORMATION: Synthetic Construct

<400> SEQUENCE: 58

Trp Val Arg Lys Ala Pro Gly Lys Gly Leu Glu Trp Val Ser
1               5                   10

<210> SEQ ID NO 59
<211> LENGTH: 112
<212> TYPE: PRT
<213> ORGANISM: Artificial Sequence
<220> FEATURE:
<223> OTHER INFORMATION: Synthetic Construct

<400> SEQUENCE: 59

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Val Asn Asn
            20                  25                  30

Ala Met Ile Trp Val Arg Lys Ala Pro Gly Lys Gly Leu Glu Trp Val
        35                  40                  45

Ser Ala Leu Ser Phe Ala Asp Asn Thr Ala Tyr Tyr Ala Thr Trp Ala
    50                  55                  60

Ser Gly Arg Phe Thr Ile Ser Arg Asp Ser Ser Lys Thr Thr Val Tyr
65                  70                  75                  80

Leu Gln Met Asn Ser Leu Arg Ala Glu Asp Thr Ala Val Tyr Tyr Cys
                85                  90                  95

Met Arg Gly Asp Leu Trp Gly Pro Gly Thr Leu Val Thr Val Ser Ser
            100                 105                 110

<210> SEQ ID NO 60
<211> LENGTH: 111
<212> TYPE: PRT
<213> ORGANISM: Artificial Sequence
<220> FEATURE:
<223> OTHER INFORMATION: Synthetic Construct

<400> SEQUENCE: 60

Asp Ile Gln Met Thr Gln Ser Pro Ser Thr Leu Ser Ala Ser Val Gly
1               5                   10                  15

Asp Arg Val Thr Ile Thr Cys Gln Ala Ser Glu Ser Ile Thr Arg Tyr
            20                  25                  30

Leu Asn Trp Tyr Gln Glu Lys Pro Gly Lys Ala Pro Lys Leu Leu Ile
        35                  40                  45

Tyr Asp Ala Ser Lys Leu Pro Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Ser Thr Ser Phe Arg Gly Arg
                85                  90                  95

Ser Tyr Gln Asn Thr Phe Gly Gly Gly Thr Lys Val Glu Ile Lys
            100                 105                 110

<210> SEQ ID NO 61
<211> LENGTH: 15
<212> TYPE: PRT
<213> ORGANISM: Artificial Sequence

```
<220> FEATURE:
<223> OTHER INFORMATION: Synthetic Construct

<400> SEQUENCE: 61

Trp Tyr Gln Glu Lys Pro Gly Lys Ala Pro Lys Leu Leu Ile Tyr
1               5                   10                  15

<210> SEQ ID NO 62
<211> LENGTH: 14
<212> TYPE: PRT
<213> ORGANISM: Artificial Sequence
<220> FEATURE:
<223> OTHER INFORMATION: Synthetic Construct

<400> SEQUENCE: 62

Trp Val Arg Lys Ala Pro Gly Gln Gly Leu Glu Trp Ile Gly
1               5                   10

<210> SEQ ID NO 63
<211> LENGTH: 15
<212> TYPE: PRT
<213> ORGANISM: Artificial Sequence
<220> FEATURE:
<223> OTHER INFORMATION: Synthetic Construct

<400> SEQUENCE: 63

Trp Tyr Gln Gln Glu Pro Gly Gln Pro Pro Lys Leu Leu Ile Tyr
1               5                   10                  15

<210> SEQ ID NO 64
<211> LENGTH: 442
<212> TYPE: PRT
<213> ORGANISM: Artificial Sequence
<220> FEATURE:
<223> OTHER INFORMATION: Synthetic Construct

<400> SEQUENCE: 64

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Val Asn Asn
            20                  25                  30

Ala Met Ile Trp Val Arg Lys Ala Pro Gly Lys Gly Leu Glu Trp Val
        35                  40                  45

Ser Ala Leu Ser Phe Ala Asp Asn Thr Ala Tyr Tyr Ala Thr Trp Ala
    50                  55                  60

Ser Gly Arg Phe Thr Ile Ser Arg Asp Ser Ser Lys Thr Thr Val Tyr
65                  70                  75                  80

Leu Gln Met Asn Ser Leu Arg Ala Glu Asp Thr Ala Val Tyr Tyr Cys
                85                  90                  95

Met Arg Gly Asp Leu Trp Gly Pro Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Glu Ser Val Val Thr Val Pro Ser Ser Ser Leu Gly Thr Gln Thr
            180                 185                 190
```

```
Tyr Ile Cys Asn Val Asn His Lys Pro Ser Asn Thr Lys Val Asp Lys
            195                 200                 205

Lys Val Glu Pro Lys Ser Cys Asp Lys Thr His Thr Cys Pro Pro Cys
    210                 215                 220

Pro Ala Pro Glu Leu Leu Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Gly Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Trp Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

<210> SEQ ID NO 65
<211> LENGTH: 218
<212> TYPE: PRT
<213> ORGANISM: Artificial Sequence
<220> FEATURE:
<223> OTHER INFORMATION: Synthetic Construct

<400> SEQUENCE: 65

Asp Ile Gln Met Thr Gln Ser Pro Ser Thr Leu Ser Ala Ser Val Gly
1               5                   10                  15

Asp Arg Val Thr Ile Thr Cys Gln Ala Ser Glu Ser Ile Thr Arg Tyr
            20                  25                  30

Leu Asn Trp Tyr Gln Glu Lys Pro Gly Lys Ala Pro Lys Leu Leu Ile
        35                  40                  45

Tyr Asp Ala Ser Lys Leu Pro Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Ser Thr Ser Phe Arg Gly Arg
                85                  90                  95

Ser Tyr Gln Asn Thr Phe Gly Gly Gly Thr Lys Val Glu Ile Lys Arg
            100                 105                 110
```

```
Thr Val Ala Ala Pro Ser Val Phe Ile Phe Pro Ser Asp Glu Gln
        115                 120                 125

Leu Lys Ser Gly Thr Ala Ser Val Lys Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 66
<211> LENGTH: 442
<212> TYPE: PRT
<213> ORGANISM: Artificial Sequence
<220> FEATURE:
<223> OTHER INFORMATION: Synthetic Construct

<400> SEQUENCE: 66

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Val Asn Asn
            20                  25                  30

Ala Met Ile Trp Val Arg Lys Ala Pro Gly Lys Gly Leu Glu Trp Val
        35                  40                  45

Ser Ala Leu Ser Phe Ala Asp Asn Thr Ala Tyr Tyr Ala Thr Trp Ala
    50                  55                  60

Ser Gly Arg Phe Thr Ile Ser Arg Asp Ser Ser Lys Thr Thr Val Tyr
65                  70                  75                  80

Leu Gln Met Asn Ser Leu Arg Ala Glu Asp Thr Ala Val Tyr Tyr Cys
                85                  90                  95

Met Arg Gly Asp Leu Trp Gly Pro Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Glu Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255
```

-continued

```
Val Val Val Asp Val Ser His Glu Asp Pro Glu Val Lys Phe Asn Trp
            260                 265                 270
Tyr Val Asp Gly Val Glu Val His Asn Ala Lys Thr Lys Pro Arg Glu
        275                 280                 285
Glu Gln Tyr Gly Ser Thr Tyr Arg Val Val Ser Val Leu Thr Val Leu
    290                 295                 300
His Gln Asp Trp Leu Asn Gly Lys Glu Tyr Lys Cys Lys Val Ser Asn
305                 310                 315                 320
Lys Ala Leu Pro Ala Pro Ile Glu Lys Thr Ile Ser Lys Ala Lys Gly
                325                 330                 335
Gln Pro Arg Glu Pro Gln Val Tyr Thr Leu Pro Pro Ser Arg Glu Glu
            340                 345                 350
Met Thr Lys Asn Gln Val Ser Leu Ser Cys Ala Val Lys Gly Phe Tyr
        355                 360                 365
Pro Ser Asp Ile Ala Val Glu Trp Glu Ser Asn Gly Gln Pro Glu Asn
    370                 375                 380
Asn Tyr Lys Thr Thr Pro Pro Val Leu Asp Ser Asp Gly Ser Phe Phe
385                 390                 395                 400
Leu Val Ser Lys Leu Thr Val Asp Lys Ser Arg Trp Gln Gln Gly Asn
                405                 410                 415
Val Phe Ser Cys Ser Val Met His Glu Ala Leu His Asn His Tyr Thr
            420                 425                 430
Gln Lys Ser Leu Ser Leu Ser Pro Gly Lys
        435                 440

<210> SEQ ID NO 67
<211> LENGTH: 449
<212> TYPE: PRT
<213> ORGANISM: Artificial Sequence
<220> FEATURE:
<223> OTHER INFORMATION: Synthetic Construct

<400> SEQUENCE: 67

Glu Val Gln Leu Val Gln Ser Gly Ala Glu Val Lys Lys Pro Gly Ala
1               5                   10                  15
Ser Val Lys Val Ser Cys Lys Ala Ser Gly Phe Thr Phe Thr Ser Tyr
            20                  25                  30
Tyr Ile His Trp Val Arg Lys Ala Pro Gly Gln Gly Leu Glu Trp Ile
        35                  40                  45
Gly Trp Ile Tyr Pro Glu Asn Asp Asn Thr Lys Tyr Asn Glu Lys Phe
    50                  55                  60
Lys Asp Arg Val Thr Ile Thr Ala Asp Thr Ser Thr Ser Thr Ala Tyr
65                  70                  75                  80
Leu Glu Leu Ser Ser Leu Arg Ser Glu Asp Thr Ala Val Tyr Tyr Cys
                85                  90                  95
Ala Arg Asp Gly Tyr Ser Arg Tyr Tyr Phe Asp Tyr Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
```

```
Gln Ser Ser Gly Leu Tyr Ser Leu Glu Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Gly Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Trp
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 68
<211> LENGTH: 449
<212> TYPE: PRT
<213> ORGANISM: Artificial Sequence
<220> FEATURE:
<223> OTHER INFORMATION: Synthetic Construct

<400> SEQUENCE: 68

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Tyr Ile His Trp Val Arg Glu Ala Pro Gly Gln Gly Leu Glu Trp Ile
            35                  40                  45

Gly Trp Ile Tyr Pro Glu Asn Asp Asn Thr Lys Tyr Asn Glu Lys Phe
        50                  55                  60

Lys Asp Arg Val Thr Ile Thr Ala Asp Thr Ser Thr Ser Thr Ala Tyr
65                  70                  75                  80
```

```
Leu Glu Leu Ser Ser Leu Arg Ser Glu Asp Thr Ala Val Tyr Tyr Cys
                85                  90                  95

Ala Arg Asp Gly Tyr Ser Arg Tyr Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gly Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Trp
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 69
<211> LENGTH: 449
<212> TYPE: PRT
<213> ORGANISM: Artificial Sequence
<220> FEATURE:
<223> OTHER INFORMATION: Synthetic Construct
```

-continued

```
<400> SEQUENCE: 69

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Tyr Ile His Trp Val Arg Glu Ala Pro Gly Gln Gly Leu Glu Trp Ile
        35                  40                  45

Gly Trp Ile Tyr Pro Glu Asn Asp Asn Thr Lys Tyr Asn Glu Lys Phe
    50                  55                  60

Lys Asp Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Gly Tyr Ser Arg Tyr Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Lys Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gly Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415
```

-continued

```
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 70
<211> LENGTH: 219
<212> TYPE: PRT
<213> ORGANISM: Artificial Sequence
<220> FEATURE:
<223> OTHER INFORMATION: Synthetic Construct

<400> SEQUENCE: 70

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Lys Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Glu Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 71

<400> SEQUENCE: 71

000

<210> SEQ ID NO 72

<400> SEQUENCE: 72

000

<210> SEQ ID NO 73
<211> LENGTH: 219
<212> TYPE: PRT
```

<213> ORGANISM: Artificial Sequence
<220> FEATURE:
<223> OTHER INFORMATION: Synthetic Construct

<400> SEQUENCE: 73

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Lys Pro Gly Gln
        35                  40                  45

Pro Pro Lys Leu Leu Ile Tyr Trp Ala Ser Thr Arg Lys Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Glu Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 74

<400> SEQUENCE: 74

000

<210> SEQ ID NO 75
<211> LENGTH: 133
<212> TYPE: PRT
<213> ORGANISM: Artificial Sequence
<220> FEATURE:
<223> OTHER INFORMATION: Synthetic Construct

<400> SEQUENCE: 75

```
Met Lys Pro Gln Phe Val Gly Ile Leu Leu Ser Ser Leu Leu Gly Ala
1               5                   10                  15

Ala Leu Gly Asn Arg Met Arg Cys Tyr Asn Cys Gly Gly Ser Pro Ser
            20                  25                  30

Ser Ser Cys Lys Glu Ala Val Thr Thr Cys Gly Glu Gly Arg Pro Gln
        35                  40                  45

Pro Gly Leu Glu Gln Ile Lys Leu Pro Gly Asn Pro Pro Val Thr Leu
    50                  55                  60

Ile His Gln His Pro Ala Cys Val Ala Ala His Cys Asn Gln Val
65                  70                  75                  80
```

```
Glu Thr Glu Ser Val Gly Asp Val Thr Tyr Pro Ala His Arg Asp Cys
            85                  90                  95

Tyr Leu Gly Asp Leu Cys Asn Ser Ala Val Ala Ser His Val Ala Pro
        100                 105                 110

Ala Gly Ile Leu Ala Ala Ala Thr Ala Leu Thr Cys Leu Leu Pro
        115                 120                 125

Gly Leu Trp Ser Gly
    130

<210> SEQ ID NO 76
<211> LENGTH: 2449
<212> TYPE: DNA
<213> ORGANISM: Artificial Sequence
<220> FEATURE:
<223> OTHER INFORMATION: Synthetic Construct

<400> SEQUENCE: 76
```

| | | | | | |
|---|---|---|---|---|---|
| atgaaacccc | agtttgttgg | gatcttgctc | agctccctgc | tagggggctgc | cttgggtaag | 60 |
| gaggcggcca | gctagcttct | cacacaggcc | ttctgccagc | cggctccacc | gagggcccag | 120 |
| gtccagcgcc | tcttttctcc | tgccaggaaa | ccgaatgcgg | tgctacaact | gtggtggaag | 180 |
| ccccagcagt | tcttgcaaag | aggccgtgac | cacctgtggc | gagggcagac | cccagccagg | 240 |
| cctggaacag | atcaagctac | ctggaaaccg | tgagtcctca | gtttctccct | cttccagcag | 300 |
| cctttccctg | cctccagccc | catgtcaatc | cttctggctt | ccagaaccct | ccaggctcag | 360 |
| tctggctctg | ggcagatggt | gcagctgtta | gaggagagca | gtctgtaccc | cttctggctc | 420 |
| ctggcacgga | gccctgaga | ggcccacagt | ccttgtgccc | ccacttcccc | acctccttat | 480 |
| tctcctaaaa | gaatctcata | ggcccattag | ctcacaaatg | aagagctctg | gccctgaaag | 540 |
| gccaaagtta | aaaccaaact | tcaaattttc | ggcattagtt | aaggaccagg | agggggtgtg | 600 |
| tgtgtgtgtg | tgtgtgtgtg | tgtgtgtgtg | tgtgtacatg | ttttaatat | tttatttaa | 660 |
| cataattttg | gattgacaga | aaagttgcag | aaatactcaa | cttctcctaa | tgctaacatc | 720 |
| ttacataacc | atagcacaat | tatcaaaatc | acaaaataac | tgatacaata | ctactaacta | 780 |
| atctacagac | tttatttgat | ttagcaagat | cctacattgc | atttagctct | catgtcttct | 840 |
| tagtctcctc | tgatctgtgc | cagttctgtt | tttctttgtc | tttcatgacc | ctgacacatt | 900 |
| tgaagagccc | tgataaatta | ttttatacct | ggagtttaaa | aaattacttt | tagggccagt | 960 |
| gcagtcactc | gcacctgtaa | tcccagcact | ttaggaggcc | aaggtgggag | gaccacttga | 1020 |
| gcccaagagt | tgagaccagc | ctgggcaaca | tagggagacc | ctgtctctac | aaaaaacaaa | 1080 |
| caaacaaaca | aacaaacaga | ttaaaaaatt | agttgggtgt | ggtggcacat | gcttgtagtc | 1140 |
| ctagctactc | aggggggctga | agagggagga | tcgcttgagc | ctgggagatt | gaagctacaa | 1200 |
| tgagccatga | tcacgccact | acactccagc | ctggggaaca | aaatgagacc | ctgtctcaaa | 1260 |
| aataataata | ataataattt | ttaggctagg | cttggtggca | cacttgta | atcccagcac | 1320 |
| tttgggaggc | caaggctgaa | gagtcacctg | aggtcaggag | tttgacacca | gcctgggcag | 1380 |
| caaagtgaga | cccccatctc | tacaaaaaat | gttttttaaaa | aattagccag | gcatagtggc | 1440 |
| acacacctgt | aatctcagtt | tcctgagagg | ctgaggcagg | aggattactt | gagcccagga | 1500 |
| gtttgaggct | atagggaggt | atgattgcac | caccacactc | cagcctgagt | gagagagcaa | 1560 |
| gatctttct | ctaaaattaa | ataaaatcat | tttagatta | aacaaaaatt | acgtgccgga | 1620 |
| tgcagtggct | cacgcctgta | atcccagcac | tttgggaggc | caaggcgggt | ggataacctg | 1680 |

```
aggtcgggag ttcaagacca gcctgatcaa tgtggagaaa tctcgtctct actaaaaata    1740
caaaattagc cgggtgtagt ggtgcccgcc tgtaatacca gctactcggg aacctgaggc    1800
aggagaattg cttgaaccca agaggtggag gtcgcggtga gccgagatca ccaccattgca   1860 ctccagctgg gcaataagag tgaaactccg tctcaaaaaa aaaaaaaaaa ttacagatac    1920
ttgaaatact aaaaattatt ttatagaatg tccctcgata tttatttatc tgatatttgc    1980
catgatgaga ttgaggtcat gcattttaag caagaatact gcagaagtga tgttgcatcc    2040
ttcttgctgc atcacatcag gagtttacaa ggtcaatgca ttaactttga tcacttggtt    2100
tcagggaggt gttttttgag ggggctgaaa atccctttgg gctccttgaa atcacatctg    2160
ctctgcccca gaaggcaagt cctgaagcca ggagtccaac accccagttt cattctctct    2220
ctcagcccca gtgaccttga ttcaccaaca tccagcctgc gtcgcagccc atcattgcaa    2280
tcaagtggag acagagtcgg tgggagacgt gacttatcca gcccacaggg actgctacct    2340
gggagacctg tgcaacagcg ccgtggcaag ccatgtggcc cctgcaggca ttttggctgc    2400
agcagctacc gccctgacct gtctcttgcc aggactgtgg agcggatag              2449
```

<210> SEQ ID NO 77
<211> LENGTH: 133
<212> TYPE: PRT
<213> ORGANISM: Artificial Sequence
<220> FEATURE:
<223> OTHER INFORMATION: Synthetic Construct

<400> SEQUENCE: 77

Met Lys Pro Gln Phe Val Gly Ile Leu Leu Ser Ser Leu Leu Gly Ala
1               5                   10                  15

Ala Leu Gly Asn Arg Met Arg Cys Tyr Asn Cys Gly Gly Ser Pro Ser
            20                  25                  30

Ser Ser Cys Lys Glu Ala Val Thr Thr Cys Gly Glu Gly Arg Pro Gln
        35                  40                  45

Pro Gly Leu Glu Gln Ile Lys Leu Pro Gly Asn Pro Val Thr Leu
    50                  55                  60

Ile His Gln His Pro Ala Cys Val Ala Ala His His Cys Asn Gln Val
65                  70                  75                  80

Glu Thr Glu Ser Val Gly Asp Val Thr Tyr Pro Ala His Arg Asp Cys
                85                  90                  95

Tyr Leu Gly Asp Leu Cys Asn Ser Ala Val Ala Ser His Val Ala Pro
            100                 105                 110

Ala Gly Ile Leu Ala Ala Ala Thr Ala Leu Thr Cys Leu Leu Pro
        115                 120                 125

Gly Leu Trp Ser Gly
    130

<210> SEQ ID NO 78
<211> LENGTH: 10
<212> TYPE: PRT
<213> ORGANISM: Artificial Sequence
<220> FEATURE:
<223> OTHER INFORMATION: Synthetic Construct

<400> SEQUENCE: 78

Arg Asp Cys Tyr Leu Gly Asp Leu Cys Asn
1               5                   10

<210> SEQ ID NO 79
<211> LENGTH: 3

```
<212> TYPE: PRT
<213> ORGANISM: Artificial Sequence
<220> FEATURE:
<223> OTHER INFORMATION: Synthetic Construct

<400> SEQUENCE: 79

Gly Asp Leu
1

<210> SEQ ID NO 80
<211> LENGTH: 207
<212> TYPE: PRT
<213> ORGANISM: Artificial Sequence
<220> FEATURE:
<223> OTHER INFORMATION: Synthetic Construct

<400> SEQUENCE: 80

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205

<210> SEQ ID NO 81
<211> LENGTH: 198
<212> TYPE: PRT
<213> ORGANISM: Artificial Sequence
<220> FEATURE:
<223> OTHER INFORMATION: Synthetic Construct

<400> SEQUENCE: 81

Met Gln Ser Gly Thr Arg Trp Arg Val Leu Gly Leu Cys Leu Leu Ser
1               5                   10                  15

Ile Gly Val Trp Gly Gln Asp Gly Asn Glu Glu Met Gly Ser Ile Thr
            20                  25                  30

Gln Thr Pro Tyr Gln Val Ser Ile Ser Gly Thr Thr Val Ile Leu Thr
        35                  40                  45
```

Cys Ser Gln His Leu Gly Ser Glu Ala Gln Trp Gln His Asn Gly Lys
        50                  55                  60

Asn Lys Glu Asp Ser Gly Asp Arg Leu Phe Leu Pro Glu Phe Ser Glu
 65              70                  75                  80

Met Glu Gln Ser Gly Tyr Tyr Val Cys Tyr Pro Arg Gly Ser Asn Pro
                85                  90                  95

Glu Asp Ala Ser His His Leu Tyr Leu Lys Ala Arg Val Cys Glu Asn
            100                 105                 110

Cys Met Glu Met Asp Val Met Ala Val Ala Thr Ile Val Ile Val Asp
        115                 120                 125

Ile Cys Ile Thr Leu Gly Leu Leu Leu Val Tyr Tyr Trp Ser Lys
        130                 135                 140

Asn Arg Lys Ala Lys Ala Lys Pro Val Thr Arg Gly Ala Gly Ala Gly
145                 150                 155                 160

Gly Arg Gln Arg Gly Gln Asn Lys Glu Arg Pro Pro Pro Val Pro Asn
                165                 170                 175

Pro Asp Tyr Glu Pro Ile Arg Lys Gly Gln Gln Asp Leu Tyr Ser Gly
            180                 185                 190

Leu Asn Gln Arg Arg Ile
            195

<210> SEQ ID NO 82
<211> LENGTH: 182
<212> TYPE: PRT
<213> ORGANISM: Artificial Sequence
<220> FEATURE:
<223> OTHER INFORMATION: Synthetic Construct

<400> SEQUENCE: 82

Met Glu Gln Gly Lys Gly Leu Ala Val Leu Ile Leu Ala Ile Ile Leu
 1               5                  10                  15

Leu Gln Gly Thr Leu Ala Gln Ser Ile Lys Gly Asn His Leu Val Lys
                20                  25                  30

Val Tyr Asp Tyr Gln Glu Asp Gly Ser Val Leu Leu Thr Cys Asp Ala
            35                  40                  45

Glu Ala Lys Asn Ile Thr Trp Phe Lys Asp Gly Lys Met Ile Gly Phe
        50                  55                  60

Leu Thr Glu Asp Lys Lys Lys Trp Asn Leu Gly Ser Asn Ala Lys Asp
 65              70                  75                  80

Pro Arg Gly Met Tyr Gln Cys Lys Gly Ser Gln Asn Lys Ser Lys Pro
                85                  90                  95

Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
        115                 120                 125

Leu Ala Val Gly Val Tyr Phe Ile Ala Gly Gln Asp Gly Val Arg Gln
        130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Asp Gln Tyr Ser His Leu Gln Gly
                165                 170                 175

Asn Gln Leu Arg Arg Asn
            180

<210> SEQ ID NO 83

<211> LENGTH: 181
<212> TYPE: PRT
<213> ORGANISM: Artificial Sequence
<220> FEATURE:
<223> OTHER INFORMATION: Synthetic Construct

<400> SEQUENCE: 83

Met Val Gln Gly Lys Gly Leu Thr Gly Phe Ile Leu Ala Ile Ile Leu
1               5                   10                  15

Leu Gln Gly Ser Leu Ala Gln Ser Phe Glu Glu Asn Arg Lys Leu Asn
            20                  25                  30

Val Tyr Asn Gln Glu Asp Gly Ser Val Leu Leu Thr Cys His Val Lys
        35                  40                  45

Asn Thr Asn Ile Thr Trp Phe Lys Glu Gly Lys Met Ile Asp Ile Leu
    50                  55                  60

Thr Ala His Lys Asn Lys Trp Asn Leu Gly Ser Asn Thr Lys Asp Pro
65                  70                  75                  80

Arg Gly Val Tyr Gln Cys Lys Gly Ser Lys Asp Lys Ser Lys Thr Leu
                85                  90                  95

Gln Val Tyr Tyr Arg Met Cys Gln Asn Cys Ile Glu Leu Asn Ala Ala
            100                 105                 110

Thr Ile Leu Gly Phe Val Phe Ala Glu Ile Ile Ser Ile Phe Phe Leu
        115                 120                 125

Ala Val Gly Val Tyr Phe Ile Ala Gly Gln Asp Gly Val Arg Gln Ser
    130                 135                 140

Arg Ala Ser Asp Lys Gln Thr Leu Leu Pro Asn Asp Gln Leu Tyr Gln
145                 150                 155                 160

Pro Leu Lys Asp Arg Glu Asp Asp Gln Tyr Ser His Leu Gln Gly Asn
                165                 170                 175

Gln Leu Arg Met Asn
            180

<210> SEQ ID NO 84
<211> LENGTH: 26
<212> TYPE: PRT
<213> ORGANISM: Artificial Sequence
<220> FEATURE:
<223> OTHER INFORMATION: Synthetic Construct

<400> SEQUENCE: 84

Met Gln Ser Gly Thr His Trp Arg Val Leu Gly Leu Cys Leu Leu Ser
1               5                   10                  15

Val Gly Val Trp Gly Gln Asp Gly Asn Glu
            20                  25

<210> SEQ ID NO 85
<211> LENGTH: 27
<212> TYPE: PRT
<213> ORGANISM: Artificial Sequence
<220> FEATURE:
<223> OTHER INFORMATION: Synthetic Construct

<400> SEQUENCE: 85

Met Gln Ser Gly Thr His Trp Arg Val Leu Gly Leu Cys Leu Leu Ser
1               5                   10                  15

Val Gly Val Trp Gly Gln Asp Gly Asn Glu Glu
            20                  25

<210> SEQ ID NO 86
<211> LENGTH: 16

```
<212> TYPE: PRT
<213> ORGANISM: Artificial Sequence
<220> FEATURE:
<223> OTHER INFORMATION: Synthetic Construct

<400> SEQUENCE: 86

Gln Asp Gly Asn Glu Glu Met Gly Gly Ile Thr Gln Thr Pro Tyr Lys
1               5                   10                  15

<210> SEQ ID NO 87
<211> LENGTH: 12
<212> TYPE: PRT
<213> ORGANISM: Artificial Sequence
<220> FEATURE:
<223> OTHER INFORMATION: Synthetic Construct

<400> SEQUENCE: 87

His Arg Asp Cys Tyr Leu Gly Asp Leu Cys Asn Ser
1               5                   10

<210> SEQ ID NO 88
<211> LENGTH: 91
<212> TYPE: PRT
<213> ORGANISM: Artificial Sequence
<220> FEATURE:
<223> OTHER INFORMATION: Synthetic Construct

<400> SEQUENCE: 88

Asn Arg Met Arg Cys Tyr Asn Cys Gly Gly Ser Pro Ser Ser Ser Cys
1               5                   10                  15

Lys Glu Ala Val Thr Thr Cys Gly Glu Gly Arg Pro Gln Pro Gly Leu
            20                  25                  30

Glu Gln Ile Lys Leu Pro Gly Asn Pro Pro Val Thr Leu Ile His Gln
        35                  40                  45

His Pro Ala Cys Val Ala Ala His His Cys Asn Gln Val Glu Thr Glu
    50                  55                  60

Ser Val Gly Asp Val Thr Tyr Pro Ala His Arg Asp Cys Tyr Leu Gly
65                  70                  75                  80

Asp Leu Cys Asn Ser Ala Gly Asn Ser Val Thr
                85                  90

<210> SEQ ID NO 89
<211> LENGTH: 119
<212> TYPE: PRT
<213> ORGANISM: Artificial Sequence
<220> FEATURE:
<223> OTHER INFORMATION: Synthetic Construct

<400> SEQUENCE: 89

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Tyr Ile His Trp Val Arg Glu Ala Pro Gly Gln Gly Leu Glu Trp Ile
        35                  40                  45

Gly Trp Ile Tyr Pro Glu Asn Asp Asn Thr Lys Tyr Asn Glu Lys Phe
    50                  55                  60

Lys Asp Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95
```

```
Ala Arg Asp Gly Tyr Ser Arg Tyr Tyr Phe Asp Tyr Trp Gly Gln Gly
            100                 105                 110

Thr Leu Val Thr Val Ser Ser
        115

<210> SEQ ID NO 90
<211> LENGTH: 112
<212> TYPE: PRT
<213> ORGANISM: Artificial Sequence
<220> FEATURE:
<223> OTHER INFORMATION: Synthetic Construct

<400> SEQUENCE: 90

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Lys Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
            100                 105                 110

<210> SEQ ID NO 91

<400> SEQUENCE: 91

000

<210> SEQ ID NO 92
<211> LENGTH: 112
<212> TYPE: PRT
<213> ORGANISM: Artificial Sequence
<220> FEATURE:
<223> OTHER INFORMATION: Synthetic Construct

<400> SEQUENCE: 92

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Lys Lys Pro Gly Gln
        35                  40                  45

Pro Pro Lys Leu Leu Ile Tyr Trp Ala Ser Thr Arg Lys Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Val Glu Ile Lys
            100                 105                 110

<210> SEQ ID NO 93
<211> LENGTH: 112
<212> TYPE: PRT
```

```
<213> ORGANISM: Artificial Sequence
<220> FEATURE:
<223> OTHER INFORMATION: Synthetic Construct

<400> SEQUENCE: 93

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Thr Ser Thr Arg Lys Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Val Glu Ile Lys
            100                 105                 110

<210> SEQ ID NO 94
<211> LENGTH: 112
<212> TYPE: PRT
<213> ORGANISM: Artificial Sequence
<220> FEATURE:
<223> OTHER INFORMATION: Synthetic Construct

<400> SEQUENCE: 94

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Lys Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Val Glu Ile Lys
            100                 105                 110

<210> SEQ ID NO 95
<211> LENGTH: 222
<212> TYPE: PRT
<213> ORGANISM: Artificial Sequence
<220> FEATURE:
<223> OTHER INFORMATION: Synthetic Construct

<400> SEQUENCE: 95

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Val Met His Trp Val Arg Gln Ala Pro Gly Gln Gly Leu Glu Trp Met
        35                  40                  45

Gly Tyr Ile Asn Pro Tyr Asn Asp Gly Thr Lys Tyr Asn Glu Lys Phe
    50                  55                  60
```

```
Lys Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Gly Arg Arg Asn Phe Asp Tyr Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr
210                 215                 220
```

<210> SEQ ID NO 96
<211> LENGTH: 216
<212> TYPE: PRT
<213> ORGANISM: Artificial Sequence
<220> FEATURE:
<223> OTHER INFORMATION: Synthetic Construct

<400> SEQUENCE: 96

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Asp Phe Val Asn Asn
             20                  25                  30

Ala Met Ile Trp Val Arg Gln Ala Pro Gly Lys Gly Leu Glu Trp Val
         35                  40                  45

Ser Ala Leu Ser Phe Ala Asp Asn Thr Ala Tyr Tyr Ala Thr Trp Ala
 50                  55                  60

Ser Gly Arg Phe Thr Ile Ser Arg Asp Ser Ser Lys Thr Thr Val Tyr
 65                  70                  75                  80

Leu Gln Met Asn Ser Leu Arg Ala Glu Asp Thr Ala Val Tyr Tyr Cys
                 85                  90                  95

Met Arg Gly Asp Leu Trp Gly Pro Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205
```

```
Lys Val Glu Pro Lys Ser Cys Asp
    210             215
```

<210> SEQ ID NO 97
<211> LENGTH: 218
<212> TYPE: PRT
<213> ORGANISM: Artificial Sequence
<220> FEATURE:
<223> OTHER INFORMATION: Synthetic Construct

<400> SEQUENCE: 97

```
Asp Ile Gln Met Thr Gln Ser Pro Ser Thr Leu Ser Ala Ser Val Gly
1               5                   10                  15

Asp Arg Val Thr Ile Thr Cys Gln Ala Ser Glu Ser Ile Thr Arg Tyr
            20                  25                  30

Leu Asn Trp Tyr Gln Gln Lys Pro Gly Lys Ala Pro Lys Leu Leu Ile
        35                  40                  45

Tyr Asp Ala Ser Lys Leu Pro Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Ser Thr Ser Phe Arg Gly Arg
                85                  90                  95

Ser Tyr Gln Asn Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210             215
```

<210> SEQ ID NO 98
<211> LENGTH: 119
<212> TYPE: PRT
<213> ORGANISM: Artificial Sequence
<220> FEATURE:
<223> OTHER INFORMATION: Synthetic Construct

<400> SEQUENCE: 98

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Ile
        35                  40                  45

Gly Trp Ile Tyr Pro Gly Asp Gly Asn Thr Lys Tyr Asn Glu Lys Phe
50                  55                  60
```

```
Lys Gly Arg Ala Thr Leu Thr Ala Asp Thr Ser Ser Thr Ala Tyr
 65                  70                  75                  80

Leu Glu Leu Ser Ser Leu Arg Ser Glu Asp Thr Ala Val Tyr Tyr Cys
             85                  90                  95

Ala Arg Asp Ser Tyr Ser Asn Tyr Tyr Phe Asp Tyr Trp Gly Gln Gly
            100                 105                 110

Thr Leu Val Thr Val Ser Ser
        115

<210> SEQ ID NO 99
<211> LENGTH: 13
<212> TYPE: PRT
<213> ORGANISM: Artificial Sequence
<220> FEATURE:
<223> OTHER INFORMATION: Synthetic Construct

<400> SEQUENCE: 99

Gln Ser Thr Ser Phe Arg Gly Arg Ser Tyr Asn Asn Thr
 1               5                  10

<210> SEQ ID NO 100
<211> LENGTH: 13
<212> TYPE: PRT
<213> ORGANISM: Artificial Sequence
<220> FEATURE:
<223> OTHER INFORMATION: Synthetic Construct

<400> SEQUENCE: 100

Gln Ser Thr Ser Phe Arg Gly Arg Ser Tyr Gln Asn Val
 1               5                  10

<210> SEQ ID NO 101
<211> LENGTH: 13
<212> TYPE: PRT
<213> ORGANISM: Artificial Sequence
<220> FEATURE:
<223> OTHER INFORMATION: Synthetic Construct

<400> SEQUENCE: 101

Gln Ser Thr Ser Phe Arg Gly Arg Ser Tyr Ser Asn Thr
 1               5                  10

<210> SEQ ID NO 102
<211> LENGTH: 13
<212> TYPE: PRT
<213> ORGANISM: Artificial Sequence
<220> FEATURE:
<223> OTHER INFORMATION: Synthetic Construct

<400> SEQUENCE: 102

Gln Ser Thr Ser Phe Arg Gly Arg Ser Tyr Ser Asn Ala
 1               5                  10

<210> SEQ ID NO 103
<211> LENGTH: 13
<212> TYPE: PRT
<213> ORGANISM: Artificial Sequence
<220> FEATURE:
<223> OTHER INFORMATION: Synthetic Construct

<400> SEQUENCE: 103

Gln Ser Thr Ser Phe Arg Gly Arg Ser Tyr Ala Asn Thr
 1               5                  10
```

-continued

<210> SEQ ID NO 104
<211> LENGTH: 13
<212> TYPE: PRT
<213> ORGANISM: Artificial Sequence
<220> FEATURE:
<223> OTHER INFORMATION: Synthetic Construct

<400> SEQUENCE: 104

Gln Ser Thr Ser Phe Arg Gly Arg Ser Tyr Asn Asn Ala
1               5                   10

<210> SEQ ID NO 105
<211> LENGTH: 13
<212> TYPE: PRT
<213> ORGANISM: Artificial Sequence
<220> FEATURE:
<223> OTHER INFORMATION: Synthetic Construct

<400> SEQUENCE: 105

Gln Ser Thr Ser Phe Arg Gly Arg Ser Tyr Asn Asn Val
1               5                   10

<210> SEQ ID NO 106
<211> LENGTH: 13
<212> TYPE: PRT
<213> ORGANISM: Artificial Sequence
<220> FEATURE:
<223> OTHER INFORMATION: Synthetic Construct

<400> SEQUENCE: 106

Gln Ser Thr Ser Phe Arg Gly Arg Ser Tyr Gly Asn Thr
1               5                   10

<210> SEQ ID NO 107
<211> LENGTH: 13
<212> TYPE: PRT
<213> ORGANISM: Artificial Sequence
<220> FEATURE:
<223> OTHER INFORMATION: Synthetic Construct

<400> SEQUENCE: 107

Gln Ser Thr Ser Phe Arg Gly Arg Ser Tyr Ser Asn Val
1               5                   10

<210> SEQ ID NO 108
<211> LENGTH: 112
<212> TYPE: PRT
<213> ORGANISM: Artificial Sequence
<220> FEATURE:
<223> OTHER INFORMATION: Synthetic Construct

<400> SEQUENCE: 108

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Lys Lys Pro Gly Gln
        35                  40                  45

Ser Pro Lys Leu Leu Ile Tyr Trp Thr Ser Thr Arg Lys Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Val Glu Ile Lys
            100                 105                 110

<210> SEQ ID NO 109
<211> LENGTH: 119
<212> TYPE: PRT
<213> ORGANISM: Artificial Sequence
<220> FEATURE:
<223> OTHER INFORMATION: Synthetic Construct

<400> SEQUENCE: 109

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Lys Ala Pro Gly Gln Gly Leu Glu Trp Ile
        35                  40                  45

Gly Trp Ile Tyr Pro Gly Asp Gly Asn Thr Lys Tyr Asn Glu Lys Phe
    50                  55                  60

Lys Gly Arg Ala Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Ser Tyr Ser Asn Tyr Tyr Phe Asp Tyr Trp Gly Gln Gly
            100                 105                 110

Thr Leu Val Thr Val Ser Ser
        115

<210> SEQ ID NO 110
<211> LENGTH: 7
<212> TYPE: PRT
<213> ORGANISM: Artificial Sequence
<220> FEATURE:
<223> OTHER INFORMATION: Synthetic Construct

<400> SEQUENCE: 110

Trp Ala Ser Thr Arg Ile Ser
1               5

<210> SEQ ID NO 111
<211> LENGTH: 5
<212> TYPE: PRT
<213> ORGANISM: Artificial Sequence
<220> FEATURE:
<223> OTHER INFORMATION: Synthetic Construct

<400> SEQUENCE: 111

Asn Asn Ala Met Ser
1               5

<210> SEQ ID NO 112
<211> LENGTH: 17
<212> TYPE: PRT
<213> ORGANISM: Artificial Sequence
<220> FEATURE:
<223> OTHER INFORMATION: Synthetic Construct

<400> SEQUENCE: 112

Ser Leu Ser Phe Ala Asp Asn Thr Ala Tyr Tyr Ala Thr Trp Ala Ser
1               5                   10                  15

Gly

```
<210> SEQ ID NO 113
<211> LENGTH: 17
<212> TYPE: PRT
<213> ORGANISM: Artificial Sequence
<220> FEATURE:
<223> OTHER INFORMATION: Synthetic Construct

<400> SEQUENCE: 113

Ile Leu Ser Phe Ala Asp Asn Thr Ala Tyr Tyr Ala Thr Trp Ala Ser
1               5                   10                  15

Gly

<210> SEQ ID NO 114
<211> LENGTH: 442
<212> TYPE: PRT
<213> ORGANISM: Artificial Sequence
<220> FEATURE:
<223> OTHER INFORMATION: Synthetic Construct

<400> SEQUENCE: 114

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Val Asn Asn
            20                  25                  30

Ala Met Ile Trp Val Arg Gln Ala Pro Gly Lys Gly Leu Glu Trp Val
        35                  40                  45

Ser Ala Leu Ser Phe Ala Asp Asn Thr Ala Tyr Tyr Ala Thr Trp Ala
    50                  55                  60

Ser Gly Arg Phe Thr Ile Ser Arg Asp Ser Ser Lys Thr Thr Val Tyr
65                  70                  75                  80

Leu Gln Met Asn Ser Leu Arg Ala Glu Asp Thr Ala Val Tyr Tyr Cys
                85                  90                  95

Met Arg Gly Asp Leu Trp Gly Pro Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285
```

```
Glu Gln Tyr Gly Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Trp Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

<210> SEQ ID NO 115
<211> LENGTH: 218
<212> TYPE: PRT
<213> ORGANISM: Artificial Sequence
<220> FEATURE:
<223> OTHER INFORMATION: Synthetic Construct

<400> SEQUENCE: 115

Asp Ile Gln Met Thr Gln Ser Pro Ser Thr Leu Ser Ala Ser Val Gly
1               5                   10                  15

Asp Arg Val Thr Ile Thr Cys Gln Ala Ser Glu Ser Ile Thr Arg Tyr
            20                  25                  30

Leu Asn Trp Tyr Gln Gln Lys Pro Gly Lys Ala Pro Lys Leu Leu Ile
        35                  40                  45

Tyr Asp Ala Ser Lys Leu Pro Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Ser Thr Ser Phe Arg Gly Arg
                85                  90                  95

Ser Tyr Gln Asn Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205
```

```
Val Thr Lys Ser Phe Asn Arg Gly Glu Cys
    210                 215

<210> SEQ ID NO 116
<211> LENGTH: 7
<212> TYPE: PRT
<213> ORGANISM: Artificial Sequence
<220> FEATURE:
<223> OTHER INFORMATION: Synthetic Construct

<400> SEQUENCE: 116

Gly Arg Ser Tyr Asn Asn Thr
1               5

<210> SEQ ID NO 117
<211> LENGTH: 111
<212> TYPE: PRT
<213> ORGANISM: Artificial Sequence
<220> FEATURE:
<223> OTHER INFORMATION: Synthetic Construct

<400> SEQUENCE: 117

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Ser Ile Thr Arg Tyr
            20                  25                  30

Leu Asn Trp Tyr Gln Gln Lys Pro Gly Lys Pro Lys Leu Leu Ile
        35                  40                  45

Tyr Asp Ala Ser Lys Leu Pro Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Thr Ser Phe Arg Gly Arg
                85                  90                  95

Ser Tyr Asn Asn Thr Phe Gly Gly Gly Thr Lys Val Glu Ile Lys
                100                 105                 110

<210> SEQ ID NO 118
<211> LENGTH: 111
<212> TYPE: PRT
<213> ORGANISM: Artificial Sequence
<220> FEATURE:
<223> OTHER INFORMATION: Synthetic Construct

<400> SEQUENCE: 118

Asp Ile Gln Met Thr Gln Ser Pro Ser Thr Leu Ser Ala Ser Val Gly
1               5                   10                  15

Asp Arg Val Thr Ile Thr Cys Gln Ala Ser Glu Ser Ile Thr Arg Tyr
            20                  25                  30

Leu Asn Trp Tyr Gln Gln Lys Pro Gly Lys Pro Pro Lys Leu Leu Ile
        35                  40                  45

Tyr Asp Ala Ser Lys Leu Pro Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Ser Thr Ser Phe Arg Gly Arg
                85                  90                  95

Ser Tyr Asn Asn Thr Phe Gly Gly Gly Thr Lys Val Glu Ile Lys
                100                 105                 110
```

```
<210> SEQ ID NO 119
<211> LENGTH: 111
<212> TYPE: PRT
<213> ORGANISM: Artificial Sequence
<220> FEATURE:
<223> OTHER INFORMATION: Synthetic Construct

<400> SEQUENCE: 119

Asp Ile Val Met Thr Gln Ser Pro Asp Ser Leu Ala Val Ser Leu Gly
1               5                   10                  15

Glu Arg Ala Thr Ile Asn Cys Gln Ala Ser Glu Ser Ile Thr Arg Tyr
            20                  25                  30

Leu Asn Trp Tyr Gln Gln Lys Pro Gly Gln Pro Pro Lys Leu Leu Ile
        35                  40                  45

Tyr Asp Ala Ser Lys Leu Pro Ser Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Ser Thr Ser Phe Arg Gly Arg
                85                  90                  95

Ser Tyr Asn Asn Thr Phe Gly Gly Gly Thr Lys Val Glu Ile Lys
            100                 105                 110

<210> SEQ ID NO 120
<211> LENGTH: 112
<212> TYPE: PRT
<213> ORGANISM: Artificial Sequence
<220> FEATURE:
<223> OTHER INFORMATION: Synthetic Construct

<400> SEQUENCE: 120

Glu Gln Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Val Asn Asn
            20                  25                  30

Ala Met Ser Trp Val Arg Gln Ala Pro Gly Lys Gly Leu Glu Trp Ile
        35                  40                  45

Ala Ala Leu Ser Phe Ala Asp Asn Thr Ala Tyr Tyr Ala Thr Trp Ala
    50                  55                  60

Ser Gly Arg Phe Thr Ile Ser Lys Asp Ser Ser Lys Thr Thr Val Tyr
65                  70                  75                  80

Leu Gln Met Asn Ser Leu Arg Ala Glu Asp Thr Ala Val Tyr Phe Cys
                85                  90                  95

Met Arg Gly Asp Leu Trp Gly Pro Gly Thr Leu Val Thr Val Ser Ser
            100                 105                 110

<210> SEQ ID NO 121
<211> LENGTH: 112
<212> TYPE: PRT
<213> ORGANISM: Artificial Sequence
<220> FEATURE:
<223> OTHER INFORMATION: Synthetic Construct

<400> SEQUENCE: 121

Glu Gln Gln Leu Val Glu Ser Gly Gly Gly Val Val Gln Pro Gly Arg
1               5                   10                  15

Ser Leu Arg Leu Ser Cys Ala Ala Ser Gly Phe Asp Phe Val Asn Asn
            20                  25                  30
```

```
Ala Met Ser Trp Val Arg Gln Ala Pro Gly Lys Gly Leu Glu Trp Ile
            35                  40                  45

Ala Ala Leu Ser Phe Ala Asp Asn Thr Ala Tyr Tyr Ala Thr Trp Ala
        50                  55                  60

Ser Gly Arg Phe Thr Ile Ser Lys Asp Ser Ser Lys Asn Thr Val Tyr
 65                  70                  75                  80

Leu Gln Met Asn Ser Leu Arg Ala Glu Asp Thr Ala Val Tyr Phe Cys
                85                  90                  95

Met Arg Gly Asp Leu Trp Gly Pro Gly Thr Leu Val Thr Val Ser Ser
            100                 105                 110
```

<210> SEQ ID NO 122
<211> LENGTH: 111
<212> TYPE: PRT
<213> ORGANISM: Artificial Sequence
<220> FEATURE:
<223> OTHER INFORMATION: Synthetic Construct

<400> SEQUENCE: 122

```
Asp Ile Gln Met Thr Gln Ser Pro Ser Thr Leu Ser Ala Ser Val Gly
 1               5                   10                  15

Asp Arg Val Thr Ile Thr Cys Gln Ala Ser Glu Ser Ile Thr Arg Tyr
            20                  25                  30

Leu Asn Trp Tyr Gln Gln Lys Pro Gly Lys Pro Pro Lys Leu Leu Ile
        35                  40                  45

Tyr Asp Ala Ser Lys Leu Pro Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Ser Thr Ser Phe Arg Gly Arg
                85                  90                  95

Ser Tyr Gln Asn Thr Phe Gly Gly Gly Thr Lys Val Glu Ile Lys
            100                 105                 110
```

<210> SEQ ID NO 123
<211> LENGTH: 112
<212> TYPE: PRT
<213> ORGANISM: Artificial Sequence
<220> FEATURE:
<223> OTHER INFORMATION: Synthetic Construct

<400> SEQUENCE: 123

```
Glu Gln Gln Leu Val Glu Ser Gly Gly Gly Val Val Gln Pro Gly Arg
 1               5                   10                  15

Ser Leu Arg Leu Ser Cys Ala Ala Ser Gly Phe Asp Phe Val Asn Asn
            20                  25                  30

Ala Met Ile Trp Val Arg Gln Ala Pro Gly Lys Gly Leu Glu Trp Ile
        35                  40                  45

Ala Ala Leu Ser Phe Ala Asp Asn Thr Ala Tyr Tyr Ala Thr Trp Ala
        50                  55                  60

Ser Gly Arg Phe Thr Ile Ser Lys Asp Ser Ser Lys Asn Thr Val Tyr
 65                  70                  75                  80

Leu Gln Met Asn Ser Leu Arg Ala Glu Asp Thr Ala Val Tyr Phe Cys
                85                  90                  95

Met Arg Gly Asp Leu Trp Gly Pro Gly Thr Leu Val Thr Val Ser Ser
            100                 105                 110
```

<210> SEQ ID NO 124
<211> LENGTH: 107
<212> TYPE: PRT
<213> ORGANISM: Artificial Sequence
<220> FEATURE:
<223> OTHER INFORMATION: Synthetic Construct

<400> SEQUENCE: 124

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Leu
                85                  90                  95

Thr Phe Gly Gly Gly Thr Lys Val Glu Ile Lys
            100                 105
```

<210> SEQ ID NO 125
<211> LENGTH: 112
<212> TYPE: PRT
<213> ORGANISM: Artificial Sequence
<220> FEATURE:
<223> OTHER INFORMATION: Synthetic Construct

<400> SEQUENCE: 125

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Asp Leu Trp Gly Arg Gly Thr Leu Val Thr Val Ser Ser
            100                 105                 110
```

<210> SEQ ID NO 126
<211> LENGTH: 112
<212> TYPE: PRT
<213> ORGANISM: Artificial Sequence
<220> FEATURE:
<223> OTHER INFORMATION: Synthetic Construct

<400> SEQUENCE: 126

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Glu Lys Pro Gly Gln
        35                  40                  45
```

```
Ser Pro Lys Leu Leu Ile Tyr Trp Thr Ser Thr Arg Lys Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Val Glu Ile Lys
                100                 105                 110

<210> SEQ ID NO 127
<211> LENGTH: 119
<212> TYPE: PRT
<213> ORGANISM: Artificial Sequence
<220> FEATURE:
<223> OTHER INFORMATION: Synthetic Construct

<400> SEQUENCE: 127

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Ile His Trp Val Arg Gln Ala Pro Gly Gln Gly Leu Glu Trp Ile
            35                  40                  45

Gly Trp Ile Tyr Pro Gly Asp Gly Asn Thr Lys Tyr Asn Glu Lys Phe
    50                  55                  60

Lys Gly Arg Ala Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Ser Tyr Ser Asn Tyr Phe Asp Tyr Trp Gly Gln Gly
                100                 105                 110

Thr Leu Val Thr Val Ser Ser
        115

<210> SEQ ID NO 128
<211> LENGTH: 112
<212> TYPE: PRT
<213> ORGANISM: Artificial Sequence
<220> FEATURE:
<223> OTHER INFORMATION: Synthetic Construct

<400> SEQUENCE: 128

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
            35                  40                  45

Pro Pro Lys Leu Leu Ile Tyr Trp Thr Ser Thr Arg Lys Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Val Glu Ile Lys
                100                 105                 110
```

```
<210> SEQ ID NO 129
<211> LENGTH: 112
<212> TYPE: PRT
<213> ORGANISM: Artificial Sequence
<220> FEATURE:
<223> OTHER INFORMATION: Synthetic Construct

<400> SEQUENCE: 129
```

Asp Ile Val Met Thr Gln Ser Pro Asp Ser Leu Ala Val Ser Leu Gly
1               5                   10                  15

Glu Arg Ala Thr Ile Asn Cys Lys Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Lys Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Val Glu Ile Lys
            100                 105                 110

```
<210> SEQ ID NO 130
<211> LENGTH: 111
<212> TYPE: PRT
<213> ORGANISM: Artificial Sequence
<220> FEATURE:
<223> OTHER INFORMATION: Synthetic Construct

<400> SEQUENCE: 130
```

Asp Ile Val Met Thr Gln Thr Pro Ser Ser Val Ser Ala Ala Val Gly
1               5                   10                  15

Gly Thr Val Thr Ile Asn Cys Gln Ala Ser Glu Ser Ile Thr Arg Tyr
            20                  25                  30

Leu Asn Trp Tyr Gln Gln Lys Pro Gly Gln Pro Pro Lys Leu Leu Ile
        35                  40                  45

Tyr Asp Ala Ser Lys Leu Pro Ser Gly Val Pro Ser Arg Phe Lys Gly
    50                  55                  60

Ser Gly Ser Gly Thr Gln Phe Thr Leu Thr Thr Ser Asp Leu Glu Cys
65                  70                  75                  80

Ala Asp Ala Ala Thr Tyr Tyr Cys Gln Ser Thr Ser Phe Arg Gly Arg
                85                  90                  95

Ser Tyr Asn Asn Thr Phe Gly Gly Gly Thr Glu Val Val Val Lys
            100                 105                 110

```
<210> SEQ ID NO 131
<211> LENGTH: 111
<212> TYPE: PRT
<213> ORGANISM: Artificial Sequence
<220> FEATURE:
<223> OTHER INFORMATION: Synthetic Construct

<400> SEQUENCE: 131
```

Gln Gln Gln Leu Glu Glu Ser Gly Gly Asp Leu Val Lys Pro Gly Ala
1               5                   10                  15

Ser Leu Thr Leu Thr Cys Thr Ala Ser Gly Phe Asp Phe Val Asn Asn
            20                  25                  30

Ala Met Cys Trp Val Arg Gln Ala Pro Gly Lys Gly Leu Glu Trp Ile
        35                  40                  45

```
Ala Cys Leu Ser Phe Ala Asp Asn Thr Ala Tyr Tyr Ala Thr Trp Ala
        50                  55                  60

Ser Gly Arg Phe Thr Ile Ser Lys Ile Ser Ser Thr Val Thr Leu
65                  70                  75                  80

Arg Met Thr Ser Leu Thr Gly Ala Asp Thr Ala Thr Tyr Phe Cys Met
                85                  90                  95

Arg Gly Asp Leu Trp Gly Pro Gly Thr Leu Val Thr Val Ser Ser
            100                 105                 110

<210> SEQ ID NO 132
<211> LENGTH: 111
<212> TYPE: PRT
<213> ORGANISM: Artificial Sequence
<220> FEATURE:
<223> OTHER INFORMATION: Synthetic Construct

<400> SEQUENCE: 132

Glu Ala Val Leu Thr Gln Ser Pro Gly Thr Leu Ser Leu Ser Pro Gly
1               5                   10                  15

Glu Arg Ala Thr Leu Ser Cys Gln Ser Ser Glu Ser Val Trp His Asn
            20                  25                  30

Asn Trp Leu Ala Trp Phe Gln Gln Lys Pro Gly Gln Arg Pro Arg Leu
        35                  40                  45

Leu Ile Tyr Gly Ala Ser Thr Leu Ala Ser Gly Val Pro Asp Arg Phe
    50                  55                  60

Ser Gly Ser Gly Ser Gly Thr Asp Phe Thr Leu Thr Ile Ser Arg Leu
65                  70                  75                  80

Glu Pro Glu Asp Phe Ala Val Tyr Tyr Cys Ala Gly Tyr Ser Ser
                85                  90                  95

Ser Asp Ala His Val Phe Gly Gly Gly Thr Lys Val Glu Ile Lys
            100                 105                 110

<210> SEQ ID NO 133
<211> LENGTH: 111
<212> TYPE: PRT
<213> ORGANISM: Artificial Sequence
<220> FEATURE:
<223> OTHER INFORMATION: Synthetic Construct

<400> SEQUENCE: 133

Asp Ala Gln Leu Thr Gln Ser Pro Ser Thr Leu Ser Ala Ser Val Gly
1               5                   10                  15

Asp Arg Val Thr Ile Thr Cys Gln Ser Ser Glu Ser Val Trp His Asn
            20                  25                  30

Asn Trp Leu Ala Trp Phe Gln Gln Lys Pro Gly Lys Arg Pro Lys Leu
        35                  40                  45

Leu Ile Tyr Gly Ala Ser Thr Leu Ala Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Asp Asp Phe Ala Thr Tyr Tyr Cys Ala Gly Tyr Ser Ser
                85                  90                  95

Ser Asp Ala His Val Phe Gly Gly Gly Thr Lys Val Glu Ile Lys
            100                 105                 110

<210> SEQ ID NO 134
<211> LENGTH: 111
<212> TYPE: PRT
```

<213> ORGANISM: Artificial Sequence
<220> FEATURE:
<223> OTHER INFORMATION: Synthetic Construct

<400> SEQUENCE: 134

```
Asp Ala Val Leu Thr Gln Ser Pro Asp Ser Leu Ala Val Ser Leu Gly
1               5                   10                  15

Glu Arg Ala Thr Ile Asn Cys Gln Ser Ser Glu Ser Val Trp His Asn
            20                  25                  30

Asn Trp Leu Ala Trp Phe Gln Gln Lys Pro Gly Gln Pro Lys Leu
        35                  40                  45

Leu Ile Tyr Gly Ala Ser Thr Leu Ala Ser Gly Val Pro Asp Arg Phe
50                  55                  60

Ser Gly Ser Gly Ser Gly Thr Asp Phe Thr Leu Thr Ile Ser Ser Leu
65                  70                  75                  80

Gln Ala Glu Asp Val Ala Val Tyr Tyr Cys Ala Gly Tyr Ser Ser
            85                  90                  95

Ser Asp Ala His Val Phe Gly Gly Gly Thr Lys Val Glu Ile Lys
            100                 105                 110
```

<210> SEQ ID NO 135
<211> LENGTH: 118
<212> TYPE: PRT
<213> ORGANISM: Artificial Sequence
<220> FEATURE:
<223> OTHER INFORMATION: Synthetic Construct

<400> SEQUENCE: 135

```
Glu Gln Gln Leu Val Glu Ser Gly Gly Gly Leu Ile Gln Pro Gly Gly
1               5                   10                  15

Ser Leu Arg Leu Ser Cys Ala Val Ser Gly Leu Ser Leu Ser Thr Asn
            20                  25                  30

Ser Ile Asn Trp Val Arg Gln Ala Pro Gly Lys Gly Leu Glu Trp Ile
        35                  40                  45

Gly Tyr Ile Tyr His Gly Asp Gly Ile Ala Asp Tyr Ala Ser Trp Ala
50                  55                  60

Lys Gly Arg Phe Thr Ile Ser Lys Asp Ser Ser Lys Asn Thr Val Tyr
65                  70                  75                  80

Leu Gln Met Asn Ser Leu Arg Ala Glu Asp Thr Ala Val Tyr Phe Cys
            85                  90                  95

Ala Ser Gly Ala Gly Tyr Ser Leu Phe Thr Leu Trp Gly Pro Gly Thr
            100                 105                 110

Leu Val Thr Val Ser Ser
        115
```

<210> SEQ ID NO 136
<211> LENGTH: 118
<212> TYPE: PRT
<213> ORGANISM: Artificial Sequence
<220> FEATURE:
<223> OTHER INFORMATION: Synthetic Construct

<400> SEQUENCE: 136

```
Glu Gln Gln Leu Gln Glu Ser Gly Pro Gly Leu Val Lys Pro Pro Gly
1               5                   10                  15

Thr Leu Ser Leu Thr Cys Ala Val Ser Gly Leu Ser Leu Ser Thr Asn
            20                  25                  30

Ser Ile Asn Trp Val Arg Gln Pro Pro Gly Lys Gly Leu Glu Trp Ile
        35                  40                  45
```

Gly Tyr Ile Tyr His Gly Asp Gly Ile Ala Asp Tyr Ala Ser Trp Ala
            50                  55                  60

Lys Gly Arg Phe Thr Ile Ser Lys Asp Ser Ser Lys Thr Gln Val Ser
 65                  70                  75                  80

Leu Lys Leu Ser Ser Val Thr Ala Ala Asp Thr Ala Val Tyr Phe Cys
                 85                  90                  95

Ala Ser Gly Ala Gly Tyr Ser Leu Phe Thr Leu Trp Gly Pro Gly Thr
                100                 105                 110

Leu Val Thr Val Ser Ser
            115

<210> SEQ ID NO 137
<211> LENGTH: 118
<212> TYPE: PRT
<213> ORGANISM: Artificial Sequence
<220> FEATURE:
<223> OTHER INFORMATION: Synthetic Construct

<400> SEQUENCE: 137

Glu Gln Gln Leu Val Glu Ser Gly Gly Gly Leu Val Gln Pro Gly Gly
 1               5                  10                  15

Ser Leu Arg Leu Ser Cys Ala Val Ser Gly Leu Ser Leu Ser Thr Asn
                 20                  25                  30

Ser Ile Asn Trp Val Arg Gln Ala Pro Gly Lys Gly Leu Glu Trp Ile
             35                  40                  45

Gly Tyr Ile Tyr His Gly Asp Gly Ile Ala Asp Tyr Ala Ser Trp Ala
            50                  55                  60

Lys Gly Arg Phe Thr Ile Ser Lys Asp Ser Ala Lys Asn Ser Val Tyr
 65                  70                  75                  80

Leu Gln Met Asn Ser Leu Arg Ala Glu Asp Thr Ala Val Tyr Phe Cys
                 85                  90                  95

Ala Ser Gly Ala Gly Tyr Ser Leu Phe Thr Leu Trp Gly Pro Gly Thr
                100                 105                 110

Leu Val Thr Val Ser Ser
            115

<210> SEQ ID NO 138
<211> LENGTH: 111
<212> TYPE: PRT
<213> ORGANISM: Artificial Sequence
<220> FEATURE:
<223> OTHER INFORMATION: Synthetic Construct

<400> SEQUENCE: 138

Ala Ala Val Leu Thr Gln Thr Pro Ser Pro Val Ser Ala Ala Val Gly
 1               5                  10                  15

Gly Thr Ile Thr Ile Asn Cys Gln Ser Ser Glu Ser Val Trp His Asn
                 20                  25                  30

Asn Trp Leu Ala Trp Phe Gln Gln Lys Pro Gly Gln Arg Pro Arg Leu
             35                  40                  45

Leu Ile Tyr Gly Ala Ser Thr Leu Ala Ser Gly Val Pro Ser Arg Phe
         50                  55                  60

Ser Gly Thr Gly Ser Gly Thr Gln Phe Thr Leu Thr Ile Ser Asp Val
 65                  70                  75                  80

Gln Cys Asp Asp Ala Ala Thr Tyr Tyr Cys Ala Gly Gly Tyr Ser Ser
                 85                  90                  95

Ser Asp Ala His Val Phe Gly Arg Gly Thr Ala Val Val Val Lys
            100                 105                 110

<210> SEQ ID NO 139
<211> LENGTH: 111
<212> TYPE: PRT
<213> ORGANISM: Artificial Sequence
<220> FEATURE:
<223> OTHER INFORMATION: Synthetic Construct

<400> SEQUENCE: 139

Asp Ala Gln Met Thr Gln Ser Pro Ser Thr Leu Ser Ala Ser Val Gly
1               5                   10                  15

Asp Arg Val Thr Ile Thr Cys Gln Ser Ser Glu Ser Val Trp His Asn
            20                  25                  30

Asn Trp Leu Ala Trp Phe Gln Gln Lys Pro Gly Lys Arg Pro Lys Leu
        35                  40                  45

Leu Ile Tyr Gly Ala Ser Thr Leu Ala Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Asp Asp Phe Ala Thr Tyr Tyr Cys Ala Gly Tyr Ser Ser
                85                  90                  95

Ser Asp Ala His Val Phe Gly Gly Gly Thr Lys Val Glu Ile Lys
            100                 105                 110

<210> SEQ ID NO 140
<211> LENGTH: 111
<212> TYPE: PRT
<213> ORGANISM: Artificial Sequence
<220> FEATURE:
<223> OTHER INFORMATION: Synthetic Construct

<400> SEQUENCE: 140

Glu Ala Val Leu Thr Gln Ser Pro Gly Thr Leu Ser Leu Ser Pro Gly
1               5                   10                  15

Glu Arg Ala Thr Leu Ser Cys Gln Ser Ser Glu Ser Val Trp His Asn
            20                  25                  30

Asn Trp Leu Ala Trp Phe Gln Gln Lys Pro Gly Gln Ala Pro Arg Leu
        35                  40                  45

Leu Ile Tyr Gly Ala Ser Thr Leu Ala Ser Gly Val Pro Asp Arg Phe
    50                  55                  60

Ser Gly Ser Gly Ser Gly Thr Asp Phe Thr Leu Thr Ile Ser Arg Leu
65                  70                  75                  80

Glu Pro Glu Asp Phe Ala Val Tyr Tyr Cys Ala Gly Tyr Ser Ser
                85                  90                  95

Ser Asp Ala His Val Phe Gly Gly Gly Thr Lys Val Glu Ile Lys
            100                 105                 110

<210> SEQ ID NO 141
<211> LENGTH: 116
<212> TYPE: PRT
<213> ORGANISM: Artificial Sequence
<220> FEATURE:
<223> OTHER INFORMATION: Synthetic Construct

<400> SEQUENCE: 141

Gln Ser Leu Glu Glu Ser Gly Gly Gly Leu Val Lys Pro Gly Gly Thr
1               5                   10                  15

```
Leu Thr Leu Thr Cys Thr Val Ser Gly Leu Ser Leu Ser Thr Asn Ser
            20                  25                  30

Ile Asn Trp Val Arg Gln Ala Pro Gly Lys Gly Leu Glu Trp Ile Gly
        35                  40                  45

Tyr Ile Tyr His Gly Asp Gly Ile Ala Asp Tyr Ala Ser Trp Ala Lys
    50                  55                  60

Gly Arg Phe Thr Ile Ser Lys Thr Ser Ser Thr Val Thr Leu Arg
65              70                  75                  80

Met Thr Ser Leu Thr Val Ala Asp Thr Ala Thr Tyr Phe Cys Ala Ser
                85                  90                  95

Gly Ala Gly Tyr Ser Leu Phe Thr Leu Trp Gly Pro Gly Thr Leu Val
            100                 105                 110

Thr Val Ser Ser
            115

<210> SEQ ID NO 142
<211> LENGTH: 118
<212> TYPE: PRT
<213> ORGANISM: Artificial Sequence
<220> FEATURE:
<223> OTHER INFORMATION: Synthetic Construct

<400> SEQUENCE: 142

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Ser Leu Ser Thr Asn
            20                  25                  30

Ser Ile Asn Trp Val Arg Gln Ala Pro Gly Lys Gly Leu Glu Trp Val
        35                  40                  45

Ser Tyr Ile Tyr His Gly Asp Gly Ile Ala Asp Tyr Ala Ser Trp Ala
    50                  55                  60

Lys Gly Arg Phe Thr Ile Ser Arg Asp Asn Ala Lys Asn Ser Leu Tyr
65              70                  75                  80

Leu Gln Met Asn Ser Leu Arg Ala Glu Asp Thr Ala Val Tyr Tyr Cys
                85                  90                  95

Ala Ser Gly Ala Gly Tyr Ser Leu Phe Thr Leu Trp Gly Arg Gly Thr
            100                 105                 110

Leu Val Thr Val Ser Ser
            115

<210> SEQ ID NO 143
<211> LENGTH: 118
<212> TYPE: PRT
<213> ORGANISM: Artificial Sequence
<220> FEATURE:
<223> OTHER INFORMATION: Synthetic Construct

<400> SEQUENCE: 143

Glu Val Gln Leu Val Glu Ser Gly Gly Gly Leu Ile Gln Pro Gly Gly
1               5                   10                  15

Ser Leu Arg Leu Ser Cys Ala Ala Ser Gly Leu Ser Leu Ser Thr Asn
            20                  25                  30

Ser Ile Asn Trp Val Arg Gln Ala Pro Gly Lys Gly Leu Glu Trp Val
        35                  40                  45

Ser Tyr Ile Tyr His Gly Asp Gly Ile Ala Asp Tyr Ala Ser Trp Ala
    50                  55                  60

Lys Gly Arg Phe Thr Ile Ser Arg Asp Asn Ser Lys Asn Thr Leu Tyr
65              70                  75                  80
```

Leu Gln Met Asn Ser Leu Arg Ala Glu Asp Thr Ala Val Tyr Tyr Cys
                85                  90                  95

Ala Ser Gly Ala Gly Tyr Ser Leu Phe Thr Leu Trp Gly Arg Gly Thr
            100                 105                 110

Leu Val Thr Val Ser Ser
        115

<210> SEQ ID NO 144
<211> LENGTH: 108
<212> TYPE: PRT
<213> ORGANISM: Artificial Sequence
<220> FEATURE:
<223> OTHER INFORMATION: Synthetic Construct

<400> SEQUENCE: 144

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105

<210> SEQ ID NO 145
<211> LENGTH: 111
<212> TYPE: PRT
<213> ORGANISM: Artificial Sequence
<220> FEATURE:
<223> OTHER INFORMATION: Synthetic Construct

<400> SEQUENCE: 145

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Phe Asp Leu Trp Gly Arg Gly Thr Leu Val Thr Val Ser Ser
            100                 105                 110

<210> SEQ ID NO 146
<211> LENGTH: 112
<212> TYPE: PRT
<213> ORGANISM: Artificial Sequence
<220> FEATURE:
<223> OTHER INFORMATION: Synthetic Construct

<400> SEQUENCE: 146

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Phe Asp Leu Trp Gly Arg Gly Thr Leu Val Thr Val Ser Ser
            100                 105                 110

<210> SEQ ID NO 147
<211> LENGTH: 220
<212> TYPE: PRT
<213> ORGANISM: Artificial Sequence
<220> FEATURE:
<223> OTHER INFORMATION: Synthetic Construct

<400> SEQUENCE: 147

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Leu Ser
            20                  25                  30

Gly Asn Gln Glu Asn Tyr Leu Ala Trp His Gln Gln Lys Pro Gly Gln
        35                  40                  45

Pro Pro Lys Thr Leu Ile Thr Trp Ala Ser Thr Arg Ile Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Tyr Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220